United States Patent
Yu et al.

(10) Patent No.: US 10,081,637 B2
(45) Date of Patent: Sep. 25, 2018

(54) PYRAZOLE COMPOUNDS AS MODULATORS OF FSHR AND USES THEREOF

(71) Applicants: MERCK PATENT GMBH, Darmstadt (DE); Henry Yu, Wellesley, MA (US); Marianne Donnelly, Reading, MA (US); Ngan Nguyen, Arlington, MA (US); Xuliang Jiang, Braintree, MA (US)

(72) Inventors: Henry Yu, Wellesley, MA (US); Marianne Donnelly, Reading, MA (US); Ngan Nguyen, Arlington, MA (US); Xuliang Jiang, Braintree, MA (US)

(73) Assignee: Merck Patent GmbH, Darmstadt (DE)

( * ) Notice: Subject to any disclaimer, the term of this patent is extended or adjusted under 35 U.S.C. 154(b) by 104 days.

(21) Appl. No.: 14/900,209

(22) PCT Filed: Jun. 24, 2014

(86) PCT No.: PCT/US2014/043838
§ 371 (c)(1),
(2) Date: Dec. 21, 2015

(87) PCT Pub. No.: WO2014/209980
PCT Pub. Date: Dec. 31, 2014

(65) Prior Publication Data
US 2016/0152626 A1 Jun. 2, 2016

Related U.S. Application Data
(60) Provisional application No. 61/898,608, filed on Nov. 1, 2013, provisional application No. 61/838,460, filed on Jun. 24, 2013.

(51) Int. Cl.
*C07D 491/052* (2006.01)
(52) U.S. Cl.
CPC ................ *C07D 491/052* (2013.01)
(58) Field of Classification Search
None
See application file for complete search history.

(56) References Cited

U.S. PATENT DOCUMENTS

| 5,670,532 | A | 9/1997 | Talley et al. |
| 6,653,338 | B2 | 11/2003 | El Tayer et al. |
| 2010/0215741 | A1 | 8/2010 | Lazzari et al. |
| 2010/0216785 | A1 | 8/2010 | Lazzari et al. |

FOREIGN PATENT DOCUMENTS

| EP | 1591443 A1 | 11/2005 | |
| WO | 2002009706 A1 | 2/2002 | |
| WO | 2003024936 A1 | 3/2003 | |
| WO | WO 2008035356 A2 * | 3/2008 | ......... C07D 491/052 |
| WO | 2009055437 A2 | 4/2009 | |
| WO | 2010049366 A1 | 5/2010 | |
| WO | 2010136438 A1 | 12/2010 | |
| WO | 2011058149 A1 | 5/2011 | |

OTHER PUBLICATIONS

Desai et al., Mutations and polymorphisms in FSH receptor: funtional implications in human reproduction, 2013, Reproduction, 146, R235-R248.*
Berge et al., J. Pharmaceutical Sciences, 1977, 66: 1-19.
Foster, Adv. Drug Res., 1985, 14:1-40.
Gillette, Biochemistry, 1994, 33(10): 2927-2937.
Hanzlik, J. Org. Chem., 1990, 55: 3992-3997.
Jarman, Carcinogenesis, 1995, 16(4): 683-688.
March's Advanced Organic Chemistry, 5th Ed., Ed.: Smith, M.B. And March, J., John Wiley & Sons, New York: 2001.
"Organic Chemistry", Thomas Sorrell, University Science Books, Sausalito: 1999.
Reider et al., J. Org. Chem., 1987, 52(15): 3326-3334.
Yanofsky et al. JBC, 2006, 281(19): 13226-13233.

* cited by examiner

*Primary Examiner* — Kortney L Klinkel
*Assistant Examiner* — Tori Strong
(74) *Attorney, Agent, or Firm* — Dwight D. Kim; EMD Serono Research and Development Institute

(57) ABSTRACT

The present invention relates to pyrazole compounds, and pharmaceutically acceptable compositions thereof, useful as positive allosteric modulators of follicle stimulating hormone receptor (FSHR).

19 Claims, No Drawings

PYRAZOLE COMPOUNDS AS MODULATORS OF FSHR AND USES THEREOF

RELATED APPLICATIONS

This application is a U.S. national stage application of PCT international application PCT/US14/43838, filed on Jun. 24, 2014, which claims the benefit of U.S. provisional application 61/838,460, filed on Jun. 24, 2013, and U.S. provisional application 61/898,608, filed on Nov. 1, 2013. The contents of the aforementioned applications are hereby incorporated by reference in their entireties.

TECHNICAL FIELD OF THE INVENTION

The present invention relates to pyrazole compounds useful as agonists of follicle stimulating hormone receptor (FSHR). The invention also provides pharmaceutically acceptable compositions comprising compounds of the present invention and methods of using said compositions in the treatment of various disorders.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The gonadotropin FSH (follicle stimulating hormone) is released from the anterior pituitary under the influence of gonadotropin-releasing hormone and estrogens, and from the placenta during pregnancy. FSH is a heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. In the female, FSH plays a pivotal role in the stimulation of follicle development and maturation and in addition, it is the major hormone regulating secretion of estrogens, whereas LH induces ovulation. In the male, FSH is responsible for the integrity of the seminiferous tubules and acts on Sertoli cells to support gametogenesis.

The hormones are relatively large (28-38 kDa) and are composed of a common α-subunit non-covalently bound to a distinct β-subunit that confers receptor binding specificity. The cellular receptor for these hormones is expressed on testicular Sertoli cells and ovarian granulosa cells. The FSH receptor is known to be members of the G protein-coupled class of membrane-bound receptors, which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: a hydrophilic amino-terminal region, considered to be the amino-terminal extracellular domain; seven hydrophobic segments of membrane-spanning length, considered to be the transmembrane domain; and a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β-2-adrenergic, rhodopsin, and substance K receptors, by the large size of the hydrophilic amino-terminal domain, which is involved in hormone binding.

Annually in the U.S. there are 2.4 million couples experiencing infertility that are potential candidates for treatment. FSH, either extracted from urine or produced by recombinant DNA technology, is a parenterally-administered protein product used by specialists for ovulation induction and for controlled ovarial hyperstimulation. Whereas ovulation induction is directed at achieving a single follicle to ovulate, controlled ovarial hyperstimulation is directed at harvesting multiple oocytes for use in various in-vitro assisted reproductive technologies, e.g. in-vitro fertilization (IVF). FSH is also used clinically to treat male hypogonadism and male infertility, e.g. some types of failure of spermatogenesis.

FSHR is a highly specific target in the ovarian follicle growth process and is exclusively expressed in the ovary. However, the use of FSH is limited by its high cost, lack of oral dosing, and need of extensive monitoring by specialist physicians. Hence, identification of a non-peptidic small molecule substitute for FSH that could potentially be developed for oral administration is desirable. Low molecular weight FSH mimetics with agonistic properties are disclosed in the international applications WO 2002/09706 and WO 2010/136438 as well as the U.S. Pat. No. 6,653,338. There is still a need for low molecular weight hormone mimetics that selectively activate FSHR.

SUMMARY OF THE INVENTION

It has now been found that compounds of this invention, and pharmaceutically acceptable compositions thereof, are effective as modulators of FSHR. Such compounds have general formula I:

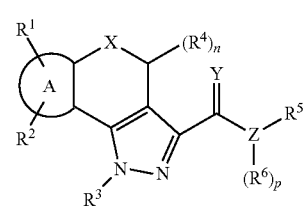

or a pharmaceutically acceptable salt thereof, wherein each of Ring A, X, Y, Z, $R^1$, $R^2$, $R^3$, $R^4$, $R^5$, $R^6$, n, and p, is as defined and described in embodiments herein.

Compounds of the present invention, and pharmaceutically acceptable compositions thereof, are useful for treating a variety of diseases, disorders or conditions, associated with abnormal cellular responses triggered by follicle stimulating hormone events. Such diseases, disorders, or conditions include those described herein.

DETAILED DESCRIPTION OF CERTAIN EMBODIMENTS

1. General Description of Compounds of the Invention

In certain embodiments, the present invention provides modulators of follicle stimulating hormone receptor (FSHR). In certain embodiments, the present invention provides positive allosteric modulators of FSHR. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^{+}$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

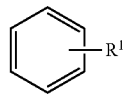

refers to at least

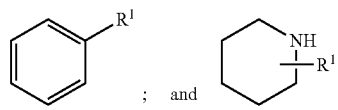
; and refers to at least

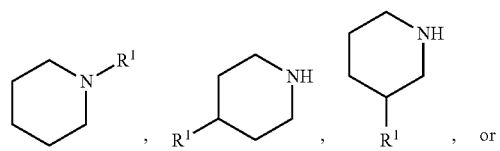

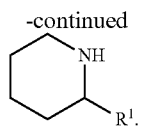

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which is optionally substituted with R°; —(CH$_2$)$_{0-4}$O(CH$_2$)$_{0-4}$Ph which is optionally substituted with R°; —CH═CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^{\bullet}$, -(haloR$^{\bullet}$), —(CH$_2$)O$_2$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R● is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR*, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, $CF_3$, $N_3$,

—NH$_2$, protected amino, —NH alkyl, —NH alkenyl, —NH alkynyl, —NH cycloalkyl, —NH— aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$-heterocyclyl, —NHC(O)NH$_2$, —NHC(O)NH— alkyl, —NHC(O)NH— alkenyl, —NHC(O)NH— alkenyl, —NHC(O)NH-carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,

—$CH_2NH_2$, —$CH_2SO_2CH_3$,

-mono-, di-, or tri-alkyl silyl,

-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms.

For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in FSHR activity between a sample comprising a compound of the present invention, or composition thereof, and FSHR, and an equivalent sample comprising FSHR, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

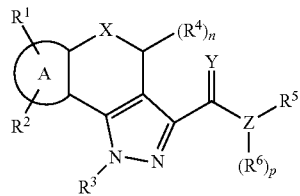

or a pharmaceutically acceptable salt thereof, wherein:
X is O, S, SO, $SO_2$, or NR;
Y is O, S, or NR;
Z is O, S, SO, $SO_2$, or N; wherein when Z is O, S, SO, or $SO_2$, then p is 0;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
Ring A is a fused $C_{3-10}$ aryl, a fused 3-8 membered saturated or partially unsaturated carbocyclic ring, a fused 3-7 membered heterocylic ring having 1-4 heteroatoms independently selected from nitrogen, oxygen, or sulfur, or a fused 5-6 membered monocyclic heteroaryl ring having 1-4 heteroatoms independently selected from nitrogen, oxygen, or sulfur;
$R^1$ is —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
$R^2$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
$R^3$ is hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
each $R^4$ is independently —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
$R^5$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
$R^6$ is hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or $R^5$ and $R^6$, together with the atom to which each is attached, form a 3-8 membered heterocyclic ring having 1-4 heteroatoms independently selected from nitrogen, oxygen, or sulfur, or a 3-8 membered heteroaryl ring having 1-4 heteroatoms independently selected from nitrogen, oxygen, or sulfur; each of which is optionally substituted;

n is 0, 1, or 2; and p is 0 or 1.

In certain embodiments, X is O. In certain embodiments, X is S. In certain embodiments, X is SO, or $SO_2$. In certain embodiments, X is NR.

In certain embodiments, Y is O. In certain embodiments, Y is S. In certain embodiments, Y is NR.

In certain embodiments, Z is O. In certain embodiments, Z is S. In certain embodiments, Z is SO or $SO_2$. In certain embodiments, Z is N.

In certain embodiments, Ring A is a fused $C_{3-10}$ aryl. In certain embodiments, Ring A is a fused 3-8 membered saturated or partially unsaturated carbocyclic ring. In certain embodiments, Ring A is a fused 3-7 membered heterocyclic ring having 1-4 heteroatoms independently selected from nitrogen, oxygen, or sulfur. In certain embodiments, Ring A is a fused 5-6 membered monocyclic heteroaryl ring having 1-4 heteroatoms independently selected from nitrogen, oxygen, or sulfur.

In certain embodiments, Ring A is phenyl, cyclopropyl, cyclobutyl, cyclopentyl, cyclohexyl, cycloheptyl, furanyl, furazanyl, imidazolidinyl, imidazolinyl, imidazolyl, 1H-indazolyl, indolenyl, isoxazolyl, morpholinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl.

In certain embodiments, Ring A is phenyl.

In certain embodiments, $R^1$ is —OR, —SR, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$. In certain embodiments, $R^1$ is —OR, —SR, —$SO_2R$, or —SOR. In certain embodiments, $R^1$ is —C(O)R, —$CO_2R$, or —C(O)N(R)$_2$. In certain embodiments, $R^1$ is —NRC(O)R, —NRC(O)N(R)$_2$, —$NRSO_2R$, or —N(R)$_2$.

In certain embodiments, $R^1$ is —OR, and R is hydrogen.

In certain embodiments, $R^1$ is —OR, and R is $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^1$ is —OR, and R is $C_{1-6}$ aliphatic. In certain embodiments, R is methyl, ethyl, propyl, i-propyl, butyl, s-butyl, t-butyl, straight or branched pentyl, or straight or branched hexyl; each of which is optionally substituted.

In certain embodiments, $R^1$ is —OR, and R is $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is hydrogen.

In certain embodiments, $R^2$ is $C_{1-6}$ aliphatic. In certain embodiments, $R^2$ is $C_{1-6}$ aliphatic wherein the aliphatic group is a $C_{1-6}$ alkyl. In certain embodiments, $R^2$ is methyl, ethyl, propyl, i-propyl, butyl, s-butyl, t-butyl, straight or branched pentyl, or straight or branched hexyl; each of which is optionally substituted. In certain embodiments, $R^2$ is $C_{1-6}$ aliphatic wherein the aliphatic group is a $C_{1-6}$ alkenyl.

In certain embodiments, $R^2$ is $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^2$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^2$ is F, Cl, Br, I, or haloalkyl.

In certain embodiments, $R^2$ is —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R is C$_1$-6 aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R is methyl, ethyl, propyl, i-propyl, butyl, s-butyl, t-butyl, straight or branched pentyl, or straight or branched hexyl; each of which is optionally substituted. In other embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is hydrogen, Br, CN,

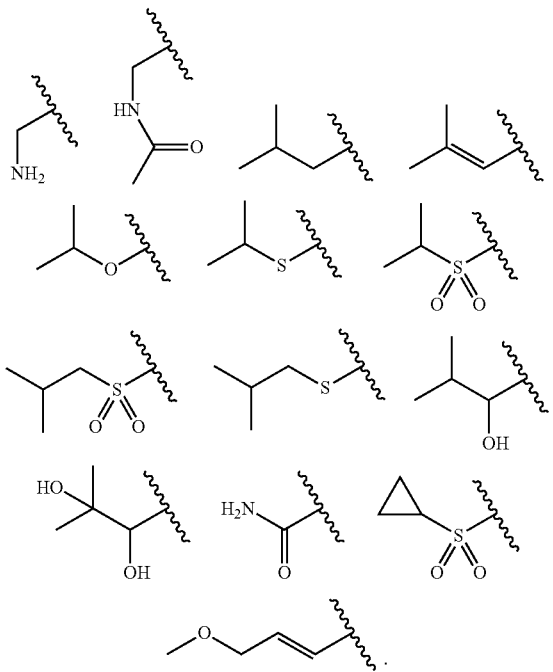

In certain embodiments, $R^2$ is

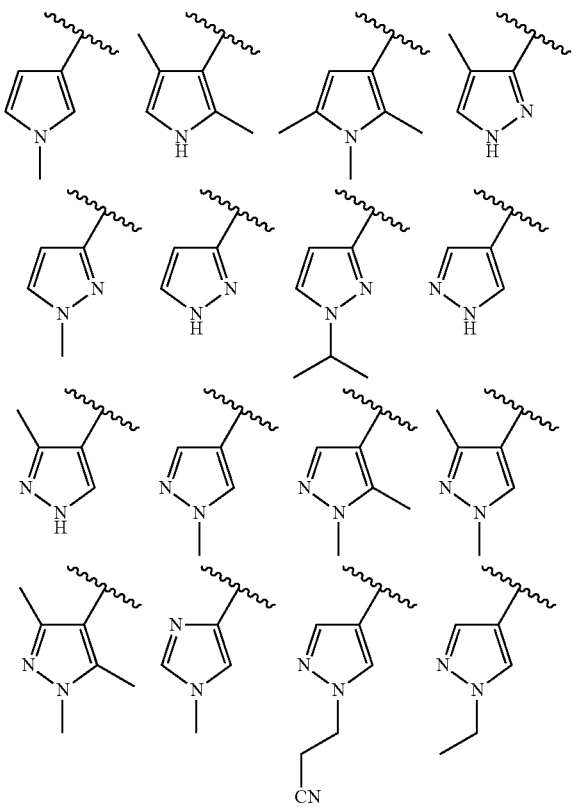

-continued
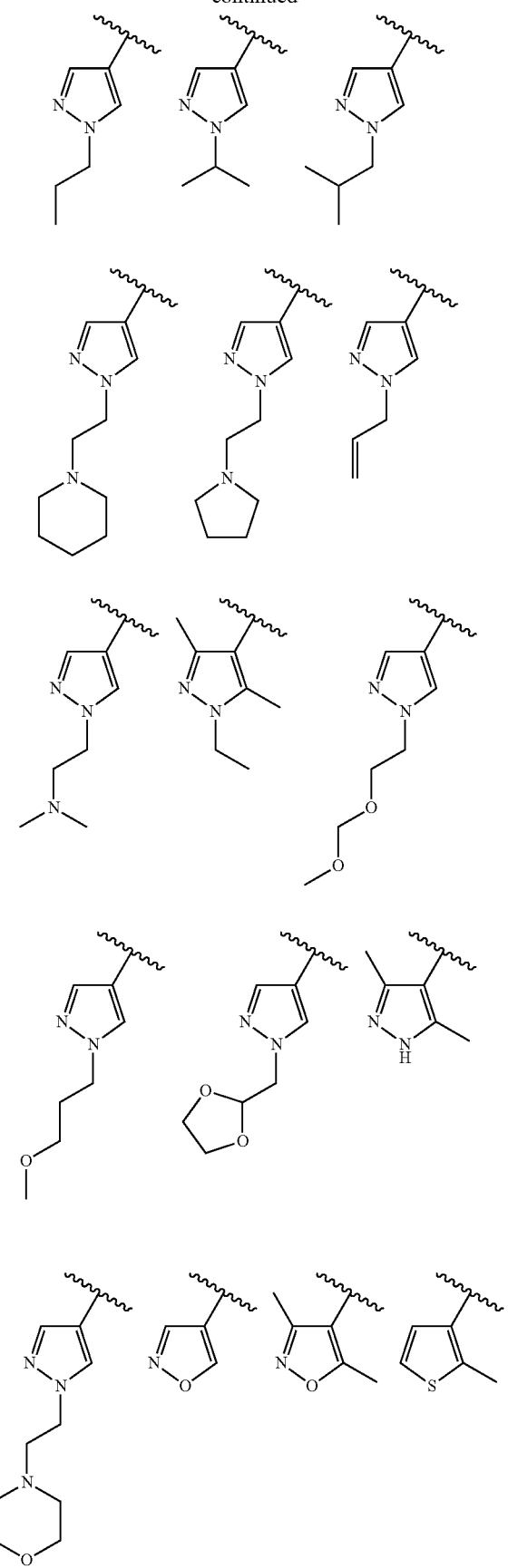
-continued
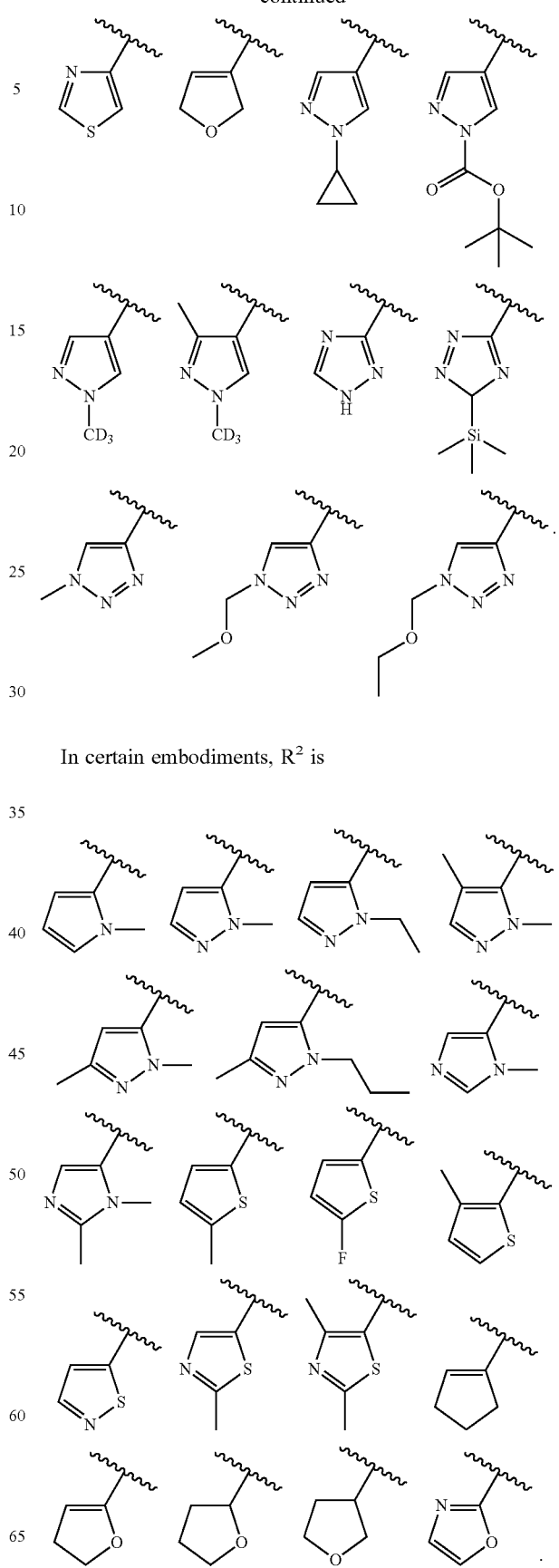
In certain embodiments, $R^2$ is

In certain embodiments, $R^2$ is

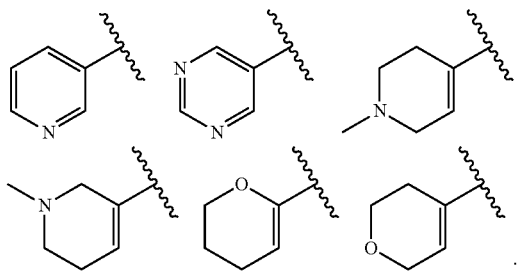

In certain embodiments, $R^3$ is hydrogen.

In certain embodiments, $R^3$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^3$ is an optionally substituted $C_{1-6}$ aliphatic. In certain embodiments, $R^3$ is an optionally substituted $C_{3-10}$ aryl. In certain embodiments, $R^3$ is an optionally substituted 3-8 membered saturated or partially unsaturated carbocyclic ring. In certain embodiments, $R^3$ is an optionally substituted 3-7 membered heterocylic ring having 1-4 heteroatoms independently selected from nitrogen, oxygen, or sulfur. In certain embodiments, $R^3$ is an optionally substituted 5-6 membered monocyclic heteroaryl ring having 1-4 heteroatoms independently selected from nitrogen, oxygen, or sulfur.

In certain embodiments, is $R^3$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, is $R^3$ is dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, purinyl, pyranyl, pyrazinyl, pyrazolidinyl, pyrazolinyl, pyrazolyl, pyridazinyl, pyrrolidinyl, pyrrolinyl, 2H-pyrrolyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl; each of which is optionally substituted.

In certain embodiments, $R^3$ is

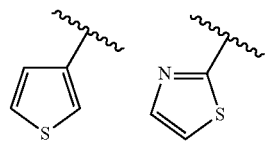

In certain embodiments, each $R^4$ is independently hydrogen.

In certain embodiments, each $R^4$ is independently $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^4$ is independently an optionally substituted $C_{1-6}$ aliphatic. In certain embodiments, each $R^4$ is independently an optionally substituted $C_3$-10 aryl. In certain embodiments, each $R^4$ is independently an optionally substituted 3-8 membered saturated or partially unsaturated carbocyclic ring. In certain embodiments, each $R^4$ is independently an optionally substituted 3-7 membered heterocylic ring having 1-4 heteroatoms independently selected from nitrogen, oxygen, or sulfur. In certain embodiments, each $R^4$ is independently an optionally substituted 5-6 membered monocyclic heteroaryl ring having 1-4 heteroatoms independently selected from nitrogen, oxygen, or sulfur.

In certain embodiments, each $R^4$ is independently halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$.

In certain embodiments, $R^5$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^5$ is an optionally substituted $C_{1-6}$ aliphatic. In certain embodiments, $R^5$ is an optionally substituted $C_{3-10}$ aryl. In certain embodiments, $R^5$ is an optionally substituted 3-8 membered saturated or partially unsaturated carbocyclic ring. In certain embodiments, $R^5$ is an optionally substituted 3-7 membered heterocylic ring having 1-4 heteroatoms independently selected from nitrogen, oxygen, or sulfur. In certain embodiments, $R^5$ is an optionally substituted 5-6 membered monocyclic heteroaryl ring having 1-4 heteroatoms independently selected from nitrogen, oxygen, or sulfur.

In certain embodiments, $R^5$ is $C_{1-6}$ aliphatic. In certain embodiments, $R^5$ is methyl, ethyl, propyl, i-propyl, butyl, s-butyl, t-butyl, straight or branched pentyl, or straight or branched hexyl; each of which is optionally substituted In certain embodiments, $R^5$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, oxetanyl, azetidinyl, or xanthenyl; each of which is optionally substituted.

In certain embodiments, $R^5$ and $R^6$, together with the atom to which each is attached, form a 3-8 membered heterocylic 1 ring having 1-4 heteroatoms independently selected from nitrogen, oxygen, or sulfur, or a 5-6 membered heteroaryl ring having 1-4 heteroatoms independently selected from nitrogen, oxygen, or sulfur; each of which is optionally substituted.

In certain embodiments, $R^5$ is methyl, t-butyl, or —$CD_3$.

In certain embodiments, $R^5$ is

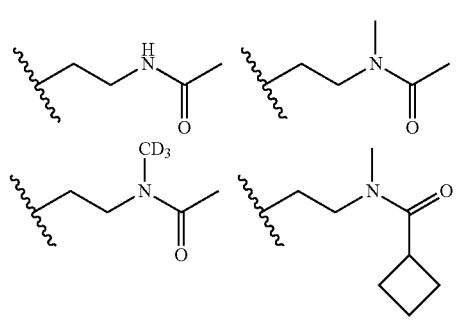

-continued

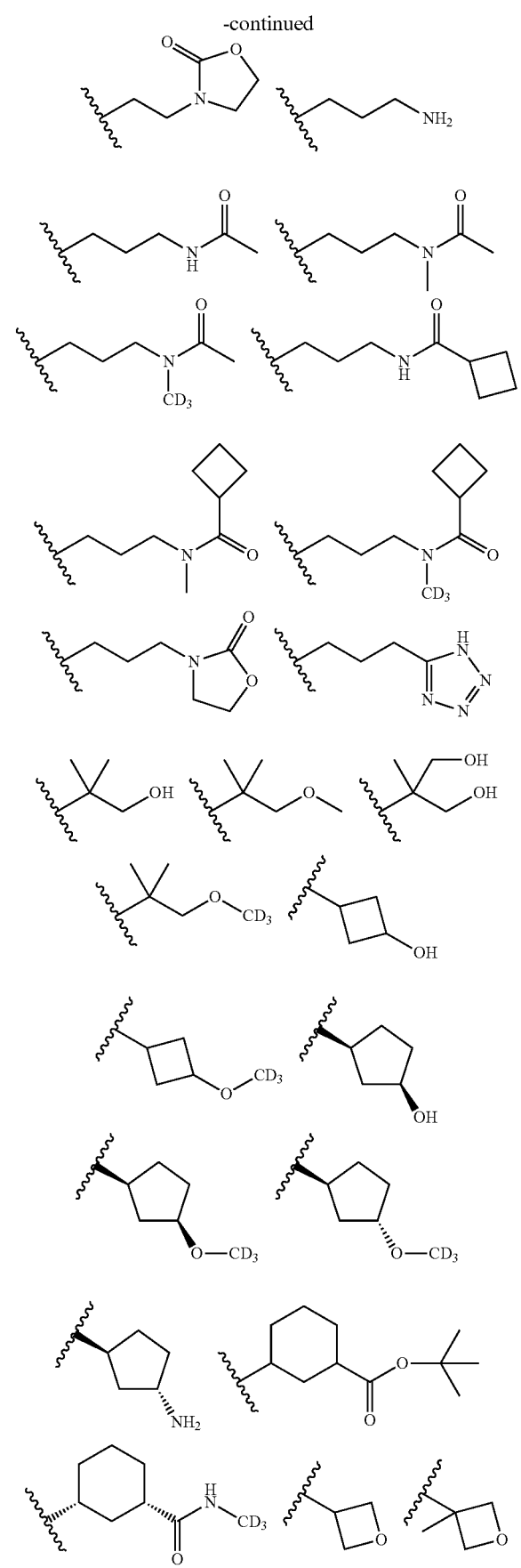

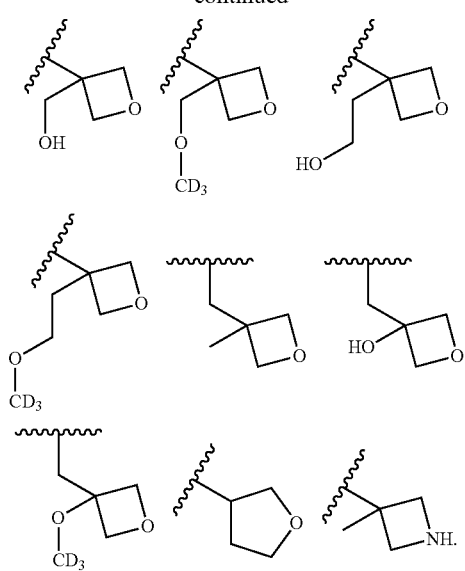
In certain embodiments, Z is N and the ring formed by Z, $R^5$ and $R^6$ is
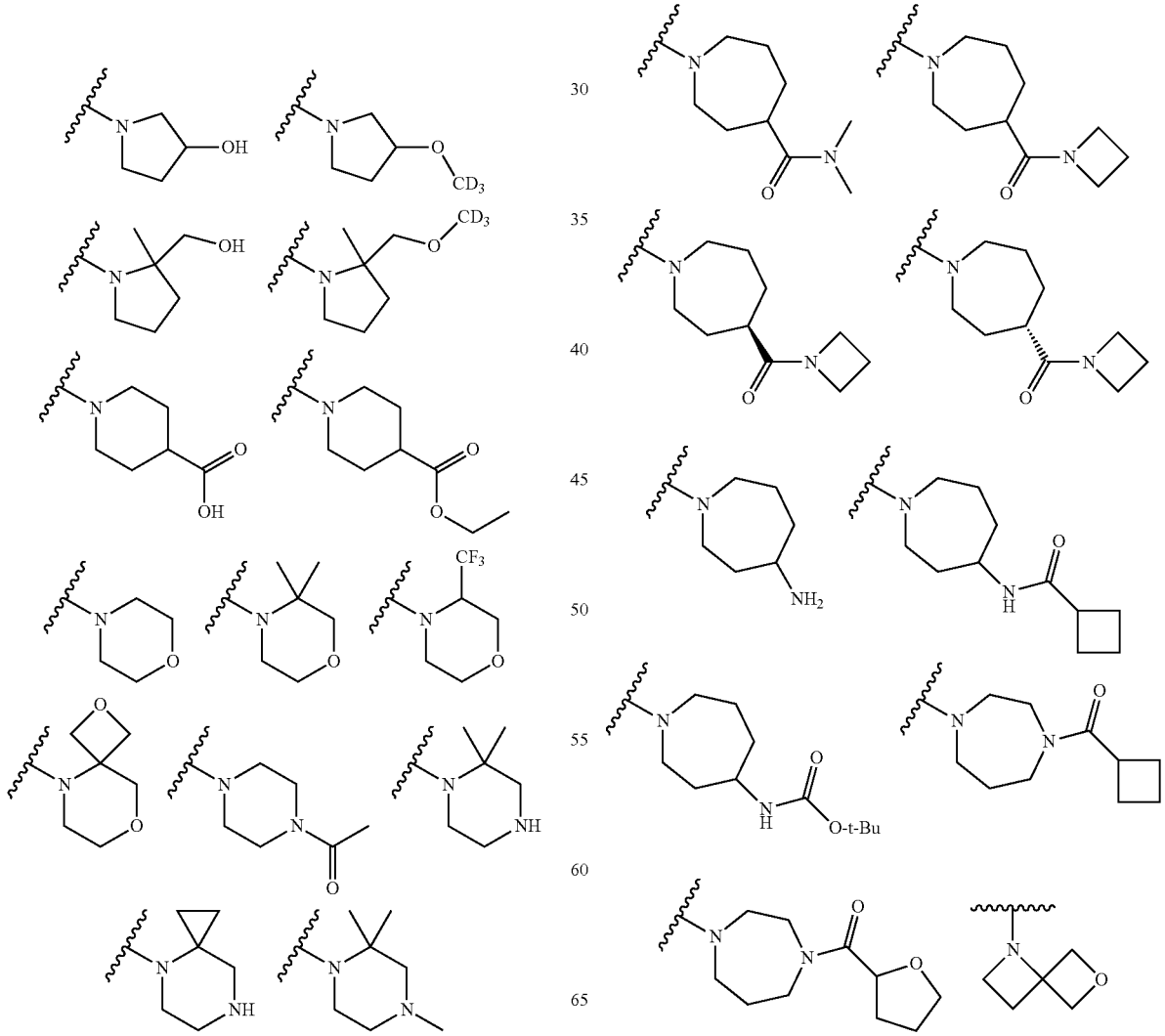
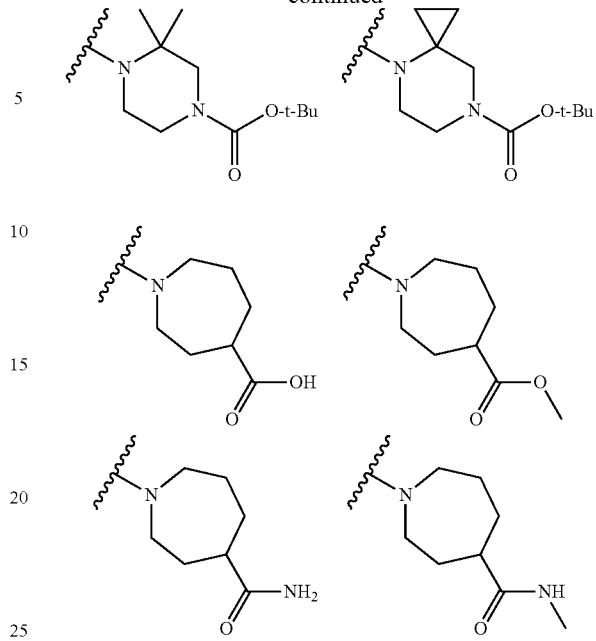

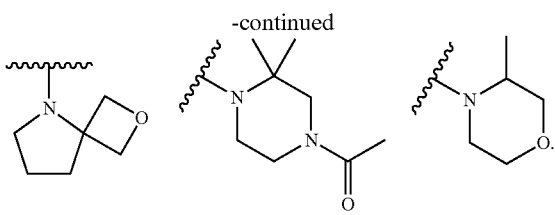

In certain embodiments, $R^6$ is hydrogen.

In certain embodiments, $R^6$ is $C_{1-6}$ aliphatic, $C_3$-10 aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^6$ is an optionally substituted $C_{1-6}$ aliphatic. In certain embodiments, $R^6$ is an optionally substituted $C_{3-10}$ aryl. In certain embodiments, $R^6$ is an optionally substituted 3-8 membered saturated or partially unsaturated carbocyclic ring. In certain embodiments, $R^6$ is an optionally substituted 3-7 membered heterocylic ring having 1-4 heteroatoms independently selected from nitrogen, oxygen, or sulfur. In certain embodiments, $R^6$ is an optionally substituted 5-6 membered monocyclic heteroaryl ring having 1-4 heteroatoms independently selected from nitrogen, oxygen, or sulfur.

In certain embodiments, $R^6$ is $C_{1-6}$ aliphatic. In certain embodiments, $R^6$ is methyl, ethyl, propyl, i-propyl, butyl, s-butyl, t-butyl, straight or branched pentyl, or straight or branched hexyl; each of which is optionally substituted.

In certain embodiments, $R^5$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^6$ is hydrogen.

In certain embodiments, $R^6$ is methyl, t-butyl, or $—CD_3$.

In certain embodiments, n is 0. In certain embodiments, n is 1. In certain embodiments, n is 2.

In certain embodiments, p is 0. In certain embodiments, p is 1.

In certain embodiments, each of $R^1$, $R^2$, $R^3$, $R^4$, $R^5$, $R^6$, X, Y, Z, n, and p is as defined above and described in embodiments, classes and subclasses above and herein, singly or in combination.

In certain embodiments, the present invention provides a compound of formula I-a,

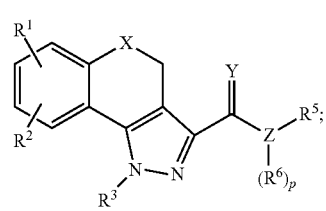

I-a or a pharmaceutically acceptable salt thereof, wherein each of $R^1$, $R^2$, $R^3$, $R^5$, $R^6$, X, Y, Z, and p is as defined above and described in embodiments, classes and subclasses above and herein, singly or in combination.

In certain embodiments, the present invention provides a compound of formula I-b,

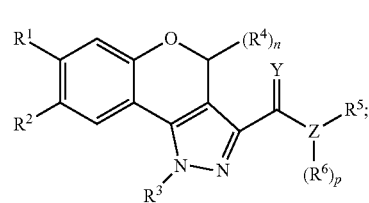

I-b or a pharmaceutically acceptable salt thereof, wherein each of $R^1$, $R^2$, $R^3$, $R^4$, $R^5$, $R^6$, Y, Z, n, and p is as defined above and described in embodiments, classes and subclasses above and herein, singly or in combination.

In certain embodiments, the compound is of formula I-c:

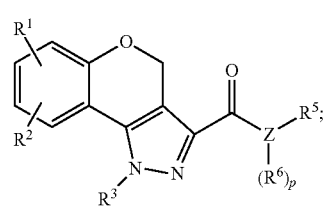

I-c or a pharmaceutically acceptable salt thereof, wherein each of $R^1$, $R^2$, $R^3$, $R^5$, $R^6$, Z, and p is as defined above and described in embodiments, classes and subclasses above and herein, singly or in combination.

In certain embodiments, the invention provides a compound of formula I-d:

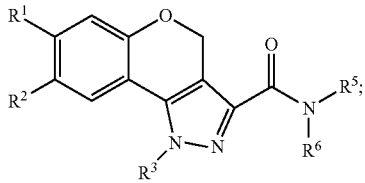

I-d or a pharmaceutically acceptable salt thereof, wherein each of $R^1$, $R^2$, $R^3$, $R^5$, and $R^6$ is as defined above and described in embodiments, classes and subclasses above and herein, singly or in combination.

In certain embodiments, the invention provides a compound of formula I-e:

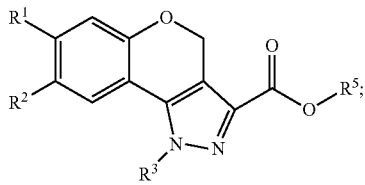

I-e or a pharmaceutically acceptable salt thereof, wherein each of $R^1$, $R^2$, $R^3$, and $R^5$ is as defined above and described in embodiments, classes and subclasses above and herein, singly or in combination.

In other embodiments, the invention provides a compound of formula I-f:

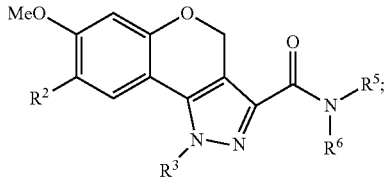

I-f or a pharmaceutically acceptable salt thereof, wherein each of $R^2$, $R^3$, $R^5$, and $R^6$ is as defined above and described in embodiments, classes and subclasses above and herein, singly or in combination.

In other embodiments, the invention provides a compound of formula I-g:

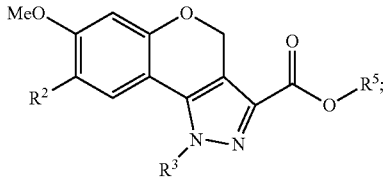

I-g or a pharmaceutically acceptable salt thereof, wherein each of $R^2$, $R^3$, and $R^5$ is as defined above and described in embodiments, classes and subclasses above and herein, singly or in combination.

In certain embodiments, the invention provides a compound of formula I-h:

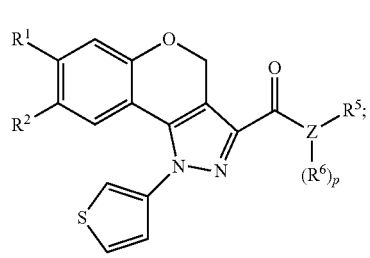

I-h or a pharmaceutically acceptable salt thereof, wherein each of $R^1$, $R^2$, $R^5$, $R^6$, Z, and p is as defined above and described in embodiments, classes and subclasses above and herein, singly or in combination.

In certain embodiments, the invention provides a compound of formula I-f, wherein $R^2$ is 5-6 membered monocyclic heteroaryl ring having 1-4 heteroatoms independently selected from nitrogen, oxygen, or sulfur; which is optionally substituted; $R^3$ is an optionally substituted 5-6 membered monocyclic heteroaryl ring having 1-4 heteroatoms independently selected from nitrogen, oxygen, or sulfur; and Z is N.

In certain embodiments, $R^5$ is an optionally substituted $C_{1-6}$ aliphatic.

In certain embodiments, $R^5$ and $R^6$, together with the atom to which each is attached, form a 3-8 membered heterocylic 1 ring having 1-4 heteroatoms independently selected from nitrogen, oxygen, or sulfur, which is optionally substituted.

In certain embodiments, $R^6$ is an optionally substituted $C_{1-6}$ aliphatic.

In certain embodiments, the invention provides a compound of formula I-h, wherein $R^1$ is —OR and R is $C_{1-6}$ aliphatic; $R^2$ is 5-6 membered monocyclic heteroaryl ring having 1-4 heteroatoms independently selected from nitrogen, oxygen, or sulfur; which is optionally substituted; and Z is N.

In certain embodiments, $R^5$ is an optionally substituted $C_{1-6}$ aliphatic.

In certain embodiments, $R^5$ and $R^6$, together with the atom to which each is attached, form a 3-8 membered heterocylic 1 ring having 1-4 heteroatoms independently selected from nitrogen, oxygen, or sulfur, which is optionally substituted.

In certain embodiments, $R^6$ is an optionally substituted $C_{1-6}$ aliphatic.

In certain embodiments, the invention provides a compound selected from Table 1:

TABLE 1
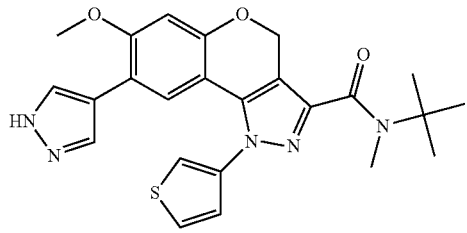 [SMILES: COc1cc2c(cc1-c1cn[nH]c1)-c1c(c(C(=O)N(C)C(C)(C)C)nn1-c1ccsc1)CO2]
1
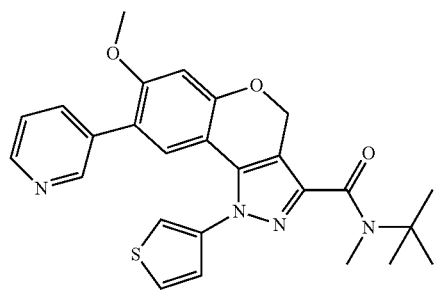 [SMILES: COc1cc2c(cc1-c1cccnc1)-c1c(c(C(=O)N(C)C(C)(C)C)nn1-c1ccsc1)CO2]
2
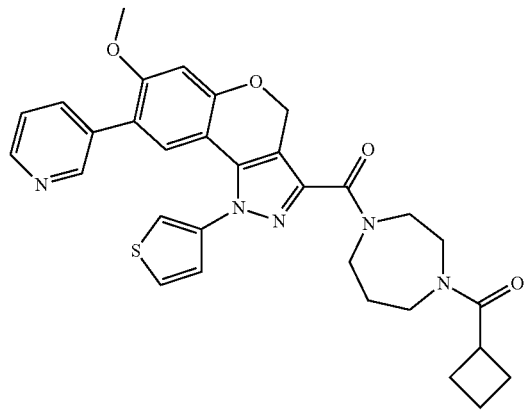 [SMILES: COc1cc2c(cc1-c1cccnc1)-c1c(c(C(=O)N3CCCN(C(=O)C4CCC4)CC3)nn1-c1ccsc1)CO2]
3
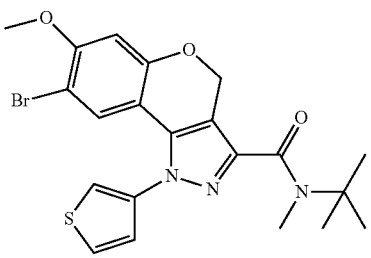 [SMILES: COc1cc2c(cc1Br)-c1c(c(C(=O)N(C)C(C)(C)C)nn1-c1ccsc1)CO2]
4
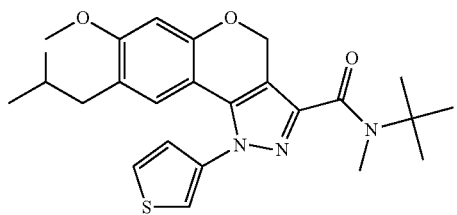 [SMILES: COc1cc2c(cc1CC(C)C)-c1c(c(C(=O)N(C)C(C)(C)C)nn1-c1ccsc1)CO2]
5

TABLE 1-continued
| | |
|---|---|
| 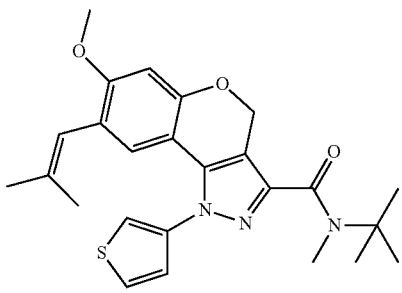 [SMILES: COc1cc2c(cc1C=C(C)C)-c1c(c(C(=O)N(C)C(C)(C)C)nn1-c1ccsc1)CO2] | 6 |
| 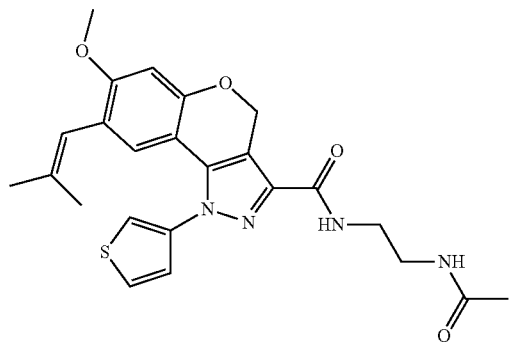 [SMILES: COc1cc2c(cc1C=C(C)C)-c1c(c(C(=O)NCCNC(C)=O)nn1-c1ccsc1)CO2] | 7 |
| 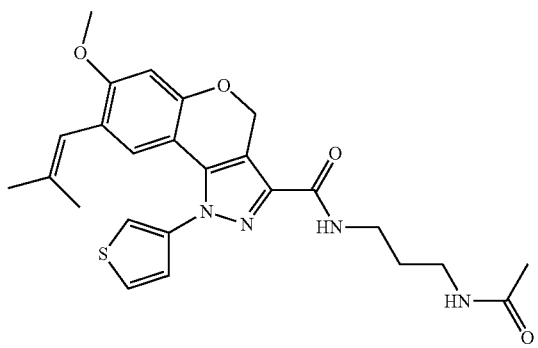 [SMILES: COc1cc2c(cc1C=C(C)C)-c1c(c(C(=O)NCCCNC(C)=O)nn1-c1ccsc1)CO2] | 8 |
| 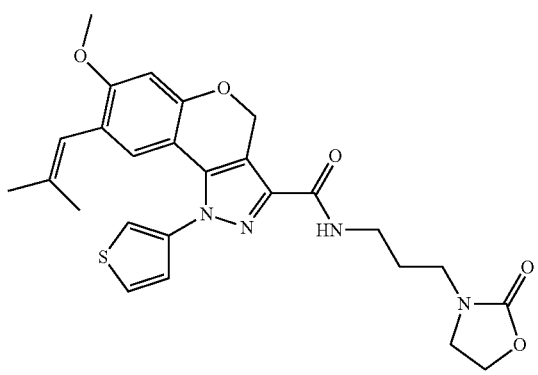 [SMILES: COc1cc2c(cc1C=C(C)C)-c1c(c(C(=O)NCCCN3CCOC3=O)nn1-c1ccsc1)CO2] | 9 |
| 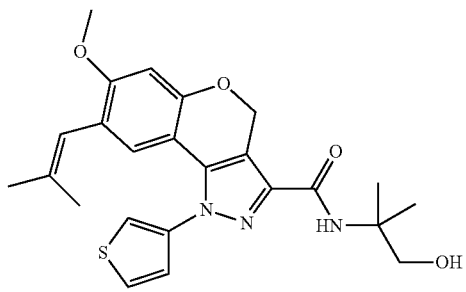 [SMILES: COc1cc2c(cc1C=C(C)C)-c1c(c(C(=O)NC(C)(C)CO)nn1-c1ccsc1)CO2] | 10 |

TABLE 1-continued
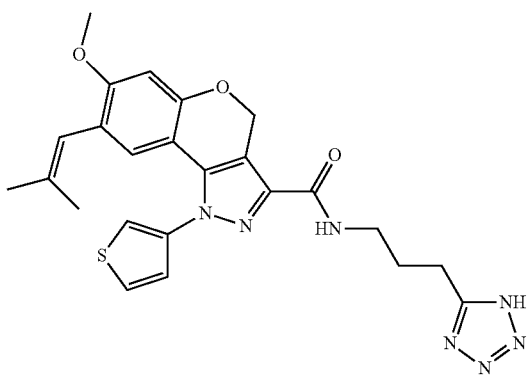 [SMILES: COc1cc2c(cc1C=C(C)C)-c1c(c(C(=O)NCCCc3nnn[nH]3)nn1-c1ccsc1)CO2]
11
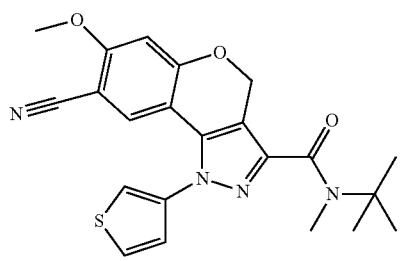 [SMILES: COc1cc2c(cc1C#N)-c1c(c(C(=O)N(C)C(C)(C)C)nn1-c1ccsc1)CO2]
12
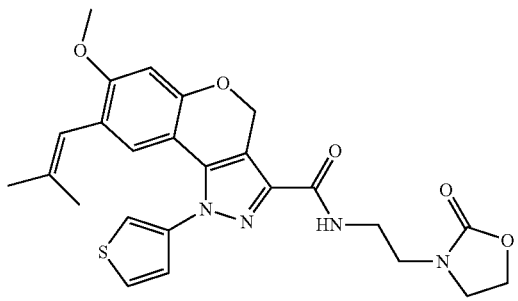 [SMILES: COc1cc2c(cc1C=C(C)C)-c1c(c(C(=O)NCCN3CCOC3=O)nn1-c1ccsc1)CO2]
13
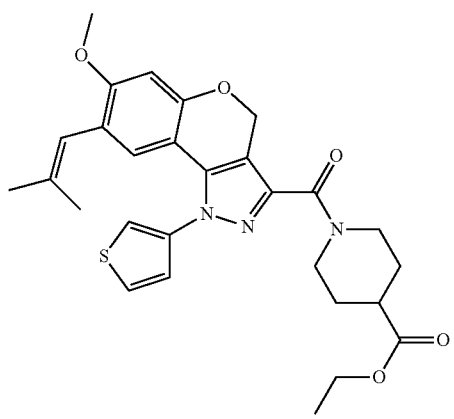 [SMILES: CCOC(=O)C1CCN(C(=O)c2nn(-c3ccsc3)c3c2COc2cc(OC)c(C=C(C)C)cc2-3)CC1]
14

TABLE 1-continued
| | |
|---|---|
| 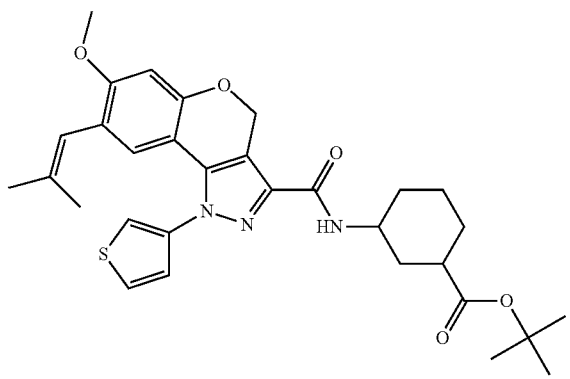 [SMILES: COc1cc2c(cc1C=C(C)C)-c1c(c(C(=O)NC3CCCC(C(=O)OC(C)(C)C)C3)nn1-c1ccsc1)CO2] | 15 |
| 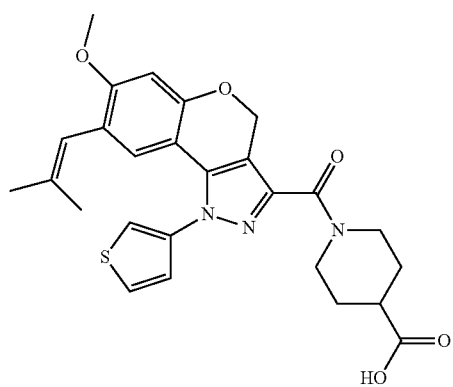 [SMILES: COc1cc2c(cc1C=C(C)C)-c1c(c(C(=O)N3CCC(C(=O)O)CC3)nn1-c1ccsc1)CO2] | 16 |
| 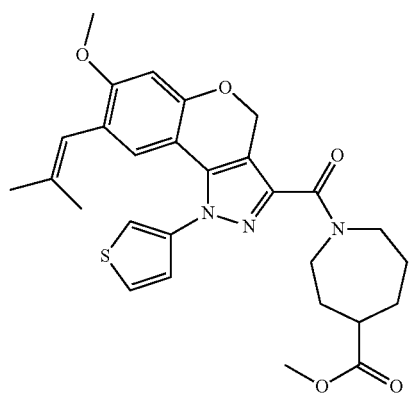 [SMILES: COC(=O)C1CCCN(C(=O)c2nn(-c3ccsc3)c3c2COc2cc(OC)c(C=C(C)C)cc2-3)CC1] | 17 |
| 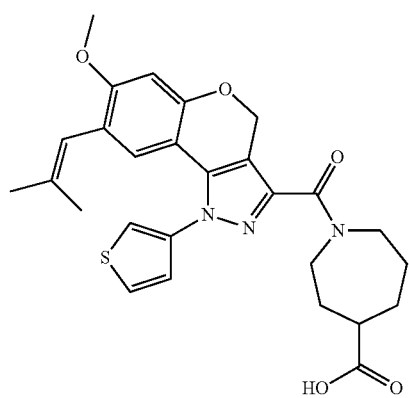 [SMILES: COc1cc2c(cc1C=C(C)C)-c1c(c(C(=O)N3CCCC(C(=O)O)CC3)nn1-c1ccsc1)CO2] | 18 |

TABLE 1-continued
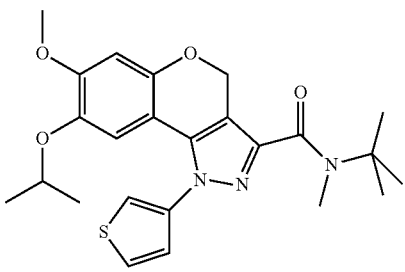 [SMILES: COc1cc2c(cc1OC(C)C)-c1c(c(C(=O)N(C)C(C)(C)C)nn1-c1ccsc1)CO2]
19
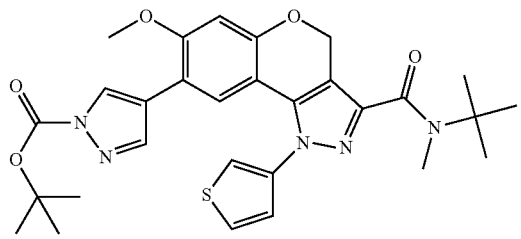 [SMILES: COc1cc2c(cc1-c1cnn(C(=O)OC(C)(C)C)c1)-c1c(c(C(=O)N(C)C(C)(C)C)nn1-c1ccsc1)CO2]
20
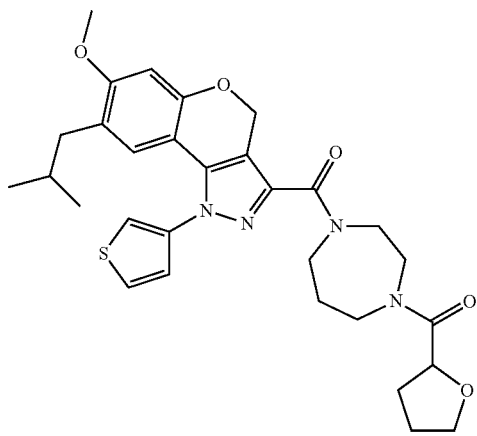 [SMILES: COc1cc2c(cc1CC(C)C)-c1c(c(C(=O)N3CCCN(C(=O)C4CCCO4)CC3)nn1-c1ccsc1)CO2]
21
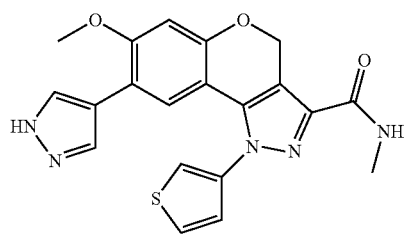 [SMILES: CNC(=O)c1nn(-c2ccsc2)c2c1COc1cc(OC)c(-c3cn[nH]c3)cc1-2]
22
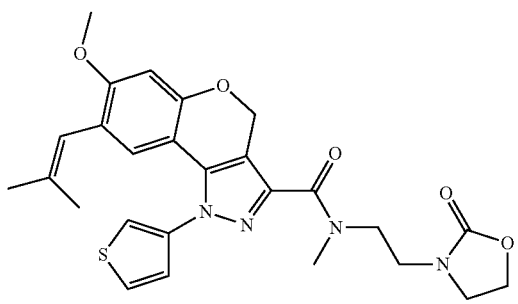 [SMILES: COc1cc2c(cc1C=C(C)C)-c1c(c(C(=O)N(C)CCN3CCOC3=O)nn1-c1ccsc1)CO2]
23

TABLE 1-continued
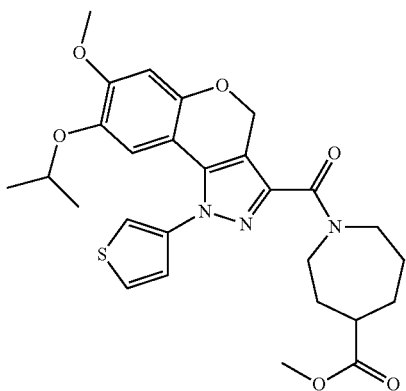 [SMILES: COC(=O)C1CCCN(C(=O)c2nn(-c3ccsc3)c3c2COc2cc(OC)c(OC(C)C)cc2-3)CC1]
24
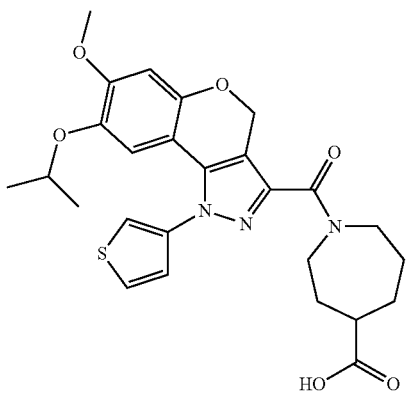 [SMILES: COc1cc2c(cc1OC(C)C)-c1c(c(C(=O)N3CCCC(C(=O)O)CC3)nn1-c1ccsc1)CO2]
25
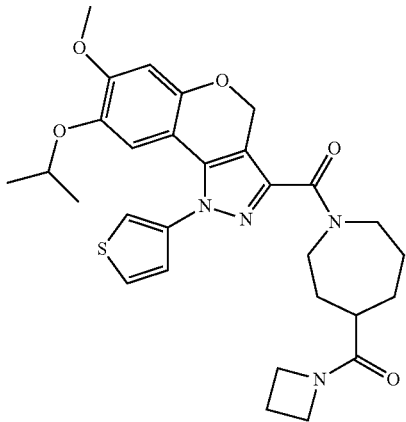 [SMILES: COc1cc2c(cc1OC(C)C)-c1c(c(C(=O)N3CCCC(C(=O)N4CCC4)CC3)nn1-c1ccsc1)CO2]
26
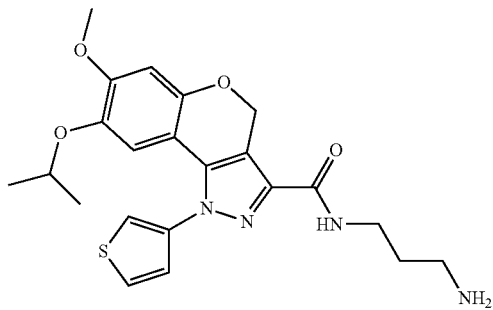 [SMILES: COc1cc2c(cc1OC(C)C)-c1c(c(C(=O)NCCCN)nn1-c1ccsc1)CO2]
27

TABLE 1-continued
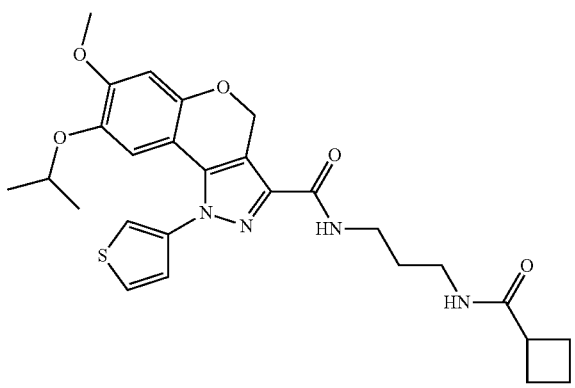 [SMILES: COc1cc2c(cc1OC(C)C)-c1c(c(C(=O)NCCCNC(=O)C3CCC3)nn1-c1ccsc1)CO2]
28
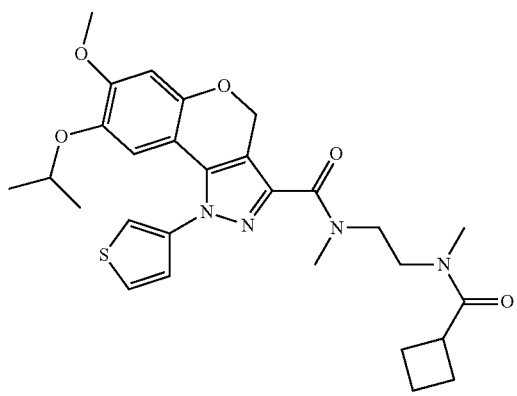 [SMILES: COc1cc2c(cc1OC(C)C)-c1c(c(C(=O)N(C)CCN(C)C(=O)C3CCC3)nn1-c1ccsc1)CO2]
29
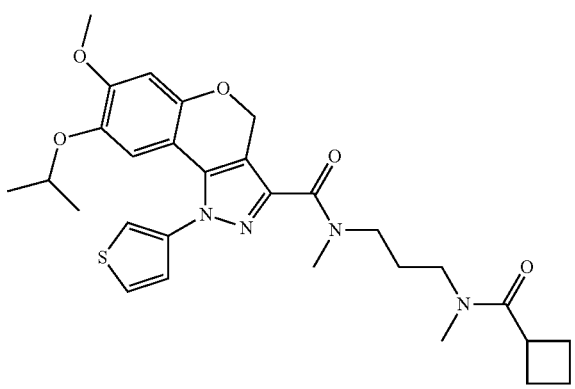 [SMILES: COc1cc2c(cc1OC(C)C)-c1c(c(C(=O)N(C)CCCN(C)C(=O)C3CCC3)nn1-c1ccsc1)CO2]
30
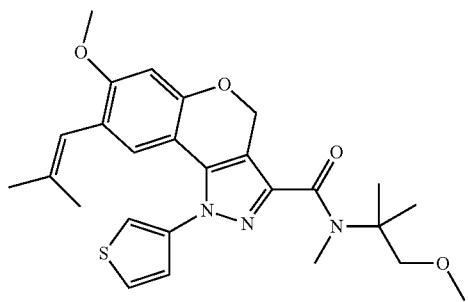 [SMILES: COCC(C)(C)N(C)C(=O)c1nn(-c2ccsc2)c2c1COc1cc(OC)c(C=C(C)C)cc1-2]
31

TABLE 1-continued
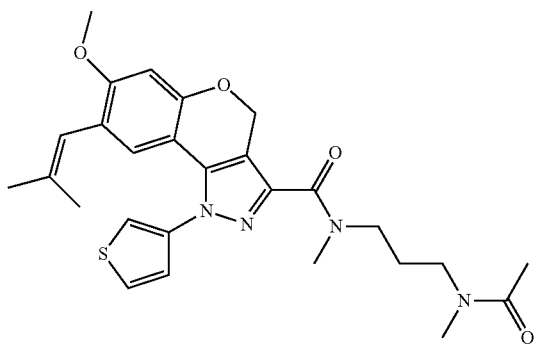 [SMILES: COc1cc2c(cc1C=C(C)C)-c1c(c(C(=O)N(C)CCCN(C)C(C)=O)nn1-c1ccsc1)CO2]
32
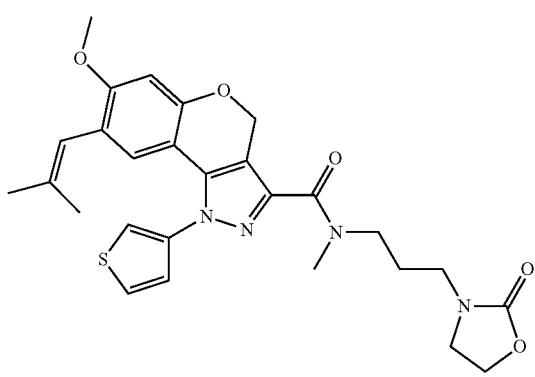 [SMILES: COc1cc2c(cc1C=C(C)C)-c1c(c(C(=O)N(C)CCCN3CCOC3=O)nn1-c1ccsc1)CO2]
33
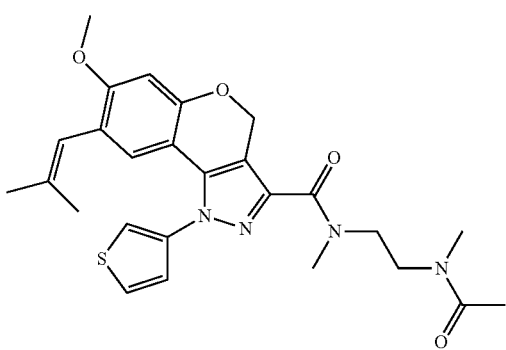 [SMILES: COc1cc2c(cc1C=C(C)C)-c1c(c(C(=O)N(C)CCN(C)C(C)=O)nn1-c1ccsc1)CO2]
34
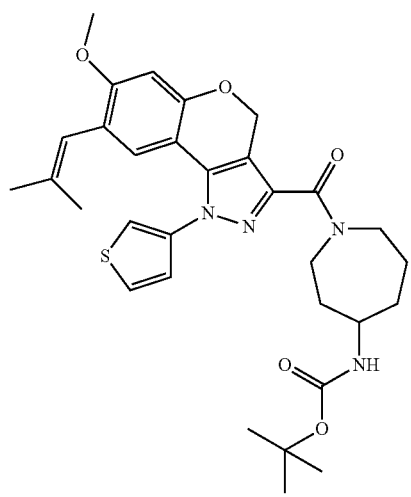 [SMILES: COc1cc2c(cc1C=C(C)C)-c1c(c(C(=O)N3CCCC(NC(=O)OC(C)(C)C)CC3)nn1-c1ccsc1)CO2]
35

TABLE 1-continued
| | |
|---|---|
| 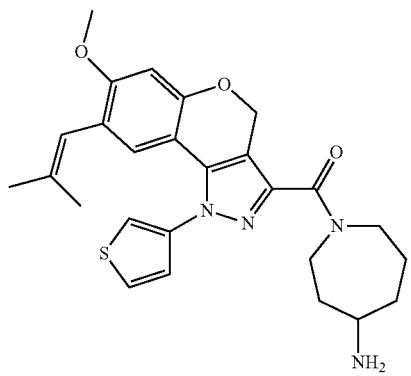 [SMILES: COc1cc2c(cc1C=C(C)C)-c1c(c(C(=O)N3CCCC(N)CC3)nn1-c1ccsc1)CO2] | 36 |
| 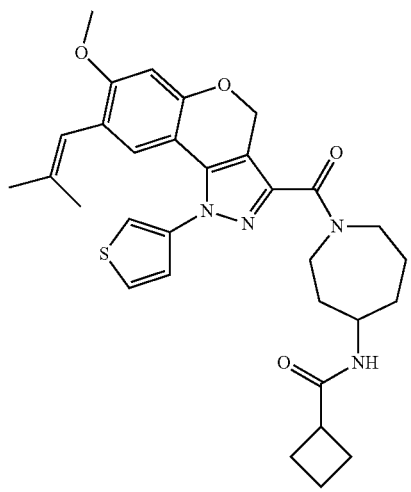 [SMILES: COc1cc2c(cc1C=C(C)C)-c1c(c(C(=O)N3CCCC(NC(=O)C4CCC4)CC3)nn1-c1ccsc1)CO2] | 37 |
| 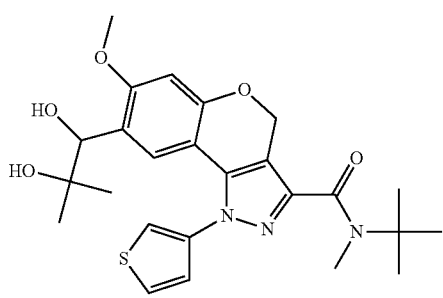 [SMILES: COc1cc2c(cc1C(O)C(C)(C)O)-c1c(c(C(=O)N(C)C(C)(C)C)nn1-c1ccsc1)CO2] | 38 |
| 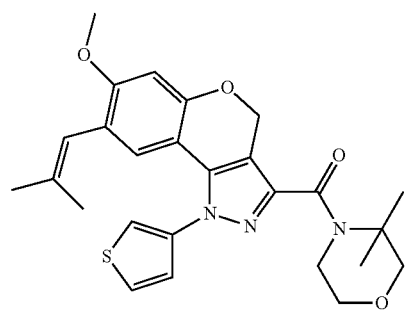 | 39 |

TABLE 1-continued
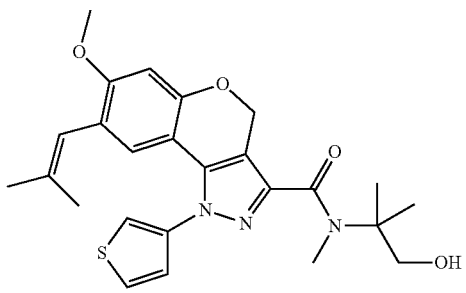 [SMILES: COc1cc2c(cc1C=C(C)C)-c1c(c(C(=O)N(C)C(C)(C)CO)nn1-c1ccsc1)CO2]
40
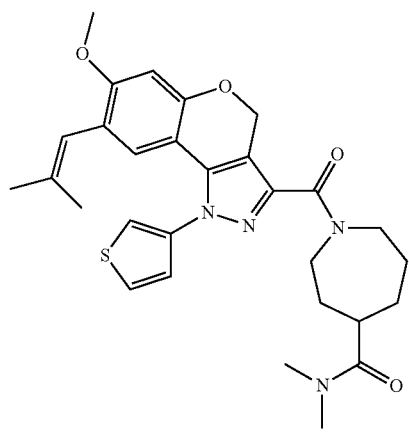 [SMILES: COc1cc2c(cc1C=C(C)C)-c1c(c(C(=O)N3CCCC(C(=O)N(C)C)CC3)nn1-c1ccsc1)CO2]
41
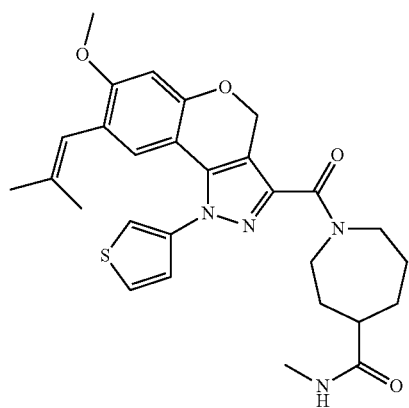 [SMILES: CNC(=O)C1CCCN(C(=O)c2nn(-c3ccsc3)c3c2COc2cc(OC)c(C=C(C)C)cc2-3)CC1]
42
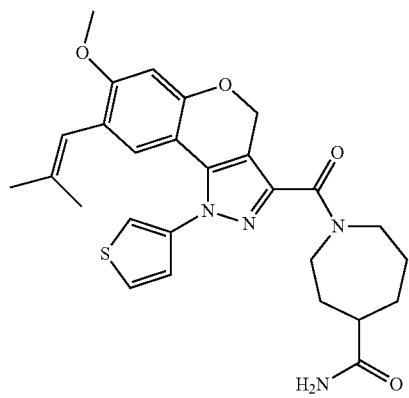 [SMILES: COc1cc2c(cc1C=C(C)C)-c1c(c(C(=O)N3CCCC(C(N)=O)CC3)nn1-c1ccsc1)CO2]
43

TABLE 1-continued
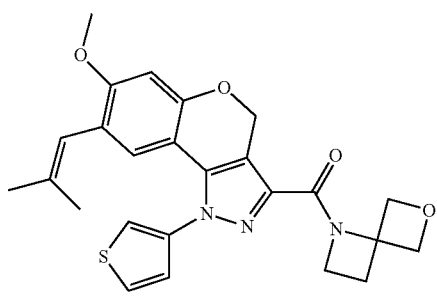 [SMILES: COc1cc2c(cc1C=C(C)C)-c1c(c(C(=O)N3CCC34COC4)nn1-c1ccsc1)CO2]
44
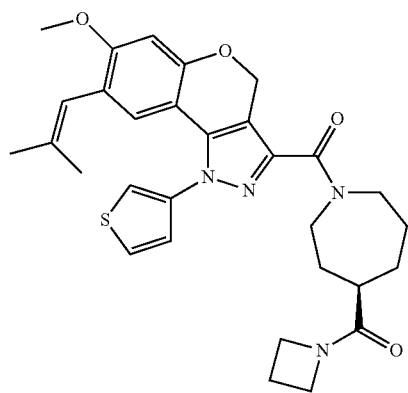 [SMILES: COc1cc2c(cc1C=C(C)C)-c1c(c(C(=O)N3CCC[C@@H](C(=O)N4CCC4)CC3)nn1-c1ccsc1)CO2]
45
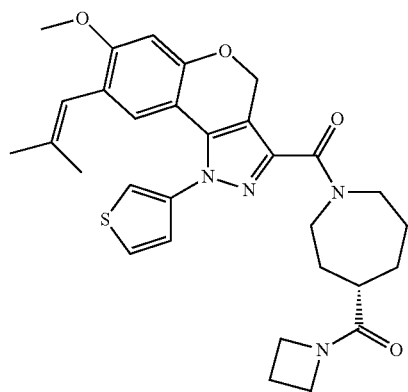 [SMILES: COc1cc2c(cc1C=C(C)C)-c1c(c(C(=O)N3CCC[C@H](C(=O)N4CCC4)CC3)nn1-c1ccsc1)CO2]
46
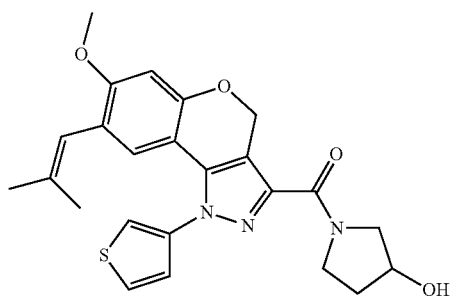 [SMILES: COc1cc2c(cc1C=C(C)C)-c1c(c(C(=O)N3CCC(O)C3)nn1-c1ccsc1)CO2]
47

TABLE 1-continued
| | |
|---|---|
| 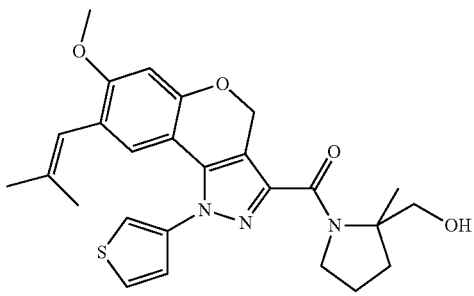 [SMILES: COc1cc2c(cc1C=C(C)C)-c1c(c(C(=O)N3CCCC3(C)CO)nn1-c1ccsc1)CO2] | 48 |
| 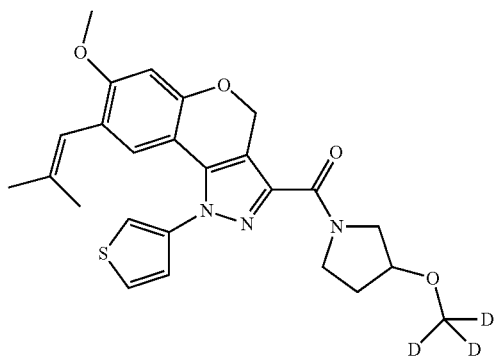 [SMILES: [2H]C([2H])([2H])OC1CCN(C(=O)c2nn(-c3ccsc3)c3c2COc2cc(OC)c(C=C(C)C)cc2-3)C1] | 49 |
| 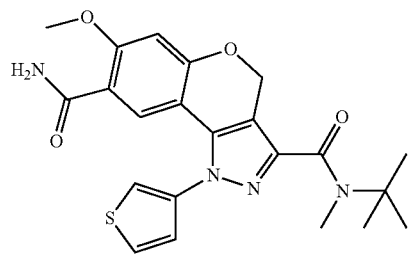 [SMILES: COc1cc2c(cc1C(N)=O)-c1c(c(C(=O)N(C)C(C)(C)C)nn1-c1ccsc1)CO2] | 50 |
| 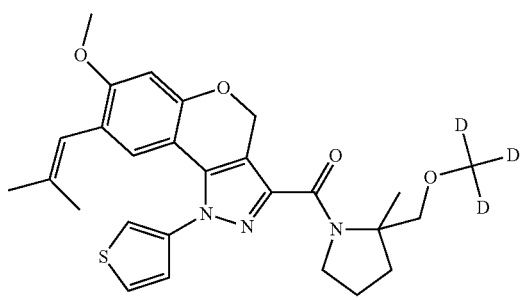 [SMILES: [2H]C([2H])([2H])OCC1(C)CCCN1C(=O)c1nn(-c2ccsc2)c2c1COc1cc(OC)c(C=C(C)C)cc1-2] | 51 |
| 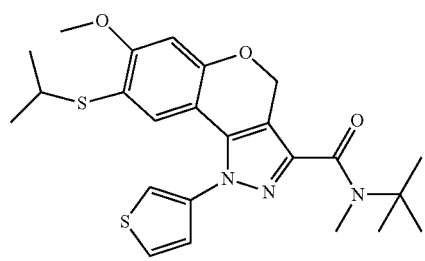 [SMILES: COc1cc2c(cc1SC(C)C)-c1c(c(C(=O)N(C)C(C)(C)C)nn1-c1ccsc1)CO2] | 52 |

TABLE 1-continued
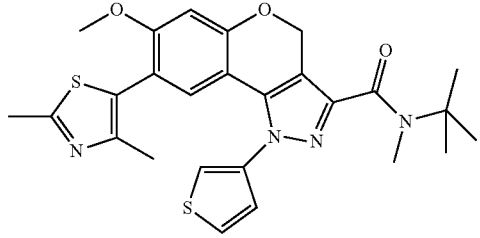 [SMILES: COc1cc2c(cc1-c1sc(C)nc1C)-c1c(c(C(=O)N(C)C(C)(C)C)nn1-c1ccsc1)CO2]
53
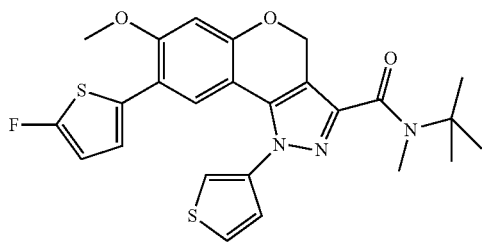 [SMILES: COc1cc2c(cc1-c1ccc(F)s1)-c1c(c(C(=O)N(C)C(C)(C)C)nn1-c1ccsc1)CO2]
54
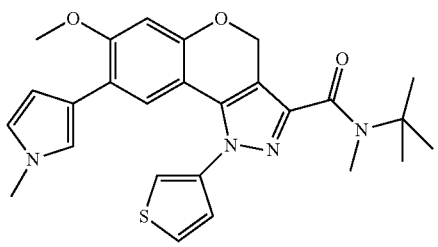 [SMILES: COc1cc2c(cc1-c1ccn(C)c1)-c1c(c(C(=O)N(C)C(C)(C)C)nn1-c1ccsc1)CO2]
55
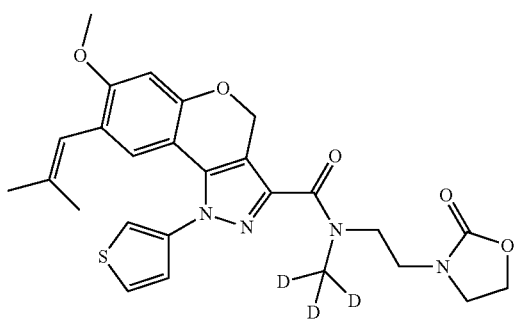 [SMILES: [2H]C([2H])([2H])N(CCN1CCOC1=O)C(=O)c1nn(-c2ccsc2)c2c1COc1cc(OC)c(C=C(C)C)cc1-2]
56
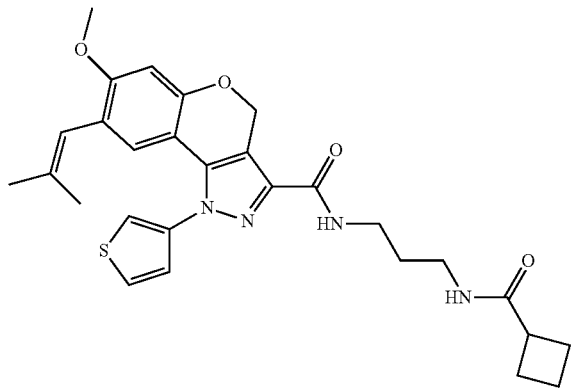 [SMILES: COc1cc2c(cc1C=C(C)C)-c1c(c(C(=O)NCCCNC(=O)C3CCC3)nn1-c1ccsc1)CO2]
57

TABLE 1-continued
58
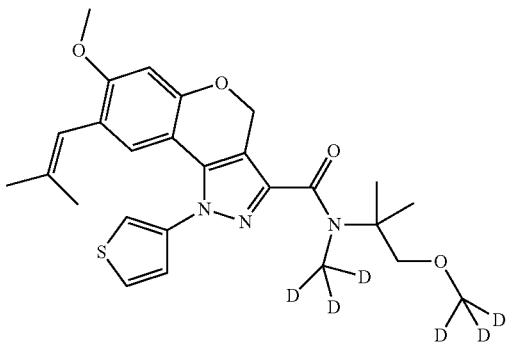 [SMILES: [2H]C([2H])([2H])OCC(C)(C)N(C(=O)c1nn(-c2ccsc2)c2c1COc1cc(OC)c(C=C(C)C)cc1-2)C([2H])([2H])[2H]]
59
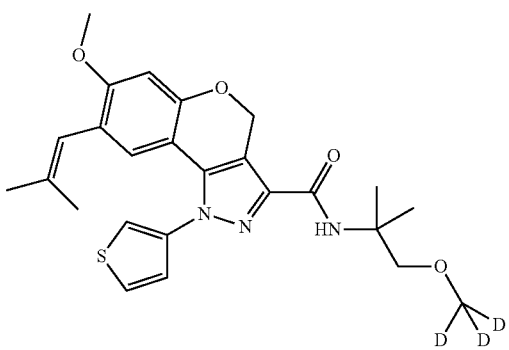 [SMILES: [2H]C([2H])([2H])OCC(C)(C)NC(=O)c1nn(-c2ccsc2)c2c1COc1cc(OC)c(C=C(C)C)cc1-2]
60
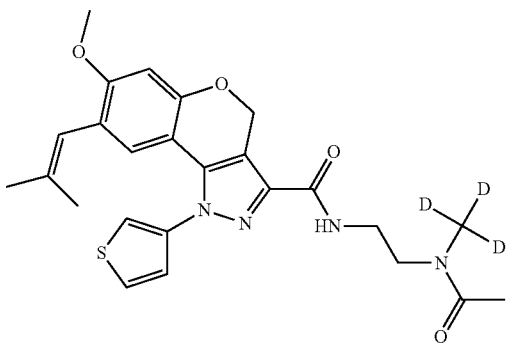 [SMILES: [2H]C([2H])([2H])N(CCNC(=O)c1nn(-c2ccsc2)c2c1COc1cc(OC)c(C=C(C)C)cc1-2)C(C)=O]
61
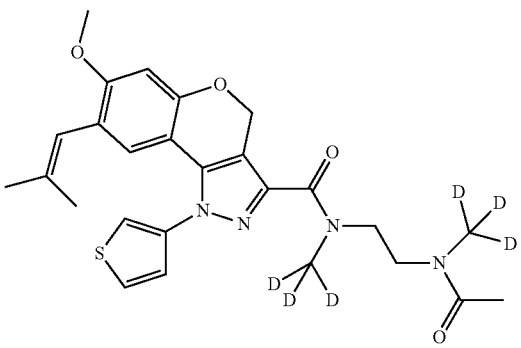 [SMILES: [2H]C([2H])([2H])N(CCN(C(=O)c1nn(-c2ccsc2)c2c1COc1cc(OC)c(C=C(C)C)cc1-2)C([2H])([2H])[2H])C(C)=O]

TABLE 1-continued
| | |
|---|---|
| 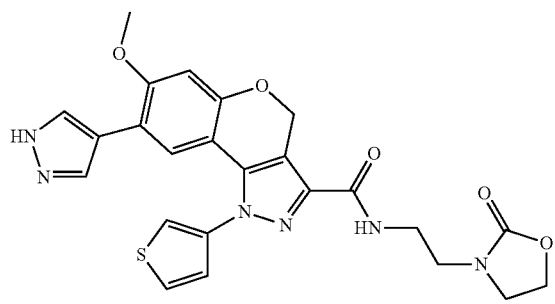 [SMILES: COc1cc2c(cc1-c1cn[nH]c1)-c1c(c(C(=O)NCCN3CCOC3=O)nn1-c1ccsc1)CO2] | 62 |
| 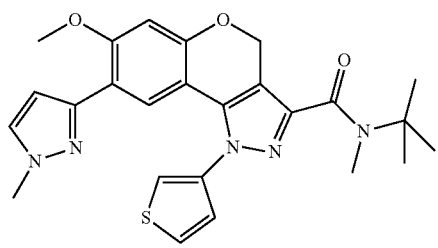 | 63 |
| 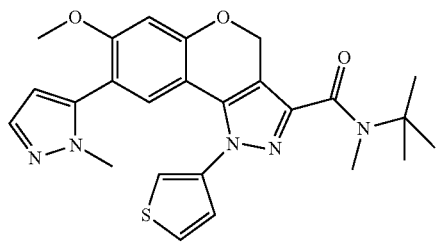 [SMILES: COc1cc2c(cc1-c1ccnn1C)-c1c(c(C(=O)N(C)C(C)(C)C)nn1-c1ccsc1)CO2] | 64 |
| 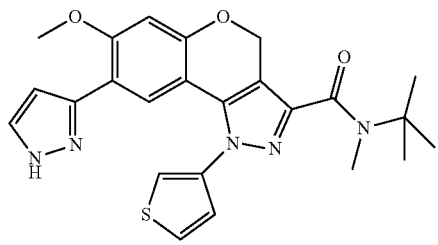 [SMILES: COc1cc2c(cc1-c1cc[nH]n1)-c1c(c(C(=O)N(C)C(C)(C)C)nn1-c1ccsc1)CO2] | 65 |
| 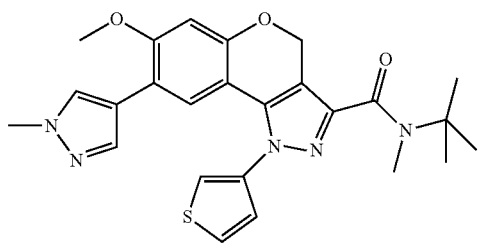 [SMILES: COc1cc2c(cc1-c1cnn(C)c1)-c1c(c(C(=O)N(C)C(C)(C)C)nn1-c1ccsc1)CO2] | 66 |
| 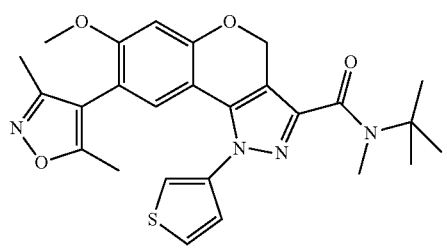 [SMILES: COc1cc2c(cc1-c1c(C)noc1C)-c1c(c(C(=O)N(C)C(C)(C)C)nn1-c1ccsc1)CO2] | 67 |

TABLE 1-continued
| | |
|---|---|
| 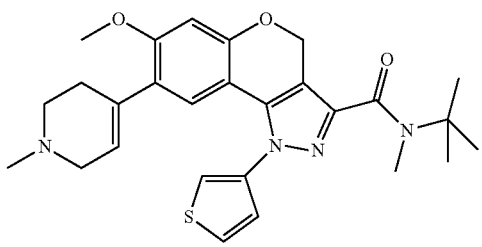 [SMILES: COc1cc2c(cc1C1=CCN(C)CC1)-c1c(c(C(=O)N(C)C(C)(C)C)nn1-c1ccsc1)CO2] | 68 |
| 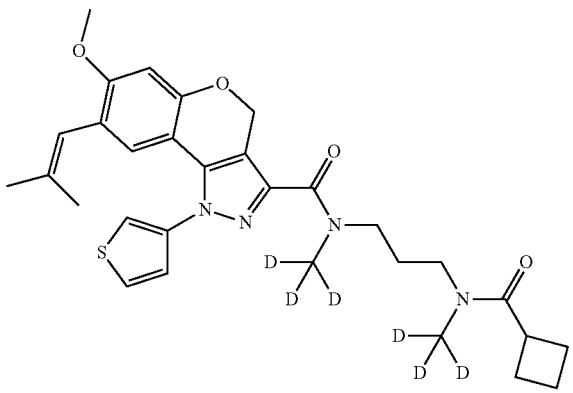 [SMILES: [2H]C([2H])([2H])N(CCCN(C(=O)C1CCC1)C([2H])([2H])[2H])C(=O)c1nn(-c2ccsc2)c2c1COc1cc(OC)c(C=C(C)C)cc1-2] | 69 |
| 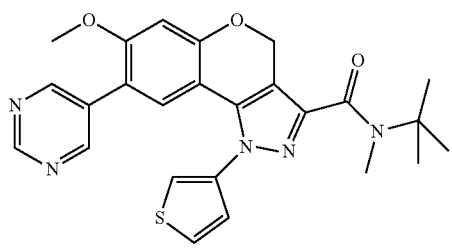 [SMILES: COc1cc2c(cc1-c1cncnc1)-c1c(c(C(=O)N(C)C(C)(C)C)nn1-c1ccsc1)CO2] | 70 |
| 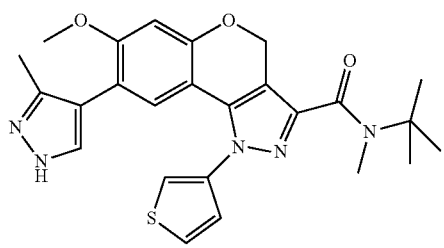 [SMILES: COc1cc2c(cc1-c1c[nH]nc1C)-c1c(c(C(=O)N(C)C(C)(C)C)nn1-c1ccsc1)CO2] | 71 |
| 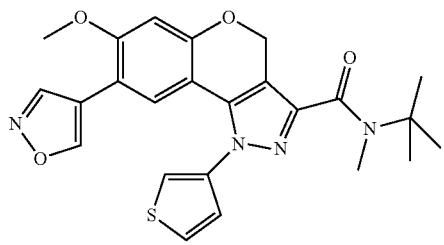 [SMILES: COc1cc2c(cc1-c1cnoc1)-c1c(c(C(=O)N(C)C(C)(C)C)nn1-c1ccsc1)CO2] | 72 |
| 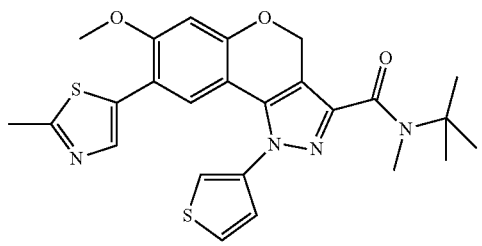 [SMILES: COc1cc2c(cc1-c1cnc(C)s1)-c1c(c(C(=O)N(C)C(C)(C)C)nn1-c1ccsc1)CO2] | 73 |

TABLE 1-continued
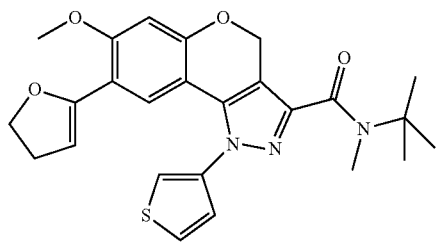 [SMILES: COc1cc2c(cc1C1=CCCO1)-c1c(c(C(=O)N(C)C(C)(C)C)nn1-c1ccsc1)CO2]
74
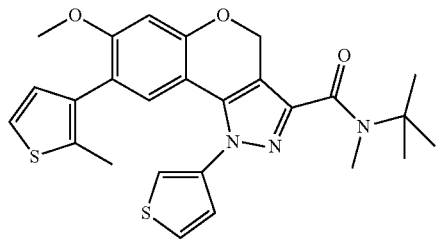 [SMILES: COc1cc2c(cc1-c1ccsc1C)-c1c(c(C(=O)N(C)C(C)(C)C)nn1-c1ccsc1)CO2]
75
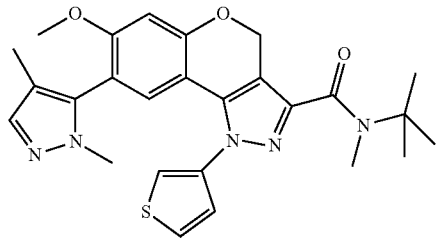 [SMILES: COc1cc2c(cc1-c1c(C)cnn1C)-c1c(c(C(=O)N(C)C(C)(C)C)nn1-c1ccsc1)CO2]
76
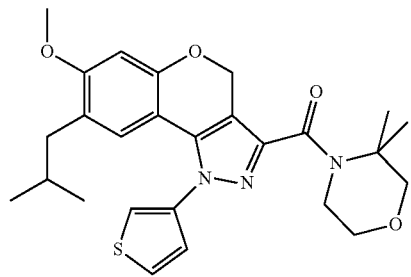 [SMILES: COc1cc2c(cc1CC(C)C)-c1c(c(C(=O)N3CCOCC3(C)C)nn1-c1ccsc1)CO2]
77
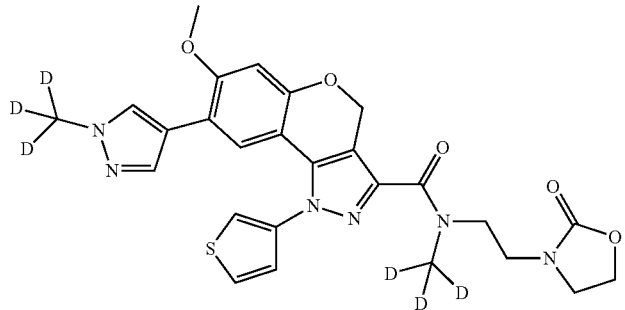 [SMILES: [2H]C([2H])([2H])N(CCN1CCOC1=O)C(=O)c1nn(-c2ccsc2)c2c1COc1cc(OC)c(-c3cnn(C([2H])([2H])[2H])c3)cc1-2]
78
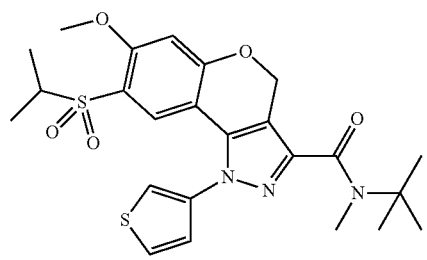 [SMILES: COc1cc2c(cc1S(=O)(=O)C(C)C)-c1c(c(C(=O)N(C)C(C)(C)C)nn1-c1ccsc1)CO2]
79

TABLE 1-continued
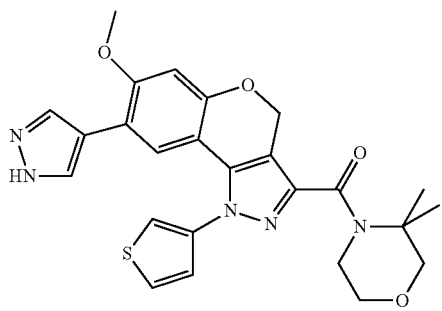 [SMILES: COc1cc2c(cc1-c1cn[nH]c1)-c1c(c(C(=O)N3CCOCC3(C)C)nn1-c1ccsc1)CO2]
80
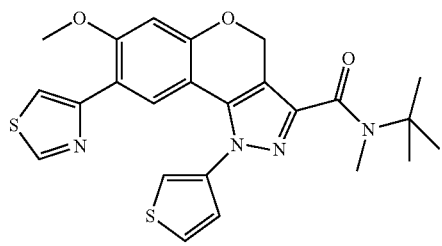 [SMILES: COc1cc2c(cc1-c1cscn1)-c1c(c(C(=O)N(C)C(C)(C)C)nn1-c1ccsc1)CO2]
81
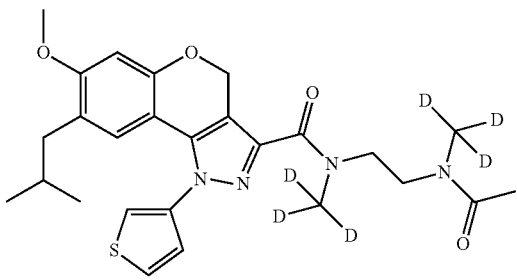 [SMILES: [2H]C([2H])([2H])N(CCN(C(=O)c1nn(-c2ccsc2)c2c1COc1cc(OC)c(CC(C)C)cc1-2)C([2H])([2H])[2H])C(C)=O]
82
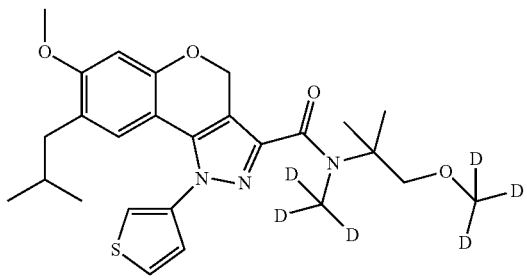 [SMILES: [2H]C([2H])([2H])OCC(C)(C)N(C(=O)c1nn(-c2ccsc2)c2c1COc1cc(OC)c(CC(C)C)cc1-2)C([2H])([2H])[2H]]
83
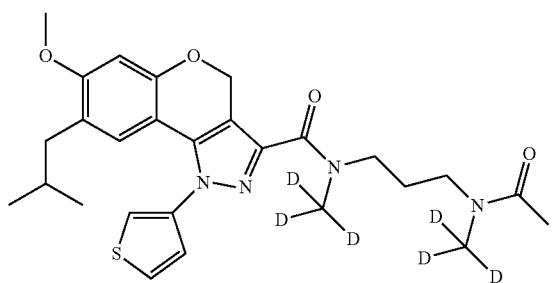 [SMILES: [2H]C([2H])([2H])N(CCCN(C(=O)c1nn(-c2ccsc2)c2c1COc1cc(OC)c(CC(C)C)cc1-2)C([2H])([2H])[2H])C(C)=O]
84

TABLE 1-continued
| | |
|---|---|
| 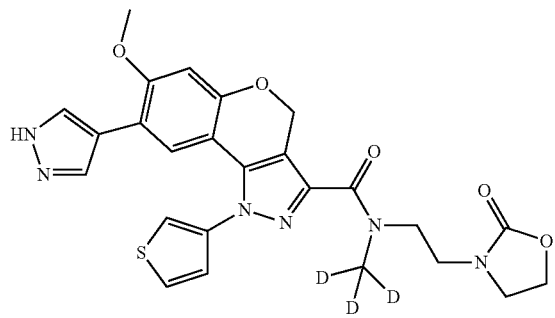 [SMILES: [2H]C([2H])([2H])N(CCN1CCOC1=O)C(=O)c1nn(-c2ccsc2)c2c1COc1cc(OC)c(-c3cn[nH]c3)cc1-2] | 85 |
| 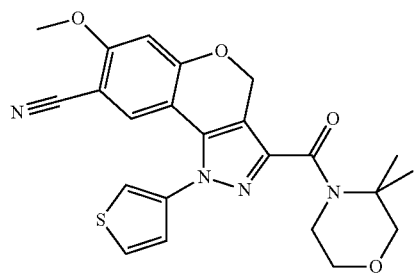 [SMILES: COc1cc2c(cc1C#N)-c1c(c(C(=O)N3CCOCC3(C)C)nn1-c1ccsc1)CO2] | 86 |
| 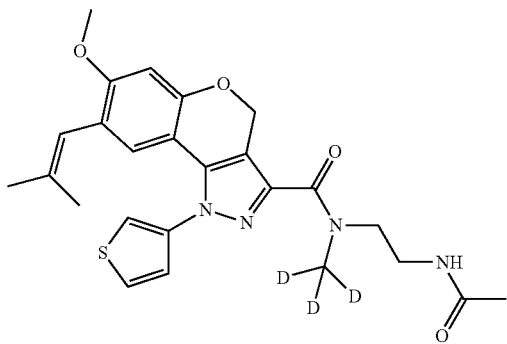 [SMILES: [2H]C([2H])([2H])N(CCNC(C)=O)C(=O)c1nn(-c2ccsc2)c2c1COc1cc(OC)c(C=C(C)C)cc1-2] | 87 |
| 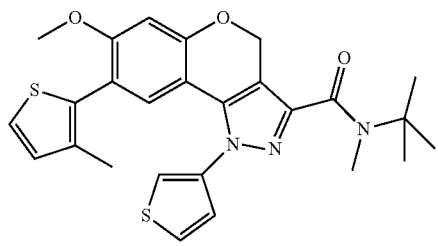 [SMILES: COc1cc2c(cc1-c1sccc1C)-c1c(c(C(=O)N(C)C(C)(C)C)nn1-c1ccsc1)CO2] | 88 |
| 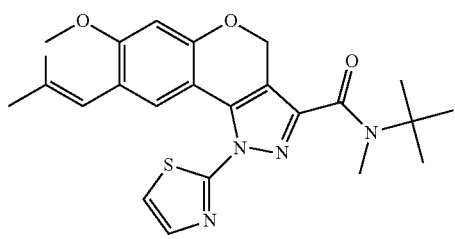 [SMILES: COc1cc2c(cc1C=C(C)C)-c1c(c(C(=O)N(C)C(C)(C)C)nn1-c1nccs1)CO2] | 89 |

TABLE 1-continued
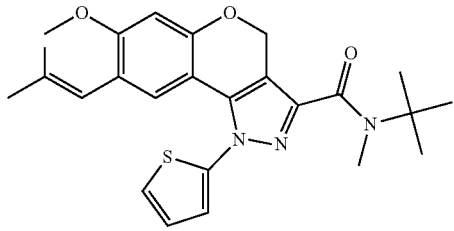 90
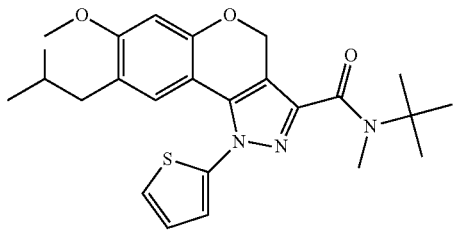 [SMILES: COc1cc2c(cc1CC(C)C)-c1c(c(C(=O)N(C)C(C)(C)C)nn1-c1cccs1)CO2] 91
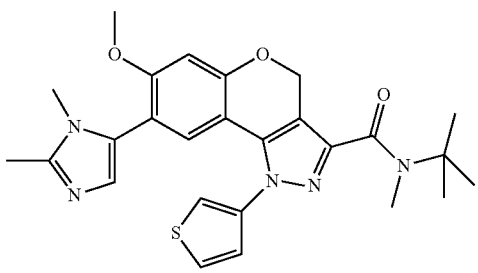 [SMILES: COc1cc2c(cc1-c1cnc(C)n1C)-c1c(c(C(=O)N(C)C(C)(C)C)nn1-c1ccsc1)CO2] 92
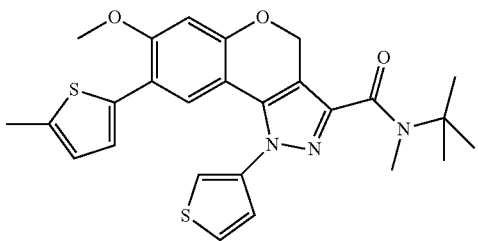 93
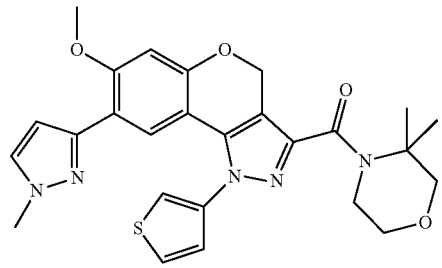 [SMILES: COc1cc2c(cc1-c1ccn(C)n1)-c1c(c(C(=O)N3CCOCC3(C)C)nn1-c1ccsc1)CO2] 94
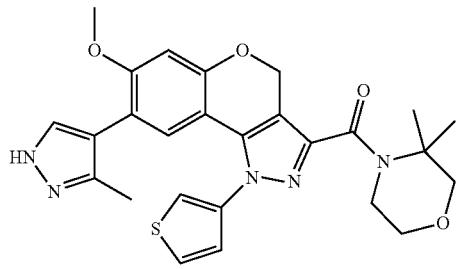 [SMILES: COc1cc2c(cc1-c1c[nH]nc1C)-c1c(c(C(=O)N3CCOCC3(C)C)nn1-c1ccsc1)CO2] 95

TABLE 1-continued
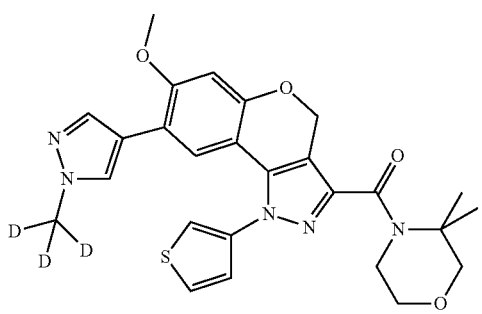 [SMILES: [2H]C([2H])([2H])n1cc(-c2cc3c(cc2OC)OCc2c(C(=O)N4CCOCC4(C)C)nn(-c4ccsc4)c2-3)cn1]
96
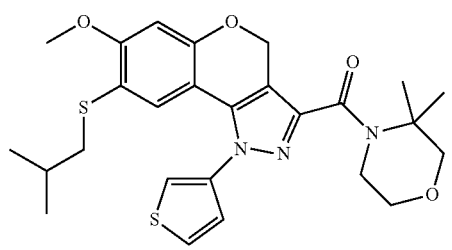 [SMILES: COc1cc2c(cc1SCC(C)C)-c1c(c(C(=O)N3CCOCC3(C)C)nn1-c1ccsc1)CO2]
97
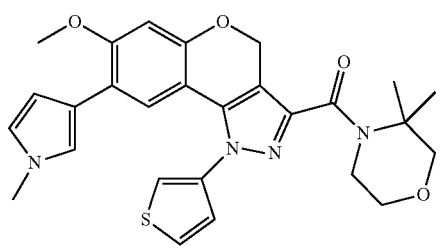 [SMILES: COc1cc2c(cc1-c1ccn(C)c1)-c1c(c(C(=O)N3CCOCC3(C)C)nn1-c1ccsc1)CO2]
98
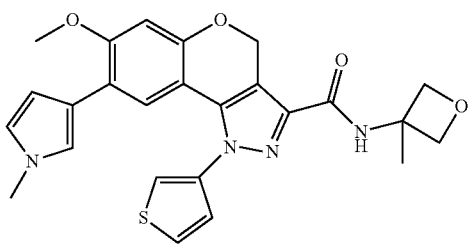 [SMILES: COc1cc2c(cc1-c1ccn(C)c1)-c1c(c(C(=O)NC3(C)COC3)nn1-c1ccsc1)CO2]
99
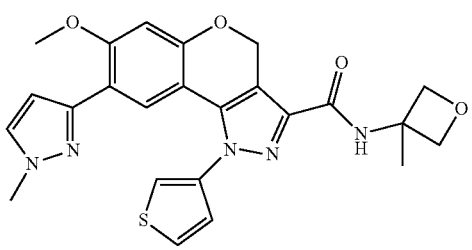 [SMILES: COc1cc2c(cc1-c1ccn(C)n1)-c1c(c(C(=O)NC3(C)COC3)nn1-c1ccsc1)CO2]
100
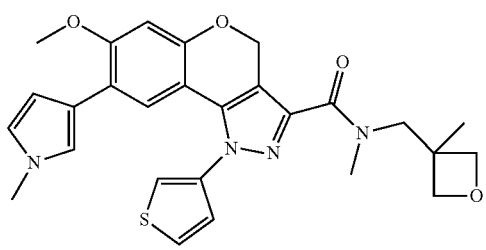
101

TABLE 1-continued
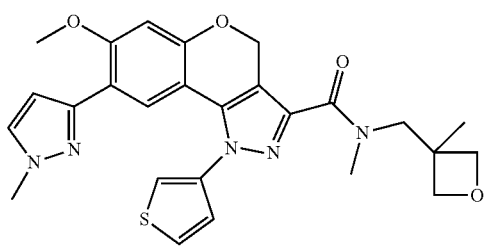 [SMILES: COc1cc2c(cc1-c1ccn(C)n1)-c1c(c(C(=O)N(C)CC3(C)COC3)nn1-c1ccsc1)CO2] 102
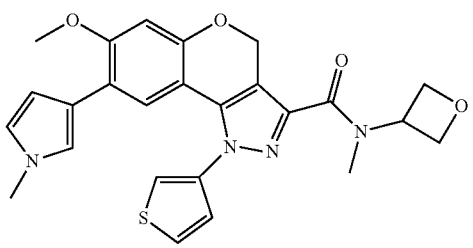 103
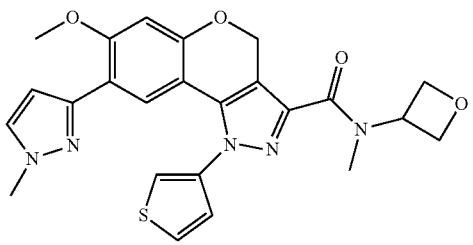 [SMILES: COc1cc2c(cc1-c1ccn(C)n1)-c1c(c(C(=O)N(C)C3COC3)nn1-c1ccsc1)CO2] 104
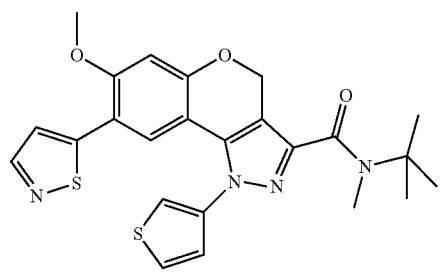 [SMILES: COc1cc2c(cc1-c1ccns1)-c1c(c(C(=O)N(C)C(C)(C)C)nn1-c1ccsc1)CO2] 105
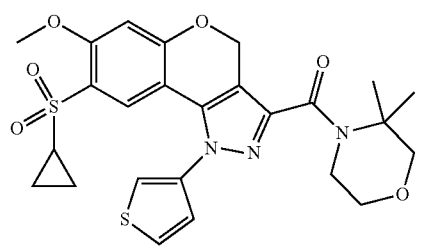 106
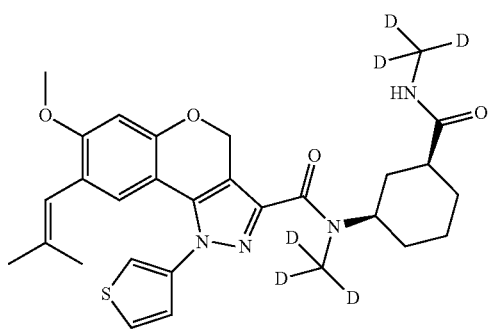 [SMILES: [2H]C([2H])([2H])NC(=O)[C@H]1CCC[C@@H](N(C(=O)c2nn(-c3ccsc3)c3c2COc2cc(OC)c(C=C(C)C)cc2-3)C([2H])([2H])[2H])C1] 107

TABLE 1-continued
| | |
|---|---|
| 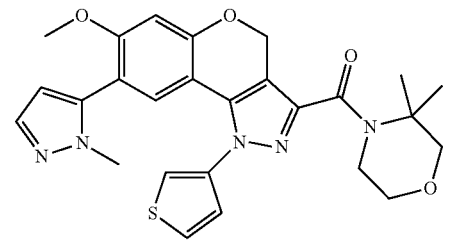 [SMILES: COc1cc2c(cc1-c1ccnn1C)-c1c(c(C(=O)N3CCOCC3(C)C)nn1-c1ccsc1)CO2] | 108 |
| 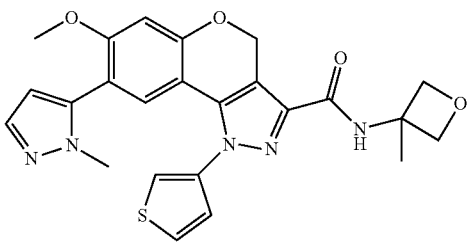 [SMILES: COc1cc2c(cc1-c1ccnn1C)-c1c(c(C(=O)NC3(C)COC3)nn1-c1ccsc1)CO2] | 109 |
| 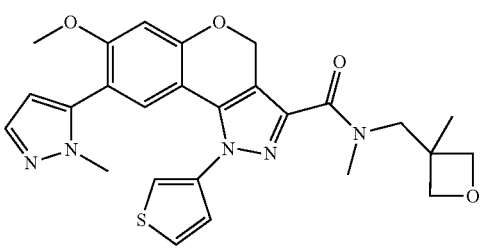 [SMILES: COc1cc2c(cc1-c1ccnn1C)-c1c(c(C(=O)N(C)CC3(C)COC3)nn1-c1ccsc1)CO2] | 110 |
| 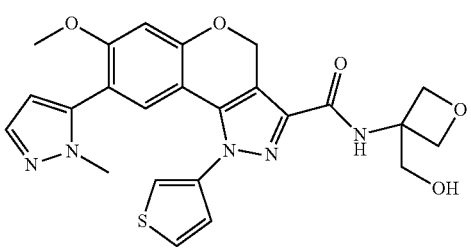 [SMILES: COc1cc2c(cc1-c1ccnn1C)-c1c(c(C(=O)NC3(CO)COC3)nn1-c1ccsc1)CO2] | 111 |
| 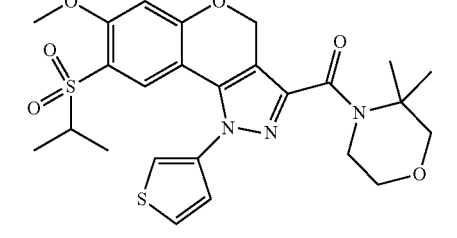 | 112 |
| 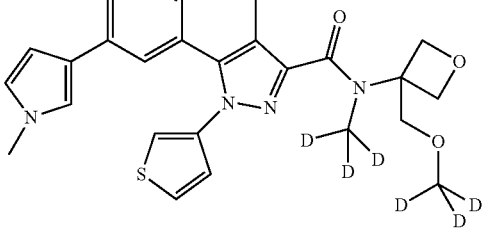 | 113 |

TABLE 1-continued
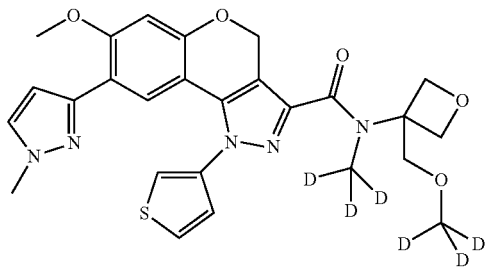 [SMILES: [2H]C([2H])([2H])OCC1(N(C(=O)c2nn(-c3ccsc3)c3c2COc2cc(OC)c(-c4ccn(C)c4)cc2-3)C([2H])([2H])[2H])COC1]
114
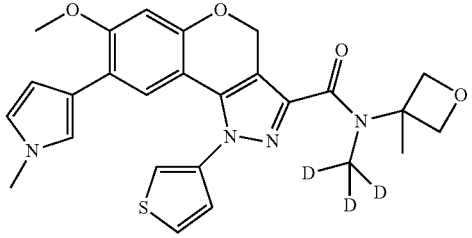
115
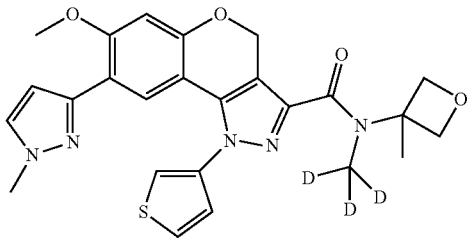 [SMILES: [2H]C([2H])([2H])N(C(=O)c1nn(-c2ccsc2)c2c1COc1cc(OC)c(-c3ccn(C)c3)cc1-2)C1(C)COC1]
116
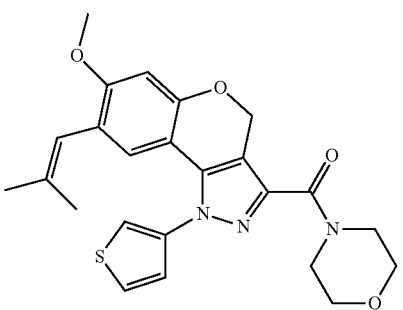 [SMILES: COc1cc2c(cc1C=C(C)C)-c1c(c(C(=O)N3CCOCC3)nn1-c1ccsc1)CO2]
117
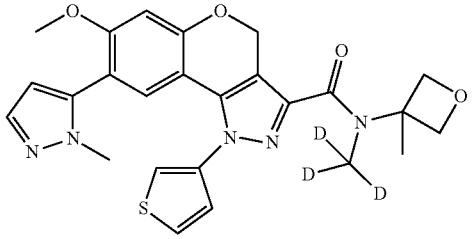 [SMILES: [2H]C([2H])([2H])N(C(=O)c1nn(-c2ccsc2)c2c1COc1cc(OC)c(-c3ccnn3C)cc1-2)C1(C)COC1]
118
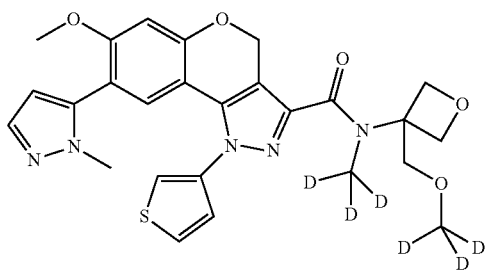 [SMILES: [2H]C([2H])([2H])OCC1(N(C(=O)c2nn(-c3ccsc3)c3c2COc2cc(OC)c(-c4ccnn4C)cc2-3)C([2H])([2H])[2H])COC1]
119

TABLE 1-continued
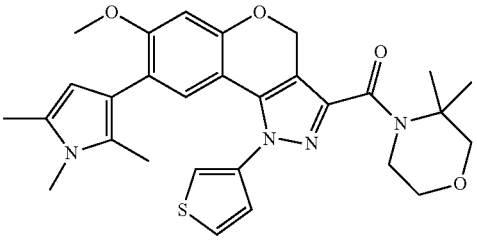 120
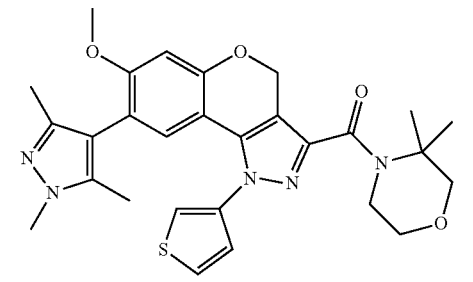 [SMILES: COc1cc2c(cc1-c1c(C)nn(C)c1C)-c1c(c(C(=O)N3CCOCC3(C)C)nn1-c1ccsc1)CO2] 121
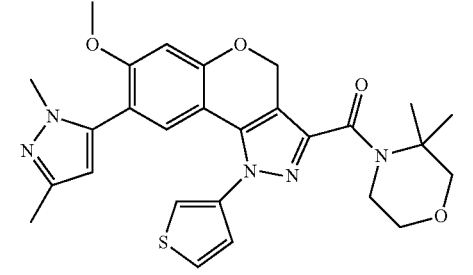 [SMILES: COc1cc2c(cc1-c1cc(C)nn1C)-c1c(c(C(=O)N3CCOCC3(C)C)nn1-c1ccsc1)CO2] 122
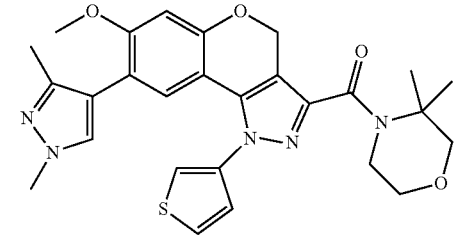 [SMILES: COc1cc2c(cc1-c1cn(C)nc1C)-c1c(c(C(=O)N3CCOCC3(C)C)nn1-c1ccsc1)CO2] 123
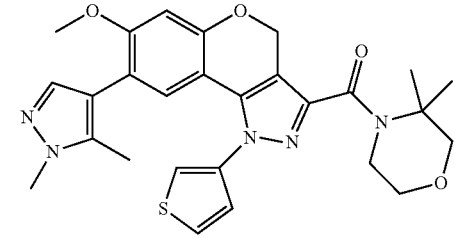 [SMILES: COc1cc2c(cc1-c1cnn(C)c1C)-c1c(c(C(=O)N3CCOCC3(C)C)nn1-c1ccsc1)CO2] 124
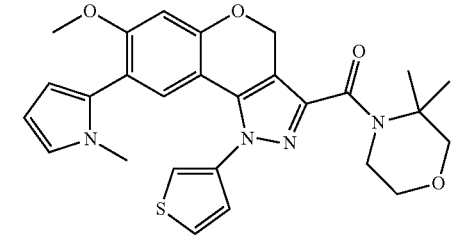 125

TABLE 1-continued
| | |
|---|---|
| 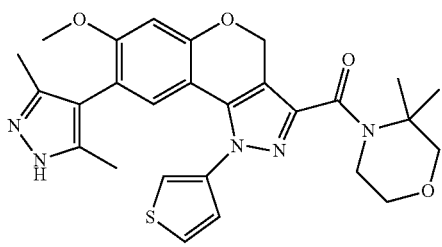 [SMILES: COc1cc2c(cc1-c1c(C)n[nH]c1C)-c1c(c(C(=O)N3CCOCC3(C)C)nn1-c1ccsc1)CO2] | 126 |
| 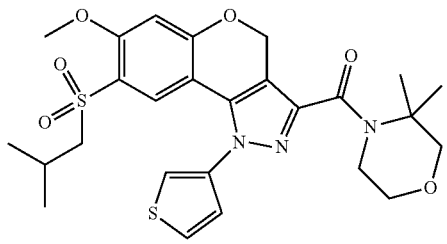 [SMILES: COc1cc2c(cc1S(=O)(=O)CC(C)C)-c1c(c(C(=O)N3CCOCC3(C)C)nn1-c1ccsc1)CO2] | 127 |
| 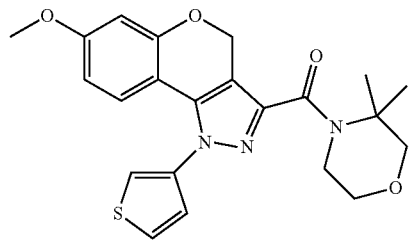 | 128 |
| 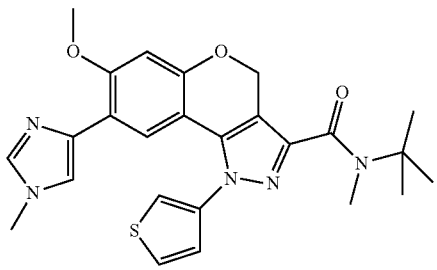 [SMILES: COc1cc2c(cc1-c1cn(C)cn1)-c1c(c(C(=O)N(C)C(C)(C)C)nn1-c1ccsc1)CO2] | 129 |
| 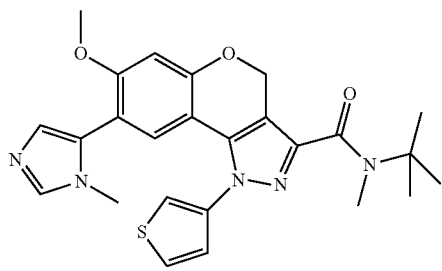 [SMILES: COc1cc2c(cc1-c1cncn1C)-c1c(c(C(=O)N(C)C(C)(C)C)nn1-c1ccsc1)CO2] | 130 |
| 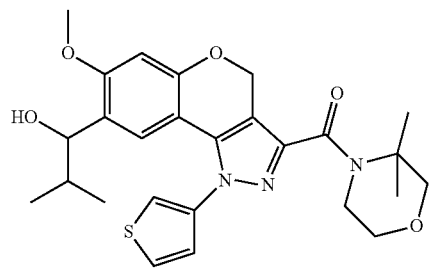 | 131 |

TABLE 1-continued
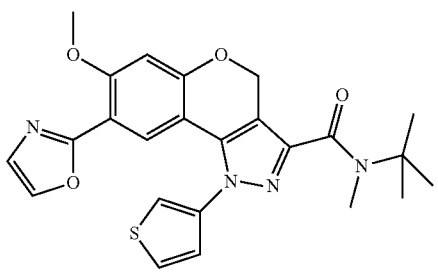 [SMILES: COc1cc2c(cc1-c1ncco1)-c1c(c(C(=O)N(C)C(C)(C)C)nn1-c1ccsc1)CO2]
132
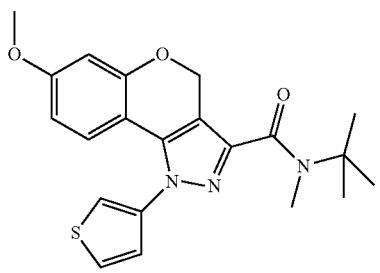 [SMILES: COc1ccc2c(c1)OCc1c(C(=O)N(C)C(C)(C)C)nn(-c3ccsc3)c1-2]
133
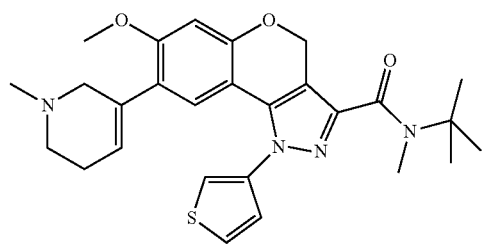 [SMILES: COc1cc2c(cc1C1=CCCN(C)C1)-c1c(c(C(=O)N(C)C(C)(C)C)nn1-c1ccsc1)CO2]
134
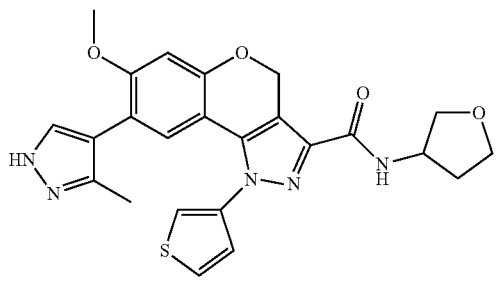 [SMILES: COc1cc2c(cc1-c1c[nH]nc1C)-c1c(c(C(=O)NC3CCOC3)nn1-c1ccsc1)CO2]
135
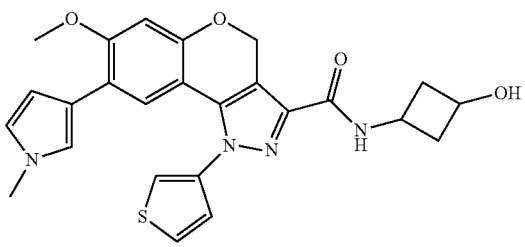 [SMILES: COc1cc2c(cc1-c1ccn(C)c1)-c1c(c(C(=O)NC3CC(O)C3)nn1-c1ccsc1)CO2]
136
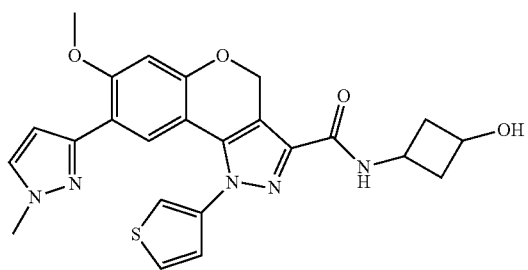 [SMILES: COc1cc2c(cc1-c1ccn(C)n1)-c1c(c(C(=O)NC3CC(O)C3)nn1-c1ccsc1)CO2]
137

TABLE 1-continued
| | |
|---|---|
| 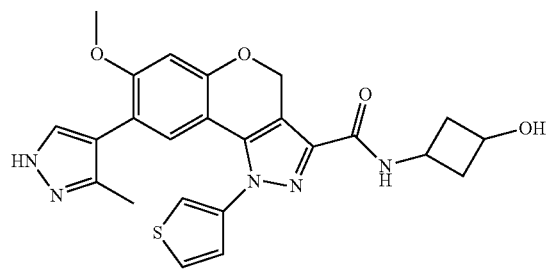 [SMILES: COc1cc2c(cc1-c1c[nH]nc1C)-c1c(c(C(=O)NC3CC(O)C3)nn1-c1ccsc1)CO2] | 138 |
| 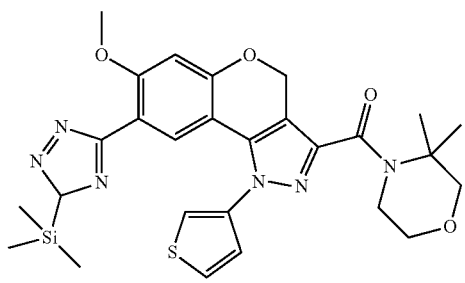 | 139 |
| 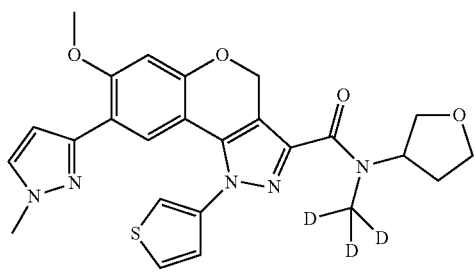 [SMILES: [2H]C([2H])([2H])N(C(=O)c1nn(-c2ccsc2)c2c1COc1cc(OC)c(-c3ccn(C)n3)cc1-2)C1CCOC1] | 140 |
| 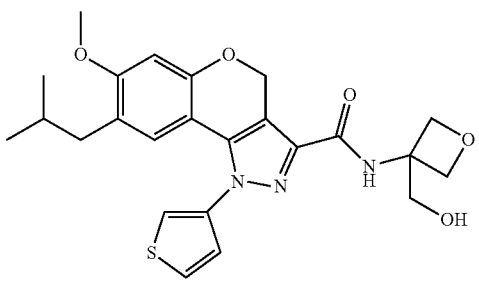 [SMILES: COc1cc2c(cc1CC(C)C)-c1c(c(C(=O)NC3(CO)COC3)nn1-c1ccsc1)CO2] | 141 |
| 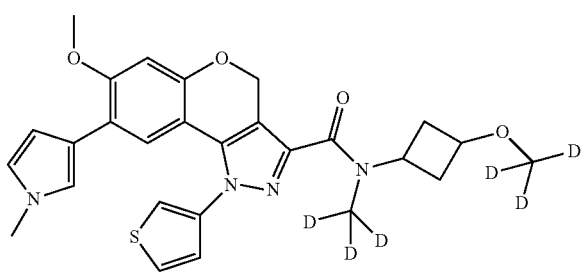 [SMILES: [2H]C([2H])([2H])OC1CC(N(C(=O)c2nn(-c3ccsc3)c3c2COc2cc(OC)c(-c4ccn(C)c4)cc2-3)C([2H])([2H])[2H])C1] | 142 |

TABLE 1-continued
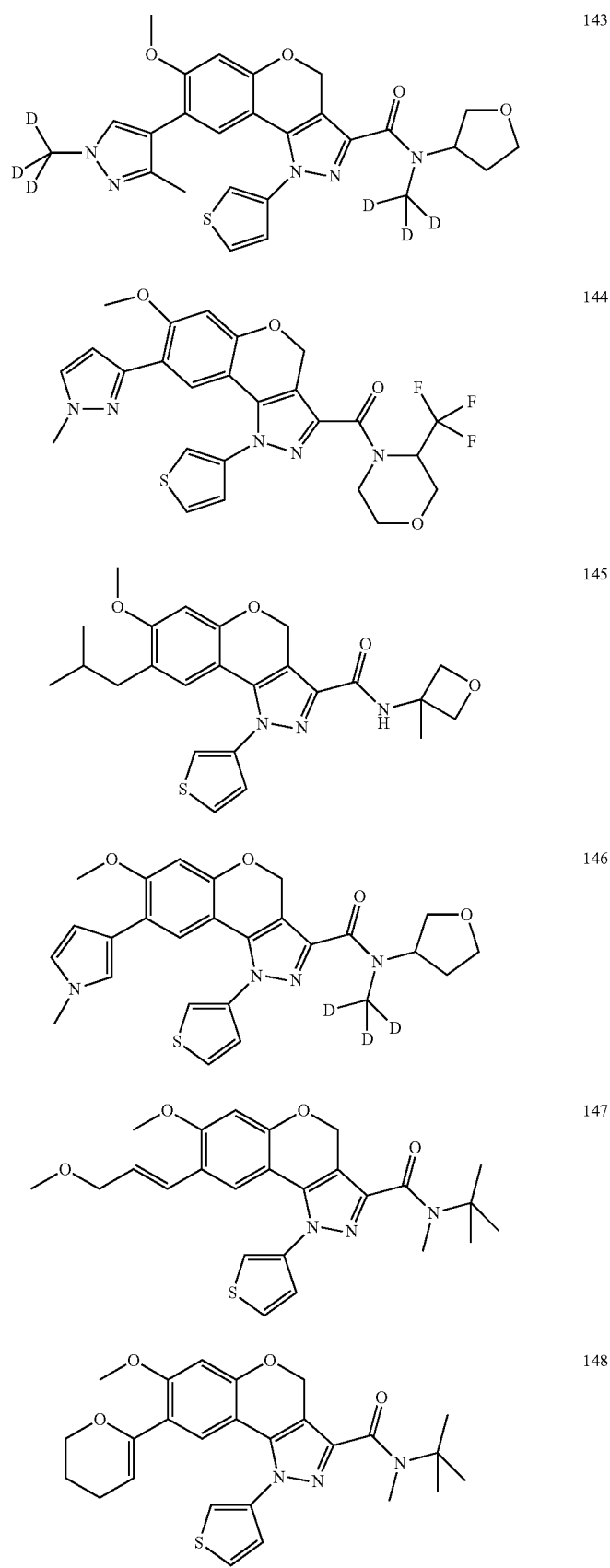

TABLE 1-continued
| | |
|---|---|
| 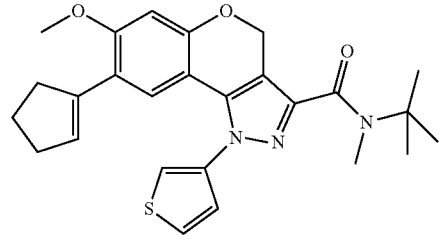 [SMILES: COc1cc2c(cc1C1=CCCC1)-c1c(c(C(=O)N(C)C(C)(C)C)nn1-c1ccsc1)CO2] | 149 |
| 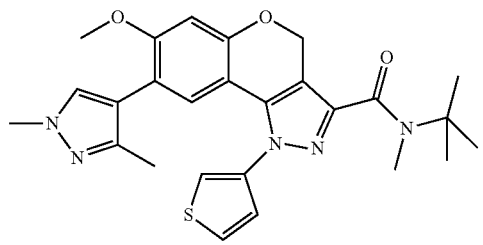 [SMILES: COc1cc2c(cc1-c1cn(C)nc1C)-c1c(c(C(=O)N(C)C(C)(C)C)nn1-c1ccsc1)CO2] | 150 |
| 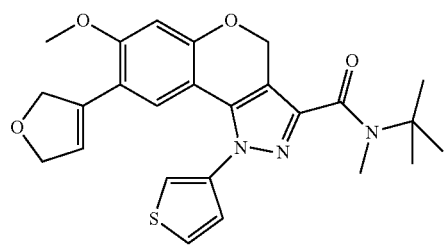 [SMILES: COc1cc2c(cc1C1=CCOC1)-c1c(c(C(=O)N(C)C(C)(C)C)nn1-c1ccsc1)CO2] | 151 |
| 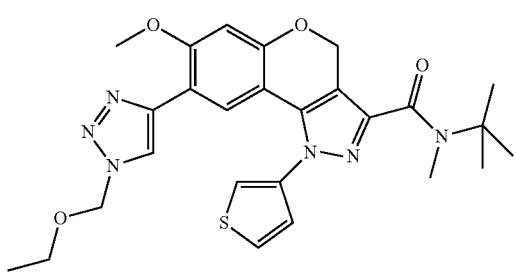 [SMILES: CCOCn1cc(-c2cc3c(cc2OC)OCc2c(C(=O)N(C)C(C)(C)C)nn(-c4ccsc4)c2-3)nn1] | 152 |
| 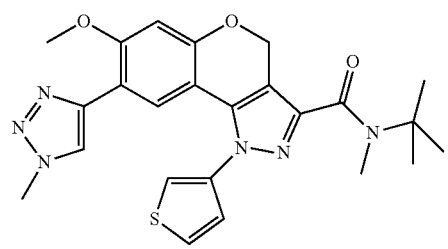 [SMILES: COc1cc2c(cc1-c1cn(C)nn1)-c1c(c(C(=O)N(C)C(C)(C)C)nn1-c1ccsc1)CO2] | 153 |
| 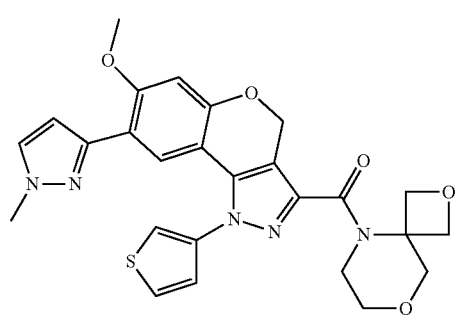 [SMILES: COc1cc2c(cc1-c1ccn(C)n1)-c1c(c(C(=O)N3CCOCC34COC4)nn1-c1ccsc1)CO2] | 154 |

TABLE 1-continued
| | |
|---|---|
| 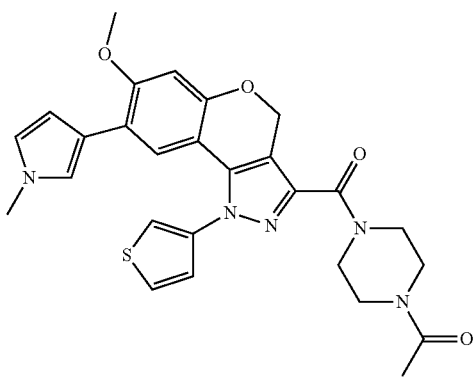 [SMILES: COc1cc2c(cc1-c1ccn(C)c1)-c1c(c(C(=O)N3CCN(C(C)=O)CC3)nn1-c1ccsc1)CO2] | 155 |
| 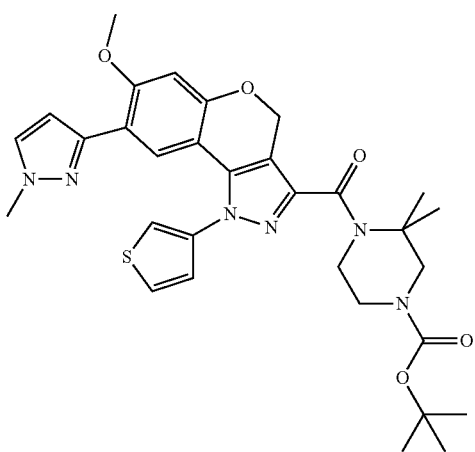 [SMILES: COc1cc2c(cc1-c1ccn(C)n1)-c1c(c(C(=O)N3CCN(C(=O)OC(C)(C)C)CC3(C)C)nn1-c1ccsc1)CO2] | 156 |
| 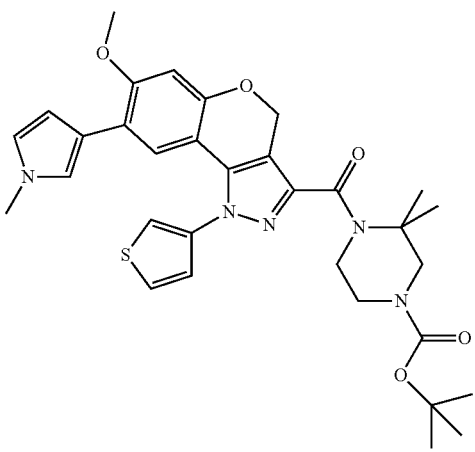 [SMILES: COc1cc2c(cc1-c1ccn(C)c1)-c1c(c(C(=O)N3CCN(C(=O)OC(C)(C)C)CC3(C)C)nn1-c1ccsc1)CO2] | 157 |

TABLE 1-continued
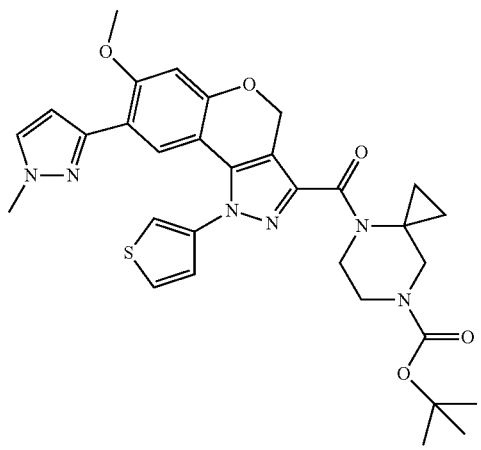 [SMILES: COc1cc2c(cc1-c1ccn(C)n1)-c1c(c(C(=O)N3CCN(C(=O)OC(C)(C)C)CC34CC4)nn1-c1ccsc1)CO2]
158
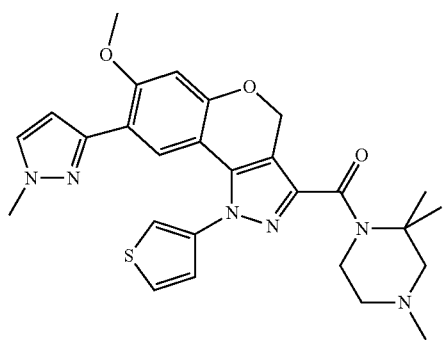
159
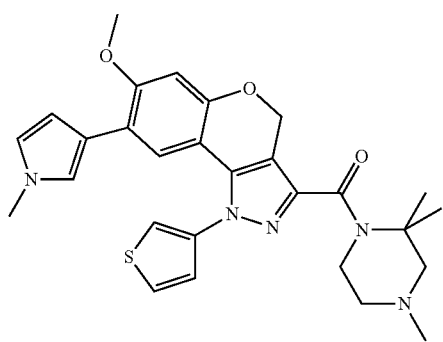
160
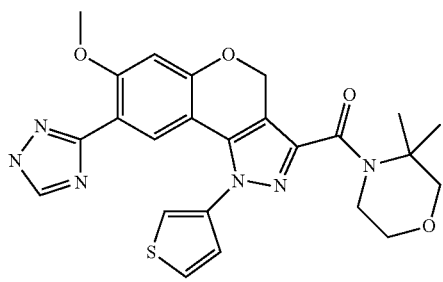 [SMILES: COc1cc2c(cc1-c1nc[nH]n1)-c1c(c(C(=O)N3CCOCC3(C)C)nn1-c1ccsc1)CO2]
161

TABLE 1-continued
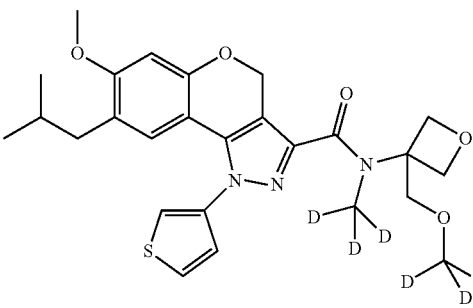
162
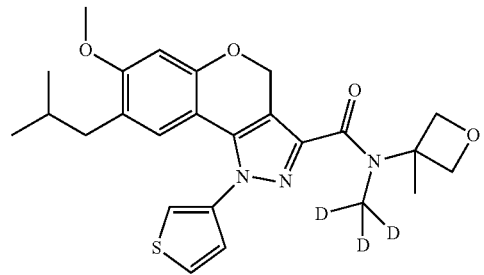 [SMILES: [2H]C([2H])([2H])N(C(=O)c1nn(-c2ccsc2)c2c1COc1cc(OC)c(CC(C)C)cc1-2)C1(C)COC1]
163
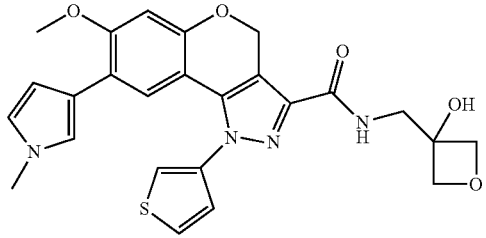 [SMILES: COc1cc2c(cc1-c1ccn(C)c1)-c1c(c(C(=O)NCC3(O)COC3)nn1-c1ccsc1)CO2]
164
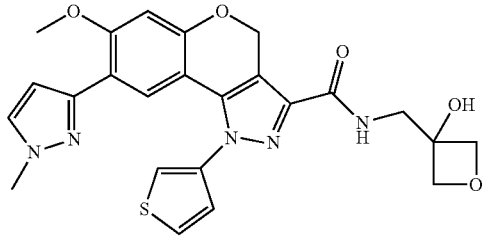 [SMILES: COc1cc2c(cc1-c1ccn(C)n1)-c1c(c(C(=O)NCC3(O)COC3)nn1-c1ccsc1)CO2]
165
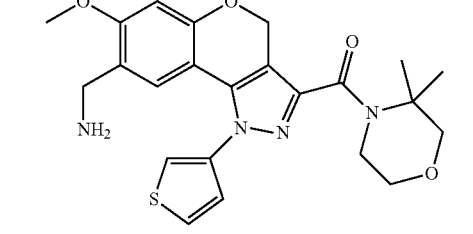
166
167

TABLE 1-continued
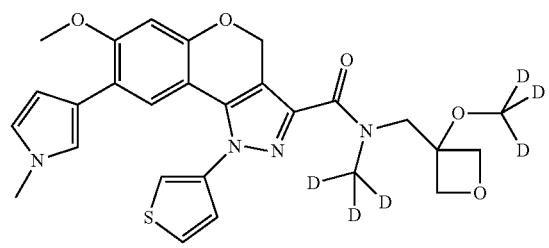 [SMILES: [2H]C([2H])([2H])OC1(CN(C(=O)c2nn(-c3ccsc3)c3c2COc2cc(OC)c(-c4ccn(C)c4)cc2-3)C([2H])([2H])[2H])COC1]
168
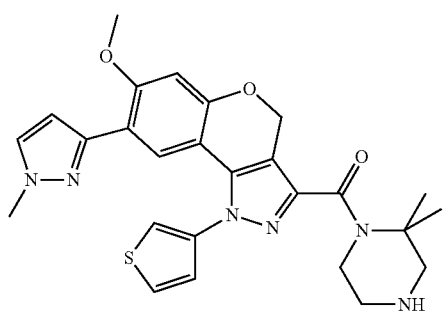
169
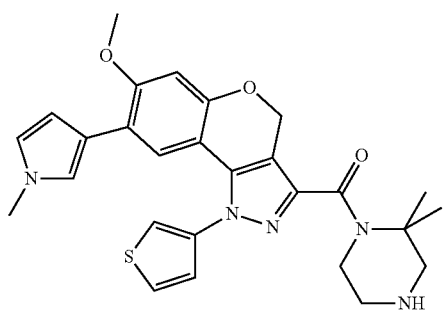
170
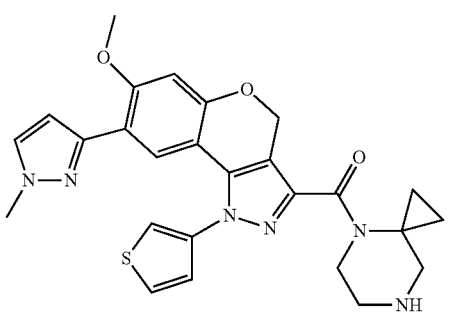 [SMILES: COc1cc2c(cc1-c1ccn(C)n1)-c1c(c(C(=O)N3CCNCC34CC4)nn1-c1ccsc1)CO2]
171
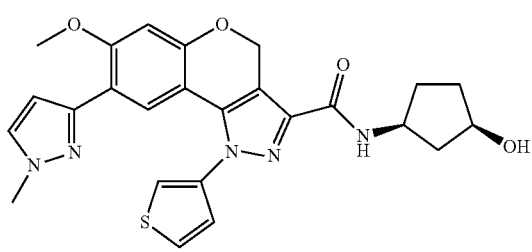 [SMILES: COc1cc2c(cc1-c1ccn(C)n1)-c1c(c(C(=O)N[C@H]3CC[C@@H](O)C3)nn1-c1ccsc1)CO2]
172

TABLE 1-continued
| | |
|---|---|
| 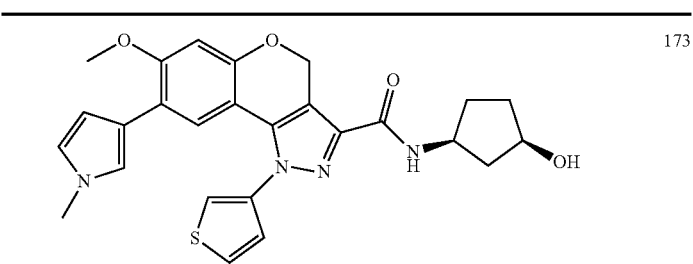 | 173 |
| 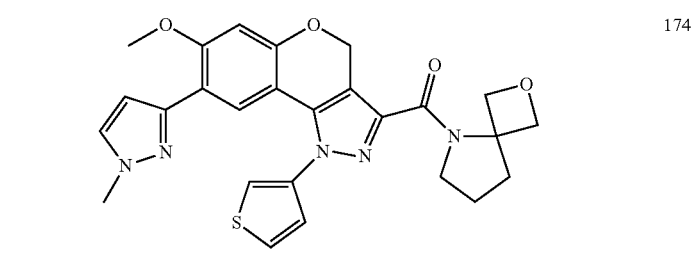 | 174 |
| 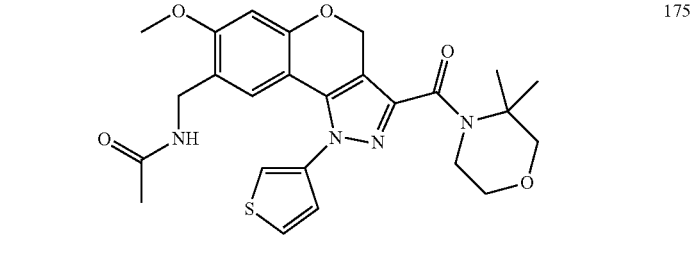 | 175 |
| 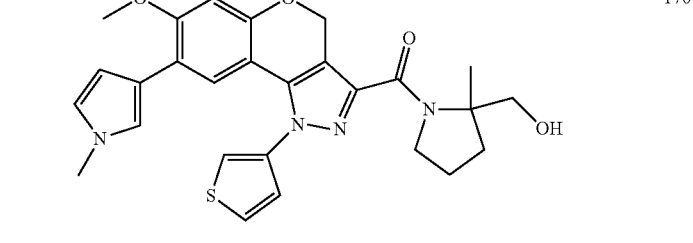 | 176 |
| 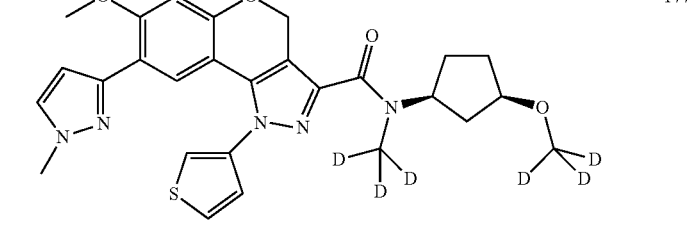 | 177 |
| 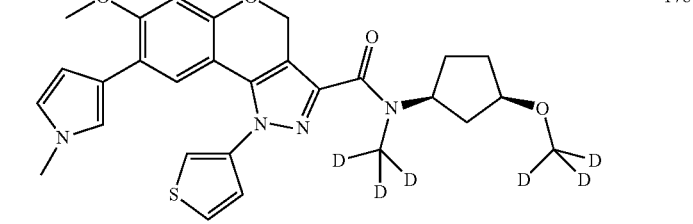 | 178 |

TABLE 1-continued
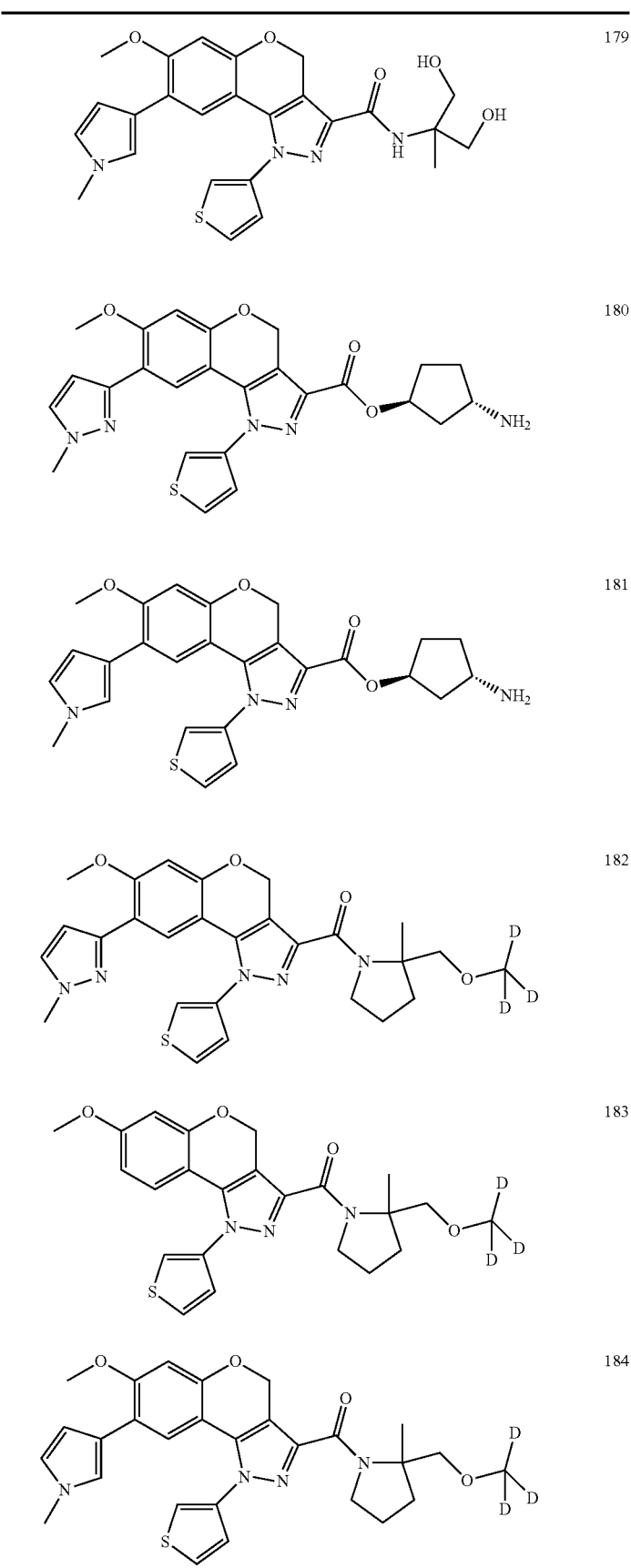

TABLE 1-continued
| | |
|---|---|
| 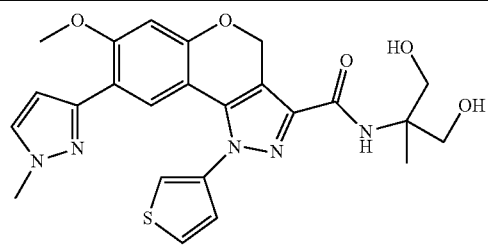 | 185 |
| 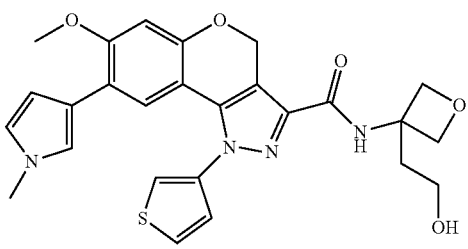 [SMILES: COc1cc2c(cc1-c1ccn(C)c1)-c1c(c(C(=O)NC3(CCO)COC3)nn1-c1ccsc1)CO2] | 186 |
| 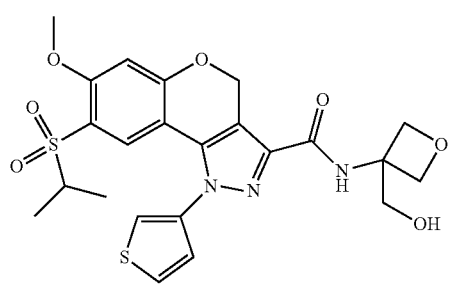 [SMILES: COc1cc2c(cc1S(=O)(=O)C(C)C)-c1c(c(C(=O)NC3(CO)COC3)nn1-c1ccsc1)CO2] | 187 |
| 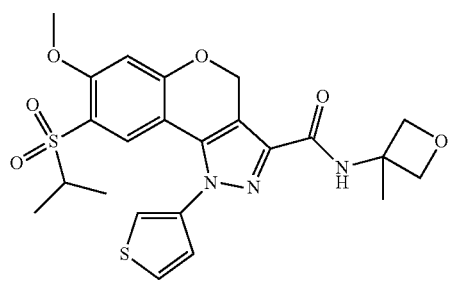 [SMILES: COc1cc2c(cc1S(=O)(=O)C(C)C)-c1c(c(C(=O)NC3(C)COC3)nn1-c1ccsc1)CO2] | 188 |
| 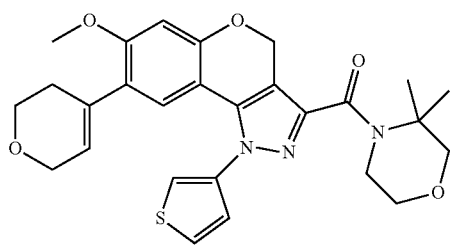 [SMILES: COc1cc2c(cc1C1=CCOCC1)-c1c(c(C(=O)N3CCOCC3(C)C)nn1-c1ccsc1)CO2] | 189 |
| 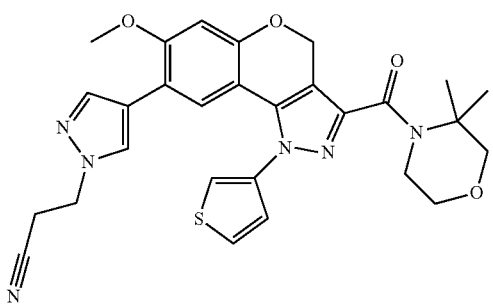 [SMILES: COc1cc2c(cc1-c1cnn(CCC#N)c1)-c1c(c(C(=O)N3CCOCC3(C)C)nn1-c1ccsc1)CO2] | 190 |

TABLE 1-continued
| | |
|---|---|
| 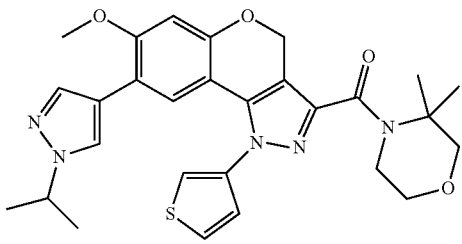 [SMILES: COc1cc2c(cc1-c1cnn(C(C)C)c1)-c1c(c(C(=O)N3CCOCC3(C)C)nn1-c1ccsc1)CO2] | 191 |
| 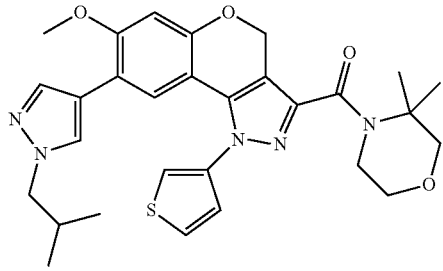 [SMILES: COc1cc2c(cc1-c1cnn(CC(C)C)c1)-c1c(c(C(=O)N3CCOCC3(C)C)nn1-c1ccsc1)CO2] | 192 |
| 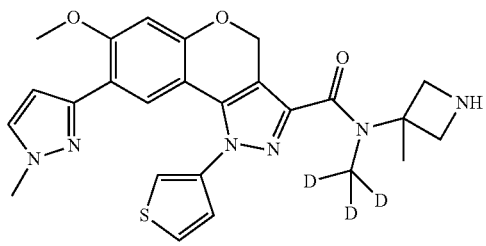 [SMILES: [2H]C([2H])([2H])N(C(=O)c1nn(-c2ccsc2)c2c1COc1cc(OC)c(-c3ccn(C)n3)cc1-2)C1(C)CNC1] | 193 |
| 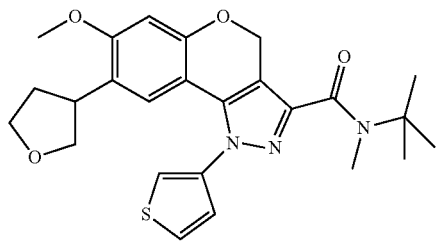 | 194 |
| 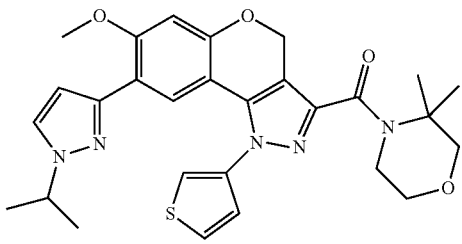 [SMILES: COc1cc2c(cc1-c1ccn(C(C)C)n1)-c1c(c(C(=O)N3CCOCC3(C)C)nn1-c1ccsc1)CO2] | 195 |
| 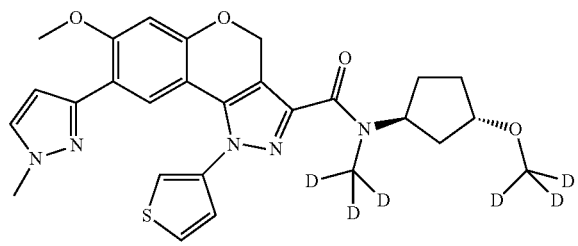 [SMILES: [2H]C([2H])([2H])O[C@H]1CC[C@H](N(C(=O)c2nn(-c3ccsc3)c3c2COc2cc(OC)c(-c4ccn(C)n4)cc2-3)C([2H])([2H])[2H])C1] | 196 |

TABLE 1-continued
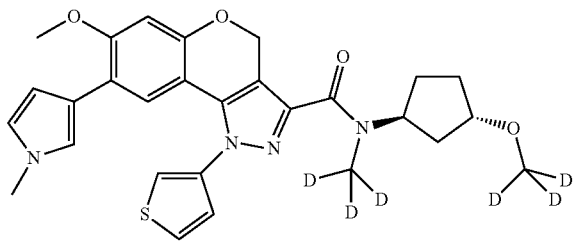 [SMILES: [2H]C([2H])([2H])O[C@H]1CC[C@H](N(C(=O)c2nn(-c3ccsc3)c3c2COc2cc(OC)c(-c4ccn(C)c4)cc2-3)C([2H])([2H])[2H])C1]
197
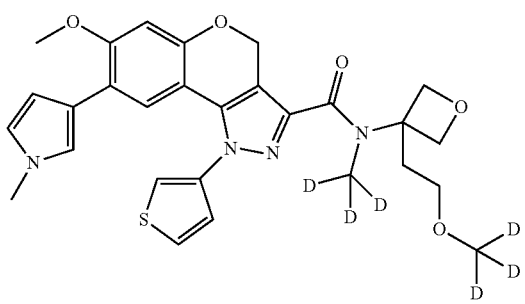 [SMILES: [2H]C([2H])([2H])OCCC1(N(C(=O)c2nn(-c3ccsc3)c3c2COc2cc(OC)c(-c4ccn(C)c4)cc2-3)C([2H])([2H])[2H])COC1]
198
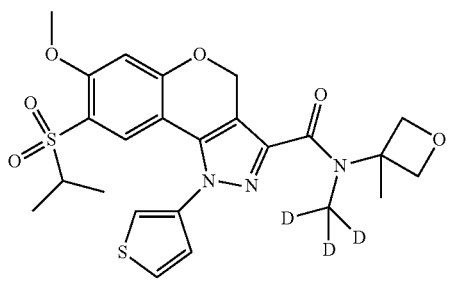 [SMILES: [2H]C([2H])([2H])N(C(=O)c1nn(-c2ccsc2)c2c1COc1cc(OC)c(S(=O)(=O)C(C)C)cc1-2)C1(C)COC1]
199
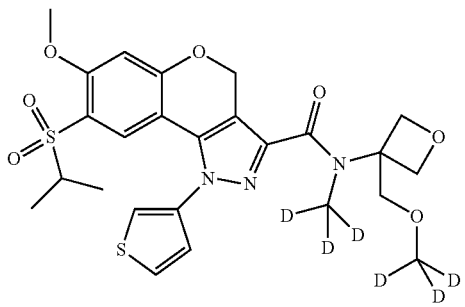 [SMILES: [2H]C([2H])([2H])OCC1(N(C(=O)c2nn(-c3ccsc3)c3c2COc2cc(OC)c(S(=O)(=O)C(C)C)cc2-3)C([2H])([2H])[2H])COC1]
200
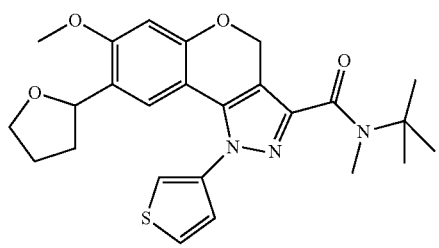 [SMILES: COc1cc2c(cc1C1CCCO1)-c1c(c(C(=O)N(C)C(C)(C)C)nn1-c1ccsc1)CO2]
201

TABLE 1-continued
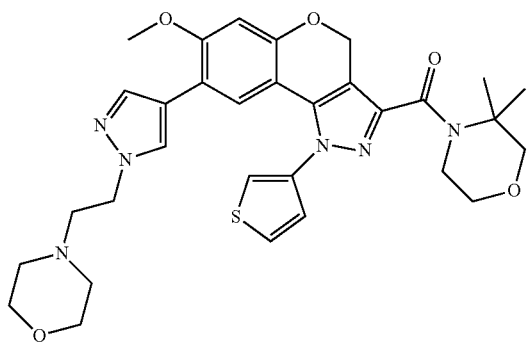 [SMILES: COc1cc2c(cc1-c1cnn(CCN3CCOCC3)c1)-c1c(c(C(=O)N3CCOCC3(C)C)nn1-c1ccsc1)CO2] 202
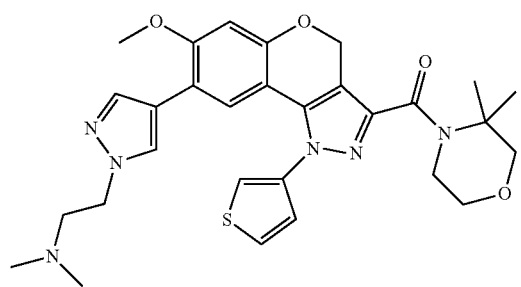 203
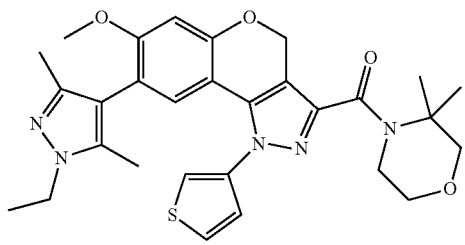 [SMILES: CCn1nc(C)c(-c2cc3c(cc2OC)OCc2c(C(=O)N4CCOCC4(C)C)nn(-c4ccsc4)c2-3)c1C] 204
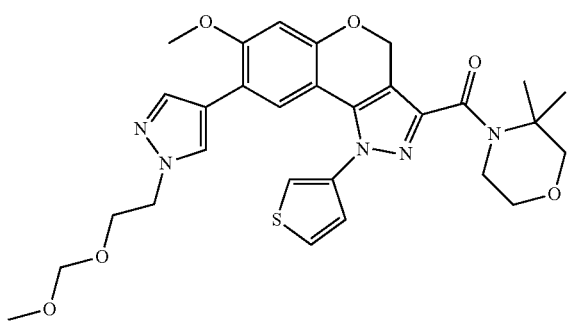 205
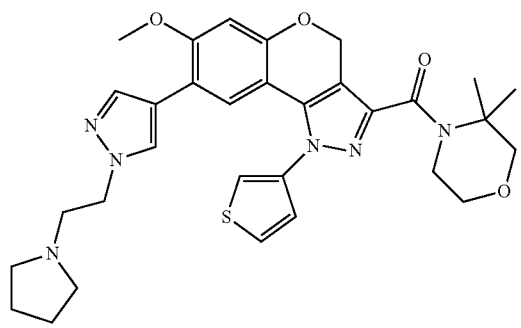 [SMILES: COc1cc2c(cc1-c1cnn(CCN3CCCC3)c1)-c1c(c(C(=O)N3CCOCC3(C)C)nn1-c1ccsc1)CO2] 206

TABLE 1-continued
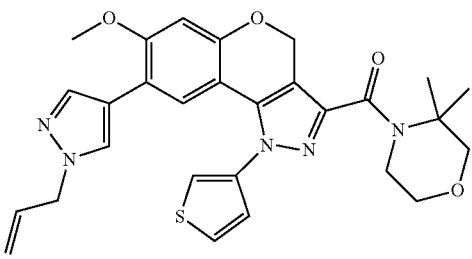 [SMILES: C=CCn1cc(-c2cc3c(cc2OC)OCc2c(C(=O)N4CCOCC4(C)C)nn(-c4ccsc4)c2-3)cn1] 207
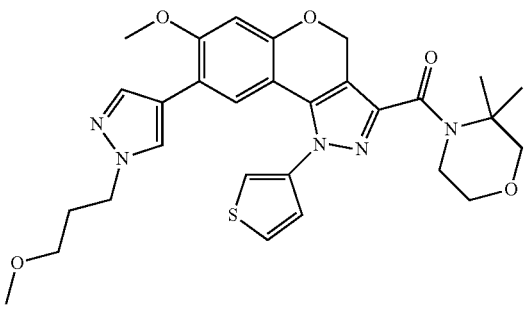 208
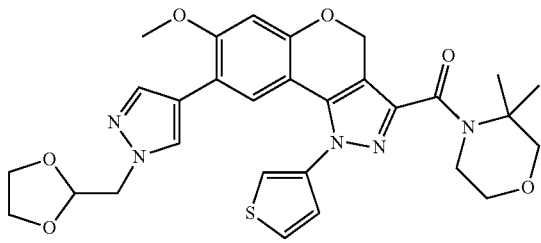 [SMILES: COc1cc2c(cc1-c1cnn(CC3OCCO3)c1)-c1c(c(C(=O)N3CCOCC3(C)C)nn1-c1ccsc1)CO2] 209
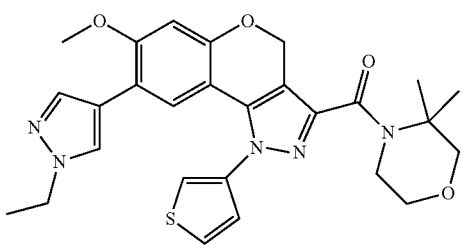 [SMILES: CCn1cc(-c2cc3c(cc2OC)OCc2c(C(=O)N4CCOCC4(C)C)nn(-c4ccsc4)c2-3)cn1] 210
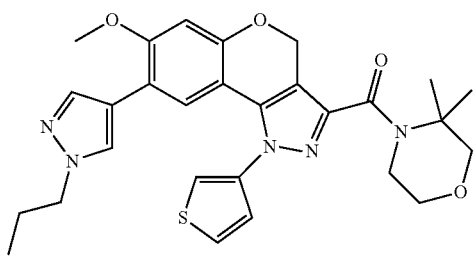 [SMILES: CCCn1cc(-c2cc3c(cc2OC)OCc2c(C(=O)N4CCOCC4(C)C)nn(-c4ccsc4)c2-3)cn1] 211
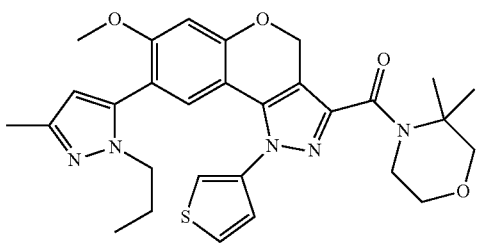 212

TABLE 1-continued
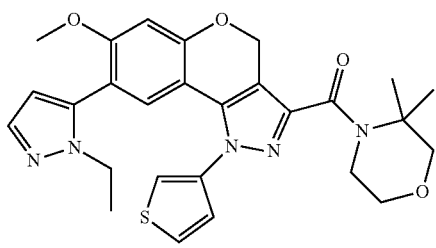 [SMILES: CCn1nccc1-c1cc2c(cc1OC)OCc1c(C(=O)N3CCOCC3(C)C)nn(-c3ccsc3)c1-2] 213
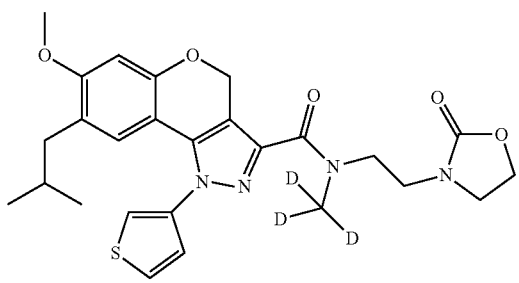 [SMILES: [2H]C([2H])([2H])N(CCN1CCOC1=O)C(=O)c1nn(-c2ccsc2)c2c1COc1cc(OC)c(CC(C)C)cc1-2] 214
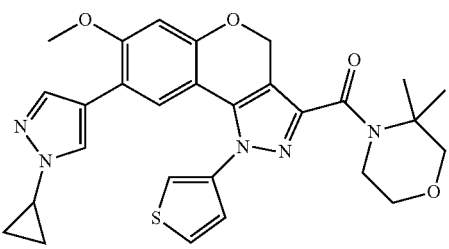 [SMILES: COc1cc2c(cc1-c1cnn(C3CC3)c1)-c1c(c(C(=O)N3CCOCC3(C)C)nn1-c1ccsc1)CO2] 215
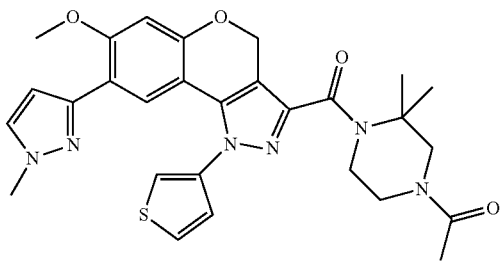 [SMILES: COc1cc2c(cc1-c1ccn(C)n1)-c1c(c(C(=O)N3CCN(C(C)=O)CC3(C)C)nn1-c1ccsc1)CO2] 216
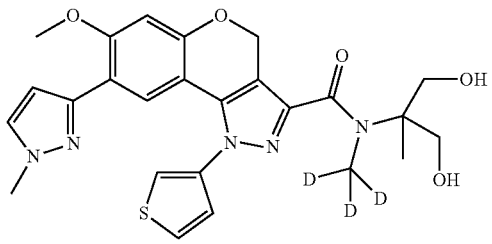 [SMILES: [2H]C([2H])([2H])N(C(=O)c1nn(-c2ccsc2)c2c1COc1cc(OC)c(-c3ccn(C)n3)cc1-2)C(C)(CO)CO] 217
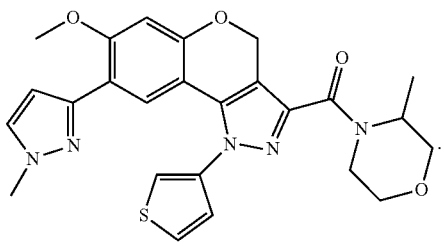 [SMILES: COc1cc2c(cc1-c1ccn(C)n1)-c1c(c(C(=O)N3CCOCC3C)nn1-c1ccsc1)CO2] 218

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen

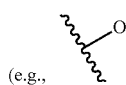

(e.g., is understood to be

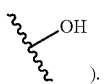

).

In certain embodiments, the compounds of the invention were synthesized in accordance with Schemes A-C below. More specific examples of compounds made utilizing Schemes A-C are provided in the Examples below.

Scheme A

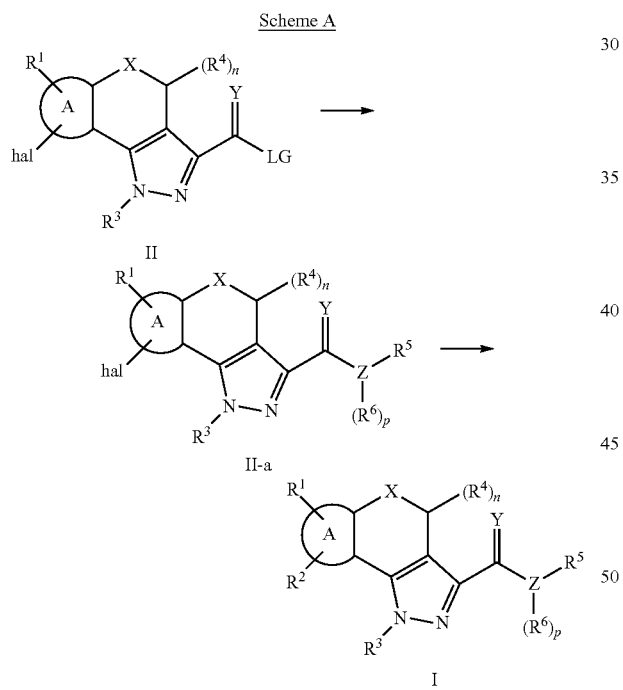

Scheme B

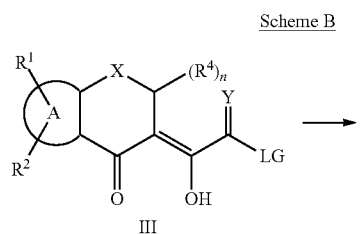

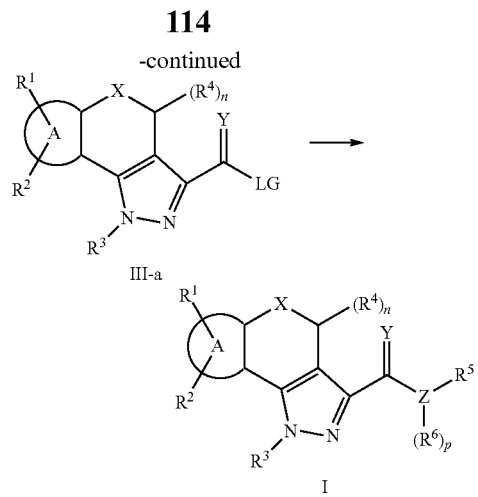

Scheme C

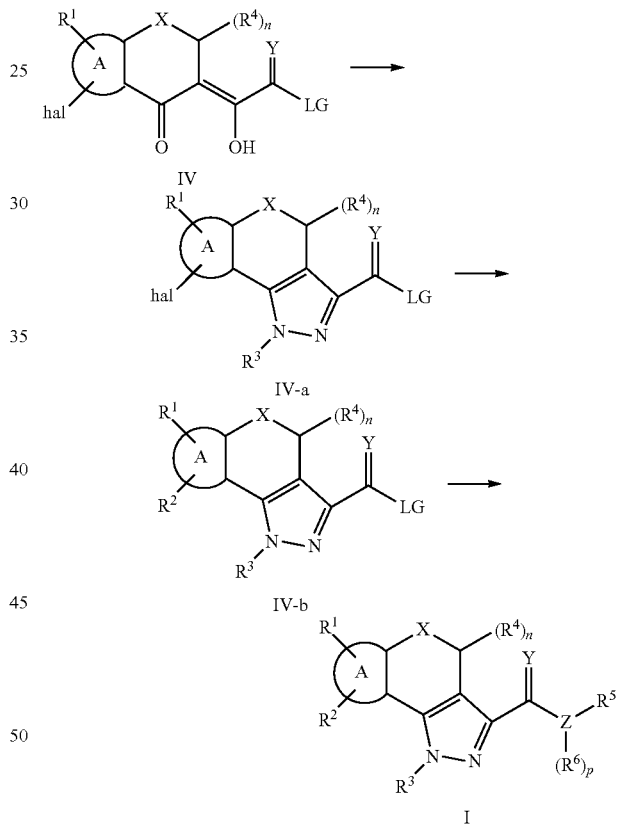

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate FSHR, or a mutant thereof, in a biological sample or in a patient. In certain embodiments, the amount of compound in compositions of this invention is such that is effective to measurably modulate FSHR, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this aremineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for allosterically agonising FSHR, or a mutant thereof, in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for modulating a FSH receptor, particularly in the presence of FSH. The term "modulation" denotes any change in FSHR-mediated signal transduction, which is based on the action of the specific inventive compounds capable to interact with the FSHR target in such a manner that makes recognition, binding and activating possible. The compounds are characterized by such a high affinity to FSHR, which ensures a reliable binding and preferably a positive allosteric modulation of FSHR. In certain embodiments, the substances are mono-specific in order to guarantee an exclusive and directed recognition with the single FSHR target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for modulating an FSH receptor, and in particular in a positive allosteric manner, wherein a system capable of expressing the FSH receptor is contacted, in the presence of FSH, with at least one compound of formula (I) according to the invention and/or physiologically acceptable salts thereof, under conditions such that said FSH receptor is modulated. In certain embodiments, modulation is in a positive allosteric manner. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating an FSH receptor is performed in-vitro. The prior teaching of the present specification concerning the compounds of formula (I), including any embodiments thereof, is valid and applicable without restrictions to the compounds according to formula (I) and their salts when used in the method for modulating FSHR. The prior teaching of the present specification concerning the compounds of formula (I), including any embodiments thereof, is valid and applicable without restrictions to the compounds according to formula (I) and their salts when used in the method for modulating FSHR.

In certain embodiments, the compounds according to the invention exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect. In certain embodiments, the compounds of the invention have an FSHR agonist activity, as expressed by an $EC_{50}$ standard, of less than 5 μM. In certain embodiments, less than 1 μM. In certain embodiments, less than 0.5 μM. In certain embodiments, less than 0.1 μM. "$EC_{50}$" is the effective concentration of a compound at which 50% of the maximal response of that obtained with FSH would be obtained.

As discussed herein, these signaling pathways are relevant for various diseases, including fertility disorders. Disorders/diseases treated by the methods of the invention include but are not limited to, hypogonadotropic hypogonadism, Isolated idiopathic hypogonadotropic hypogonadism, Kallmann syndrome, Idiopathic hypogonadotropic hypogonadism, Craniopharyngiomas, Combined pituitary hormone deficiency, Fertile eunuch syndrome, Abnormal beta subunit of LH, Abnormal beta subunit of FSH, mass lesions, pituitary adenomas, cysts, metastatic cancer to the sella (breast in women, lung and prostate in men), Infiltrative lesions, Hemochromatosis, sarcoidosis, histiocytosis, lymphoma, Lymphocytic hypophysitis, Infections, Meningitis, Pituitary apoplexy, Hyperprolactinemia, hypothyroidism, Intentional (iatrogenic) secondary hypogonadism, Empty sella, Pituitary infarction, Sheehan syndrome, Anorexia nervosa, Congenital adrenal hyperplasia, and disorders related to GnRH deficiency. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably agonists, more preferably positive allosteric modulators, of the signaling pathways described herein, preferably of the FSHR-mediated signaling pathway. The compounds of the invention are supposed to bind to the intracellular receptor domain without a competitive interaction with FSH, but they act as an allosteric enhancer of FSH on its receptor. The non-competitive interaction refers to the nature of the agonist activity exhibited by the compounds of the invention, wherein the compounds activate FSHR without substantially reducing the magnitude of binding of FSH to FSHR.

In certain embodiments, the invention is directed towards the stimulation of follicular development, ovulation induction, controlled ovarial hyperstimulation, assisted reproductive technology, including in-vitro fertilization, male hypogonadism and male infertility, including some types of failure of spermatogenesis.

It is another object of the invention to provide a method for treating diseases that are caused, mediated and/or propagated by FSHR activity, wherein at least one compound of formula (I) according to the invention and/or physiologically acceptable salts thereof is administered to a mammal in need of such treatment. In certain embodiments, the invention provides a method for treating fertility disorders, wherein at least one compound of formula (I) according to the invention and/or physiologically acceptable salts thereof is administered to a mammal in need of such treatment. In certain embodiments, the compound is administered in an effective amount as defined above. In certain embodiments, the treatment is an oral administration.

In certain embodiments, the method of treatment aims to achieve ovulation induction and/or controlled ovarian hyperstimulation. In still another embodiment, the method of treatment forms the basis for a method for in-vitro fertilization comprising the steps of: (a) treating a mammal according to the method of treatment as described above, (b) collecting ova from said mammal, (c) fertilizing said ova, and (d) implanting said fertilized ova into a host mammal. The host mammal can be either the treated mammal (i.e. the patient) or a surrogate. The prior teaching of the invention and its embodiments is valid and applicable without restrictions to the methods of treatment if expedient.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate FSHR activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing FSHR-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. In certain embodiments, the in-vitro use is preferably applied to samples of humans suffering from fertility disorders. Testing of several specific compounds and/or derivatives thereof makes the selection of that active ingredient possible that is best suited for the treatment of the human subject. The in-vivo dose rate of the chosen derivative is advantageously pre-adjusted to the FSHR susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the modulation of FSHR activity if expedient.

The invention also relates to the use of compounds according to formula (I) and/or physiologically acceptable salts thereof for the prophylactic or therapeutic treatment and/or monitoring of diseases that are caused, mediated and/or propagated by FSHR activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by FSHR activity. In certain embodiments, the invention provides the use of a compound according to formula I or physiologically acceptable salts thereof, for the production of a medicament for the prophylactic or therapeutic treatment of a FSHR-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by FSHR activity. Another preferred object of the invention concerns compounds of formula (I) according to the invention and/or physiologically acceptable salts thereof for use in the prophylactic or therapeutic treatment and/or monitoring of fertility disorders. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of fertility disorders.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The methods of the invention can also be used to reducing the likelihood of developing a disorder or even prevent the initiation of disorders associated with FSHR activity in advance or to treat the arising and continuing symptoms. In certain embodiments, the disorders are fertility disorders.

In the meaning of the invention, prophylactic treatment is advisable if the subject possesses any preconditions for the aforementioned physiological or pathological conditions, such as a familial disposition, a genetic defect, or a previously passed disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with FSHR activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with known fertility-inducing agents. In certain embodiments, the other active pharmaceutical ingredient is selected from the group of FSH, $\alpha$-FSH (Gonal F), $\beta$-FSH, LH, hMG and 2-(4-(2-chloro-1,2-diphenylethenyl)-phenoxy)-N,N-diethyl-ethanamine citrate (Chlomifene citrate). Further ovulation adjuncts are known to those of skill in the art (cf. e.g. WO 2002/09706, which is incorporated herein by reference) and are useful with the compounds of the present invention.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like.

Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection.

This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of allosterically modulating FSHR activity in a biological sample comprising the step of contacting said biological sample with a compound of this invention, or a composition comprising said compound.

According to another embodiment, the invention relates to a method of allosterically modulating FSHR, or a mutant thereof, activity in a biological sample in a positive manner, comprising the step of contacting said biological sample with a compound of this invention, or a composition comprising said compound.

The compounds of the invention are strong and selective modulators of the FSH receptor. Their selectivity to the FSH receptor is 3 to 10-fold over the LH receptor and even 10 to 100-fold over the TSH receptor while the $EC_{50}$ or $IC_{50}$ amounts to more than 10 µM on unrelated G protein-coupled receptors (GPCR) or non-GPCR targets. The current invention comprises the use of the compounds of the invention in the regulation and/or modulation of the FSHR signal cascade, which can be advantageously applied as research tool, for diagnosis and/or in treatment of any disorder arising from FSHR signaling.

For example, the compounds of the invention are useful in-vitro as unique tools for understanding the biological role of FSH, including the evaluation of the many factors thought to influence, and be influenced by, the production of FSH and the interaction of FSH with the FSHR (e. g. the mechanism of FSH signal transduction/receptor activation). The present compounds are also useful in the development of other compounds that interact with FSHR since the present compounds provide important structure-activity relationship (SAR) information that facilitate that development. Compounds of the present invention that bind to FSHR can be used as reagents for detecting FSHR on living cells, fixed cells, in biological fluids, in tissue homogenates, in purified, natural biological materials, etc. For example, by labeling such compounds, one can identify cells having FSHR on their surfaces. In addition, based on their ability to bind FSHR, compounds of the present invention can be used in in-situ staining, FACS (fluorescence-activated cell sorting), western blotting, ELISA (enzyme-linked immunoadsorptive assay), etc., receptor purification, or in purifying cells expressing FSHR on the cell surface or inside permeabilized cells.

The compounds of the invention can also be utilized as commercial research reagents for various medical research and diagnostic uses. Such uses can include but are not limited to: use as a calibration standard for quantifying the activities of candidate FSH agonists in a variety of functional assays; use as blocking reagents in random compound screening, i.e. in looking for new families of FSH receptor ligands, the compounds can be used to block recovery of the presently claimed FSH compounds; use in the co-crystallization with FSHR receptor, i.e. the compounds of the present invention will allow formation of crystals of the compound bound to FSHR, enabling the determination of receptor/compound structure by x-ray crystallography; other research and diagnostic applications, wherein FSHR is preferably activated or such activation is conveniently calibrated against a known quantity of an FSH agonist, etc.; use in assays as probes for determining the expression of FSHR on the surface of cells; and developing assays for detecting compounds which bind to the same site as the FSHR binding ligands.

The compounds of the invention can be applied either themselves and/or in combination with physical measurements for diagnostics of treatment effectiveness. Pharmaceutical compositions containing said compounds and the use of said compounds to treat FSHR-mediated conditions is a promising, novel approach for a broad spectrum of therapies causing a direct and immediate improvement in the state of health, whether in human or animal. The impact is of special benefit to efficiently combat infertility, either alone or in combination with other fertility-inducing treatments. In particular, the compounds of the invention potentiate the native FSH effect for both ovulation induction and assisted reproductive technology. The orally bioavailable and active new chemical entities of the invention improve convenience for patients and compliance for physicians.

The compounds of the invention are active in the primary screen (CHO with or without FSH), selective in secondary screen (no or low activity against TSHR and LHR) and potent in the granulosa cell estrodiol assay. Neither hERG nor any toxic effects could be observed in-vitro.

In certain embodiments, the invention provides a method for in-vitro fertilization comprising the steps of:
(a) treating a mammal according to the method as described above,
(b) collecting ova from said mammal,
(c) fertilizing said ova, and
(d) implanting said fertilized ova into a host mammal.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of FSHR, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

$^1$H NMR was recorded on a Bruker 400 MHz spectrometer, using residual signal of deuterated solvent as internal reference. Chemical shifts ($\delta$) are reported in ppm relative to the residual solvent signal ($\delta$=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under the following conditions:
Method: A: 0.1% TFA in H$_2$O, B: 0.1% TFA in ACN:
Runtime: 6.5 min
Flow Rate: 1.0 mL/min
Gradient: 5-95% B in 4.5 min, wavelength 254 and 215 nM.
Column: Waters Sunfire C18, 3.0×50 mm, 3.5 um, +ve mode
Mass Scan: 100-900 Da Scheme 1:

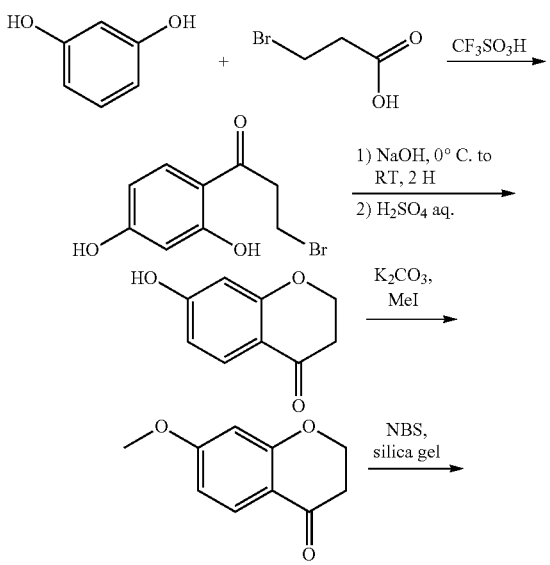

Example 1

7-Methoxy-8-(1H-pyrazol-4-yl)-1-thiophen-3-yl-1,4-dihydro-chromeno[4,3-c]pyrazole-3-carboxylic acid tert-butyl-methyl-amide (1)

Step 1: 3-Bromo-1-(2,4-dihydroxyphenyl)propan-1-one

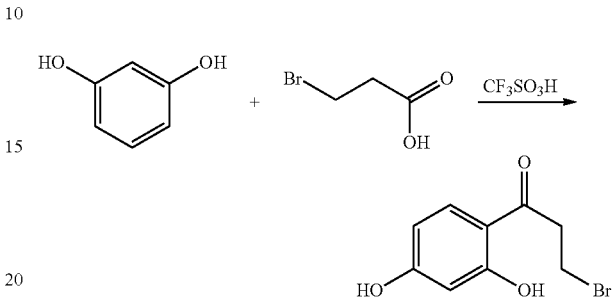

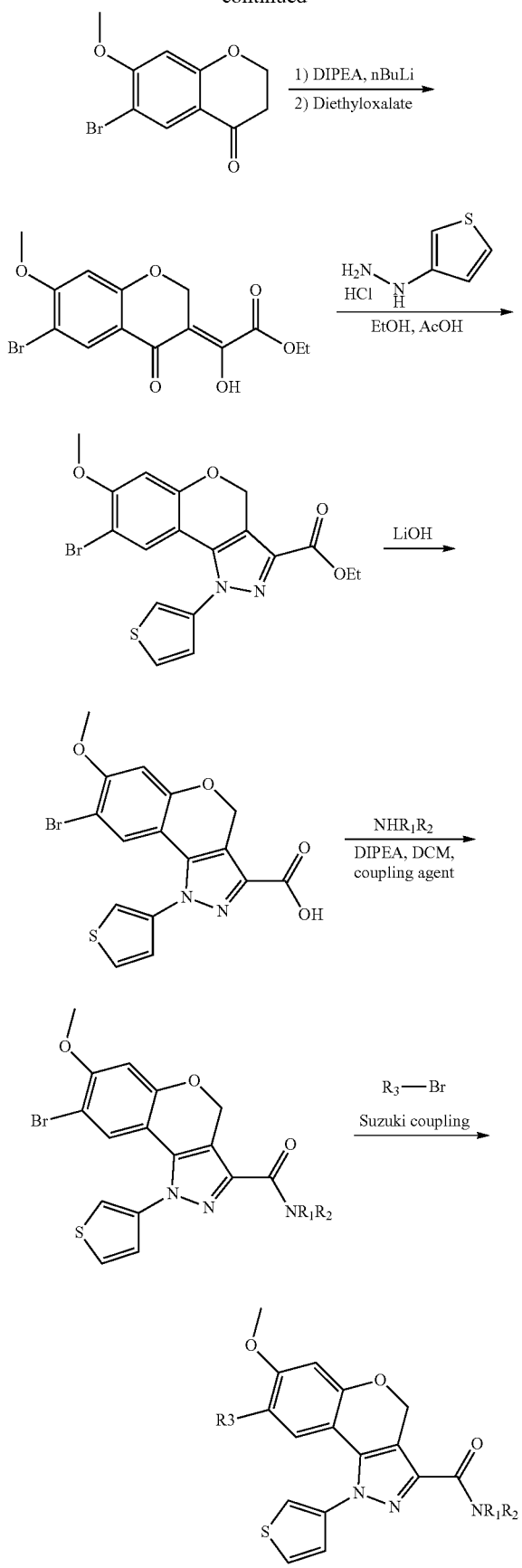

To a stirred suspension of resorcinol (25 g, 0.22 mol) and 3-Bromopropanoic acid (38.3 g, 0.25 mol) was added trifluoromethanesulfonic acid (75 mL, 0.84 mol) drop wise at 0° C. under nitrogen atmosphere. After the addition, the reaction mixture was heated to 80° C. for 30 min. The reaction mixture was cooled to RT and quenched with ice water (200 mL) and extracted with DCM (500 mL). The aqueous layer was re-extracted with DCM (2×100 mL); the combined organic layer was dried over sodium sulphate and concentrated under vacuum to afford the desired compound (40 g, 72%) as an orange solid.

$^1$H NMR (400 MHz, DMSO-$d_6$) δ 12.2 (bs, 1H), 10.6 (bs, 1H), 7.77-7.75 (d, J=8 Hz, 1H), 6.38-6.35 (dd, J=2.0, 8.8 Hz, 1H), 6.26-6.26 (d, J=4.0 Hz, 1H), 3.74 (t, J=6.8 Hz, 2H), 3.61-3.57 (dd, J=6.0, 11.2 Hz, 2H).

Step 2: 7-Hydroxy-2,3-dihydro-4H-chromen-4-one

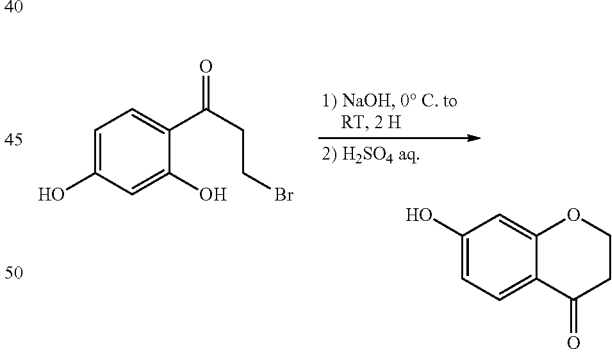

To an ice cold solution of 2M NaOH (92 mL, 2.33 mol), was added 3-Bromo-1-(2,4-dihydroxyphenyl)propan-1-one (38 g, 0.155 mol) in lots over a period of 30 min. The resulting suspension was stirred at RT for 2 h. The reaction mixture was cooled to 0° C.; pH was adjusted to ~2 using 50% aqueous solution of sulfuric acid. The solid separated out was stirred for additional 10 min at RT, filtered and dried under high vacuum to afford the desired compound (16 g, 63%) as brown solid.

$^1$H NMR (400 MHz, DMSO-$d_6$) δ 10.52 (bs, 1H), 7.61-7.59 (d, J=8.0 Hz, 1H), 6.48-6.45 (dd, J=4.0, 12.0 Hz, 1H), 6.29-6.20 (d, J=4.0 Hz, 1H), 4.44 (t, J=4.0 Hz, 2H), 2.65 (t, J=4.0 Hz, 2H).

Step 3: 7-Methoxy-2,3-dihydro-4H-chromen-4-one

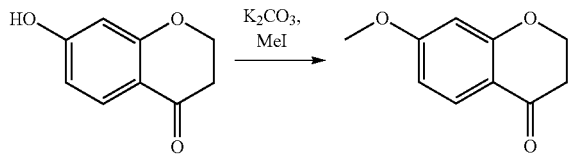

To a stirred solution of 7-Hydroxy-2,3-dihydro-4H-chromen-4-one (27 g, 0.16 mol) in acetone (700 mL) was added dry K$_2$CO$_3$ (45.6 g, 0.32 mol) in lots at RT under nitrogen. The reaction mixture was stirred at RT for 10 min and then methyl iodide (65.4 g, 0.46 mol) was added drop wise at RT. The reaction mixture was stirred at RT for 4 h. The reaction mixture was filtered and filtrate was concentrated under vacuum. The crude product was dissolved in DCM (200 mL), washed with water (100 mL), brine (50 mL), dried over sodium sulphate and concentrated under vacuum to afford the desired compound (15 g, 89%) as light yellow solid.

$^1$H NMR (400 MHz, CDCl$_3$) δ 7.85-7.83 (d, J=8.0 Hz, 1H), 6.60-6.57 (dd, J=4.0, 12.0 Hz, 1H), 6.41-6.41 (d, J=4.0 Hz, 1H), 4.52 (t, J=8.0 Hz, 2H), 3.77 (s, 3H), 2.76 (t, J=4.0 Hz, 2H).

Step 4: 6-Bromo-7-methoxy-2,3-dihydro-4H-chromen-4-one

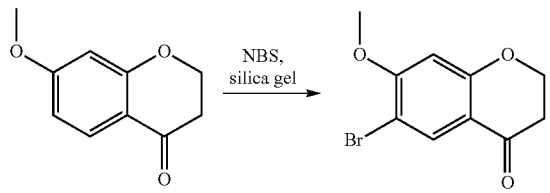

To a solution of 7-Methoxy-2,3-dihydro-4H-chromen-4-one (30 g, 0.16 mol) in acetonitrile:diethyl ether mixture (100:300 mL) was added silica gel 60-120 mesh (1.5 g) and NBS (33 g, 0.18 mol) in lots at RT under nitrogen. The reaction mixture was stirred at RT for 14 h. The reaction mixture was filtered and concentrated under vacuum. The crude product was purified by column chromatography by using pet ether/ethyl acetate (9:1) as eluent to afford the desired compound (10 g, 72%) as a light brown solid.

$^1$H NMR (400 MHz, DMSO-d$_6$) δ 7.82 (s, 1H), 6.73 (s, 1H), 4.53 (t, J=8.0 Hz, 2H), 3.89 (s, 3H), 2.72 (t, J=8.0 Hz, 2H).

Step 5: Ethyl-(6-bromo-7-methoxy-4-oxo-2H-chromen-3(4H)-ylidene)(hydroxy)acetate

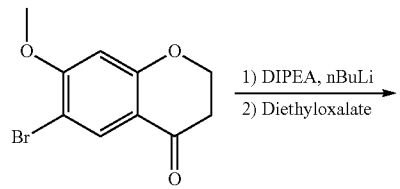

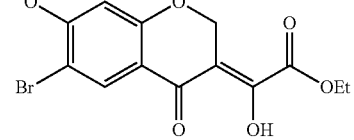

Diisopropylamine (7 mL, 0.3958 mol) was taken in dry THF (50 mL) at RT under nitrogen atmosphere. The reaction mixture was cooled to −78° C. and n-Butyl lithium (1.6 M solution in hexane, 29.2 mL, 0.04 mol) was added drop wise over a period of 30 min. After the addition, the reaction mixture was stirred at the same temperature for 15 min and then slowly warmed to −10° C. and stirred further for 30 min. The reaction mixture was again cooled to −78° C., 6-Bromo-7-methoxy-2,3-dihydro-4H-chromen-4-one (10 g, 0.03 mol) in THF (50 mL) was added drop wise over period of 30 min and stirred at −78° C. After 1 h, diethyl oxalate (7.8 mL, 0.05 mol) was added drop wise at −78° C.; the reaction mixture was slowly brought to 0° C. and stirred for 1 h. The reaction mixture was cooled to −5° C., quenched with a solution of 1.5N HCl and extracted with ethyl acetate (100 mL×2). The combined organic layer was washed with water (100 mL), brine (50 mL), dried over sodium sulphate and concentrated to afford the desired compound (10 g, 72%) as pale yellow solid.

$^1$H NMR (400 MHz, DMSO-d$_6$) δ. 8.04 (s, 1H), 6.43 (s, 1H), 5.32 (s, 2H), 4.40-4.32 (m, 2H), 3.95 (s, 3H), 1.42-1.37 (m, 3H).

Step 6: tert-Butyl 1-(3-thienyl)hydrazinecarboxylate

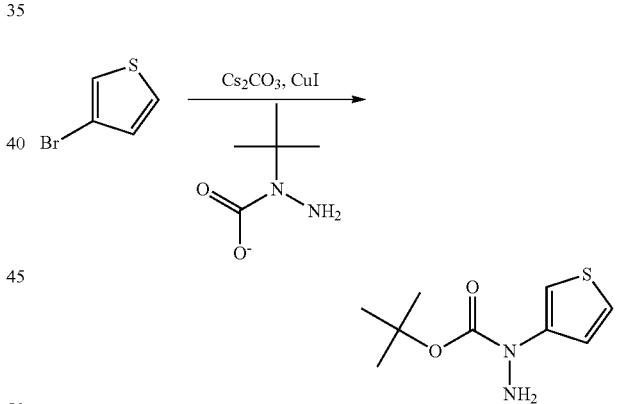

To a solution of 3-Bromo thiophene (10 g, 0.061 mol) in DMSO (100 mL) was added tert-butyl carbazate (16.3 g, 0.122 mol), cesium carbonate (40 g, 0.122 mol) followed by CuI (1.2 g, 0.006 mol) and 4-Hydroxy-L-Proline (1.6 g, 0.01 mol) at RT under nitrogen. The reaction mixture was stirred at 80° C. for 14 h. The reaction mixture was cooled to RT, quenched with water (100 mL) and extracted with ethyl acetate (3×200 mL). The combined organic layer was washed with water (100 mL×2), brine (100 mL), dried over sodium sulphate and evaporated under vacuum. The crude product was purified by column chromatography by using pet ether and ethyl acetate (7:3) as eluent to afford the title compound (3.5 g, 27%) as pale brown liquid.

$^1$H NMR (400 MHz, DMSO-d$_6$) δ 7.37-7.35 (dd, J=4.0, 5.2 Hz, 1H), 7.31-7.29 (d, J=8.0 Hz, 1H), 7.14-7.13 (dd, J=4.0, 5.2 Hz, 1H), 5.09 (bs, 2H), 1.47 (s, 9H).

131

Step 7: 3-Thienylhydrazine hydrochloride

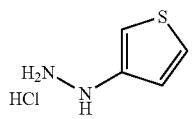

To a stirred solution of tert-Butyl 1-(3-thienyl)hydrazinecarboxylate (3.5 g, 0.0163 mol) in diethyl ether (10 mL) was added HCl in dioxane (30 mL) at RT under nitrogen. The reaction mixture was stirred at RT for 8 h. The organic solvent was removed under reduced pressure to afford the desired compound (2.4 g, 97%) as pale brown solid.

$^1$H NMR (400 MHz, DMSO-$d_6$) δ 10.08 (bs, 3H), 8.20 (bs, 1H), 7.48-7.46 (dd, J=3.2, 5.2 Hz, 1H), 6.87-6.85 (dd, J=1.2, 4.8 Hz, 1H), 6.72-6.71 (dd, J=1.6, 3.2 Hz, 1H).

Step 8: Ethyl 8-bromo-7-methoxy-1-(3-thienyl)-1,4-dihydrochromeno[4,3-c]pyrazole-3-carboxylate

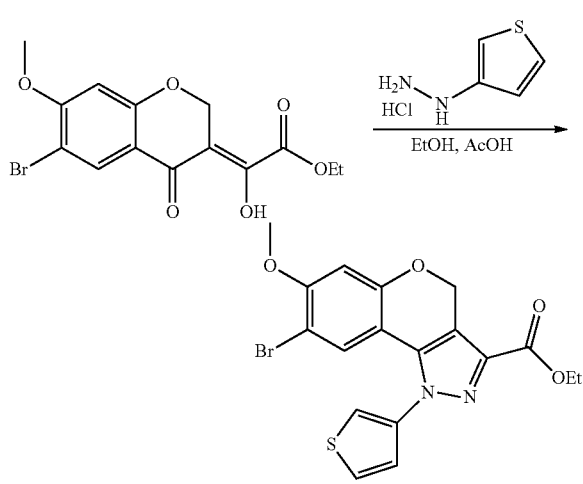

To a solution of ethyl-(6-bromo-7-methoxy-4-oxo-2H-chromen-3(4H)-ylidene)(hydroxy)acetate (8.0 g, 0.0224 mol) in a mixture of ethanol (200 mL) and acetic acid (200 mL) was added 3-thienylhydrazine hydrochloride (4.4 g, 0.0291 mol) at RT under nitrogen. The reaction mixture was stirred at 100° C. for 4 h. The reaction mixture was concentrated under high vacuum. The residue was dissolved with ethyl acetate (40 mL), washed with water (20 mL), brine (20 mL), dried over sodium sulphate and concentrated under vacuum. The crude product was purified by column chromatography using pet ether/ethyl acetate as eluent to afford the desired compound (8.5 g, 87%) as a pale yellow solid.

$^1$H NMR (400 MHz, CDCl$_3$) δ 7.57-7.55 (dd, J=4.0, 5.2 Hz, 1H), 7.52-7.50 (dd, J=4.0, 5.2 Hz, 1H), 7.22-7.21 (dd, J=1.2, 5.2 Hz, 1H), 6.94 (s, 1H), 6.60 (s, 1H), 5.56 (s, 2H), 4.47-4.41 (dd, J=8.0, 12 Hz. 2H), 3.88 (s, 3H), 1.42 (t, J=8.0 Hz, 3H).

132

Step 9: 8-Bromo-7-methoxy-1-(3-thienyl)-1,4-dihydrochromeno[4,3-c]pyrazole-3-carboxylic acid

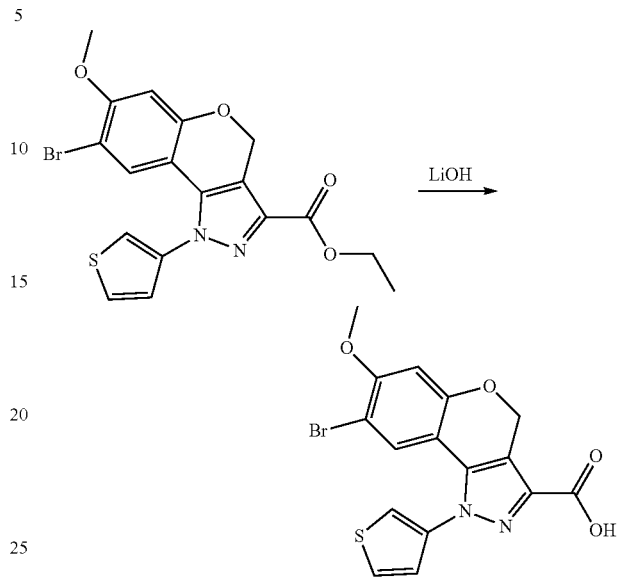

To a solution of Ethyl 8-bromo-7-methoxy-1-(3-thienyl)-1,4-dihydrochromeno[4,3-c]pyrazole-3-carboxylate (3 g, 0.0069 mol) in mixture of THF (70 mL), H$_2$O (20 mL), MeOH (10 mL) was added LiOH.H$_2$O (0.857 g, 0.0207 mol) at RT. The reaction mixture was stirred at RT for 4 h. The reaction mixture was evaporated and acidified with a solution of 1.5N HCl. The solid was filtered and dried to afford the desired compound (2.8 g, 99%) as an off-white solid.

$^1$H NMR (400 MHz, DMSO-$d_6$) δ 13.28 (bs, 1H), 8.01-8.00 (dd, J=1.2, 5.2 Hz, 1H), 7.87-7.85 (dd, J=4.0, 5.2 Hz, 1H), 7.35-7.33 (dd, J=4.0, 8.0 Hz, 1H), 6.83 (s, 1H), 6.73 (s, 1H), 5.50 (s, 2H), 3.82 (s, 3H). m/z: 407 [M+H]$^+$

Step 10: 8-Bromo-7-methoxy-1-thiophen-3-yl-1,4-dihydro-chromeno[4,3-c]pyrazole-3-carboxylic acid tert-butyl-methyl-amide (4)

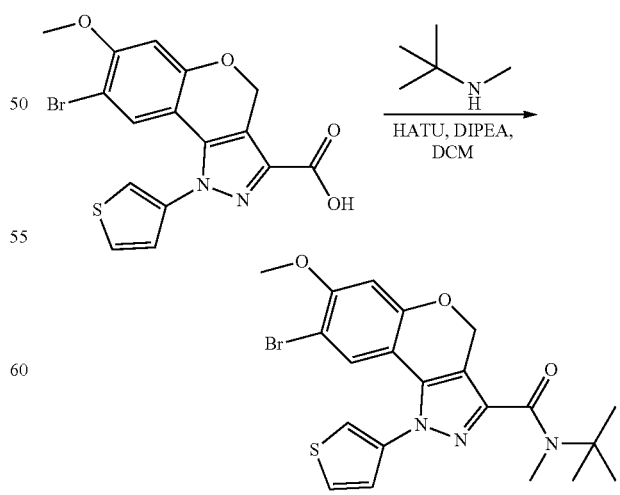

To a solution of 8-bromo-7-methoxy-1-(3-thienyl)-1,4-dihydrochromeno[4, 3-c]pyrazole-3-carboxylic acid (2.8 g, 0.0069 mol) in DCM (50 mL) was added N-tert-butyl methyl amine (718 mg, 0.0083 mol), HATU (3.14 g, 0.0083 mol) and diisopropyl ethyl amine (1.8 mL, 0.0103 mol) at RT under nitrogen. The reaction mixture was stirred at RT for 16 h. The reaction mixture was quenched to sodium bicarbonate (10 mL, 10%), extracted with DCM (2×50 mL). The combined organic layer was washed with NaHCO$_3$ solution (1×100 mL, 10% solution), brine (100 mL) and dried over anhydrous sodium sulphate. The solvent was removed under vacuum; the crude product was purified by column chromatography by using pet ether and ethyl acetate (9:1) as eluent to afford the desired compound (3.2 g, 98%) as a white solid.

$^1$H NMR (400 MHz, DMSO-d$_6$) δ 7.98-7.97 (dd, J=1.4, 3.2 Hz, 1H), 7.80-7.85 (dd, J=3.2, 4.7 Hz, 1H), 7.33-7.32 (dd, J=1.3, 5.1 Hz, 1H), 6.83 (s, 1H), 6.76 (s, 1H), 5.37 (s, 2H), 3.81 (s, 3H), 3.15 (s, 3H), 1.47 (s, 9H). m/z: 476 [M+H]$^+$

Step 11: 7-Methoxy-8-(1H-pyrazol-4-yl)-1-thiophen-3-yl-1,4-dihydro-chromeno[4,3-c]pyrazole-3-carboxylic acid tert-butyl-methyl-amide (1)

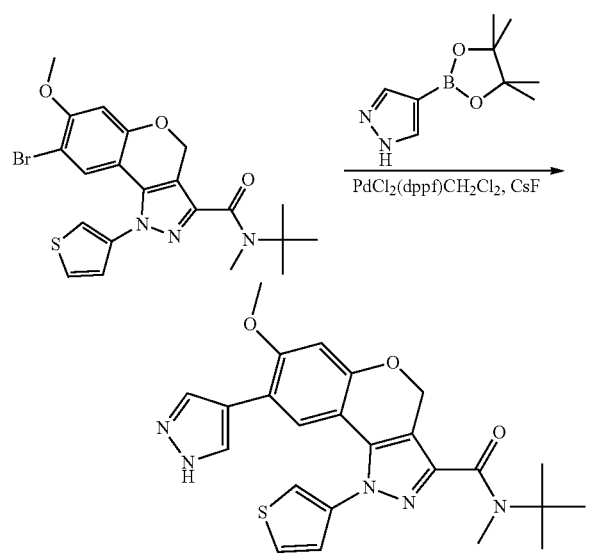

To a solution of 8-bromo-N-(tert-butyl)-7-methoxy-N-methyl-1-(thiophen-3-yl)-1,4-dihydrochromeno[4,3-c]pyrazole-3-carboxamide (1 g, 0.0021 mol) in dioxane (20 mL) was added 4-(4,4,5,5-tetramethyl-1,3,2-dioxaborolan-2-yl)-1H-pyrazole (611 mg, 0.0031 mol), PdCl$_2$(dppf)CH$_2$Cl$_2$ (86 mg, 0.0001 mol) and cesium fluoride (800 mg, 0.0053 mol) at RT under nitrogen. The reaction mixture was degassed with nitrogen for 20 min and water (4 mL) was added at RT. The reaction mixture was stirred at 100° C. for 12 h. The reaction mixture was filtered through celite and washed with DCM (20 mL). The filtrate was concentrated under vacuum; the crude product was dissolved in DCM (200 mL), washed with water (10 ml), brine (10 mL) and dried over sodium sulphate. The organic solvent was removed under vacuum; the crude product was purified by column chromatograph using pet ether: ethyl acetate as eluent to afford the desired compound (0.5 g, 51%) as an off-white solid.

$^1$H NMR (400 MHz, DMSO-d$_6$) δ 8.02-8.01 (dd, J=1.4, 3.2 Hz, 1H), 7.89-7.87 (dd, J=3.2, 5.1 Hz, 1H), 7.54 (bs, 2H), 7.37-7.36 (dd, J=1.4, 5.1 Hz, 1H), 6.85 (s, 1H), 6.74 (s, 1H), 5.35 (s, 2H), 3.83 (s, 3H), 3.16 (s, 3H), 1.42 (s, 9H). m/z: 464 [M+H]$^+$

Example 2

7-Methoxy-8-pyridin-3-yl-1-thiophen-3-yl-1,4-dihydro-chromeno[4,3-c]pyrazole-3-carboxylic acid tert-butyl-methyl-amide (2)

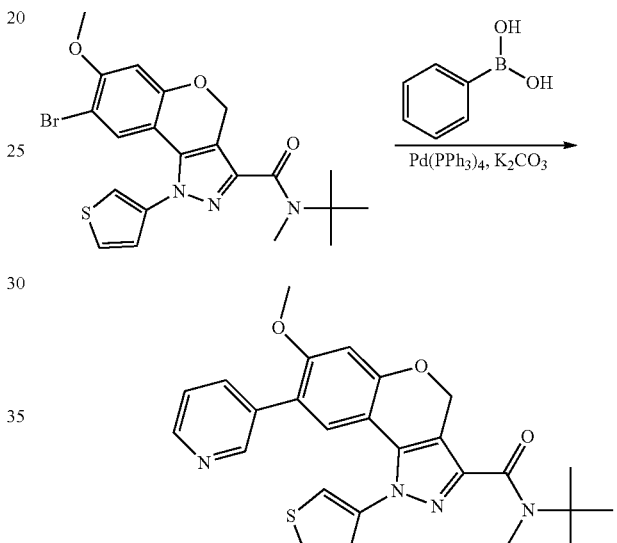

To a solution of 8-bromo-7-methoxy-1-thiophen-3-yl-1,4-dihydro-chromeno[4,3-c]pyrazole-3-carboxylic acid tert-butyl-methyl-amide (Example 1 step 10) (100 mg, 0.2 mmol) in DME (10 mL) was added pyridine-3-boronic acid (52 mg, 0.4 mmol), tetra kis (triphenylphospine)palladium (13 mg, 0.01 mmol) and potassium carbonate (90 mg, 0.6 mmol) at RT under nitrogen. The reaction mixture was degassed with nitrogen for 10 min and water was added (1 mL). The reaction mixture was stirred at 90° C. for 16 h. The reaction mixture was filtered through celite. Filtrate was concentrated under vacuum; the crude product was dissolved in DCM (200 mL), washed with water (10 ml), brine (10 mL) and dried over sodium sulphate. The solvent was removed under vacuum to provide the crude product. The crude product was slurried with diethyl ether (5 mL), filtered and dried to afford the desired compound (95 mg, 98%) as an off white solid.

$^1$H NMR (400 MHz, CDCl$_3$) δ 8.50-8.47 (m, 2H), 7.67-7.64 (m, 1H), 7.53-7.52 (dd, J=1.2, 3.2 Hz, 1H), 7.49-7.47 (dd, J=3.2, 5.2 Hz, 1H), 7.27-7.22 (m, 2H), 6.77 (s, 1H), 6.69 (s, 1H), 5.52 (s, 2H), 3.82 (s, 3H), 3.28 (s, 3H), 1.52 (s, 9H). m/z: 475 [M+H]$^+$

Example 3

(4-Cyclobutanecarbonyl-[1,4]diazepan-1-yl)-(7-methoxy-8-pyridin-3-yl-1-thiophen-3-yl-1,4-dihydro-chromeno[4,3-c]pyrazol-3-yl)-methanone (3)

Step 1: (8-Bromo-7-methoxy-1-thiophen-3-yl-1,4-dihydro-chromeno[4,3-c]pyrazol-3-yl)-(4-cyclobutanecarbonyl-[1,4]diazepan-1-yl)-methanone

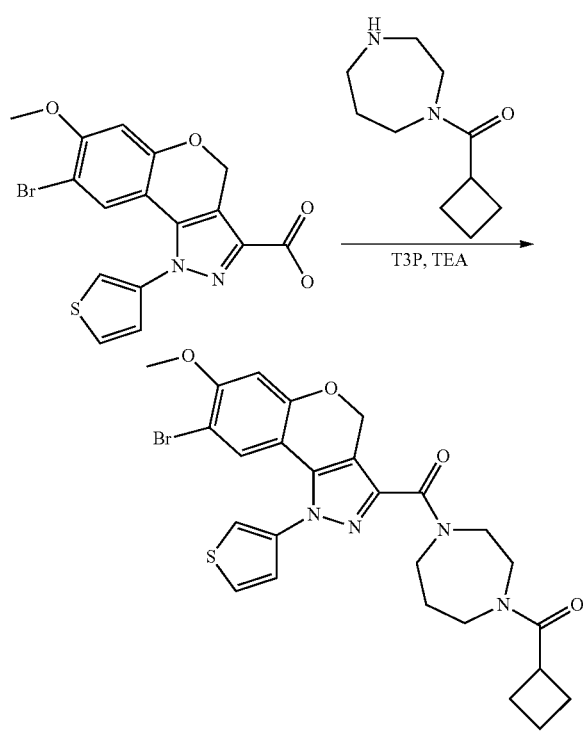

To a solution of 8-bromo-7-methoxy-1-(3-thienyl)-1,4-dihydrochromeno[4,3-c]pyrazole-3-carboxylic acid (example 1 step 9) (0.5 g, 0.001 mol) in DCM (10 mL) was added 1-(cyclobutyl carbonyl)-1,4 diazepane (0.25 g, 0.001 mol), $T_3P$ (1 mL, 0.001 mol, 50% soln in EtOAc) and TEA (0.2 mL, 0.003 mol) at RT under nitrogen. The reaction mixture was stirred at RT for 16 h. The reaction mixture was quenched with saturated sodium bicarbonate (10 mL), extracted with DCM (2×25 mL). The combined organic layer was washed with $NaHCO_3$ solution (1×100 mL, 100%), brine (100 mL) and dried over anhydrous sodium sulphate. The solvent was removed under vacuum, the crude product was purified by column chromatography using pet ether and ethyl acetate (9:1) as eluent to afford the desired compound as (0.4 g, 57%) an off white solid.

$^1$H NMR (400 MHz, $CDCl_3$) δ 7.51-7.48 (m, 2H), 7.22-7.20 (m, 1H), 6.99 (t, J=4.0 Hz, 1H), 6.60 (t, J=2.4 Hz, 1H), 5.54-5.51 (dd, J=4.0, 12.0 Hz, 2H), 4.18-4.17 (m, 2H), 3.86 (s, 3H), 3.81-3.79 (m, 3H), 3.71-3.60 (m, 3H), 3.57-3.54 (m, 1H), 2.36-2.34 (m, 2H), 1.99-1.95 (m, 2H), 1.94-1.90 (m, 4H). m/z: 571 [M+H]$^+$

Step 2: (4-Cyclobutanecarbonyl-[1,4]diazepan-1-yl)-(7-methoxy-8-pyridin-3-yl-1-thiophen-3-yl-1,4-dihydro-chromeno[4,3-c]pyrazol-3-yl)-methanone

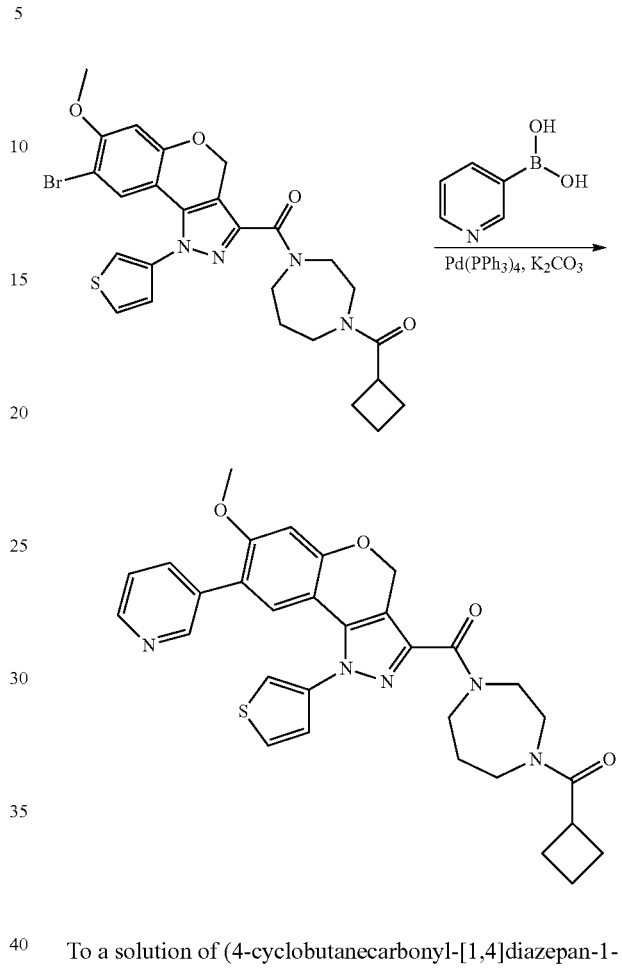

To a solution of (4-cyclobutanecarbonyl-[1,4]diazepan-1-yl)-(7-methoxy-8-pyridin-3-yl-1-thiophen-3-yl-1,4-dihydro-chromeno[4,3-c]pyrazol-3-yl)-methanone (250 mg, 0.4 mmol) in DME (10 mL) was added pyridine-3-boronic acid (100 mg, 0.8 mmol), tetra kis (triphenylphospine) palladium (30 mg, 0.02 mmol) and potassium carbonate (150 mg, 0.001 mol) at RT under nitrogen. The reaction mixture was degassed with nitrogen for 10 min and water (2 mL) was added. The reaction mixture was stirred at 90° C. for 16 h. The reaction mixture was filtered through celite and washed with DCM (20 mL). Filtrate was concentrated under vacuum; crude product was dissolved in DCM (200 mL), washed with water (10 ml), brine (10 mL) and dried over sodium sulphate. The solvent was removed under vacuum; crude product was slurred with diethyl ether (10 mL), filtered and dried to afford the desired compound as (240 mg, 96%) an off white solid.

$^1$H NMR (400 MHz, $CDCl_3$) δ 8.49-8.47 (dd, J=1.6, 4.8 Hz, 2H), 7.67 (t, J=2.0 Hz, 1H), 7.52-7.47 (m, 2H), 7.27-7.24 (m, 2H), 6.83-6.80 (dd, J=1.6, 4.8 Hz, 1H), 6.68 (t, J=4.0, Hz, 1H), 5.59-5.56 (dd, J=1.6, 10.4 Hz, 2H), 4.18-4.17 (m, 2H), 3.86 (s, 4H), 3.81-3.79 (m, 1H), 3.71-3.60 (m, 2H), 3.57-3.54 (m, 1H), 3.36-3.34 (m, 1H), 2.36-2.349 m, 2H), 2.12-1.99 (m, 6H), 0.98-0.97 (m, 1H). m/z: 570 [M+H]

Example 4

8-Isobutyl-7-methoxy-1-thiophen-3-yl-1,4-dihydrochromeno[4,3-c]pyrazole-3-carboxylic acid tert-butyl-methyl-amide (5)

Step 1: 7-Methoxy-8-(2-methyl-propenyl)-1-thiophen-3-yl-1,4-dihydro-chromeno[4,3-c]pyrazole-3-carboxylic acid ethyl ester

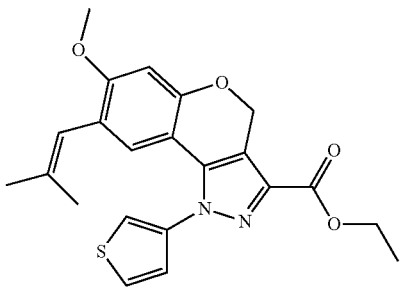 [SMILES: CCOC(=O)c1nn(-c2ccsc2)c2c1COc1cc(OC)c(C=C(C)C)cc1-2]

To a solution of ethyl 8-bromo-7-methoxy-1-(3-thienyl)-1,4-dihydrochromeno[4,3-c]pyrazole-3-carboxylate (example 1 step 8) (1 g, 0.002 mol) in THF (20 mL) was added 2,4,6-Tris-(2-methyl-propenyl)-cyclotriboroxanepyridine complex (380 mg, 0.001 mol), bis (triphenylphospine)palladium (II) dichloride (80 mg, 0.1 mmol) and potassium tri phosphate (63 mg, 0.004 mol) at RT under nitrogen. The reaction mixture was degassed with nitrogen for 10 min and water (2 mL) was added at RT. The reaction mixture was stirred at 70° C. for 4 h. The reaction mixture was filtered through celite and washed with DCM (50 mL). The filtrate was concentrated under vacuum; crude product was dissolved in DCM (200 mL), washed with water (20 ml), brine (20 mL) and dried over sodium sulphate. The organic solvent was removed under vacuum; crude product was purified by column chromatograph with pet ether: ethyl acetate as eluent to afford the desired product as (0.9 g, 96%) a light yellow solid.

$^1$H NMR (400 MHz, DMSO-$d_6$) δ 8.00 (m, 1H), 7.83-7.82 (d, J=3.2 Hz, 1H), 7.33-7.32 (dd, J=1.6, 5.2 Hz, 1H), 6.65 (s, 1H), 6.56 (s, 1H), 6.00 (s, 1H), 5.56 (s, 2H), 4.32-4.26 (m, 2H), 3.78 (s, 3H), 1.76 (s, 3H), 4.52 (s, 3H), 1.23-1.18 (m, 3H). m/z: 411.5 [M+H]$^+$

Step 2: 8-Isobutyl-7-methoxy-1-(3-thienyl)-1,4-dihydrochromeno[4,3-c]pyrazole-3-carboxylate

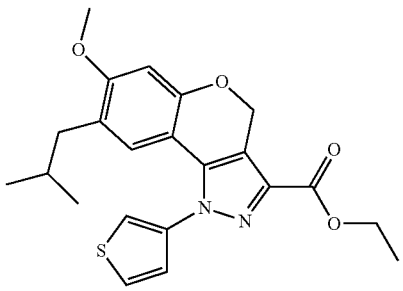 [SMILES: CCOC(=O)c1nn(-c2ccsc2)c2c1COc1cc(OC)c(CC(C)C)cc1-2]

To a solution of ethyl 7-methoxy-8-(2-methylprop-1-en-1-yl)-1-(thiophen-3-yl)-1,4-dihydrochromeno[4,3-c]pyrazole-3-carboxylate (step 1) (1 g, 0.02 mol) in methanol and ethyl acetate mixture (40 mL) was added palladium on carbon (10%, 0.5 g). The reaction mixture was hydrogenated under 3 bar of pressure hydrogen for 4 h at RT. The reaction mixture was filtered through a celite bed and filtrate was concentrated under vacuum. The residue was purified by column chromatography using pet ether: ethyl acetate as eluent to afford the title compound (0.7 g, 70%) as an off white solid.

$^1$H NMR (400 MHz, DMSO-$d_6$) δ 7.97-7.96 (dd, J=1.2, 3.2 Hz, 1H), 7.83-7.82 (dd, J=3.2, 5.2 Hz, 1H), 7.31-7.30 (dd, J=1.2, 5.2 Hz, 1H), 6.64 (s, 1H), 6.37 (s, 1H), 5.43 (s, 2H), 4.32-4.27 (m, 2H), 3.75 (s, 3H), 2.12-2.10 (m, 2H), 1.62-1.55 (m, 1H), 1.31-1.22 (m, 3H), 0.85-0.83 (d, J=4.0 Hz, 6H). m/z: 413 [M+H]$^+$

Step 3: 8-Isobutyl-7-methoxy-1-(3-thienyl)-1,4-dihydrochromeno[4,3-c]pyrazole-3-carboxylic acid

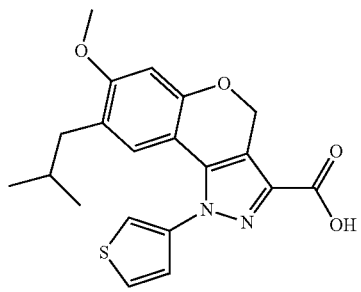 [SMILES: COc1cc2c(cc1CC(C)C)-c1c(c(C(=O)O)nn1-c1ccsc1)CO2]

To a solution of ethyl 8-isobutyl-7-methoxy-1-(thiophen-3-yl)-1,4-dihydrochromeno[4,3-c]pyrazole-3-carboxylate (250 mg, 0.006 mol) in mixture of THF (21 mL), H$_2$O (6 mL), MeOH (3 mL) was added LiOH (0.08 g, 0.001 mol) at RT. The reaction mixture was stirred at RT for 2 h. The reaction mixture was evaporated and acidified with 1.5N HCl solution. The solid was filtered and dried under high vacuum to afford the desired compound (200 mg, 87%) as a white solid.

$^1$H NMR (400 MHz, DMSO-$d_6$) δ 13.02 (bs, 1H), 7.96-7.95 (dd, J=1.6, 3.2 Hz, 1H), 7.83-7.81 (dd, J=3.2, 5.2 Hz, 1H), 7.31-7.29 (dd, J=1.2, 5.2 Hz, 1H), 6.64 (s, 1H), 6.37 (s, 1H), 5.42 (s, 2H), 3.73 (s, 3H), 2.12-2.11 (m, 2H), 1.62-1.55 (m, 1H), 0.72-0.711 (d, J=4.0 Hz, 6H). m/z: 385 [M+H]$^+$

Step 4: 8-Isobutyl-7-methoxy-1-thiophen-3-yl-1,4-dihydro-chromeno[4,3-c]pyrazole-3-carboxylic acid tert-butyl-methyl-amide (5)

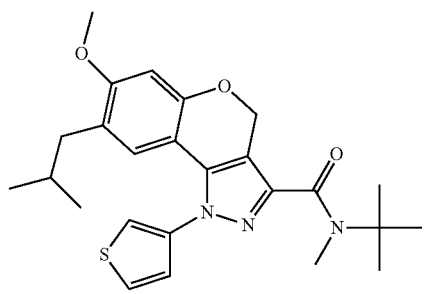 [SMILES: COc1cc2c(cc1CC(C)C)-c1c(c(C(=O)N(C)C(C)(C)C)nn1-c1ccsc1)CO2]

To a solution of 8-isobutyl-7-methoxy-1-(3-thienyl)-1,4-dihydrochromeno[4,3-c]pyrazole-3-carboxylic acid (step 3) (180 mg, 0.4 mmol) in DCM (20 mL) was added N-tert-butyl methyl amine (50 mg, 0.5 mmol), HATU (0.22 g, 5 mmol) and diisopropyl ethyl amine (0.2 mL, 0.7 mmol) at RT under nitrogen. The reaction mixture was stirred at RT for 16 h. The reaction mixture was quenched with sodium bicarbonate (10 mL, 10%), extracted with DCM (2×25 mL). The combined organic layer was washed with NaHCO$_3$ solution (1×100 mL, 10%), brine (100 mL) and dried over anhydrous sodium sulphate. The solvent was removed under vacuum; the crude product was purified by column chromatography using pet ether and ethyl acetate (9:1) as eluent to afford the desired compound (140 mg, 66%) as a white solid.

$^1$H NMR (400 MHz, DMSO-d$_6$) δ 7.91-7.90 (dd, J=1.6, 3.2 Hz, 1H), 7.80-7.85 (dd, J=3.2, 5.2 Hz, 1H), 7.29-7.28 (dd, J=1.2, 5.2 Hz, 1H), 6.64 (s, 1H), 6.40 (s, 1H), 5.29 (s, 2H), 3.73 (s, 3H), 3.14 (s, 3H), 2.13-2.11 (m, 2H), 1.63-1.55 (m, 1H), 1.41 (s, 9H), 0.72-0.711 (d, J=4.0 Hz, 6H). m/z: 454 [M+H]$^+$

Example 5

7-Methoxy-8-(2-methyl-propenyl)-1-thiophen-3-yl-1,4-dihydro-chromeno[4,3-c]pyrazole-3-carboxylic acid tert-butyl-methyl-amide (6)

Step 1: 8-Bromo-7-methoxy-1-thiophen-3-yl-1,4-dihydro-chromeno[4,3-c]pyrazole-3-carboxylic acid tert-butyl-methyl-amide (4)

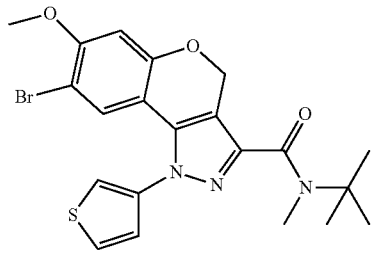 [SMILES: COc1cc2c(cc1Br)-c1c(c(C(=O)N(C)C(C)(C)C)nn1-c1ccsc1)CO2]

To a solution of 8-bromo-7-methoxy-1-(3-thienyl)-1,4-dihydrochromeno[4,3-c]pyrazole-3-carboxylic acid (example 1 step 9) (150.00 mg; 0.37 mmol; 1.00 eq.) in DCM (0.50 ml; 7.80 mmol; 21.18 eq.) was added N,N-Diisopropylamine (0.12 ml; 0.74 mmol; 2.00 eq.), o-(benzotriazol-1-yl)-n,n,n',n'-tetramethyluronium tetrafluoroborate (TBTU) (236.53 mg; 0.74 mmol; 2.00 eq.), and n-tert-butyl-methylamine (48.16 mg, 0.55 mmol, 1.5 eq.). The reaction was stirred at RT for 2 h. The crude product was purified by column chromatography (Biotage) using EtOAc/Hex as eluent to afford the desired compound (120 mg, 68%) as a white solid.

Step 2: 7-Methoxy-8-(2-methyl-propenyl)-1-thiophen-3-yl-1,4-dihydro-chromeno[4,3-c]pyrazole-3-carboxylic acid tert-butyl-methyl-amide (6)

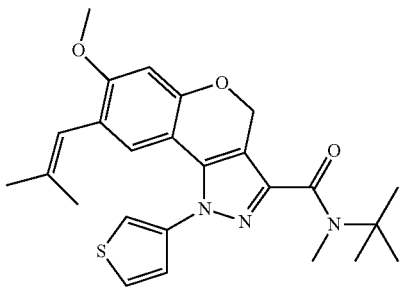 [SMILES: COc1cc2c(cc1C=C(C)C)-c1c(c(C(=O)N(C)C(C)(C)C)nn1-c1ccsc1)CO2]

To 8-bromo-7-methoxy-1-thiophen-3-yl-1,4-dihydro-chromeno[4,3-c]pyrazole-3-carboxylic acid tert-butyl-methyl-amide (50.00 mg; 0.10 mmol; 1.00 eq.) (example 5 step 1) in a microwave vial, was added 2,4,6-Tris-(2-methyl-propenyl)-cyclotriboroxane pyridine (51.14 mg; 0.16 mmol; 1.50 eq.), [1,1'-bis(diphenylphosphino)ferrocene]dichloropalladium(ii), complex with dichloromethane (1:1) (8.57 mg; 0.01 mmol; 0.10 eq.), dioxane (1.00 ml; 11.74 mmol; 111.82 eq.) and cesium carbonate (0.16 ml; 0.31 mmol; 3.00 eq., 3M). The vessel was sealed, vacuumed and backfilled with nitrogen (3 times). Reaction was microwaved at 120° C. for 2 h. The crude product was purified by column chromatography (Biotage) using EtOAc/Hex as eluent to afford the desired compound (6.6 mg, 14%) as a white solid.

$^1$H NMR (400 MHz, MeOD) δ 7.75 (dd, J=3.2, 1.4 Hz, 1H), 7.69 (dd, J=5.1, 3.2 Hz, 1H), 7.27 (dd, J=5.1, 1.4 Hz, 1H), 6.70 (s, 1H), 6.63 (s, 1H), 6.07 (s, 1H), 5.33 (s, 2H), 3.80 (s, 3H), 3.20 (s, 3H), 1.80 (d, J=1.3 Hz, 3H), 1.54 (s, 9H), 1.50 (d, J=1.2 Hz, 3H). m/z: 452 [M+H]$^+$

Example 6

7-Methoxy-8-(2-methyl-propenyl)-1-thiophen-3-yl-1,4-dihydro-chromeno[4,3-c]pyrazole-3-carboxylic acid (2-acetylamino-ethyl)-amide (7)

Step 1: Ethyl 7-methoxy-8-(2-methylprop-1-en-1-yl)-1-(thiophen-3-yl)-1,4-dihydrochromeno[4,3-c]pyrazole-3-carboxylate

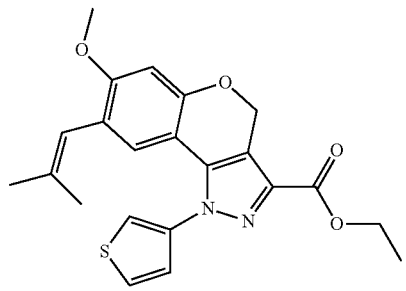 [SMILES: CCOC(=O)c1nn(-c2ccsc2)c2c1COc1cc(OC)c(C=C(C)C)cc1-2]

To a solution of ethyl 8-bromo-7-methoxy-1-(3-thienyl)-1,4-dihydrochromeno[4,3-c]pyrazole-3-carboxylate (6 g, 0.0138 mol) in THF (100 mL) was added 2,4,6-Tris-(2-methyl-propenyl)-cyclotriboroxanepyridine complex (5.8 g, 0.018 mol), bis(triphenylphospine)palladium (II) dichloride (1.0 g, 1.38 mmol) and potassium triphosphate (3.8 g, 0.0276 mol) at RT under nitrogen. The reaction mixture was degassed with nitrogen for 10 min and water (10 mL) was added at RT. The reaction mixture was stirred at 80° C. for 8 h. The reaction mixture was filtered through celite and washed with DCM (50 mL). The filtrate was concentrated under vacuum; crude product was dissolved in DCM (200 mL), washed with water (20 ml), brine (20 mL) and dried over sodium sulphate. The organic solvent was removed under vacuum; crude product was purified by column chromatograph using pet ether: ethyl acetate as eluent to afford the desired compound as (5.5 g, 98%) a pale yellow solid.

$^1$H NMR (400 MHz, DMSO-d$_6$) δ 8.00 (m, 1H), 7.83-7.82 (d, J=3.2 Hz, 1H), 7.33-7.32 (dd, J=1.6, 5.2 Hz, 1H), 6.65 (s, 1H), 6.56 (s, 1H), 6.00 (s, 1H), 5.56 (s, 2H), 4.32-4.26 (m, 2H), 3.78 (s, 3H), 1.76 (s, 3H), 4.52 (s, 3H), 1.23-1.18 (m, 3H). m/z: 411.5 [M+H]$^+$

Step 2: 7-Methoxy-8-(2-methyl-propenyl)-1-thiophen-3-yl-1,4-dihydro-chromeno[4,3-c]pyrazole-3-carboxylic acid

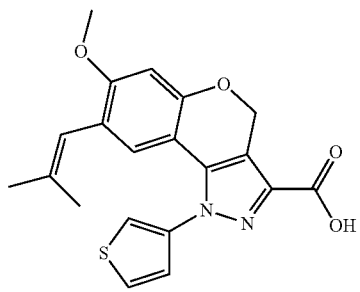 [SMILES: COc1cc2c(cc1C=C(C)C)-c1c(c(C(=O)O)nn1-c1ccsc1)CO2]

To a solution of ethyl 7-methoxy-8-(2-methylprop-1-en-1-yl)-1-(thiophen-3-yl)-1,4-dihydrochromeno[4,3-c]pyrazole-3-carboxylate (7 g, 0.0171 mol) in mixture of THF (70 mL), H$_2$O (20 mL), MeOH (10 mL) was added LiOH.H$_2$O (2.1 g, 0.0512 mol) at RT. The reaction mixture was stirred at RT for 4 h. The reaction mixture was evaporated and acidified with 1.5N HCl solution. The solid was filtered and dried under high vacuum to afford the desired compound (5.5 g, 85%) as an off-white solid.

$^1$H NMR (400 MHz, DMSO-d$_6$) δ 13.02 (bs, 1H), 7.96-7.95 (dd, J=1.6, 3.2 Hz, 1H), 7.83-7.81 (dd, J=3.2, 5.2 Hz, 1H), 7.31-7.29 (dd, J=1.2, 5.2 Hz, 1H), 6.64 (s, 1H), 6.37 (s, 1H), 5.42 (s, 2H), 3.73 (s, 3H), 2.12-2.11 (m, 2H), 1.62-1.55 (m, 1H), 0.72-0.711 (d, J=4.0 Hz, 6H). m/z: 383 [M+H]$^+$

Step 3: 7-Methoxy-8-(2-methyl-propenyl)-1-thiophen-3-yl-1,4-dihydro-chromeno[4,3-c]pyrazole-3-carboxylic acid (2-acetylamino-ethyl)-amide (7)

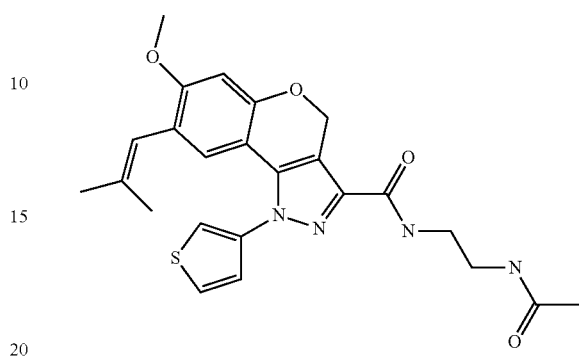

To 7-methoxy-8-(2-methyl-propenyl)-1-thiophen-3-yl-1,4-dihydro-chromeno[4,3-c]pyrazole-3-carboxylic acid (30 mg 0.08 mmol) in DCM (1.00 ml; 15.60 mmol; 198.87 eq.) was added N,N-Diisopropylethylamine (0.02 ml; 0.09 mmol; 1.20 eq.), N-acetylethylenediamine (9.61 mg, 0.09 mmol, 1.2 eq.) and T3P (0.03 ml; 0.12 mmol; 1.50 eq.). The reaction was stirred at RT for 1.5 h. The crude product was purified by column chromatography using EtOAc/Hex as eluent to afford the desired compound (27.4 mg, 73%) as a white solid.

$^1$H NMR (500 MHz, CD$_3$OD) δ 7.74 (dd, J=3.1, 1.2 Hz, 1H), 7.67 (dd, J=5.0, 3.2 Hz, 1H), 7.26 (dd, J=5.1, 1.1 Hz, 1H), 6.66 (s, 1H), 6.58 (s, 1H), 6.04 (s, 1H), 5.48 (s, 2H), 3.76 (s, 3H), 3.46 (t, J=6.0 Hz, 2H), 3.41-3.33 (m, 2H), 1.94 (s, 3H), 1.78 (s, 3H), 1.48 (s, 3H). m/z: 467 [M+H]$^+$

The following compounds were prepared using procedures analogous to those disclosed in Example 6.

| Product | Amine | LC/MS | NMR |
|---|---|---|---|
| ![compound 11 structure] 7-Methoxy-8-(2-methyl-propenyl)-1-thiophen-3-yl-1,4-dihydro-chromeno[4,3-c]pyrazole-3-carboxylic acid [3-(1H-tetrazol-5-yl)-propyl]-amide; trifluoroacetic acid salt (11) | ![amine structure] | m/z: 492 [M + H]$^+$ | $^1$H NMR (400 MHz, CDCl$_3$) δ 7.59-7.56 (m, 1H), 7.54 (dd, J = 5.0, 3.3 Hz, 1H), 7.40-7.34 (m, 1H), 7.26 (dd, J = 5.1, 1.4 Hz, 1H), 6.71 (s, 1H), 6.60 (s, 1H), 6.12 (s, 1H), 5.63 (s, 2H), 3.84 (s, 3H), 3.49 (dd, J = 12.3, 6.5 Hz, 2H), 3.15-3.09 (m, 2H), 1.98 (dtd, J = 8.5, 6.0, 2.6 Hz, 2H), 1.85 (d, J = 1.2 Hz, 3H), 1.52 (d, J = 1.1 Hz, 3H). |

-continued

| Product | Amine | LC/MS | NMR |
| --- | --- | --- | --- |
| 7-Methoxy-8-(2-methyl-propenyl)-1-thiophen-3-yl-1,4-dihydro-chromeno[4,3-c]pyrazole-3-carboxylic acid (3-acetylamino-propyl)-amide (8) | (3-acetylaminopropylamine) | m/z: 481 [M + H]+ | $^1$H NMR (400 MHz, MeOD) δ 7.74 (dd, J = 3.2, 1.4 Hz, 1H), 7.67 (dd, J = 5.1, 3.2 Hz, 1H), 7.26 (dd, J = 5.1, 1.4 Hz, 1H), 6.66 (s, 1H), 6.58 (s, 1H), 6.05 (d, J = 0.6 Hz, 1H), 5.49 (s, 2H), 3.78 (s, 3H), 3.39 (dd, J = 10.1, 3.4 Hz, 2H), 3.26 (t, J = 6.7 Hz, 2H), 1.95 (s, 3H), 1.82-1.73 (m, 5H), 1.48 (d, J = 1.2 Hz, 3H). |
| 7-Methoxy-8-(2-methyl-propenyl)-1-thiophen-3-yl-1,4-dihydro-chromeno[4,3-c]pyrazole-3-carboxylic acid [2-(2-oxo-oxazolidin-3-yl)-ethyl]-amide (13) | (2-(2-oxo-oxazolidin-3-yl)ethylamine) | m/z: 495 [M + H]+ | $^1$H NMR (400 MHz, CDCl$_3$) δ 7.55 (dd, J = 3.1, 1.3 Hz, 1H), 7.50 (dd, J = 5.1, 3.2 Hz, 1H), 7.24 (dd, J = 5.1, 1.4 Hz, 1H), 7.11 (s, 1H), 6.71 (s, 1H), 6.57 (s, 1H), 6.12 (s, 1H), 5.60 (s, 2H), 4.39-4.31 (m, 2H), 3.82 (s, 3H), 3.72 (dd, J = 8.7, 7.2 Hz, 2H), 3.66 (dd, J = 12.3, 6.0 Hz, 2H), 3.52 (t, J = 6.1 Hz, 2H), 1.85 (d, J = 1.3 Hz, 3H), 1.52 (d, J = 1.2 Hz, 3H). |
| 7-Methoxy-8-(2-methyl-propenyl)-1-thiophen-3-yl-1,4-dihydro-chromeno[4,3-c]pyrazole-3-carboxylic acid [3-(2-oxo-oxazolidin-3-yl)-propyl]-amide (9) | (3-(2-oxo-oxazolidin-3-yl)propylamine) | m/z: 509 [M + H]+ | $^1$H NMR (400 MHz, CDCl$_3$) δ 7.54 (dd, J = 3.2, 1.4 Hz, 1H), 7.49 (dd, J = 5.1, 3.2 Hz, 1H), 7.24 (dd, J = 5.1, 1.4 Hz, 1H), 7.19 (s, 1H), 6.71 (s, 1H), 6.57 (s, 1H), 6.11 (s, 1H), 5.61 (s, 2H), 4.38-4.30 (m, 2H), 3.81 (s, 3H), 3.65-3.58 (m, 2H), 3.48 (q, J = 6.7 Hz, 2H), 3.39 (t, J = 6.8 Hz, 2H), 1.89 (dd, J = 13.7, 6.8 Hz, 2H), 1.84 (d, J = 1.2 Hz, 3H), 1.52 (d, J = 1.2 Hz, 3H). |

-continued

| Product | Amine | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid (2-hydroxy-1,1-dimethyl-ethyl)-amide (10) | H₂N–C(CH₃)₂–CH₂OH | m/z: 454 [M + H]⁺ | $^1$H NMR (400 MHz, CDCl$_3$) δ 7.55 (dd, J = 3.2, 1.4 Hz, 1H), 7.51 (dd, J = 5.1, 3.2 Hz, 1H), 7.24 (dd, J = 5.1, 1.4 Hz, 1H), 6.95 (s, 1H), 6.68 (s, 1H), 6.57 (s, 1H), 6.11 (s, 1H), 5.59 (s, 2H), 3.82 (s, 3H), 3.72 (s, 2H), 1.85 (d, J = 1.3 Hz, 3H), 1.52 (d, J = 1.2 Hz, 3H), 1.41 (s, 6H). |
| 1-[7-Methoxy-8-(2-methyl-propenyl)-1-thiophen-3-yl-1,4-dihydro-chromeno[4,3-c]pyrazole-3-carbonyl]-piperidine-4-carboxylic acid ethyl ester (14) | ethyl piperidine-4-carboxylate | m/z: 522 [M + H]⁺ | $^1$H NMR (400 MHz, CDCl$_3$) δ 7.52 (dd, J = 3.2, 1.4 Hz, 1H), 7.48 (dd, J = 5.1, 3.2 Hz, 1H), 7.24 (dd, J = 5.1, 1.4 Hz, 1H), 6.74 (s, 1H), 6.58 (s, 1H), 6.12 (s, 1H), 5.52 (s, 2H), 5.00 (d, J = 13.1 Hz, 1H), 4.55 (d, J = 13.4 Hz, 1H), 4.17 (q, J = 7.1 Hz, 2H), 3.83 (s, 3H), 3.47-3.36 (m, 1H), 3.09-2.96 (m, 1H), 2.66-2.54 (m, 1H), 2.08-1.92 (m, 2H), 1.85 (d, J = 1.3 Hz, 3H), 1.81 (d, J = 11.8 Hz, 2H), 1.54 (d, J = 1.2 Hz, 3H), 1.28 (t, J = 7.1 Hz, 3H). |
| 3-{[7-Methoxy-8-(2-methyl-propenyl)-1-thiophen-3-yl-1,4-dihydro-chromeno[4,3-c]pyrazole-3-carbonyl]-amino}-cyclohexanecarboxylic acid tert-butyl ester (15) | tert-butyl 3-aminocyclohexanecarboxylate | m/z: 564 [M + H]⁺ | $^1$H NMR (400 MHz, CDCl$_3$) δ 7.55 (ddd, J = 4.6, 3.2, 1.4 Hz, 2H), 7.51 (dd, J = 5.1, 3.2 Hz, 1H), 7.25 (td, J = 4.7, 1.4 Hz, 1H), 6.69 (s, 1H), 6.57 (s, 1H), 6.11 (s, 1H), 5.63 (s, 2H), 4.33 (s, 1H), 3.98 (dd, J = 8.2, 4.0 Hz, 2H), 3.83 (d, J = 3.7 Hz, 3H), 2.28-2.4 (m, 1H), 2.56 (s, 1H), 2.42-2.26 (m, 2H), 2.05 (d, J = 13.2 Hz, 1H), 1.92 (dd, J = 21.8, 15.1 Hz, 2H), 1.85 (s, 3H), 1.52 (s, 3H), 1.48-1.42 (m, 9H). |

-continued

| Product | Amine | LC/MS | NMR |
|---|---|---|---|
| 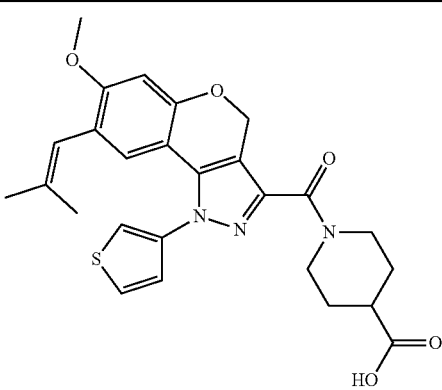<br>1-[7-Methoxy-8-(2-methyl-propenyl)-1-thiophen-3-yl-1,4-dihydro-chromeno[4,3-c]pyrazole-3-carbonyl]-piperidine-4-carboxylic acid (16) | | m/z: 494 [M + H]$^+$ | $^1$H NMR (400 MHz, CDCl$_3$) δ 7.52 (dd, J = 3.2, 1.4 Hz, 1H), 7.48 (dd, J = 5.1, 3.3 Hz, 1H), 7.24 (dd, J = 5.1, 1.4 Hz, 1H), 6.73 (s, 1H), 6.58 (s, 1H), 6.12 (s, 1H), 5.52 (s, 2H), 5.12-5.03 (m, 2H), 4.62-4.52 (m, 2H), 3.82 (s, 3H), 3.11-3.00 (m, 2H), 3.42-3.48 (m, 2H), 2.81-2.68 (m, 1H), 1.85 (d, J = 1.2 Hz, 3H), 1.53 (d, J = 1.2 Hz, 3H). |
| <br>1-[7-Methoxy-8-(2-methyl-propenyl)-1-thiophen-3-yl-1,4-dihydro-chromeno[4,3-c]pyrazole-3-carbonyl]-azepane-4-carboxylic acid methyl ester (17) | 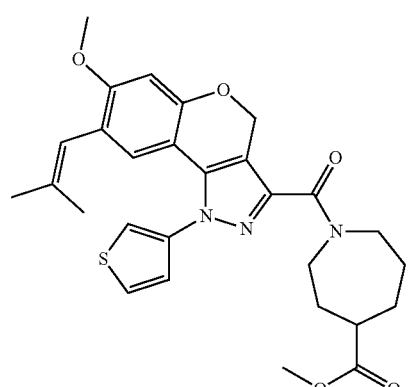 | m/z: 522 [M + H]$^+$ | $^1$H NMR (400 MHz, CDCl$_3$) δ 7.51-7.49 (m, 1H), 7.47 (dd, J = 5.1, 3.3 Hz, 1H), 7.25-7.22 (m, 1H), 6.76 (d, J = 3.4 Hz, 1H), 6.58 (s, 1H), 6.12 (s, 1H), 5.55 (d, J = 3.4 Hz, 2H), 4.40-4.23 (m, 2H), 4.11-4.00 (m, 2H), 3.86 (d, J = 5.2 Hz, 1H), 3.82 (s, 3H), 3.79-3.74 (m, 1H), 3.69 (d, J = 5.9 Hz, 3H), 2.62-2.54 (m, 2H), 2.30-2.20 (m, 1H), 2.04-1.94 (m, 1H), 1.85 (d, J = 1.2 Hz, 2H), 1.81-1.73 (m, 3H), 1.55 (s, 3H). |
| 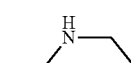<br>1-[7-Methoxy-8-(2-methyl-propenyl)-1-thiophen-3-yl-1,4-dihydro-chromeno[4,3-c]pyrazole-3-carbonyl]-azepane-4-carboxylic acid (18) | 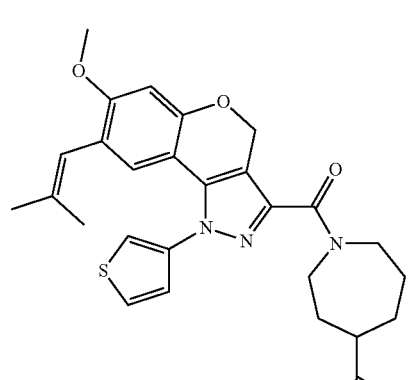 | m/z: 508 [M + H]$^+$ | $^1$H NMR (400 MHz, CDCl$_3$) δ 7.52-7.47 (m, 1H), 7.46 (d, J = 4.7 Hz, 1H), 7.23 (d, J = 3.7 Hz, 1H), 6.75 (d, J = 4.3 Hz, 1H), 6.57 (s, 1H), 6.12 (s, 1H), 5.53 (d, J = 6.1 Hz, 2H), 4.35-4.21 (m, 1H), 4.04 (dd, J = 17.7, 16.6 Hz, 1H), 3.91-3.73 (m, 5H), 3.51 (s, 1H), 2.68-2.52 (m, 1H), 2.30-2.18 (m, 1H), 2.13-1.94 (m, 3H), 1.85 (s, 3H), 1.82-1.72 (m, 1H), 1.54 (s, 3H). |

-continued

| Product | Amine | LC/MS | NMR |
|---|---|---|---|
| 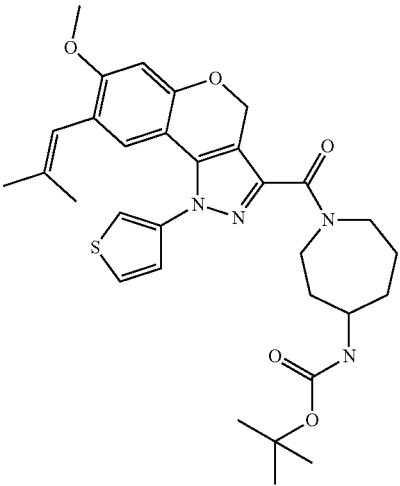<br>{1-[7-Methoxy-8-(2-methyl-propenyl)-1-thiophen-3-yl-1,4-dihydro-chromeno[4,3-c]pyrazole-3-carbonyl]-azepan-4-yl}-carbamic acid tert-butyl ester (35) | 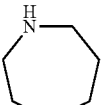 | m/z: 579 [M + H]+ | $^1$H NMR (400 MHz, CDCl$_3$) δ 7.52-7.48 (m, 1H), 7.46 (dd, J = 5.1, 3.3 Hz, 1H), 7.26-7.21 (m, 1H), 6.76 (d, J = 7.6 Hz, 1H), 6.57 (s, 1H), 6.12 (s, 1H), 5.53 (s, 2H), 4.63-4.51 (m, 1H), 4.51-4.39 (m, 1H), 4.27-4.18 (m, 1H), 4.05-3.91 (m, 1H), 3.82 (s, 3H), 3.75-3.51 (m, 2H), 2.22-2.11 (m, 1H), 2.03-1.90 (m, 2H), 1.85 (s, 3H), 1.82-1.68 (m, 2H), 1.54 (d, J = 1.2 Hz, 3H), 1.45 (d, J = 8.1 Hz, 9H). |
| 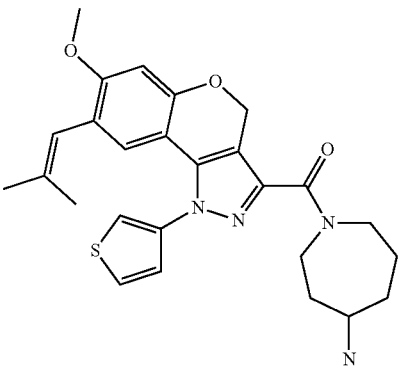<br>(4-Amino-azepan-1-yl)-[7-methoxy-8-(2-methyl-propenyl)-1-thiophen-3-yl-1,4-dihydro-chromeno[4,3-c]pyrazol-3-yl]-methanone (36) | | m/z: 479 [M + H]+ | $^1$H NMR (400 MHz, CDCl$_3$) δ 7.51 (d, J = 10.5 Hz, 1H), 7.47-7.41 (m, 1H), 7.23 (d, J = 5.0 Hz, 1H), 6.76 (s, 1H), 6.57 (s, 1H), 6.12 (s, 1H), 5.53 (s, 2H), 4.35-4.16 (m, 2H), 4.02-3.85 (m, 3H), 3.82 (s, 2H), 3.64-3.50 (m, 2H), 3.29-3.19 (m, 2H), 2.34-2.23 (m, 1H), 2.10-1.97 (m, 2H), 1.85 (s, 3H), 1.54 (s, 3H). |
| 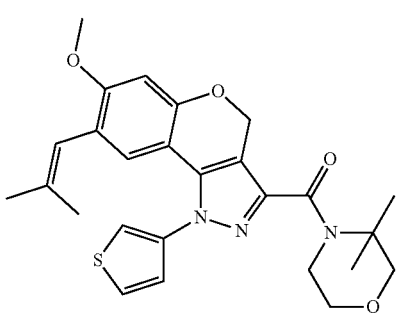<br>(3,3-Dimethyl-morpholin-4-yl)-[7-methoxy-8-(2-methyl-propenyl)-1-thiophen-3-yl-1,4-dihydro-chromeno[4,3-c]pyrazol-3-yl]-methanone (39) |  | m/z: 480 [M + H]+ | $^1$H NMR (400 MHz, CDCl$_3$) δ 7.51 (dd, J = 3.2, 1.4 Hz, 1H), 7.47 (dd, J = 5.1, 3.3 Hz, 1H), 7.22 (dd, J = 5.1, 1.3 Hz, 1H), 6.72 (s, 1H), 6.58 (s, 1H), 6.12 (s, 1H), 5.47 (s, 2H), 4.10-4.06 (m, 2H), 3.88-3.84 (m, 2H), 3.82 (s, 3H), 3.50 (s, 2H), 1.85 (d, J = 1.0 Hz, 3H), 1.55 (s, 6H), 1.53 (d, J = 0.9 Hz, 3H). |

| Product | Amine | LC/MS | NMR |
| --- | --- | --- | --- |
| 7-Methoxy-8-(2-methyl-propenyl)-1-thiophen-3-yl-1,4-dihydro-chromeno[4,3-c]pyrazole-3-carboxylic acid (2-hydroxy-1,1-dimethyl-ethyl)-methyl-amide (40) | | m/z: 468 [M + H]+ | ¹H NMR (400 MHz, CDCl₃) δ 7.53 (d, J = 2.2 Hz, 1H), 7.48 (dd, J = 5.0, 3.3 Hz, 1H), 7.23 (d, J = 5.1 Hz, 1H), 6.72 (s, 1H), 6.58 (s, 1H), 6.12 (s, 1H), 5.44 (s, 2H), 5.07 (t, J = 6.3 Hz, 1H), 3.83 (s, 3H), 3.80 (d, J = 6.2 Hz, 2H), 3.32 (s, 3H), 1.85 (s, 3H), 1.52 (s, 3H), 1.46 (s, 6H). |
| [7-Methoxy-8-(2-methyl-propenyl)-1-thiophen-3-yl-1,4-dihydro-chromeno[4,3-c]pyrazol-3-yl]-(6-oxa-1-aza-spiro[3.3]hept-1-yl)-methanone (44) | | m/z: 464 [M + H]+ | ¹H NMR (400 MHz, CDCl₃) δ 7.51-7.44 (m, 2H), 7.22 (d, J = 4.8 Hz, 1H), 6.73 (s, 1H), 6.58 (s, 1H), 6.12 (s, 1H), 5.64 (s, 2H), 5.62 (d, J = 6.7 Hz, 2H), 4.69 (d, J = 6.8 Hz, 2H), 4.51-4.43 (m, 2H), 3.82 (s, 3H), 2.63-2.55 (m, 2H), 1.85 (s, 3H), 1.54 (s, 3H). |
| [(R)-4-(Azetidine-1-carbonyl)-azepan-1-yl]-[7-methoxy-8-(2-methyl-propenyl)-1-thiophen-3-yl-1,4-dihydro-chromeno[4,3-c]pyrazol-3-yl]-methanone (45) Chiral | Followed by chiral separation | m/z: 547 [M + H]+ | |

| Product | Amine | LC/MS | NMR |
|---|---|---|---|
| [(S)-4-(Azetidine-1-carbonyl)-azepan-1-yl]-[7-methoxy-8-(2-methyl-propenyl)-1-thiophen-3-yl-1,4-dihydro-chromeno[4,3-c]pyrazol-3-yl]-methanone (46) | Followed by chiral separation | m/z: 547 [M + H]⁺ | |
| (2-Hydroxymethyl-2-methyl-pyrrolidin-1-yl)-[7-methoxy-8-(2-methyl-propenyl)-1-thiophen-3-yl-1,4-dihydro-chromeno[4,3-c]pyrazol-3-yl]-methanone (48) | | m/z: 480 [M + H]⁺ | $^1$H NMR (400 MHz, CDCl$_3$) δ 7.57-7.44 (m, 2H), 7.23 (d, J = 5.0 Hz, 1H), 6.72 (s, 1H), 6.58 (s, 1H), 6.12 (s, 1H), 5.83 (s, 1H), 5.54 (s, 2H), 4.47-4.37 (m, 1H), 3.99-3.88 (m, 1H), 3.82 (s, 3H), 3.68 (d, J = 11.9 Hz, 1H), 2.04-1.87 (m, 3H), 1.85 (s, 3H), 1.82-1.74 (m, 2H), 1.54 (d, J = 4.6 Hz, 6H). |
| [7-Methoxy-8-(2-methyl-propenyl)-1-thiophen-3-yl-1,4-dihydro-chromeno[4,3-c]pyrazol-3-yl]-morpholin-4-yl-methanone (117) | | m/z: 452 [M + H]⁺ | $^1$H NMR (400 MHz, CDCl$_3$) δ 7.52 (dd, J = 3.2, 1.4 Hz, 1H), 7.48 (dd, J = 5.1, 3.3 Hz, 1H), 7.23 (dd, J = 5.1, 1.4 Hz, 1H), 6.72 (s, 1H), 6.58 (s, 1H), 6.12 (s, 1H), 5.55 (s, 2H), 4.32 (t, J = 7.0 Hz, 2H), 3.83 (s, 3H), 3.82-3.71 (m, 6H), 1.85 (d, J = 1.0 Hz, 3H), 1.53 (d, J = 0.9 Hz, 3H). |

-continued

| Product | Amine | LC/MS | NMR |
|---|---|---|---|
| (3-Hydroxy-pyrrolidin-1-yl)-[7-methoxy-8-(2-methyl-propenyl)-1-thiophen-3-yl-1,4-dihydro-chromeno[4,3-c]pyrazol-3-yl]-methanone (47) | 3-hydroxypyrrolidine | m/z: 452 [M + H]+ | ¹H NMR (500 MHz, cdcl₃) δ 7.49 (dd, J = 3.1, 1.5 Hz, 1H), 7.48-7.42 (m, 1H), 7.22 (dd, J = 6.5, 2.8 Hz, 1H), 6.71 (d, J = 6.3 Hz, 1H), 6.54 (s, 1H), 6.10 (s, 1H), 5.65-5.54 (m, 1H), 4.57-4.50 (m, 1H), 4.16 (t, J = 12.8 Hz, 1H), 4.13-4.04 (m, 2H), 3.85-3.81 (m, 1H), 3.80 (s, 3H), 3.75 (d, J = 2.7 Hz, 1H), 2.10-1.94 (m, 2H), 1.83 (s, 3H), 1.52 (s, 3H). |

The following compounds were prepared using procedures analogous to those disclosed in example 4:

| Compound | Starting material | LC/MS | NMR |
|---|---|---|---|
| (3,3-Dimethyl-morpholin-4-yl)-(8-isobutyl-7-methoxy-1-thiophen-3-yl-1,4-dihydro-chromeno[4,3-c]pyrazol-3-yl)-methanone (77) | 3,3-dimethylmorpholine | m/z = 482 [M + H]+ | ¹H-NMR (DMSO-d6): δ 7.94 (s, 1H), 7.84-7.79 (m, 1H), 7.31 (d, 1H), 6.66 (s, 1H), 6.41 (s, 1H), 5.34 (s, 2H), 3.94 (t, 2H), 3.78-3.70 (m, 5H), 3.42 (s, 2H), 2.14 (d, 2H), 1.62 (septet, 1H), 1.42 (s, 6H), 0.74 (d, J = 6.5 Hz, 6H). |
| 8-Isobutyl-7-methoxy-1-thiophen-3-yl-1,4-dihydro-chromeno[4,3-c]pyrazole-3-carboxylic acid (3-hydroxymethyl-oxetan-3-yl)-amide (141) | 3-amino-3-(hydroxymethyl)oxetane | m/z = 470 [M + H]+ | ¹H-NMR (DMSO-d6): δ 8.67 (s, 1H), 7.99 (dd, 1H), 7.84 (dd, 1H), 7.34 (dd, 1H), 6.66 (s, 1H), 6.38 (s, 1H), 5.45 (s, 2H), 5.14 (s, 1H), 4.68 (d, 2H), 4.51 (d, 2H), 3.76 (s, 3H), 3.68 (s, 2H), 2.14 (d, 2H), 1.61 (septet, 1H), 0.74 (d, 6H). |

| Compound | Starting material | LC/MS | NMR |
|---|---|---|---|
| 8-Isobutyl-7-methoxy-1-thiophen-3-yl-1,4-dihydro-chromeno[4,3-c]pyrazole-3-carboxylic acid (3-methyl-oxetan-3-yl)-amide (145) | (3-amino-3-methyl-oxetane) | m/z = 454 [M + H]+ | $^1$H-NMR (DMSO-d6): δ 8.87 (s, 1H), 8.00 (dd, 1H), 7.84 (dd, 1H), 7.35 (dd, 1H), 6.66 (s, 1H), 6.38 (s, 1H), 5.46 (s, 2H), 4.70 (d, 2H), 4.31 (d, 2H), 3.75 (s, 3H), 2.14 (d, 2H), 1.66-1.54 (m, 4H), 0.73 (d, 6H). |
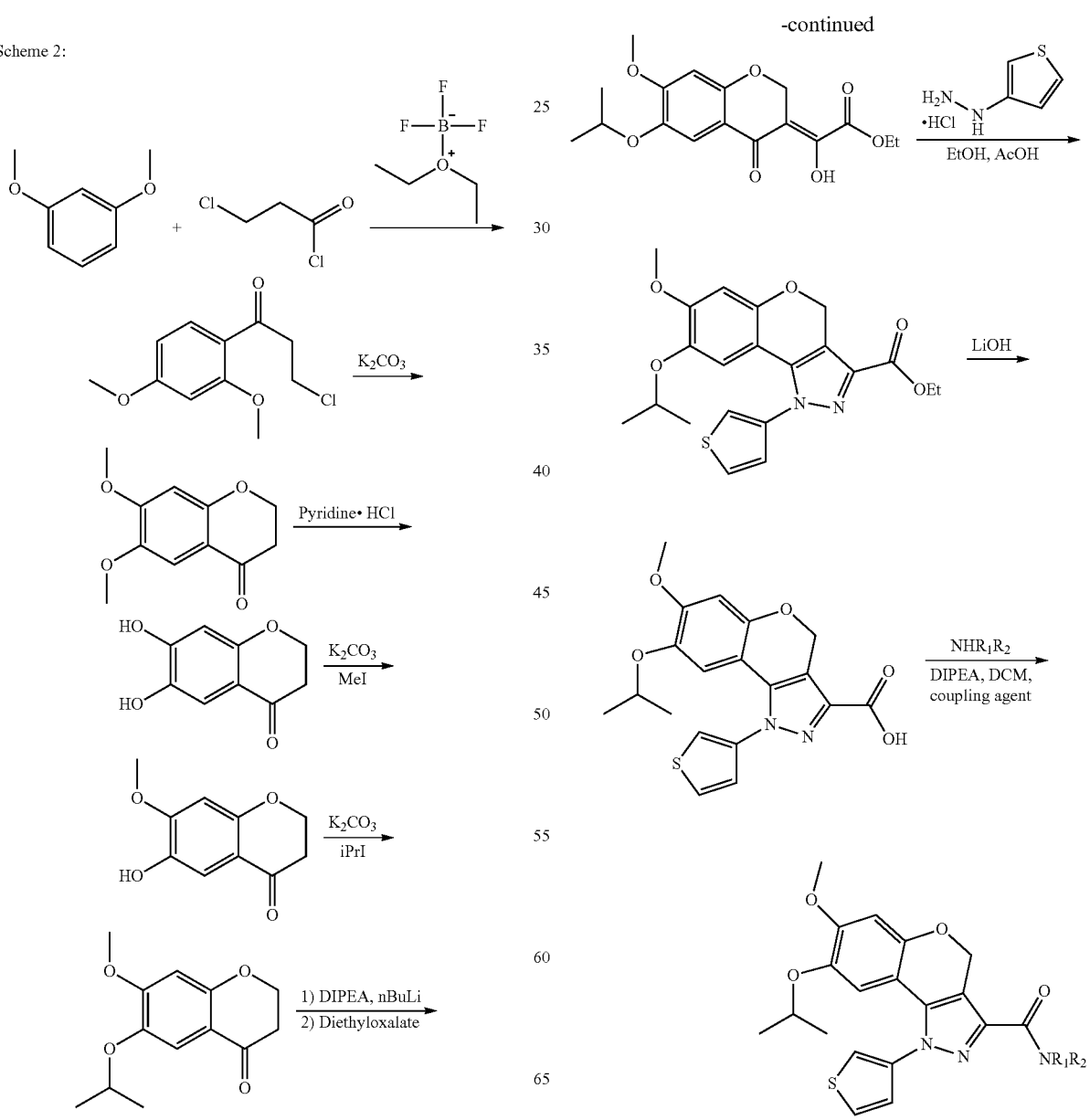
Scheme 2:

Example 7

8-Isopropoxy-7-methoxy-1-thiophen-3-yl-1,4-di-hydro-chromeno[4,3-c]pyrazole-3-carboxylic acid tert-butyl-methyl-amide (19)

Step 1: 3-Chloro-1-(2-hydroxy-4,5-dimethoxyphenyl)propan-1-one

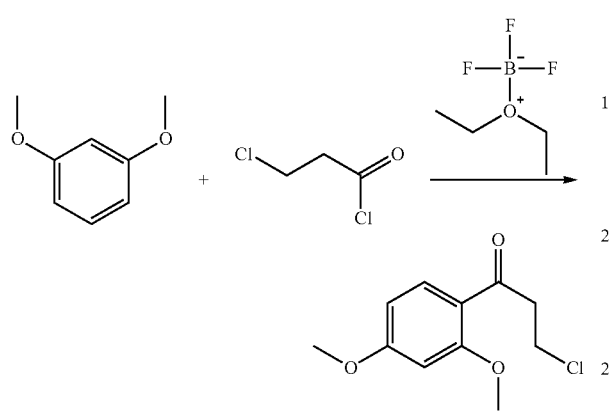

To a stirred suspension of 3, 4-dimethoxy phenol (10 g, 0.06 mol) and chloropropanoyl chloride (12.5 g, 0.12 mol) was added boron trifluorideethylethrate (8.8 mL, 0.06 mol) in drops at 60° C. under nitrogen atmosphere. After the complete addition, the reaction mixture was heated to 70° C. for 1 h. The reaction mixture was cooled to RT and quenched with ice-water (200 mL) and extracted with DCM (500 mL). The aqueous layer was re-extracted (2×100 mL) DCM, the combined organic layer was dried over sodium sulphate and concentrated under vacuum. The crude mass was purified by column chromatography using pet ether/ethyl acetate (8:2) as eluent to afford the desired compound (12 g, 76%) as a light yellow solid.

$^1$H NMR (400 MHz, DMSO-$d_6$) δ 12.2 (bs, 1H), 7.27 (s, 1H), 6.55 (s, 1H), 4.12-4.10 (m, 2H), 3.79 (s, 3H), 3.71 (s, 3H), 2.48-2.43 (m, 2H).

Step 2: 6,7-Dimethoxy-2,3-dihydro-4H-chromen-4-one

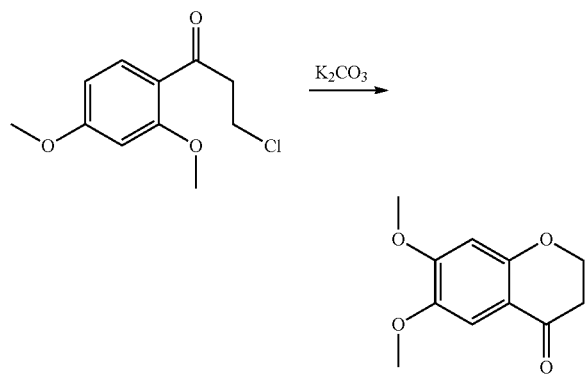

To a stirred solution of 3-Chloro-1-(2-hydroxy-4,5-dimethoxyphenyl)propan-1-one (13 g, 0.05 mol) in ethanol was added dry $K_2CO_3$ (16.3 g, 0.10 mol) in lots at RT under nitrogen. The resulting suspension was stirred at RT for 16 h. The reaction mixture was filtered and concentrated under vacuum. The crude mass was dissolved in ethyl acetate (200 mL), washed with 5% sodium bicarbonate (50 mL), brine (50 mL) and dried over sodium sulphate. The organic solvent was concentrated; the residue was purified by column chromatography using pet ether/ethyl acetate (8:2) as eluent to afford the desired compound (9 g, 81%) as a light brown solid.

$^1$H NMR (400 MHz, DMSO-$d_6$) δ 7.12 (s, 1H), 6.59 (s, 1H), 4.47-4.44 (m, 2H), 3.80 (s, 3H), 3.72 (s, 3H), 2.69-2.65 (m, 2H).

Step 3: 6,7-Dihydroxy-2,3-dihydro-4H-chromen-4-one

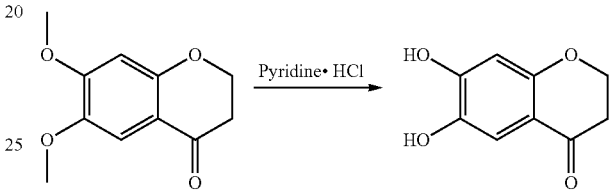

The mixture of 6,7-dimethoxy-2,3-dihydro-4H-chromen-4-one (2.5 g, 0.01 mol) and pyridine hydrochloride (20 g, 0.20 mol) was heated at 170° C. under nitrogen for 12 h. The reaction mixture was slurried with DCM (100 mL), the separated solid was filtered and filtrate was concentrated under vacuum. The crude product was purified by column chromatography using pet ether/ethyl acetate (5:5) as eluent to afford the desired compound (1 g, 50%) as a light white solid.

$^1$H NMR (400 MHz, DMSO-$d_6$) δ 9.72 (bs, 2H), 7.04 (s, 1H), 6.30 (s, 1H), 4.37-4.34 (m, 2H), 2.60-2.57 (m, 2H).

Step 4: 6-Hydroxy-7-methoxy-2,3-dihydro-4H-chromen-4-one

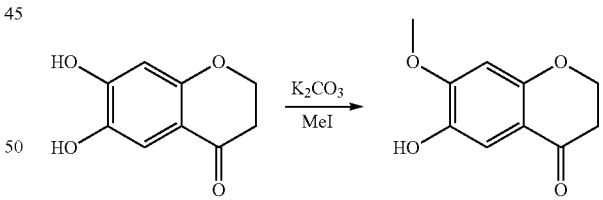

To a stirred solution of 6,7-dihydroxy-2,3-dihydro-4H-chromen-4-one (5.5 g, 0.0305 mol) in DMF (60 mL) was added dry $K_2CO_3$ (4.2 g, 0.0305 mol) at RT under nitrogen. The reaction mixture was stirred at RT for 15 min and then added methyl iodide (1.3 mL, 0.0214 mol) in drops at RT. The reaction mixture was stirred at RT for 2 h. The reaction mixture was filtered and filtrate was concentrated under vacuum. The crude product was purified by column chromatography using pet ether/ethyl acetate (9:1) as eluent to afford the desired compound (4 g, 68%) as a light brown solid.

$^1$H NMR (400 MHz, DMSO-$d_6$) δ 9.05 (bs, 1H), 7.05 (s, 1H), 6.53 (s, 1H), 4.43-4.40 (m, 2H), 3.80 (s, 3H), 2.64-2.61 (m, 2H).

Step 5: 6-Isopropoxy-7-methoxy-2,3-dihydro-4H-chromen-4-one

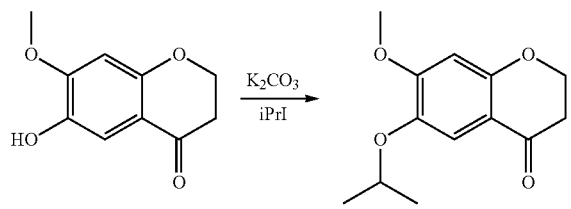

To a stirred solution of 6-hydroxy-7-methoxy-2,3-dihydro-4H-chromen-4-one (4.0 g, 0.0206 mol) in DMF (80 mL) was added dry K$_2$CO$_3$ (5.7 g, 0.0412 mol) at RT under nitrogen. The reaction mixture was stirred at RT for 15 min and then added 2-Iodo propane (6.2 mL, 0.0618 mol) in drops at RT. The reaction mixture was stirred at 65° C. for 8 h. The reaction mixture was filtered and filtrate was concentrated under vacuum. The crude product was dissolved in ethyl acetate (2×200 mL), washed with water (50 mL), brine (50 mL) and dried over sodium sulphate. The organic solvent was concentrated, crude mass was purified by column chromatography using pet ether/ethyl acetate (8:2) as eluent to afford the desired compound (4.1 g, 87%) as a light brown solid.

$^1$H NMR (400 MHz, DMSO-d$_6$) δ 7.13 (s, 1H), 6.59 (s, 1H), 4.48-4.40 (m, 3H), 3.80 (s, 3H), 2.68-2.65 (m, 2H), 1.21 (s, 3H), 1.20 (s, 3H).

Step 6: Ethyl (2Z)-hydroxy(6-isopropoxy-7-methoxy-4-oxo-2H-chromen-3(4H)-ylidene)acetate

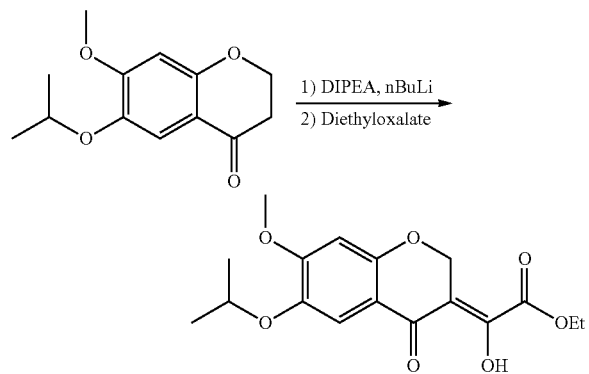

Diisopropyl amine (6.9 mL, 0.0495 mol) was taken in dry THF (150 mL) at RT under nitrogen atmosphere. The reaction mixture was cooled to −78° C. and n-Butyl lithium (1.6 M solution in hexane, 28.6 mL, 0.0457 mol) was added in drops over a period of 30 min. After the addition, the reaction mixture stirred at same temperature for 15 min and then slowly warmed to −10° C. and stirred further for 30 min. Reaction mixture was again re-cooled to −78° C., 6-Isopropoxy-7-methoxy-2,3-dihydro-4H-chromen-4-one (9 g, 0.0381 mol) in THF (50 mL) was added in drops over period of 30 min and stirred at −78° C. After 1 h, diethyl oxalate (7.8 mL, 0.0571 mol) was added in drops at −78° C.; the reaction mixture was slowly brought to 0° C. and stirred for 1 h. The reaction mixture was cooled to −5° C., quenched with a solution of 1.5N HCl and extracted with ethyl acetate (100 mL×2). The combined organic layer was washed with water (100 mL), brine (50 mL), dried over sodium sulphate and concentrated to afford the desired compound (10.5 g, 92%) as a pale yellow solid.

$^1$H NMR (400 MHz, DMSO-d$_6$) δ. 7.17-7.13 (d, J=16 Hz, 1H), 6.61-6.59 (d, J=24 Hz, 1H), 5.16-5.12 (m, 1H), 4.47-4.24 (m, 1H), 4.21 (s, 3H), 2.97 (s, 3H), 2.54-5.53 (m, 1H), 1.21 (s, 6H).

Step 7: 8-Isopropoxy-7-methoxy-1-(3-thienyl)-1,4-dihydrochromeno[4,3-c]pyrazole-3-carboxylate

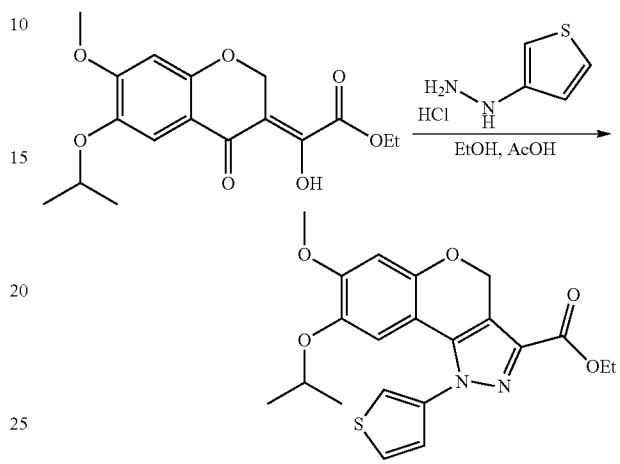

To a solution of (ethyl (2Z)-hydroxy(6-isopropoxy-7-methoxy-4-oxo-2H-chromen-3(4H)-ylidene)acetate (6.0 mg, 0.0223 mol) in a mixture of ethanol (150 mL) and acetic acid (150, mL) was added 3-thienylhydrazine hydrochloride (2.7 g, 0.0223 mol) at RT under nitrogen. The reaction mixture was stirred at 100° C. for 4 h. The reaction mixture was concentrated under high vacuum. The residue was dissolved with ethyl acetate (20 mL), washed with water (20 mL), brine (20 mL), dried over sodium sulphate and concentrated under vacuum. The crude product was purified by column chromatography using pet ether/ethyl acetate as eluent to afford desired compound (6.5 g, 88%) as an off white solid.

$^1$H NMR (400 MHz, DMSO-d$_6$) δ 8.02-8.01 (dd, J=1.2, 2.4 Hz, 1H), 7.86-7.83 (dd, J=4, 16 Hz, 1H), 7.35-7.34 (dd, J=1.2, 4 Hz, 1H), 6.68 (s, 1H), 6.19 (s, 1H), 5.40 (s, 2H), 4.31-4.26 (m, 2H), 3.94-3.88 (m, 1H), 3.72 (s, 3H), 1.31-1.287 (m, 3H), 1.07 (s, 6H).

Step 8: 8-Isopropoxy-7-methoxy-1-(3-thienyl)-1,4-dihydrochromeno[4,3-c]pyrazole-3-carboxylic acid

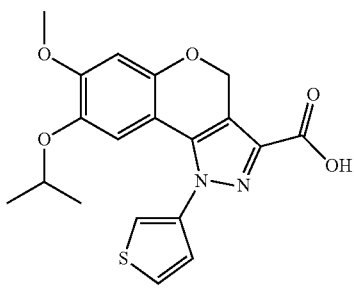 [SMILES: COc1cc2c(cc1OC(C)C)-c1c(c(C(=O)O)nn1-c1ccsc1)CO2]

To a solution of 8-isopropoxy-7-methoxy-1-(3-thienyl)-1,4-dihydrochromeno[4,3-c]pyrazole-3-carboxylate (4 g, 0.0108 mol) in mixture of THF (70 mL), H$_2$O (20 mL), MeOH (10 mL) was added LiOH.H$_2$O (1.4 g, 0.0326 mol) at RT. The reaction mixture was stirred at RT for 4 h. The reaction mixture was evaporated and acidified with a solution of 1.5N HCl. The filtrate was dried under high vacuum to afford the desired compound (3.3 g, 79%) as an off white solid.

¹H NMR (400 MHz, DMSO-d₆) δ 13.16 (bs, 1H), 8.01-8.00 (dd, J=1.2, 2.4 Hz, 1H), 7.85-7.83 (dd, J=4, 16 Hz, 1H), 7.35-7.33 (dd, J=1.2, 4 Hz, 1H), 6.69 (s, 1H), 6.19 (s, 1H), 5.39 (s, 2H), 3.94-3.88 (m, 2H), 3.72 (s, 3H), 1.07 (s, 6H).

Step 9: 8-Isopropoxy-7-methoxy-1-thiophen-3-yl-1,4-dihydro-chromeno[4,3-c]pyrazole-3-carboxylic acid tert-butyl-methyl-amide (19)

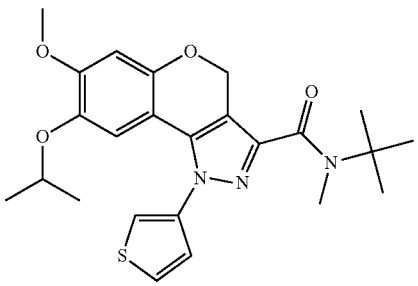 [SMILES: COc1cc2c(cc1OC(C)C)-c1c(c(C(=O)N(C)C(C)(C)C)nn1-c1ccsc1)CO2]

To a stirred solution of 8-isopropoxy-7-methoxy-1-(3-thienyl)-1,4-dihydrochromeno[4,3-c]pyrazole-3-carboxylic acid (1.1 g, 0.0028 mol) in DCM (50 mL) was added N-tert-butyl methyl amine (0.3 g, 0.0034 mol), HATU (1.3 g, 0.0034 mol) and DIPEA (0.8 mL, 0.0043 mol) at RT under nitrogen. The reaction mixture was stirred at RT for 16 h. The reaction mixture was quenched to water (20 mL), extracted with dichloromethane (2×100 mL). The combined organic layer was washed with brine (100 mL) and dried over anhydrous sodium sulphate. The solvent was removed under vacuum; the crude product was purified by column chromatography using pet ether/ethyl acetate (8:2) as eluent to afford the desired compound (1.1 g, 85%) as an off white solid.

¹H NMR (400 MHz, DMSO-d₆) δ 7.97-7.96 (dd, J=1.2, 2.4 Hz, 1H), 7.82-7.80 (dd, J=4, 16 Hz, 1H), 7.34-7.32 (dd, J=1.2, 4 Hz, 1H), 6.69 (s, 1H), 6.22 (s, 1H), 5.27 (s, 2H), 3.39-3.89 (m, 1H), 3.72 (s, 3H), 3.14 (s, 3H), 1.41 (s, 9H), 1.06 (s, 6H). m/z: 456 [M+H]⁺

The following compounds were prepared using procedures analogous to those disclosed in example 7.

| Compound | Starting material | LC/MS | NMR |
|---|---|---|---|
| 1-(8-Isopropoxy-7-methoxy-1-thiophen-3-yl-1,4-dihydro-chromeno[4,3-c]pyrazole-3-carbonyl)-azepane-4-carboxylic acid methyl ester (24) | | m/z: 526 [M + H]⁺ | ¹H NMR (400 MHz, CDCl₃) δ 7.53-7.46 (m, 2H), 7.25 (d, J = 4.9 Hz, 1H), 6.62 (s, 1H), 6.44 (d, J = 4.2 Hz, 1H), 5.50 (d, J = 3.4 Hz, 2H), 4.39-4.22 (m, 1H), 4.06 (dt, J = 12.9, 6.4 Hz, 1H), 3.83 (s, 3H), 3.77 (dd, J = 11.0, 5.2 Hz, 1H), 3.69 (d, J = 5.5 Hz, 3H), 3.60-3.50 (m, 1H), 2.63-2.53 (m, 1H), 2.30-2.16 (m, 1H), 2.11-1.99 (m, 2H), 1.87-1.68 (m, 2H), 1.56 (d, J = 6.7 Hz, 1H), 1.47 (d, J = 6.7 Hz, 1H), 1.22 (d, J = 6.1 Hz, 6H) |
| 1-(8-Isopropoxy-7-methoxy-1-thiophen-3-yl-1,4-dihydro-chromeno[4,3-c]pyrazole-3-carbonyl)-azepane-4-carboxylic acid (25) | | m/z: 512 [M + H]⁺ | ¹H NMR (400 MHz, MeOD) δ 7.74 (d, J = 2.8Hz, 1H), 7.72-7.66 (m, 1H), 7.28 (dd, J = 3.2, 1.9 Hz, 1H), 6.64 (s, 1H), 6.37 (d, J = 3.3 Hz, 1H), 5.36 (d, J = 3.0 Hz, 2H), 4.21 (ddt, J = 30.6, 14.1, 4.9 Hz, 1H), 4.04 (dt, J = 12.1, 6.1 Hz, 1H), 3.96-3.82 (m, 2H), 3.80 (s, 3H), 3.71-3.58 (m, 1H), 2.58-2.44 (m, 1H), 2.24-2.11 (m, 1H), 2.11-1.91 (m, 3H), 1.86-1.66 (m, 2H), 1.15 (d, J = 6.1 Hz, 6H). |

The following compounds were prepared using procedures analogous to those disclosed in example 1:

| Compound | Boronic acid Starting material | Amine Starting material | LC/MS | NMR |
|---|---|---|---|---|
| 4-[3-(tert-Butyl-methyl-carbamoyl)-7-methoxy-1-thiophen-3-yl-1,4-dihydro-chromeno[4,3-c]pyrazole-8-yl]-pyrazole-1-carboxylic acid tert-butyl ester (20) | | | m/z: 564 [M + H]⁺ | ¹H NMR (400 MHz, CDCl₃) δ 8.31 (d, J = 0.6 Hz, 1H), 7.63 (d, J = 0.7 Hz, 1H), 7.58 (dd, J = 3.2, 1.4 Hz, 1H), 7.55-7.52 (m, 1H), 7.28-7.26 (m, 1H), 6.96 (s, 1H), 6.67 (s, 1H), 5.53 (s, 2H), 3.92 (s, 3H), 3.30 (s, 3H), 1.70 (s, 9H), 1.54 (s, 9H). |
| 8-(2,4-Dimethyl-thiazol-5-yl)-7-methoxy-1-thiophen-3-yl-1,4-dihydro-chromeno[4,3-c]pyrazole-3-carboxylic acid tert-butyl-methyl-amide (53) | | | m/z = 509 [M + H]⁺ | ¹H-NMR (DMSO-d6): δ 7.99 (s, 1H), 7.81 (s, 1H), 7.34 (d, 1H), 6.83 (s, 1H), 6.66 (s, 1H), 5.42 (s, 2H), 3.78 (s, 3H), 3.17 (s, 3H), 2.56 (s, 3H), 2.00 (s, 3H), 1.44 (s, 9H). |

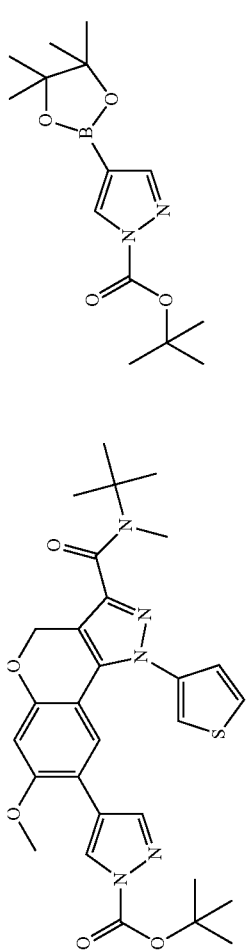
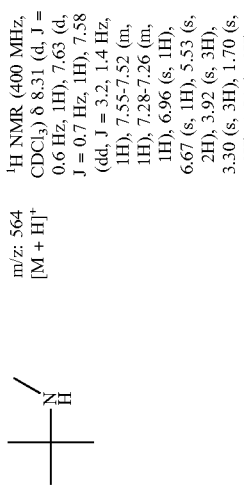
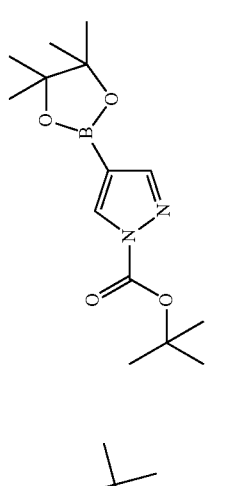
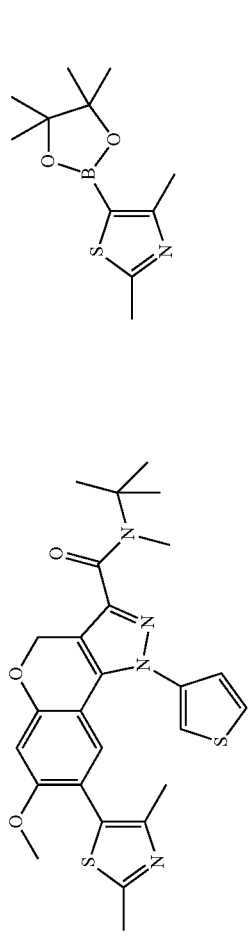
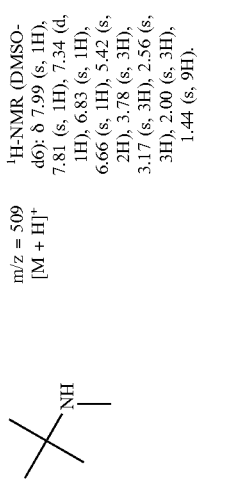
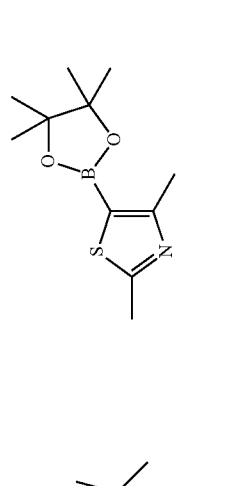

| Compound | Boronic acid Starting material | Amine Starting material | LC/MS | NMR |
|---|---|---|---|---|
| 8-(5-Fluoro-thiophen-2-yl)-7-methoxy-1-thiophen-3-yl-1,4-dihydro-chromeno[4,3-c]pyrazole-3-carboxylic acid tert-butyl-methyl-amide (54) | 5-fluorothiophene-2-boronic acid pinacol ester | N-methyl-tert-butylamine | m/z = 498 [M + H]⁺ | ¹H-NMR (CDCl₃): δ 7.57 (m, 2H), 7.02 (s, 1H), 6.65-6.62 (m, 2H), 6.38 (s, 1H), 5.52 (s, 2H), 3.92 (s, 3H), 3.29 (s, 3H), 1.54 (s, 9H). |
| 7-Methoxy-8-(1-methyl-1H-pyrrol-3-yl)-1-thiophen-3-yl-1,4-dihydro-chromeno[4,3-c]pyrazole-3-carboxylic acid tert-butyl-methyl-amide (55) | 1-methyl-1H-pyrrole-3-boronic acid pinacol ester | N-methyl-tert-butylamine | m/z = 477 [M + H]⁺ | ¹H-NMR (CDCl₃): δ 7.50 (s, 1H), 7.45 (d, 1H), 7.23 (d, 1H), 6.83 (s, 1H), 6.67 (s, 2H), 6.15 (s, 1H), 5.94 (s, 1H), 5.51 (s, 2H), 3.81 (s, 3H), 3.41 (s, 3H), 3.28 (s, 3H), 1.54 (s, 9H). |

| Compound | Boronic acid Starting material | Amine Starting material | LC/MS | NMR |
|---|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid tert-butyl-methyl-amide (63) | 1-methyl-1H-pyrazole-3-boronic acid pinacol ester | N-methyl-tert-butylamine | m/z = 478 [M + H]+ | 1H-NMR (DMSO-d6): δ 7.94 (s, 1H), 7.83 (d, 1H), 7.60 (s, 1H), 7.48 (s, 1H), 7.32 (d, 1H), 6.76 (s, 1H), 6.50 (s, 1H), 5.38 (s, 2H), 3.84 (s, 3H), 3.78 (s, 3H), 3.19 (s, 3H), 1.45 (s, 9H). |
| 7-Methoxy-8-(1H-pyrazol-4-yl)-1-thiophen-3-yl-1,4-dihydro-chromeno[4,3-c]pyrazole-3-carboxylic acid [2-(2-oxo-oxazolidin-3-yl)-ethyl]-amide (62) | 1H-pyrazole-4-boronic acid pinacol ester | 3-(2-aminoethyl)-2-oxazolidinone | m/z = 507 [M + H]+ | 1H NMR (400 MHz, MeOD) δ 8.35 (t, J = 6.4 Hz, 1H), 7.81 (s, 1H), 7.76 (d, J =3.7 Hz, 1H), 7.62 (s, 2H), 7.34 (d, J = 4.9 Hz, 1H), 6.97 (s, 1H), 6.71 (s, 1H), 5.55 (s, 2H), 4.36 (t, J = 8.1 Hz, 2H), 3.91 (s, 3H), 3.76 (t, J = 8.0 Hz, 2H), 3.63-3.54 (m, 2H), 3.53-3.46 (m, 2H). |

| Compound | Boronic acid Starting material | Amine Starting material | LC/MS | NMR |
|---|---|---|---|---|
| 7-Methoxy-8-(2-methyl-2H-pyrazol-3-yl)-1-thiophen-3-yl-1,4-dihydro-chromeno[4,3-c]pyrazole-3-carboxylic acid tert-butyl-methyl-amide (64) | (1-methylpyrazole boronic acid pinacol ester) | (N-methyl tert-butylamine) | m/z = 478 [M + H]+ | 1H-NMR (DMSO-d6): δ 7.96 (s, 1H), 7.82-7.77 (m, 1H), 7.40-7.32 (m, 2H), 6.87 (s, 1H), 6.61 (s, 1H), 6.01 (s, 1H), 5.44 (s, 2H), 3.80 (s, 3H), 3.53 (s, 3H), 3.18 (s, 3H), 1.45 (s, 9H). |
| 7-Methoxy-8-(1H-pyrazol-3-yl)-1-thiophen-3-yl-1,4-dihydro-chromeno[4,3-c]pyrazole-3-carboxylic acid tert-butyl-methyl-amide (65) | (pyrazole boronic acid pinacol ester) | (N-methyl tert-butylamine) | m/z = 464 [M + H]+ | 1H-NMR (DMSO-d6): δ 12.71 (s, 1H), 8.01-7.33 (m, 4.5H), 6.96 (s, 0.5H), 6.81 (d, 1H), 6.56 (s, 0.5H), 5.97 (s, 0.5H), 5.40 (d, 2H), 3.87 (d, 3H), 3.19 (s, 3H), 1.45 (s, 9H). |

-continued

| Compound | Boronic acid Starting material | Amine Starting material | LC/MS | NMR |
|---|---|---|---|---|
| 7-Methoxy-8-(1-methyl-1H-pyrazol-4-yl)-1-thiophen-3-yl-1,4-dihydro-chromeno[4,3-c]pyrazole-3-carboxylic acid tert-butyl-methyl-amide (66) | 1-methyl-1H-pyrazol-4-yl pinacol boronate | N-methyl-tert-butylamine | m/z = 478 [M + H]$^+$ | $^1$H-NMR (DMSO-d6): δ 8.02 (s, 1H), 7.91 (d, 1H), 7.80 (s, 1H), 7.38 (d, 1H), 7.21 (s, 1H), 6.85 (s, 1H), 6.77 (s, 1H), 5.38 (s, 2H), 3.86 (s, 3H), 3.82 (s, 3H), 3.19 (s, 3H), 1.45 (s, 9H). |
| 8-(3,5-Dimethyl-isoxazol-4-yl)-7-methoxy-1-thiophen-3-yl-1,4-dihydro-chromeno[4,3-c]pyrazole-3-carboxylic acid tert-butyl-methyl-amide (67) | 3,5-dimethylisoxazole-4-boronic acid | N-methyl-tert-butylamine | m/z = 493 [M + H]$^+$ | $^1$H-NMR (DMSO-d6): δ 8.00 (s, 1H), 7.84-7.78 (m, 1H), 7.36 (d, 1H), 6.84 (s, 1H), 6.48 (s, 1H), 5.43 (s, 2H), 3.78 (s, 3H), 3.18 (s, 3H), 2.12 (s, 3H), 1.94 (s, 3H), 1.45 (s, 9H). |

| Compound | Boronic acid Starting material | Amine Starting material | LC/MS | NMR |
|---|---|---|---|---|
| 7-Methoxy-8-(1-methyl-1,2,3,6-tetrahydro-pyridin-4-yl)-1-thiophen-3-yl-1,4-dihydro-chromeno[4,3-c]pyrazole-3-carboxylic acid tert-butyl-methyl-amide (68) | (1-methyl-1,2,3,6-tetrahydropyridin-4-yl pinacol boronate) | (N-methyl-tert-butylamine) | m/z = 493 [M + H]⁺ | ¹H-NMR (DMSO-d6): δ 7.94 (s, 1H), 7.84–7.80 (m, 1H), 7.33 (d, 1H), 6.68 (s, 1H), 6.56 (s, 1H), 5.63 (s, 1H), 5.35 (s, 2H), 3.75 (s, 3H), 3.17 (s, 3H), 2.88 (s, 2H), 2.42 (t, 2H), 2.25–2.15 (m, 5H), 1.44 (s, 9H). |
| 7-Methoxy-8-pyrimidin-5-yl-1-thiophen-3-yl-1,4-dihydro-chromeno[4,3-c]pyrazole-3-carboxylic acid tert-butyl-methyl-amide (70) | (pyrimidin-5-yl pinacol boronate) | (N-methyl-tert-butylamine) | m/z = 476 [M + H]⁺ | ¹H-NMR (DMSO-d6): δ 9.08 (s, 1H), 8.69 (s, 2H), 8.00 (s, 1H), 7.82 (t, 1H), 7.38 (d, J = 5.0 Hz, 1H), 6.91 (s, 1H), 6.74 (s, 1H), 5.45 (s, 2H), 3.83 (s, 3H), 3.23–3.15 (m, 4H), 1.45 (s, 9H). |

| Compound | Boronic acid Starting material | Amine Starting material | LC/MS | NMR |
|---|---|---|---|---|
| 7-Methoxy-8-(3-methyl-1H-pyrazol-4-yl)-1-thiophen-3-yl-1,4-dihydro-chromeno[4,3-c]pyrazole-3-carboxylic acid tert-butyl-methyl-amide (71) | | | m/z = 478 [M + H]⁺ | ¹H-NMR (DMSO-d6): δ 7.97 (s, 1H), 7.81 (s, 1H), 7.41-7.32 (m, 2H), 6.77 (s, 1H), 6.67 (s, 1H), 5.37 (s, 2H), 3.77 (s, 3H), 3.18 (s, 3H), 1.95 (s, 3H), 1.45 (s, 9H). |
| 8-Isoxazol-4-yl-7-methoxy-1-thiophen-3-yl-1,4-dihydro-chromeno[4,3-c]pyrazole-3-carboxylic acid tert-butyl-methyl-amide (72) | | | m/z = 465 [M + H]⁺ | ¹H-NMR (DMSO-d6): δ 9.04 (s, 1H), 8.33 (s, 1H), 8.02 (s, 1H), 7.90 (s, 1H), 7.39 (d, 1H), 6.86 (d, 2H), 5.42 (s, 2H), 3.90 (s, 3H), 3.19 (s, 3H), 1.45 (s, 9H). |

-continued

| Compound | Boronic acid Starting material | Amine Starting material | LC/MS | NMR |
|---|---|---|---|---|
| 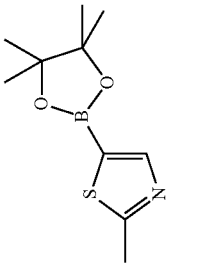 7-Methoxy-8-(2-methyl-thiazol-5-yl)-1-thiophen-3-yl-1,4-dihydro-chromeno[4,3-c]pyrazole-3-carboxylic acid tert-butyl-methyl-amide (73) | 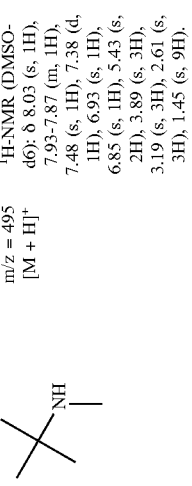 | 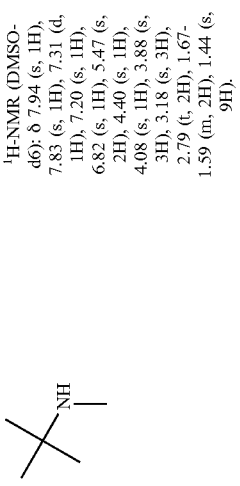 | m/z = 495 [M + H]+ | 1H-NMR (DMSO-d6): δ 8.03 (s, 1H), 7.93-7.87 (m, 1H), 7.48 (s, 1H), 7.38 (d, 1H), 6.93 (s, 1H), 6.85 (s, 1H), 5.43 (s, 2H), 3.89 (s, 3H), 3.19 (s, 3H), 2.61 (s, 3H), 1.45 (s, 9H). |
| 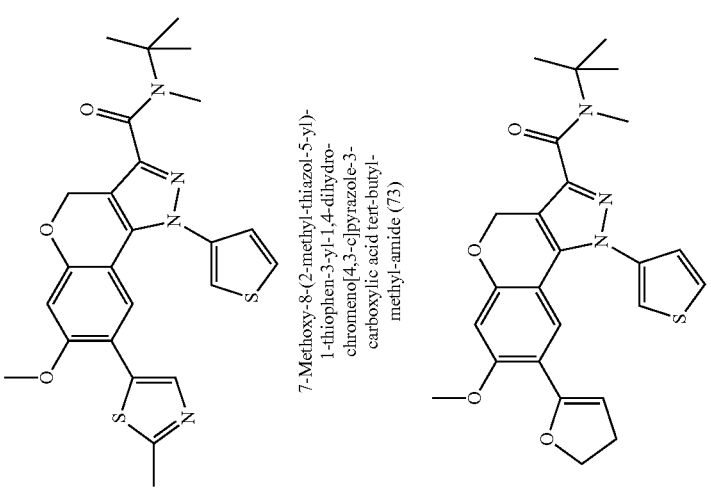 8-(4,5-Dihydro-furan-2-yl)-7-methoxy-1-thiophen-3-yl-1,4-dihydro-chromeno[4,3-c]pyrazole-3-carboxylic acid tert-butyl-methyl-amide (74) |  |  | | 1H-NMR (DMSO-d6): δ 7.94 (s, 1H), 7.83 (s, 1H), 7.31 (d, 1H), 7.20 (s, 1H), 6.82 (s, 1H), 5.47 (s, 2H), 4.40 (s, 1H), 4.08 (s, 1H), 3.88 (s, 3H), 3.18 (s, 3H), 2.79 (t, 2H), 1.67-1.59 (m, 2H), 1.44 (s, 9H). |

-continued

| Compound | Boronic acid Starting material | Amine Starting material | LC/MS | NMR |
|---|---|---|---|---|
| 7-Methoxy-8-(2-methyl-thiophen-3-yl)-1-thiophen-3-yl-1,4-dihydro-chromeno[4,3-c]pyrazole-3-carboxylic acid tert-butyl-methyl-amide (75) | (2-methylthiophen-3-yl pinacol boronate) | tert-butyl methylamine | m/z = 494 [M + H]+ | 1H-NMR (DMSO-d6): δ 7.97 (s, 1H), 7.81-7.76 (m, 1H), 7.34 (d, 1H), 7.21 (d, 1H), 6.82-6.77 (m, 2H), 6.59 (s, 1H), 5.40 (s, 2H), 3.75 (s, 3H), 3.18 (s, 3H), 2.12 (s, 3H), 1.45 (s, 9H). |
| 8-(2,4-Dimethyl-2H-pyrazol-3-yl)-7-methoxy-1-thiophen-3-yl-1,4-dihydro-chromeno[4,3-c]pyrazole-3-carboxylic acid tert-butyl-methyl-amide (76) | (1,4-dimethyl-1H-pyrazol-5-yl pinacol boronate) | tert-butyl methylamine | m/z = 492 [M + H]+ | 1H-NMR (DMSO-d6): δ 7.98 (s, 1H), 7.79 (s, 1H), 7.34 (d, 1H), 7.21 (s, 1H), 6.88 (s, 1H), 6.52 (s, 1H), 5.45 (d, 2H), 3.78 (s, 3H), 3.45 (s, 3H), 3.18 (s, 3H), 1.71 (s, 3H), 1.45 (s, 9H). |

-continued

| Compound | Boronic acid Starting material | Amine Starting material | LC/MS | NMR |
|---|---|---|---|---|
| (3,3-Dimethyl-morpholin-4-yl)-[7-methoxy-8-(1H-pyrazol-4-yl)-1-thiophen-3-yl-1,4-dihydro-chromeno[4,3-c]pyrazol-3-yl]-methanone (80) | | | m/z: 492 [M + H]+ | 1H NMR (400 MHz, MeOD) δ 7.85-7.80 (m, 3H), 7.79-7.73 (m, 1H), 7.34 (d, J = 5.2 Hz, 1H), 6.99 (s, 1H), 6.78 (s, 1H), 5.42 (s, 2H), 4.02-3.96 (m, 2H), 3.93 (s, 3H), 3.87-3.81 (m, 2H), 1.54 (s, 6H). |
| 7-Methoxy-8-thiazol-4-yl-1-thiophen-3-yl-1,4-dihydro-chromeno[4,3-c]pyrazole-3-carboxylic acid tert-butyl-methyl-amide (81) | | | m/z = 481 [M + H]+ | 1H-NMR (DMSO-d6): δ 8.99 (s, 1H), 7.95 (s, 2H), 7.85 (s, 1H), 7.82-7.79 (m, 1H), 7.32 (d, 1H), 6.86 (s, 1H), 5.76 (s, 1H), 5.41 (s, 2H), 4.09 (s, 5H), 3.93 (s, 3H), 3.19 (s, 3H), 1.45 (s, 9H). |

-continued

| Compound | Boronic acid Starting material | Amine Starting material | LC/MS | NMR |
|---|---|---|---|---|
| 7-Methoxy-8-(3-methyl-thiophen-2-yl)-1-thiophen-3-yl-1,4-dihydro-chromeno[4,3-c]pyrazole-3-carboxylic acid tert-butyl-methyl-amide (88) | (3-methylthiophen-2-yl boronic acid pinacol ester) | N-methyl-tert-butylamine | m/z = 494 [M + H]⁺ | ¹H-NMR (DMSO-d6): δ 7.97 (d, 1H), 7.81-7.76 (m, 1H), 7.35 (dd, 2H), 6.87 (d, 1H), 6.82 (s, 1H), 6.67 (s, 1H), 5.42 (s, 2H), 3.78 (s, 3H), 3.18 (s, 3H), 1.92 (s, 3H), 1.45 (s, 9H). |
| 8-(2,3-Dimethyl-3H-imidazol-4-yl)-7-methoxy-1-thiophen-3-yl-1,4-dihydro-chromeno[4,3-c]pyrazole-3-carboxylic acid tert-butyl-methyl-amide (92) | (1,2-dimethylimidazole-5-boronic acid pinacol ester) | N-methyl-tert-butylamine | m/z = 492 [M + H]⁺ | ¹H-NMR (DMSO-d6): δ 7.97-7.92 (m, 1H), 7.81-7.77 (m, 1H), 7.33 (d, 1H), 6.83 (s, 1H), 6.59 (s, 1H), 6.45 (s, 1H), 5.42 (s, 2H), 3.78 (s, 3H), 3.19 (d, 6H), 2.27 (s, 3H), 1.45 (s, 9H). |

-continued

| Compound | Boronic acid Starting material | Amine Starting material | LC/MS | NMR |
|---|---|---|---|---|
| 7-Methoxy-8-(5-methyl-thiophen-2-yl)-1-thiophen-3-yl-1,4-dihydro-chromeno[4,3-c]pyrazole-3-carboxylic acid tert-butyl-methyl-amide (93) | 5-methylthiophene-2-boronic acid pinacol ester | N-methyl-tert-butylamine | m/z = 494 [M + H]+ | 1H-NMR (DMSO-d6): δ 8.04-8.00 (m, 1H), 7.91-7.86 (m, 1H), 7.37 (d, 1H), 6.96 (s, 1H), 6.83-6.79 (m, 2H), 6.70 (d, 1H), 5.40 (s, 2H), 3.87 (s, 3H), 3.19 (s, 3H), 2.41 (s, 3H), 1.45 (s, 9H). |
| (3,3-Dimethyl-morpholin-4-yl)-[7-methoxy-8-(1-methyl-1H-pyrazol-3-yl)-1-thiophen-3-yl-1,4-dihydro-chromeno[4,3-c]pyrazol-3-yl]-methanone (94) | 1-methyl-1H-pyrazole-3-boronic acid pinacol ester | 3,3-dimethylmorpholine | m/z = 506 [M + H]+ | 1H-NMR (DMSO-d6): δ 7.96 (d, 1H), 7.82 (dd, 1H), 7.60 (d, 1H), 7.46 (s, 1H), 7.32 (d, 1H), 6.76 (s, 1H), 6.49 (d, 1H), 5.40 (s, 2H), 3.96 (t, 2H), 3.84 (s, 3H), 3.79-3.71 (m, 5H), 3.43 (s, 2H), 1.43 (s, 6H). |

| Compound | Boronic acid Starting material | Amine Starting material | LC/MS | NMR |
|---|---|---|---|---|
| (3,3-Dimethyl-morpholin-4-yl)-[7-methoxy-8-(3-methyl-1H-pyrazol-4-yl)-1-thiophen-3-yl-1,4-dihydro-chromeno[4,3-c]pyrazol-3-yl]-methanone (95) | | | m/z = 506 [M + H]⁺ | ¹H-NMR (DMSO-d6): δ 12.41 (s, 1H), 7.97 (s, 1H), 7.84-7.79 (m, 1H), 7.45-7.30 (m, 2H), 6.77 (s, 1H), 6.64 (s, 1H), 5.39 (s, 2H), 3.95 (t, 2H), 3.79-3.70 (m, 5H), 3.42 (s, 2H), 1.94 (s, 3H), 1.42 (s, 6H). |
| (3,3-Dimethyl-morpholin-4-yl)-[7-methoxy-8-(1-methyl-1H-pyrrol-3-yl)-1-thiophen-3-yl-1,4-dihydro-chromeno[4,3-c]pyrazol-3-yl]-methanone (98) | | | m/z = 505 [M + H]⁺ | ¹H-NMR (DMSO-d6): δ 8.02 (dd, 1H), 7.89 (dd, 1H), 7.37 (dd, 1H), 7.00 (s, 1H), 6.84 (s, 1H), 6.71 (s, 1H), 6.63 (t, 1H), 5.79 (t, 1H), 5.37 (s, 2H), 3.96 (t, 2H), 3.84 (s, 3H), 3.73 (t, 2H), 3.59 (s, 3H), 3.42 (s, 2H), 1.42 (s, 6H). |

| Compound | Boronic acid Starting material | Amine Starting material | LC/MS | NMR |
|---|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid (3-methyl-oxetan-3-yl)-amide (99) | (1-methyl-1H-pyrrol-3-yl boronic acid pinacol ester) | (3-methyl-3-aminooxetane) | m/z = 477 [M + H]+ | 1H-NMR (DMSO-d6): δ 8.89 (s, 1H), 8.08 (dd, 1H), 7.91 (dd, 1H), 7.41 (dd, 1H), 7.00 (t, 1H), 6.81 (s, 1H), 6.71 (s, 1H), 6.63 (t, 1H), 5.78 (t, 1H), 5.48 (s, 2H), 4.71 (d, 2H), 4.32 (d, 2H), 3.83 (s, 3H), 3.59 (s, 3H), 1.59 (s, 3H). |
| 7-Methoxy-8-(1-methyl-1H-pyrazol-3-yl)-1-thiophen-3-yl-1,4-dihydro-chromeno[4,3-c]pyrazole-3-carboxylic acid (3-methyl-oxetan-3-yl)-amide (100) | (1-methyl-1H-pyrazol-3-yl boronic acid pinacol ester) | (3-methyl-3-aminooxetane) | m/z = 478 [M + H]+ | 1H-NMR (DMSO-d6): δ 8.90 (s, 1H), 8.02 (dd, 1H), 7.85 (dd, 1H), 7.60 (d, 1H), 7.42 (s, 1H), 7.35 (dd, 1H), 6.76 (s, 1H), 6.49 (d, 1H), 5.52 (s, 2H), 4.71 (d, 2H), 4.32 (d, 2H), 3.84 (s, 3H), 3.77 (s, 3H), 1.60 (s, 3H). |

| Compound | Boronic acid Starting material | Amine Starting material | LC/MS | NMR |
|---|---|---|---|---|
| 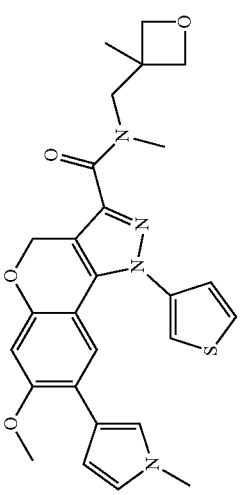 7-Methoxy-8-(1-methyl-1H-pyrrol-3-yl)-1-thiophen-3-yl-1,4-dihydro-chromeno[4,3-c]pyrazole-3-carboxylic acid methyl-(3-methyl-oxetan-3-ylmethyl)-amide (101) | 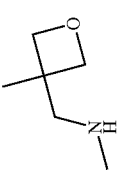 | 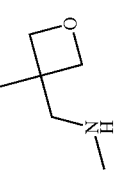 | m/z = 505 [M + H]⁺ | ¹H-NMR (DMSO-d6): δ 8.02 (d, 1H), 7.92-7.86 (m, 1H), 7.38 (dd, 1H), 7.00 (s, 1H), 6.88 (d, 1H), 6.71 (s, 1H), 6.63 (t, 1H), 5.80 (s, 1H), 5.39 (s, 2H), 4.54 (dd, 2H), 4.23-4.10 (m, 3H), 3.84 (s, 3H), 3.72 (s, 1H), 3.59 (s, 3H), 3.35 (d, 3H), 2.98 (s, 1H), 1.27 (d, 3H). |
| 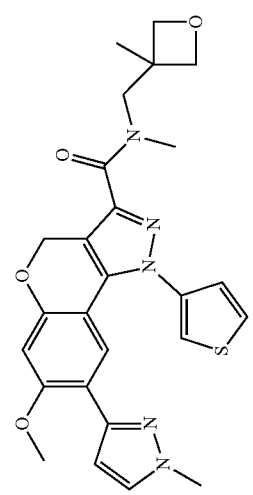 7-Methoxy-8-(1-methyl-1H-pyrazol-3-yl)-1-thiophen-3-yl-1,4-dihydro-chromeno[4,3-c]pyrazole-3-carboxylic acid methyl-(3-methyl-oxetan-3-ylmethyl)-amide (102) | 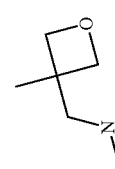 |  | m/z = 506 [M + H]⁺ | ¹H-NMR (DMSO-d6): δ 7.96 (d, 1H), 7.84 (s, 1H), 7.60 (s, 1H), 7.50 (d, 1H), 7.32 (dd, 1H), 6.76 (s, 1H), 6.50 (s, 1H), 5.43 (s, 2H), 4.55 (dd, 2H), 4.23-4.08 (m, 3H), 3.84 (s, 3H), 3.78 (s, 3H), 3.72 (s, 1H), 3.37 (s, 3H), 3.18 (d, 1H), 2.99 (s, 1H), 1.27 (d, 3H). |

| Compound | Boronic acid Starting material | Amine Starting material | LC/MS | NMR |
|---|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid methyl-oxetan-3-yl-amide (103) | (1-methyl-1H-pyrrole-3-boronic acid pinacol ester) | N-methyl-oxetan-3-amine | m/z = 477 [M + H]+ | 1H-NMR (DMSO-d6): δ 8.05 (d, 1H), 7.91 (dd, 1H), 7.40 (d, 1H), 7.00 (d, 1H), 6.87 (s, 1H), 6.71 (s, 1H), 6.64 (t, 1H), 5.94 (s, 0.5H), 5.80 (s, 1H), 5.38 (s, 2H), 5.22 (s, 0.5H), 4.71 (s, 4H), 3.84 (s, 3H), 3.59 (s, 3H), 3.41 (s, 1H), 3.24-3.12 (m, 2H). |
| 7-Methoxy-8-(1-methyl-1H-pyrazol-3-yl)-1-thiophen-3-yl-1,4-dihydro-chromeno[4,3-c]pyrazole-3-carboxylic acid methyl-oxetan-3-yl-amide (104) | (1-methyl-1H-pyrazole-3-boronic acid pinacol ester) | N-methyl-oxetan-3-amine | m/z = 478 [M + H]+ | 1H-NMR (DMSO-d6): δ 7.99 (d, 1H), 7.84 (dd, 1H), 7.60 (d, 1H), 7.49 (s, 1H), 7.35 (d, 1H), 6.76 (s, 1H), 6.50 (d, 1H), 5.94 (s, 0.5H), 5.42 (s, 2H), 5.22 (s, 0.5H), 4.72 (s, 4H), 4.09 (q, 1H), 3.84 (s, 3H), 3.78 (s, 3H), 3.41 (s, 1H), 3.18 (d, 5H). |

-continued

| Compound | Boronic acid Starting material | Amine Starting material | LC/MS | NMR |
|---|---|---|---|---|
| 8-Isothiazol-5-yl-7-methoxy-1-thiophen-3-yl-1,4-dihydro-chromeno[4,3-c]pyrazole-3-carboxylic acid tert-butyl-methyl-amide (105) | (isothiazol-5-yl pinacol boronate) | N-methyl-tert-butylamine | m/z = 481 [M + H]⁺ | ¹H-NMR (DMSO-d6): δ 8.45 (d, 1H), 8.08 (dd, 1H), 7.94 (dd, 1H), 7.42 (dd, 1H), 7.15 (s, 1H), 7.02 (d, 1H), 6.95 (s, 1H), 5.49 (s, 2H), 4.01 (s, 3H), 3.20 (s, 3H), 1.45 (s, 9H). |
| (3,3-Dimethyl-morpholin-4-yl)-[7-methoxy-8-(2-methyl-2H-pyrazol-3-yl)-1-thiophen-3-yl-1,4-dihydro-chromeno[4,3-c]pyrazol-3-yl]-methanone (108) | (1-methyl-pyrazol-5-yl pinacol boronate) | 3,3-dimethylmorpholine | m/z = 506 [M + H]⁺ | ¹H-NMR (DMSO-d6): δ 7.97 (dd, 1H), 7.79 (dd, 1H), 7.38-7.32 (m, 2H), 6.87 (s, 1H), 6.59 (s, 1H), 6.00 (d, 1H), 5.46 (s, 2H), 3.99-3.92 (m, 2H), 3.80 (s, 3H), 3.73 (t, 2H), 3.52 (s, 3H), 3.42 (s, 2H), 1.42 (s, 6H). |

| Compound | Boronic acid Starting material | Amine Starting material | LC/MS | NMR |
|---|---|---|---|---|
| 7-Methoxy-8-(2-methyl-2H-pyrazol-3-yl)-1-thiophen-3-yl-1,4-dihydro-chromeno[4,3-c]pyrazole-3-carboxylic acid (3-methyl-oxetan-3-yl)-amide (109) | (pyrazole pinacol boronate) | (3-methyl-3-aminooxetane) | m/z = 478 [M + H]⁺ | ¹H-NMR (DMSO-d6): δ 8.92 (s, 1H), 8.03 (dd, 1H), 7.81 (dd, 1H), 7.39-7.35 (m, 2H), 6.87 (s, 1H), 6.56 (s, 1H), 5.99 (d, 1H), 5.57 (s, 2H), 4.71 (d, 2H), 4.32 (d, 2H), 3.80 (s, 3H), 3.52 (s, 3H), 1.59 (s, 3H). |
| 7-Methoxy-8-(2-methyl-2H-pyrazol-3-yl)-1-thiophen-3-yl-1,4-dihydro-chromeno[4,3-c]pyrazole-3-carboxylic acid methyl-(3-methyl-oxetan-3-ylmethyl)-amide (110) | (pyrazole pinacol boronate) | (N-methyl-(3-methyloxetan-3-yl)methanamine) | m/z = 506 [M + H]⁺ | ¹H-NMR (DMSO-d6): δ 7.97 (dd, 1H), 7.80 (dd, 1H), 7.39-7.31 (m, 2H), 6.86 (s, 1H), 6.62 (d, 1H), 6.03-6.00 (d, 1H), 5.48 (s, 2H), 4.54 (dd, 2H), 4.25-4.09 (m, 3H), 3.80 (s, 3H), 3.72 (s, 1H), 3.52 (s, 3H), 3.36 (s, 2H), 2.99 (s, 1H), 1.26 (d, 3H). |

| Compound | Boronic acid Starting material | Amine Starting material | LC/MS | NMR |
|---|---|---|---|---|
| 7-Methoxy-8-(2-methyl-2H-pyrazol-3-yl)-1-thiophen-3-yl-1,4-dihydro-chromeno[4,3-c]pyrazole-3-carboxylic acid (3-hydroxymethyl-oxetan-3-yl)-amide (111) | 1-methyl-pyrazole-5-boronic acid pinacol ester | 3-amino-3-(hydroxymethyl)oxetane | m/z = 494 [M + H]⁺ | ¹H-NMR (DMSO-d6): δ 8.73 (s, 1H), 8.02 (dd, 1H), 7.82 (dd, 1H), 7.37 (dd, 2H), 6.87 (s, 1H), 6.56 (s, 1H), 5.99 (d, 1H), 5.56 (s, 2H), 5.15 (s, 1H), 4.68 (d, 2H), 4.52 (d, 2H), 3.80 (s, 3H), 3.69 (s, 2H), 3.52 (s, 3H). |
| (3,3-Dimethyl-morpholin-4-yl)-[7-methoxy-1-thiophen-3-yl-8-(1,2,5-trimethyl-1H-pyrrol-3-yl)-1,4-dihydro-chromeno[4,3-c]pyrazol-3-yl]-methanone (120) | 1,2,5-trimethylpyrrole-3-boronic acid pinacol ester | 3,3-dimethylmorpholine | m/z: 533 [M + H]⁺ | ¹H NMR (400 MHz, CDCl₃) δ 7.50 (dd, J = 3.2, 1.4 Hz, 1H), 7.44 (dd, J = 5.1, 3.2 Hz, 1H), 7.24 (dd, J = 5.1, 1.4 Hz, 1H), 6.81 (s, 1H), 6.66 (s, 1H), 5.83 (s, 1H), 5.47 (s, 2H), 4.11-4.05 (m, 2H), 3.89-3.83 (m, 2H), 3.82 (s, 3H), 3.50 (s, 2H), 3.39 (s, 3H), 2.22 (s, 3H), 2.01 (s, 3H), 1.27 (s, 6H). |

| Compound | Boronic acid Starting material | Amine Starting material | LC/MS | NMR |
|---|---|---|---|---|
| (3,3-Dimethyl-morpholin-4-yl)-[7-methoxy-1-thiophen-3-yl-8-(1,3,5-trimethyl-1H-pyrazol-4-yl)-1,4-dihydro-chromeno[4,3-c]pyrazol-3-yl]-methanone (121) | | | m/z: 534 [M + H]⁺ | ¹H NMR (400 MHz, CDCl₃) δ 7.49 (dd, J = 3.1, 1.2 Hz, 1H), 7.44 (dd, J = 5.0, 3.3 Hz, 1H), 7.21 (dd, J = 5.1, 1.2 Hz, 1H), 6.68 (s, 1H), 6.63 (s, 1H), 5.51 (s, 2H), 4.12-4.05 (m, 2H), 3.90-3.84 (m, 2H), 3.80 (s, 3H), 3.74 (s, 3H), 3.50 (s, 2H), 2.01 (d, J = 5.5 Hz, 6H), 1.55 (s, 6H). |
| (3,3-Dimethyl-morpholin-4-yl)-[8-(2,5-dimethyl-2H-pyrazol-3-yl)-7-methoxy-1-thiophen-3-yl-1,4-dihydro-chromeno[4,3-c]pyrazol-3-yl]-methanone (122) | | | m/z: 520 [M + H]⁺ | ¹H NMR (400 MHz, CDCl₃) δ 7.50-7.47 (m, 1H), 7.47-7.44 (m, 1H), 7.19 (dd, J = 5.0, 1.5 Hz, 1H), 6.72 (s, 1H), 6.68 (s, 1H), 5.83 (s, 1H), 5.53 (s, 2H), 4.09 (dd, J = 8.4, 3.0 Hz, 2H), 3.88-3.83 (m, 2H), 3.82 (s, 3H), 3.56 (s, 3H), 3.49 (s, 2H), 2.27 (s, 3H), 1.54 (s, 6H). |

-continued

| Compound | Boronic acid Starting material | Amine Starting material | LC/MS | NMR |
|---|---|---|---|---|
| (3,3-Dimethyl-morpholin-4-yl)-[8-(1,3-dimethyl-1H-pyrazol-4-yl)-7-methoxy-1-thiopheno-1,4-dihydro-chromeno[4,3-c]pyrazol-3-yl]-methanone (123) | | | m/z: 520 [M + H]⁺ | ¹H NMR (400 MHz, CDCl₃) δ 7.51 (dd, J = 3.2, 1.3 Hz, 1H), 7.46 (dd, J = 5.1, 3.3 Hz, 1H), 7.37 (s, 1H), 7.22 (dd, J = 5.1, 1.3 Hz, 1H), 6.84 (s, 1H), 6.67 (s, 1H), 5.50 (s, 2H), 4.13-4.06 (m, 2H), 3.89-3.82 (m, 8H), 3.50 (s, 2H), 2.03 (s, 3H), 1.55 (s, 6H). |
| (3,3-dimethyl-morpholin-4-yl)-[8-(1,5-dimethyl-1H-pyrazol-4-yl)-7-methoxy-1-thiophen-3-yl-1,4-dihydro-chromeno[4,3-c]pyrazol-3-yl]-methanone (124) | | | m/z: 520 [M + H]⁺ | ¹H NMR (400 MHz, CDCl₃) δ 7.53-7.49 (m, 1H), 7.49-7.44 (m, 1H), 7.35 (s, 1H), 7.23 (d, J = 5.0 Hz, 1H), 6.70 (s, 1H), 6.67 (s, 1H), 5.50 (s, 2H), 4.13-4.05 (m, 2H), 3.90-3.83 (m, 2H), 3.81 (d, J = 8.9 Hz, 6H), 3.50 (s, 2H), 2.07 (s, 3H), 1.55 (s, 6H). |

| Compound | Boronic acid Starting material | Amine Starting material | LC/MS | NMR |
|---|---|---|---|---|
| (3,3-Dimethyl-morpholin-4-yl)-[7-methoxy-8-(1-methyl-1H-pyrrol-2-yl)-1-thiophen-3-yl-1,4-dihydro-chromeno[4,3-c]pyrazol-3-yl]-methanone (125) | | | m/z: 505 [M + H]⁺ | ¹H NMR (400 MHz, CDCl₃) δ 7.62 (d, J = 7.3 Hz, 1H), 7.51-7.42 (m, 2H), 7.22 (d, J = 5.0 Hz, 1H), 6.83 (s, 1H), 6.67 (s, 1H), 6.17-6.12 (m, 1H), 5.96-5.89 (m, 1H), 5.51 (s, 2H), 4.15-4.05 (m, 2H), 3.91-3.84 (m, 2H), 3.82 (s, 3H), 3.50 (s, 2H), 3.41 (s, 3H), 1.55 (s, 6H). |
| (3,3-Dimethyl-morpholin-4-yl)-[8-(3,5-dimethyl-1H-pyrazol-4-yl)-7-methoxy-1-thiophen-3-yl-1,4-dihydro-chromeno[4,3-c]pyrazol-3-yl]-methanone (126) | | | m/z: 520 [M + H]⁺ | ¹H NMR (400 MHz, MeOD) δ 7.79-7.74 (m, 1H), 7.66 (dd, J = 5.0, 3.2 Hz, 1H), 7.27 (d, J = 5.1 Hz, 1H), 6.76 (s, 1H), 6.58 (s, 1H), 5.42 (s, 2H), 4.01-3.95 (m, 2H), 3.86-3.80 (m, 2H), 3.79 (s, 3H), 3.51 (s, 2H), 2.01 (s, 6H), 1.53 (s, 6H). |

-continued

| Compound | Boronic acid Starting material | Amine Starting material | LC/MS | NMR |
|---|---|---|---|---|
| 7-Methoxy-8-(1-methyl-1H-imidazol-4-yl)-1-thiophen-3-yl-1,4-dihydro-chromeno[4,3-c]pyrazole-3-carboxylic acid tert-butyl-methyl-amide (129) | 1-methyl-1H-imidazole-4-boronic acid pinacol ester | N-methyl-tert-butylamine | m/z = 478 [M + H]$^+$ | $^1$H-NMR (DMSO-d6): δ 7.89 (dd, 1H), 7.79 (dd, 1H), 7.74 (s, 1H), 7.47 (s, 1H), 7.39 (d, 1H), 7.30 (dd, 1H), 6.76 (s, 1H), 5.33 (s, 2H), 3.89 (s, 3H), 3.64 (s, 3H), 3.18 (s, 3H), 1.45 (s, 9H). |
| 7-Methoxy-8-(3-methyl-3H-imidazol-4-yl)-1-thiophen-3-yl-1,4-dihydro-chromeno[4,3-c]pyrazole-3-carboxylic acid tert-butyl-methyl-amide (130) | 1-methyl-1H-imidazole-5-boronic acid pinacol ester | N-methyl-tert-butylamine | m/z = 478 [M + H]$^+$ | $^1$H-NMR (DMSO-d6): δ 7.95 (d, 1H), 7.79 (dd, 1H), 7.59 (s, 1H), 7.35-7.32 (m, 1H), 6.84 (s, 1H), 6.62 (d, 2H), 5.42 (s, 2H), 3.79 (s, 3H), 3.35 (s, 3H), 3.18 (s, 3H), 1.45 (s, 9H). |

| Compound | Boronic acid Starting material | Amine Starting material | LC/MS | NMR |
|---|---|---|---|---|
| 7-Methoxy-8-oxazol-2-yl-1-thiophen-3-yl-1,4-dihydro-chromeno[4,3-c]pyrazole-3-carboxylic acid tert-butyl-methyl-amide (132) | (oxazol-2-yl pinacol boronate) | (N-methyl-tert-butylamine) | m/z = 465 [M + H]⁺ | ¹H-NMR (DMSO-d6): δ 8.07 (d, 1H), 7.98 (dd, 1H), 7.83 (dd, 1H), 7.37-7.33 (m, 2H), 7.24 (d, 1H), 6.88 (s, 1H), 5.46 (s, 2H), 3.87 (s, 3H), 3.19 (s, 3H), 1.45 (s, 9H). |
| 7-Methoxy-8-(1-methyl-1,2,5,6-tetrahydro-pyridin-3-yl)-1-thiophen-3-yl-1,4-dihydro-chromeno[4,3-c]pyrazole-3-carboxylic acid tert-butyl-methyl-amide (134) | (1-methyl-1,2,5,6-tetrahydropyridine-3-boronic acid pinacol ester) | (N-methyl-tert-butylamine) | m/z = 493 [M + H]⁺ | ¹H-NMR (DMSO-d6): δ 7.96 (dd, 1H), 7.83 (dd, 1H), 7.33 (dd, 1H), 6.68 (s, 1H), 6.54 (s, 1H), 5.67-5.63 (m, 1H), 5.36 (s, 2H), 3.75 (s, 3H), 3.17 (s, 3H), 2.85 (d, 2H), 2.38 (t, 2H), 2.22 (s, 3H), 2.14 (d, 2H), 1.44 (s, 9H). |

-continued

| Compound | Boronic acid Starting material | Amine Starting material | LC/MS | NMR |
|---|---|---|---|---|
| 7-Methoxy-8-(3-methyl-1H-pyrazol-4-yl)-1-thiophen-3-yl-1,4-dihydro-chromeno[4,3-c]pyrazole-3-carboxylic acid (tetrahydro-furan-3-yl)-amide (135) | 3-methyl-1H-pyrazol-4-yl pinacol boronate | 3-aminotetrahydrofuran | m/z = 478 [M + H]$^+$ | $^1$H-NMR (DMSO-d6): δ 12.45 (s, 1H), 8.43 (d, 1H), 8.03 (dd, 1H), 7.82 (dd, 1H), 7.37 (dd, 2H), 6.76 (s, 1H), 6.62 (s, 1H), 5.52 (s, 2H), 4.49-4.40 (m, 1H), 3.86-3.67 (m, 6H), 3.56 (dd, 1H), 2.17-2.06 (m, 1H), 2.02-1.91 (m, 4H). |
| 7-Methoxy-8-(1-methyl-1H-pyrrol-3-yl)-1-thiophen-3-yl-1,4-dihydro-chromeno[4,3-c]pyrazole-3-carboxylic acid (3-hydroxy-cyclobutyl)-amide (136) | 1-methyl-1H-pyrrol-3-yl pinacol boronate | 3-aminocyclobutanol | m/z = 477 [M + H]$^+$ | $^1$H-NMR (DMSO-d6): δ 8.50 (dd, 1H), 8.09-8.03 (m, 1H), 7.90 (dd, 1H), 7.40 (d, 1H), 7.00 (s, 1H), 6.82 (d, 1H), 6.70 (s, 1H), 6.63 (s, 1H), 5.78 (s, 1H), 5.48 (s, 2H), 4.97 (dd, 1H), 4.53-4.43 (m, 1H), 4.32-4.24 (m, 1H), 3.89-3.76 (m, 4H), 3.59 (s, 3H), 2.37-2.29 (m, 1H), 2.15-2.07 (m, 1H), 2.03-1.91 (m, 1H). |

| Compound | Boronic acid Starting material | Amine Starting material | LC/MS | NMR |
|---|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid (3-hydroxy-cyclobutyl)-amide (137) | (1-methyl-1H-pyrazol-3-yl pinacol boronate) | (3-aminocyclobutanol) | m/z = 478 [M + H]+ | 1H-NMR (DMSO-d6): δ 8.50 (dd, 1H), 8.00 (s, 1H), 7.88-7.80 (m, 1H), 7.60 (d, 1H), 7.43 (d, 1H), 7.34 (d, 1H), 6.75 (s, 1H), 6.49 (d, 1H), 5.52 (s, 2H), 4.99 (s, 1H), 4.54-4.43 (m, 1H), 4.33-4.24 (m, 1H), 3.94-3.70 (m, 7H), 2.39-2.28 (m, 1H), 2.16-2.06 (m, 1H), 2.04-1.91 (m, 1H). |
| 7-Methoxy-8-(3-methyl-1H-pyrazol-4-yl)-1-thiophen-3-yl-1,4-dihydro-chromeno[4,3-c]pyrazole-3-carboxylic acid (3-hydroxy-cyclobutyl)-amide (138) | (3-methyl-1H-pyrazol-4-yl pinacol boronate) | (3-aminocyclobutanol) | m/z = 478 [M + H]+ | 1H-NMR (DMSO-d6): δ 8.50 (dd, 1H), 8.06-8.01 (m, 1H), 7.82 (dd, 1H), 7.40-7.35 (m, 2H), 6.76 (s, 1H), 6.62 (d, 1H), 5.51 (d, 2H), 4.97 (s, 1H), 4.51-4.44 (m, 1H), 4.31-4.23 (m, 1H), 3.90-3.74 (m, 5H), 2.37-2.29 (m, 1H), 2.15-2.06 (m, 1H), 2.02-1.90 (m, 4H). |

-continued

| Compound | Boronic acid Starting material | Amine Starting material | LC/MS | NMR |
|---|---|---|---|---|
| [7-Methoxy-8-(1-methyl-1H-pyrazol-3-yl)-1-thiophen-3-yl-1,4-dihydro-chromeno[4,3-c]pyrazol-3-yl]-(3-trifluoromethyl-morpholin-4-yl)-methanone (144) | 1-methyl-1H-pyrazole-3-boronic acid pinacol ester | 3-(trifluoromethyl)morpholine | m/z: 546 [M + H]+ | 1H NMR (400 MHz, CDCl3) δ 7.61-7.48 (m, 3H), 7.32 (d, J = 2.0 Hz, 1H), 6.66 (s, 1H), 6.54 (d, J = 1.9 Hz, 1H), 6.36 (s, 1H), 5.69-5.49 (m, 2H), 5.31 (d, J = 13.8 Hz, 1H), 4.44-4.22 (m, 2H), 4.04 (dd, J = 43.8, 13.6 Hz, 1H), 3.90 (s, 3H), 3.88 (s, 3H), 3.84-3.70 (m, 1H), 3.62 (dd, J = 24.9, 12.6 Hz, 1H), 3.36 (t, J = 14.2 Hz, 1H). |
| 7-Methoxy-8-((E)-3-methoxy-propenyl)-1-thiophen-3-yl-1,4-dihydro-chromeno[4,3-c]pyrazole-3-carboxylic acid tert-butyl-methyl-amide (147) | (E)-3-methoxypropenyl boronic acid pinacol ester | N-methyl-tert-butylamine | 468 [M + H]+ | 1H-NMR (DMSO-d6): δ 7.99 (dd, 1H), 7.85 (dd, 1H), 7.35 (dd, 1H), 6.80 (s, 1H), 6.71 (s, 1H), 6.61 (d, 1H), 5.63 (dt, 1H), 5.37 (d, 2H), 3.93 (dd, 2H), 3.80 (s, 3H), 3.23 (s, 3H), 3.18 (s, 3H), 1.44 (s, 9H). |

| Compound | Boronic acid Starting material | Amine Starting material | LC/MS | NMR |
|---|---|---|---|---|
| 8-(5,6-Dihydro-4H-pyran-2-yl)-7-methoxy-1-thiophen-3-yl-1,4-dihydro-chromeno[4,3-c]pyrazole-3-carboxylic acid tert-butyl-methyl-amide (148) | (3,4-dihydro-2H-pyran-6-yl boronic acid pinacol ester) | (N-methyl-tert-butylamine) | m/z = 480 [M + H]⁺ | ¹H-NMR (DMSO-d6): δ 7.92 (dd, 1H), 7.82 (dd, 1H), 7.30 (dd, 1H), 6.93 (s, 1H), 6.69 (s, 1H), 5.38 (s, 2H), 5.29 (t, 1H), 3.89 (t, 2H), 3.78 (s, 3H), 3.18 (s, 3H), 2.12-2.03 (m, 2H), 1.74 (quintet, 2H), 1.44 (s, 9H). |
| 8-Cyclopent-1-enyl-7-methoxy-1-thiophen-3-yl-1,4-dihydro-chromeno[4,3-c]pyrazole-3-carboxylic acid tert-butyl-methyl-amide (149) | (cyclopentenyl boronic acid pinacol ester) | (N-methyl-tert-butylamine) | m/z = 464 [M + H]⁺ | ¹H-NMR (DMSO-d6): δ 7.97 (dd, 1H), 7.85 (dd, 1H), 7.34 (dd, 1H), 6.71 (s, 1H), 6.68 (s, 1H), 6.28 (s, 1H), 5.38 (s, 2H), 3.82 (s, 3H), 3.18 (s, 3H), 2.46-2.38 (m, 2H), 2.29-2.19 (m, 2H), 1.76 (quintet, 2H), 1.44 (s, 9H). |

-continued

| Compound | Boronic acid Starting material | Amine Starting material | LC/MS | NMR |
|---|---|---|---|---|
| 8-(1,3-Dimethyl-1H-pyrazol-4-yl)-7-methoxy-1-thiophen-3-yl-1,4-dihydro-chromeno[4,3-c]pyrazole-3-carboxylic acid tert-butyl-methyl-amide (150) | 1,3-dimethylpyrazole-4-boronic acid pinacol ester | N-methyl-tert-butylamine | m/z = 492 [M + H]⁺ | ¹H-NMR (DMSO-d6): δ 7.97 (dd, 1H), 7.80 (dd, 1H), 7.56 (s, 1H), 7.33 (dd, 1H), 6.77 (s, 1H), 6.72 (s, 1H), 5.37 (s, 2H), 3.77 (s, 3H), 3.73 (s, 3H), 3.17 (s, 3H), 1.84 (s, 3H), 1.44 (s, 9H). |
| 8-(2,5-Dihydro-furan-3-yl)-7-methoxy-1-thiophen-3-yl-1,4-dihydro-chromeno[4,3-c]pyrazole-3-carboxylic acid tert-butyl-methyl-amide (151) | 2,5-dihydrofuran-3-boronic acid pinacol ester | N-methyl-tert-butylamine | m/z = 466 [M + H]⁺ | ¹H-NMR (DMSO-d6): δ 7.98 (dd, 1H), 7.88 (dd, 1H), 7.34 (dd, 1H), 6.77 (s, 1H), 6.44 (s, 1H), 6.34 (t, 1H), 5.41 (s, 2H), 4.69-4.62 (m, 2H), 4.49-4.41 (m, 2H), 3.85 (s, 3H), 3.18 (s, 3H), 1.44 (s, 9H). |

| Compound | Boronic acid Starting material | Amine Starting material | LC/MS | NMR |
|---|---|---|---|---|
| 8-(1-Ethoxymethyl-1H-[1,2,3]triazol-4-yl)-7-methoxy-1-thiophen-3-yl-1,4-dihydro-chromeno[4,3-c]pyrazole-3-carboxylic acid tert-butyl-methyl-amide (152) | Li+ trimethylene borate ester of 1-ethoxymethyl-1H-[1,2,3]triazole | tert-butyl(methyl)amine | m/z = 523 [M + H]+ | 1H-NMR (DMSO-d6): δ 7.92 (dd, 1H), 7.76 (dd, 1H), 7.60 (s, 1H), 7.30 (dd, 1H), 6.91 (s, 1H), 6.67 (s, 1H), 5.48 (s, 2H), 5.45 (s, 2H), 3.79 (s, 3H), 3.27 (q, 2H), 3.18 (s, 3H), 1.45 (s, 9H), 0.92 (t, 3H). |
| 7-Methoxy-8-(1-methyl-1H-[1,2,3]triazol-4-yl)-1-thiophen-3-yl-1,4-dihydro-chromeno[4,3-c]pyrazole-3-carboxylic acid tert-butyl-methyl amide (153) | Li+ trimethylene borate ester of 1-methyl-1H-[1,2,3]triazole | tert-butyl(methyl)amine | m/z = 478 [M + H]+ | 1H-NMR (DMSO-d6): δ 8.21 (s, 1H), 7.95 (dd, 1H), 7.82 (dd, 1H), 7.72 (s, 1H), 7.33 (dd, 1H), 6.84 (s, 1H), 5.39 (s, 2H), 4.04 (s, 3H), 3.91 (s, 3H), 3.19 (s, 3H), 1.45 (s, 9H). |

-continued

| Compound | Boronic acid Starting material | Amine Starting material | LC/MS | NMR |
|---|---|---|---|---|
| (2,8-Dioxa-5-aza-spiro[3.5]non-5-yl)-[7-methoxy-8-(1-methyl-1H-pyrazol-3-yl)-1-thiophen-3-yl-1,4-dihydro-chromeno[4,3-c]pyrazol-3-yl]-methanone (154) | | | m/z: 520 [M + H]+ | 1H NMR (400 MHz, CDCl3) δ 7.58 (d, J = 2.0 Hz, 1H), 7.53–7.49 (m, 2H), 7.32 (d, J = 2.0 Hz, 1H), 7.27 (s, 1H), 6.67 (s, 1H), 6.54 (d, J = 2.1 Hz, 1H), 5.54 (s, 2H), 4.90 (s, 2H), 4.57 (d, J = 6.6 Hz, 2H), 4.17 (s, 3H), 3.90 (s, 3H), 3.88 (s, 3H), 3.63 (t, J = 4.5 Hz, 2H). |
| 1-{4-[7-Methoxy-8-(1-methyl-1H-pyrrol-3-yl)-1-thiophen-3-yl-1,4-dihydro-chromeno[4,3-c]pyrazole-3-carbonyl]-piperazin-1-yl}-ethanone (155) | | | m/z: 518 [M + H]+ | 1H NMR (400 MHz, CDCl3) δ 7.59–7.53 (m, 2H), 7.30 (d, J = 1.5 Hz, 1H), 7.06 (s, 1H), 7.01 (s, 1H), 6.65 (s, 1H), 6.55 (t, J = 2.4 Hz, 1H), 6.04 (s, 1H), 5.55 (s, 2H), 4.40–4.25 (m, 2H), 3.89 (s, 3H), 3.86–3.70 (m, 4H), 3.67 (s, 3H), 3.59 (s, 2H), 2.16 (d, J = 7.8 Hz, 3H). |

| Compound | Boronic acid Starting material | Amine Starting material | LC/MS | NMR |
|---|---|---|---|---|
| 4-[7-Methoxy-8-(1-methyl-1H-pyrazol-3-yl)-1-thiophen-3-yl-1,4-dihydro-chromeno[4,3-c]pyrazole-3-carbonyl]-3,3-dimethyl-piperazine-1-carboxylic acid tert-butyl ester (156) | 1-methyl-3-(4,4,5,5-tetramethyl-1,3,2-dioxaborolan-2-yl)-1H-pyrazole | tert-butyl 3,3-dimethylpiperazine-1-carboxylate | m/z: 605 [M + H]+ | 1H NMR (400 MHz, CDCl3) δ 7.55 (dd, J = 3.2, 1.3 Hz, 1H), 7.53-7.47 (m, 2H), 7.32 (d, J = 2.2 Hz, 1H), 7.29-7.24 (m, 1H), 6.67 (s, 1H), 6.54 (d, J = 2.2 Hz, 1H), 5.52 (s, 2H), 4.35-4.26 (m, 2H), 3.89 (s, 3H), 3.88 (s, 3H), 3.61-3.47 (m, 4H), 1.61 (s, 6H), 1.50 (s, 9H). |

| Compound | Boronic acid Starting material | Amine Starting material | LC/MS | NMR |
|---|---|---|---|---|
| 4-[7-Methoxy-8-(1-methyl-1H-pyrrol-3-yl)-1-thiophen-3-yl-1,4-dihydro-chromeno[4,3-c]pyrazole-3-carbonyl]-3,3-dimethyl-piperazine-1-carboxylic acid tert-butyl ester (157) | (1-methyl-1H-pyrrol-3-yl boronic acid pinacol ester) | (tert-butyl 3,3-dimethylpiperazine-1-carboxylate) | m/z: 604 [M + H]⁺ | ¹H NMR (400 MHz, CDCl₃) δ 7.58-7.51 (m, 2H), 7.28 (d, J = 1.5 Hz, 1H), 7.05 (s, 1H), 7.00 (t, J = 1.9 Hz, 1H), 6.64 (s, 1H), 6.55 (t, J = 2.5 Hz, 1H), 6.04 (s, 1H), 5.49 (s, 2H), 4.34-4.26 (m, 2H), 3.90 (s, 3H), 3.66 (s, 3H), 3.61-3.47 (m, 4H), 1.61 (s, 6H), 1.50 (s, 9H). |

| Compound | Boronic acid Starting material | Amine Starting material | LC/MS | NMR |
|---|---|---|---|---|
| 4-[7-Methoxy-8-(1-methyl-1H-pyrazol-3-yl)-1-thiophen-3-yl-1,4-dihydro-chromeno[4,3-c]pyrazole-3-carbonyl]-4,7-diaza-spiro[2.5]octane-7-carboxylic acid tert-butyl ester (158) | 1-methyl-1H-pyrazole-3-boronic acid pinacol ester | tert-butyl 4,7-diazaspiro[2.5]octane-7-carboxylate | m/z: 603 [M + H]⁺ | ¹H NMR (400 MHz, CDCl₃) δ 7.59-7.48 (m, 3H), 7.32 (d, J = 2.1 Hz, 1H), 7.28-7.25 (m, 1H), 6.66 (s, 1H), 6.54 (d, J = 2.1 Hz, 1H), 5.54 (s, 2H), 4.42-4.23 (m, 2H), 3.90 (s, 3H), 3.88 (s, 4H), 3.63-3.41 (m, 4H), 1.61 (s, 3H), 1.48 (s, 9H). |
| [7-Methoxy-8-(1-methyl-1H-pyrazol-3-yl)-1-thiophen-3-yl-1,4-dihydro-chromeno[4,3-c]pyrazol-3-yl]-(2,2,4-trimethyl-piperazin-1-yl)-methanone (159) | 1-methyl-1H-pyrazole-3-boronic acid pinacol ester | 1,3,3-trimethylpiperazine | m/z: 519 [M + H]⁺ | ¹H NMR (400 MHz, CDCl₃) δ 7.56 (dd, J = 3.2, 1.4 Hz, 1H), 7.52 (s, 1H), 7.48 (dd, J = 5.1, 3.2 Hz, 1H), 7.32 (d, J = 2.2 Hz, 1H), 7.27 (d, J = 1.3 Hz, 1H), 6.66 (s, 1H), 6.53 (d, J = 2.2 Hz, 1H), 5.48 (s, 2H), 4.05-3.97 (m, 2H), 3.89 (s, 3H), 3.88 (s, 3H), 2.56-2.51 (m, 2H), 2.33-2.29 (m, 5H), 1.59 (s, 6H). |

-continued

| Compound | Boronic acid Starting material | Amine Starting material | LC/MS | NMR |
|---|---|---|---|---|
| [7-Methoxy-8-(1-methyl-1H-pyrrol-3-yl)-1-thiophen-3-yl-1,4-dihydro-chromeno[4,3-c]pyrazol-3-yl]-(2,2,4-trimethyl-piperazin-1-yl)-methanone (160) | 1-methyl-pyrrole-3-boronic acid pinacol ester | 1,3,3-trimethylpiperazine | m/z: 518 [M + H]$^+$ | $^1$H NMR (400 MHz, CDCl$_3$) δ 7.56 (dd, J = 3.2, 1.4 Hz, 1H), 7.52 (dd, J = 5.0, 3.3 Hz, 2H), 7.06 (s, 1H), 7.00 (t, J = 1.9 Hz, 1H), 6.64 (s, 1H), 6.55 (t, J = 2.5 Hz, 1H), 6.06-6.01 (m, 1H), 5.46 (s, 2H), 4.03-3.97 (m, 2H), 3.90 (s, 3H), 3.66 (s, 3H), 2.55-2.49 (m, 2H), 2.30 (s, 5H), 1.59 (s, 6H). |
| 7-Methoxy-8-(1-methyl-1H-pyrrol-3-yl)-1-thiophen-3-yl-1,4-dihydro-chromeno[4,3-c]pyrazole-3-carboxylic acid (3-hydroxy-oxetan-3-ylmethyl)-amide (164) | 1-methyl-pyrrole-3-boronic acid pinacol ester | 3-(aminomethyl)oxetan-3-ol | m/z = 493 [M + H]$^+$ | $^1$H-NMR (DMSO-d6): δ 8.31 (t, 1H), 8.08 (dd, 1H), 7.91 (dd, 1H), 7.41 (dd, 1H), 7.00 (t, 1H), 6.81 (s, 1H), 6.71 (s, 1H), 6.63 (t, 1H), 5.89 (s, 1H), 5.80-5.75 (m, 1H), 5.51 (s, 2H), 4.48 (d, 2H), 4.38 (d, 2H), 3.84 (s, 3H), 3.61-3.53 (m, 5H). |

-continued

| Compound | Boronic acid Starting material | Amine Starting material | LC/MS | NMR |
|---|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid (3-hydroxy-oxetan-3-ylmethyl)-amide (165) | 1-methyl-1H-pyrazole-3-boronic acid pinacol ester | (3-aminomethyl)-3-hydroxyoxetane (cyclobutane variant shown) | 494 [M + H]+ | 1H-NMR (DMSO-d6): δ 8.32 (t, 1H), 8.03 (dd, 1H), 7.85 (dd, 1H), 7.60 (d, 1H), 7.42 (s, 1H), 7.35 (dd, 1H), 6.76 (s, 1H), 6.49 (d, 1H), 5.88 (s, 1H), 5.55 (s, 2H), 4.48 (d, 2H), 4.38 (d, 2H), 3.84 (s, 3H), 3.77 (s, 3H), 3.56 (d, 2H). |
| (2,2-Dimethyl-piperazin-1-yl)-[7-methoxy-8-(1-methyl-1H-pyrazol-3-yl)-1-thiophen-3-yl-1,4-dihydro-chromeno[4,3-c]pyrazol-3-yl]-methanone (169) | 1-methyl-1H-pyrazole-3-boronic acid pinacol ester | tert-butyl 3,3-dimethylpiperazine-1-carboxylate | m/z: 505 [M + H]+ | 1H NMR (400 MHz, CDCl3) δ 8.39 (s, 1H), 7.63-7.36 (m, 2H), 7.35-7.31 (m, 2H), 6.67 (s, 1H), 6.54 (s, 1H), 5.50 (s, 2H), 4.13 (s, 1H), 3.89 (s, 3H), 3.77-3.62 (m, 1H), 3.21 (s, 1H), 3.16-3.05 (m, 2H), 2.94 (s, 1H), 1.64 (s, 3H), 1.51-1.42 (m, 6H). |

| Compound | Boronic acid Starting material | Amine Starting material | LC/MS | NMR |
|---|---|---|---|---|
| (2,2-Dimethyl-piperazin-1-yl)-[7-methoxy-8-(1-methyl-1H-pyrrol-3-yl)-1-thiophen-3-yl-1,4-dihydro-chromeno[4,3-c]pyrazol-3-yl]-methanone (170) | 1-methyl-1H-pyrrol-3-yl pinacol boronate | N-Boc-2,2-dimethylpiperazine | m/z: 504 [M + H]⁺ | ¹H NMR (400 MHz, CDCl₃) δ 7.54 (dd, J = 8.0, 2.4 Hz, 2H), 7.27 (d, J = 5.0 Hz, 1H), 7.05 (s, 1H), 7.00 (s, 1H), 6.64 (s, 1H), 6.55 (d, J = 2.2 Hz, 1H), 6.03 (d, J = 1.7 Hz, 1H), 5.48 (s, 2H), 4.28 (s, 2H), 3.89 (s, 3H), 3.66 (s, 3H), 3.34 (s, 2H), 3.07 (s, 2H), 1.69 (s, 6H). |
| (4,7-Diaza-spiro[2.5]oct-4-yl)-[7-methoxy-8-(1-methyl-1H-pyrazol-3-yl)-1-thiophen-3-yl-1,4-dihydro-chromeno[4,3-c]pyrazol-3-yl]-methanone (171) | 1-methyl-1H-pyrazol-3-yl pinacol boronate | N-Boc-4,7-diazaspiro[2.5]octane | m/z: 503 [M + H]⁺ | ¹H NMR (400 MHz, CDCl₃) δ 8.26 (s, 1H), 7.61–7.46 (m, 3H), 7.35–7.31 (m, 1H), 6.67 (s, 1H), 6.54 (s, 1H), 5.54 (s, 2H), 4.37 (m, 2H), 3.93–3.85 (m, 2H), 3.20–2.99 (m, 6H), 1.16–0.95 (m, 4H). |

-continued

| Compound | Boronic acid Starting material | Amine Starting material | LC/MS | NMR |
|---|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid ((1S,3R)-3-hydroxy-cyclopentyl)-amide (172) | 1-methyl-1H-pyrazole-3-boronic acid pinacol ester | (1S,3R)-3-aminocyclopentanol | m/z = 492 [M + H]+ | 1H-NMR (DMSO-d6): δ 8.11 (d, 1H), 8.00 (s, 1H), 7.84 (s, 1H), 7.60 (s, 1H), 7.42 (s, 1H), 7.34 (s, 1H), 6.76 (s, 1H), 6.49 (s, 1H), 5.54 (s, 2H), 4.75 (s, 1H), 4.32 (s, 1H), 4.15 (s, 1H), 3.84 (s, 3H), 3.78 (s, 3H), 2.06-1.85 (m, 2H), 1.78-1.53 (m, 4H). |
| 7-Methoxy-8-(1-methyl-1H-pyrrol-3-yl)-1-thiophen-3-yl-1,4-dihydro-chromeno[4,3-c]pyrazole-3-carboxylic acid ((1S,3R)-3-hydroxy-cyclopentyl)-amide (173) | 1-methyl-1H-pyrrole-3-boronic acid pinacol ester | (1S,3R)-3-aminocyclopentanol | m/z = 491 [M + H]+ | 1H-NMR (DMSO-d6): δ 8.14-8.04 (m, 2H), 7.91 (s, 1H), 7.39 (s, 1H), 7.00 (s, 1H), 6.80 (s, 1H), 6.71 (s, 1H), 6.63 (s, 1H), 5.78 (s, 1H), 5.50 (s, 2H), 4.75 (s, 1H), 4.33 (s, 1H), 3.84 (s, 3H), 3.59 (s, 3H), 2.06-1.84 (m, 2H), 1.78-1.52 (m, 4H). |

| Compound | Boronic acid Starting material | Amine Starting material | LC/MS | NMR |
|---|---|---|---|---|
| 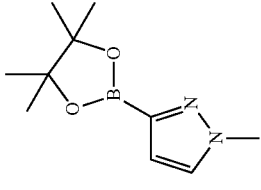 [7-Methoxy-8-(1-methyl-1H-pyrazol-3-yl)-1-thiophen-3-yl-1,4-dihydro-chromeno[4,3-c]pyrazol-3-yl]-(2-oxa-5-aza-spiro[3.4]oct-5-yl)-methanone (174) | | | m/z = 504 [M + H]+ | 1H-NMR (DMSO-d6): δ 7.96 (s, 1H), 7.84 (s, 1H), 7.60 (s, 1H), 7.49 (s, 1H), 7.32 (s, 1H), 6.78 (s, 1H), 6.50 (s, 1H), 5.55 (s, 2H), 5.45 (s, 2H), 4.31 (s, 2H), 3.91 (s, 2H), 3.85 (s, 3H), 3.78 (s, 3H), 2.29 (s, 2H), 1.75 (s, 2H). |
| 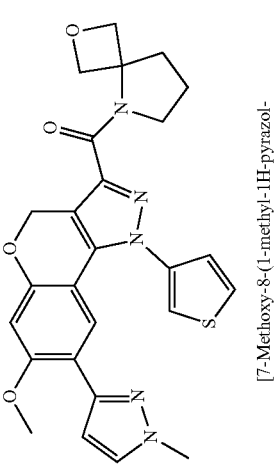 (2-Hydroxymethyl-2-methyl-pyrrolidin-1-yl)-[7-methoxy-8-(1-methyl-1H-pyrrol-3-yl)-1-thiophen-3-yl-1,4-dihydro-chromeno[4,3-c]pyrazol-3-yl]-methanone (176) | | | m/z = 505 [M + H]+ | 1H-NMR (DMSO-d6): δ 8.01 (s, 1H), 7.89 (d, 1H), 7.37 (s, 1H), 7.00 (s, 1H), 6.85 (s, 1H), 6.71 (s, 1H), 6.63 (s, 1H), 5.80 (s, 1H), 5.44 (s, 2H), 4.88 (s, 1H), 4.10 (s, 1H), 3.91-3.80 (m, 5H), 3.59 (s, 4H), 2.15-2.06 (m, 1H), 1.89-1.72 (m, 2H), 1.64-1.54 (m, 1H), 1.40 (s, 3H). |

| Compound | Boronic acid Starting material | Amine Starting material | LC/MS | NMR |
|---|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid [3-(2-hydroxy-ethyl)-oxetan-3-yl]-amide (186) | (1-methyl-1H-pyrrol-3-yl boronic acid pinacol ester) | 3-(2-aminoethyl)oxetan-3-ol type amine (H₂N-containing oxetane with hydroxyethyl) | m/z = 507 [M + H]⁺ | ¹H-NMR (DMSO-d6): δ 8.06 (dd, 1H), 7.91 (dd, 1H), 7.80 (s, 1H), 7.39 (dd, 1H), 7.00 (t, 1H), 6.81 (s, 1H), 6.71 (s, 1H), 6.63 (t, 1H), 5.78 (dd, 1H), 5.49 (s, 2H), 5.10 (s, 1H), 3.91-3.75 (m, 8H), 3.63-3.56 (m, 5H), 2.35-2.27 (m, 1H), 2.02-1.93 (m, 1H). |
| [8-(3,6-Dihydro-2H-pyran-4-yl)-7-methoxy-1-thiophen-3-yl-1,4-dihydro-chromeno[4,3-c]pyrazol-3-yl]-(3,3-dimethyl-morpholin-4-yl)-methanone (189) | 3,6-dihydro-2H-pyran-4-boronic acid pinacol ester | 3,3-dimethylmorpholine | m/z = 494 [M + H]⁺ | ¹H-NMR (DMSO-d6): δ 8.23 (s, 1H), 8.02 (dd, 1H), 7.86 (dd, 1H), 7.60 (d, 1H), 7.42 (s, 1H), 7.34 (dd, 1H), 6.76 (s, 1H), 6.49 (d, 1H), 5.54 (s, 2H), 5.18 (s, 1H), 3.84 (s, 3H), 3.77 (s, 3H), 3.44-3.36 (m, 4H), 1.05 (s, 3H). |

-continued

| Compound | Boronic acid Starting material | Amine Starting material | LC/MS | NMR |
|---|---|---|---|---|
| 3-{4-[3-(3,3-Dimethyl-morpholine-4-carbonyl)-7-methoxy-1-thiophen-3-yl-1,4-dihydro-chromeno[4,3-c]pyrazol-8-yl]-pyrazol-1-yl}-propionitrile (190) | pyrazole-boronic ester with CH2CH2CN | 3,3-dimethylmorpholine | m/z = 545 [M + H]+ | 1H-NMR (DMSO-d6): δ 8.04 (dd, 1H), 7.97 (s, 1H), 7.91 (dd, 1H), 7.39 (dd, 1H), 7.28 (s, 1H), 6.85 (s, 1H), 6.79 (s, 1H), 5.41 (s, 2H), 4.38 (t, 2H), 3.99-3.94 (m, 2H), 3.87 (s, 3H), 3.76-3.71 (m, 2H), 3.43 (s, 2H), 3.06 (t, 2H), 1.43 (s, 6H). |
| (3,3-Dimethyl-morpholin-4-yl)-[8-(1-isopropyl-1H-pyrazol-4-yl)-7-methoxy-1-thiophen-3-yl-1,4-dihydro-chromeno[4,3-c]pyrazol-3-yl]-methanone (191) | 1-isopropylpyrazole boronic ester | 3,3-dimethylmorpholine | m/z = 534 [M + H]+ | 1H-NMR (DMSO-d6): δ 8.04 (dd, 1H), 7.92 (dd, 1H), 7.78 (s, 1H), 7.39 (dd, 1H), 7.26 (s, 1H), 6.82 (s, 1H), 6.76 (s, 1H), 5.41 (s, 2H), 4.48 (septet, 1H), 3.97 (t, 2H), 3.86 (s, 3H), 3.73 (t, 2H), 3.43 (s, 2H), 1.44-1.39 (m, 12H). |

| Compound | Boronic acid Starting material | Amine Starting material | LC/MS | NMR |
|---|---|---|---|---|
| (3,3-Dimethyl-morpholin-4-yl)-[8-(1-isobutyl-1H-pyrazol-4-yl)-7-methoxy-1-thiophen-3-yl-1,4-dihydro-chromeno[4,3-c]pyrazol-3-yl]-methanone (192) | | | m/z = 548 [M + H]+ | ¹H-NMR (DMSO-d6): δ 8.04 (dd, 1H), 7.91 (dd, 1H), 7.78 (s, 1H), 7.39 (dd, 1H), 7.25 (s, 1H), 6.83 (s, 1H), 6.77 (s, 1H), 5.40 (s, 2H), 3.99-3.94 (m, 2H), 3.91-3.84 (m, 5H), 3.76-3.71 (m, 2H), 3.43 (s, 2H), 2.08 (septet, 1H), 1.43 (s, 6H), 0.84 (d, 6H). |
| (3,3-Dimethyl-morpholin-4-yl)-[8-(1-isopropyl-1H-pyrazol-3-yl)-7-methoxy-1-thiophen-3-yl-1,4-dihydro-chromeno[4,3-c]pyrazol-3-yl]-methanone (195) | | | m/z = 534 [M + H]+ | ¹H-NMR (DMSO-d6): δ 8.05 (dd, 1H), 7.92 (dd, 1H), 7.78 (s, 1H), 7.39 (dd, 1H), 7.26 (s, 1H), 6.82 (s, 1H), 6.76 (s, 1H), 5.41 (s, 2H), 4.48 (septet, 1H), 4.00-3.94 (m, 2H), 3.86 (s, 3H), 3.76-3.71 (m, 2H), 3.43 (s, 2H), 1.45-1.39 (m, 12H). |

| Compound | Boronic acid Starting material | Amine Starting material | LC/MS | NMR |
|---|---|---|---|---|
| 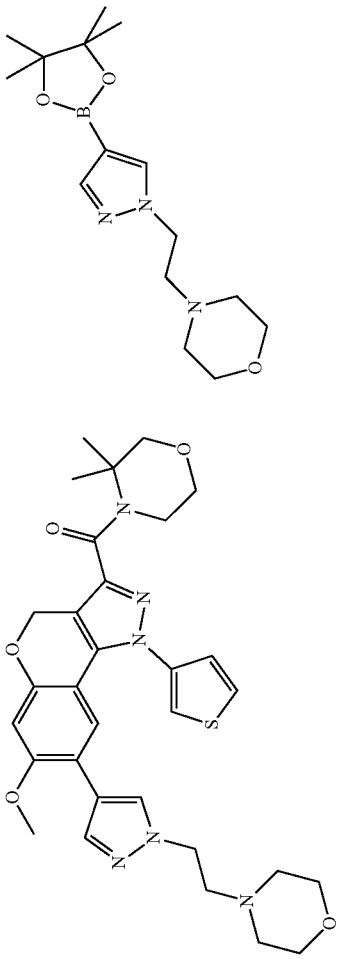<br>(3,3-Dimethyl-morpholin-4-yl)-{7-methoxy-8-[1-(2-morpholin-4-yl-ethyl)-1H-pyrazol-4-yl]-1-thiophen-3-yl-1,4-dihydro-chromeno[4,3-c]pyrazol-3-yl}-methanone (202) | 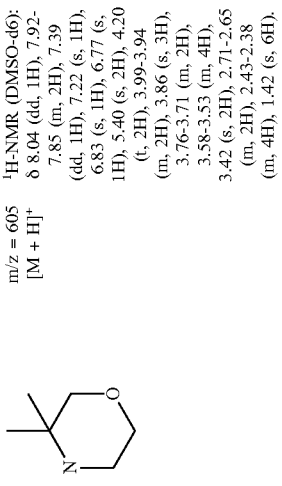 | 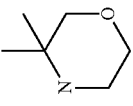 | m/z = 605 [M + H]⁺ | ¹H-NMR (DMSO-d6): δ 8.04 (dd, 1H), 7.92-7.85 (m, 2H), 7.39 (dd, 1H), 7.22 (s, 1H), 6.83 (s, 1H), 6.77 (s, 1H), 5.40 (s, 2H), 4.20 (t, 2H), 3.99-3.94 (m, 2H), 3.86 (s, 3H), 3.76-3.71 (m, 2H), 3.58-3.53 (m, 4H), 3.42 (s, 2H), 2.71-2.65 (m, 2H), 2.43-2.38 (m, 4H), 1.42 (s, 6H). |
| 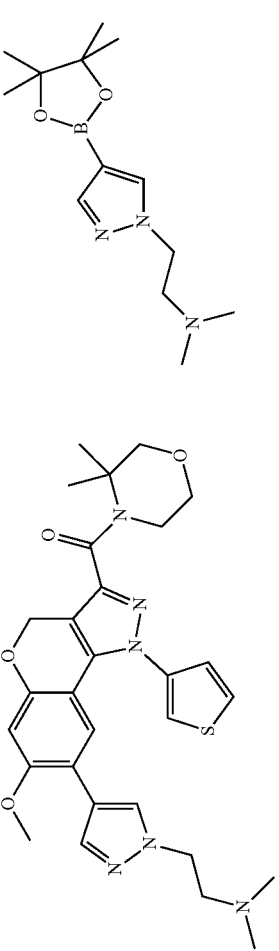<br>{8-[1-(2-Dimethylamino-ethyl)-1H-pyrazol-4-yl]-7-methoxy-1-thiophen-3-yl-1,4-dihydro-chromeno[4,3-c]pyrazol-3-yl}-(3,3-dimethyl-morpholin-4-yl)-methanone (203) | 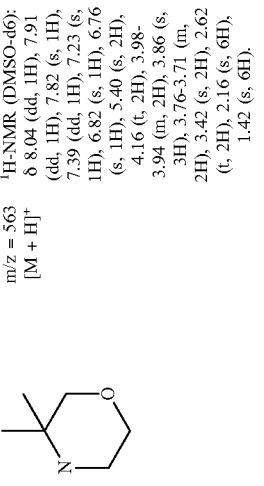 | 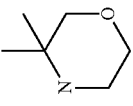 | m/z = 563 [M + H]⁺ | ¹H-NMR (DMSO-d6): δ 8.04 (dd, 1H), 7.91 (dd, 1H), 7.82 (s, 1H), 7.39 (dd, 1H), 7.23 (s, 1H), 6.82 (s, 1H), 6.76 (s, 1H), 5.40 (s, 2H), 4.16 (t, 2H), 3.98-3.94 (m, 2H), 3.86 (s, 3H), 3.76-3.71 (m, 2H), 3.42 (s, 2H), 2.62 (t, 2H), 2.16 (s, 6H), 1.42 (s, 6H). |

| Compound | Boronic acid Starting material | Amine Starting material | LC/MS | NMR |
|---|---|---|---|---|
| 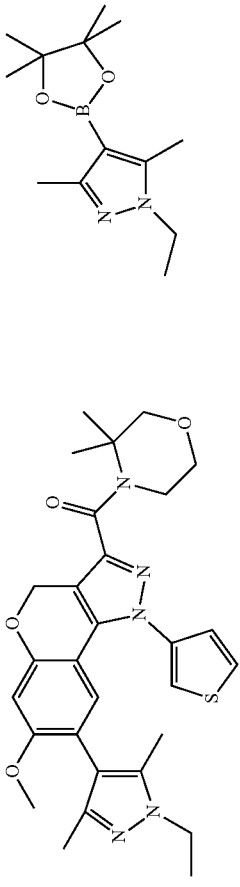<br>(3,3-Dimethyl-morpholin-4-yl)-[8-(1-ethyl-3,5-dimethyl-1H-pyrazol-4-yl)-7-methoxy-1-thiophen-3-yl-1,4-dihydro-chromeno[4,3-c]pyrazol-3-yl]-methanone (204) | 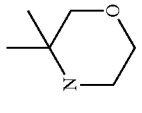 | 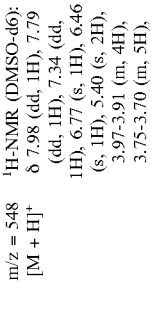 | m/z = 548 [M + H]$^+$ | $^1$H-NMR (DMSO-d6): δ 7.98 (dd, 1H), 7.79 (dd, 1H), 7.34 (dd, 1H), 6.77 (s, 1H), 6.46 (s, 1H), 5.40 (s, 2H), 3.97-3.91 (m, 4H), 3.75-3.70 (m, 5H), 3.42 (s, 2H), 1.92 (s, 3H), 1.82 (s, 3H), 1.42 (s, 6H), 1.27 (t, 3H). |
| 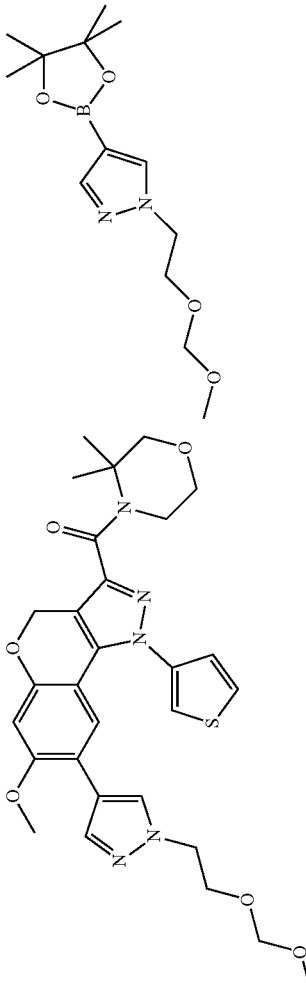<br>(3,3-Dimethyl-morpholin-4-yl)-{7-methoxy-8-[1-(2-methoxymethoxy-ethyl)-1H-pyrazol-4-yl]-1-thiophen-3-yl-1,4-dihydro-chromeno[4,3-c]pyrazol-3-yl}-methanone (205) | 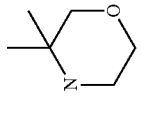 | 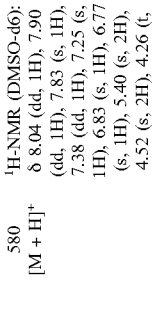 | 580 [M + H]$^+$ | $^1$H-NMR (DMSO-d6): δ 8.04 (dd, 1H), 7.90 (dd, 1H), 7.83 (s, 1H), 7.38 (dd, 1H), 7.25 (s, 1H), 6.83 (s, 1H), 6.77 (s, 1H), 5.40 (s, 2H), 4.52 (s, 2H), 4.26 (t, 2H), 3.96 (t, 2H), 3.86 (s, 3H), 3.80 (t, J = 5.3 Hz, 2H), 3.73 (t, 2H), 3.42 (s, 2H), 3.16 (s, 3H), 1.42 (s, 6H). |

| Compound | Boronic acid Starting material | Amine Starting material | LC/MS | NMR |
|---|---|---|---|---|
| 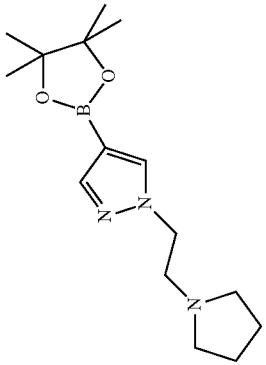 (3,3-Dimethyl-morpholin-4-yl)-{7-methoxy-8-[1-(2-pyrrolidin-1-yl-ethyl)-1H-pyrazol-4-yl]-1-thiophen-3-yl-1,4-dihydro-chromeno[4,3-c]pyrazol-3-yl}-methanone (206) | 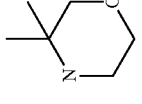 | 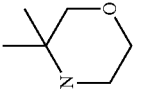 | m/z = 589 [M + H]⁺ | ¹H-NMR (DMSO-d6): δ 8.04 (dd, 1H), 7.90 (dd, 1H), 7.83 (s, 1H), 7.39 (dd, 1H), 7.23 (s, 1H), 6.83 (s, 1H), 6.76 (s, 1H), 5.40 (s, 2H), 4.18 (t, 2H), 3.98-3.94 (m, 2H), 3.86 (s, 3H), 3.75-3.71 (m, 2H), 3.42 (s, 2H), 2.79 (t, 2H), 2.47-2.43 (m, 4H), 1.69-1.64 (m, 4H), 1.42 (s, 6H). |
| 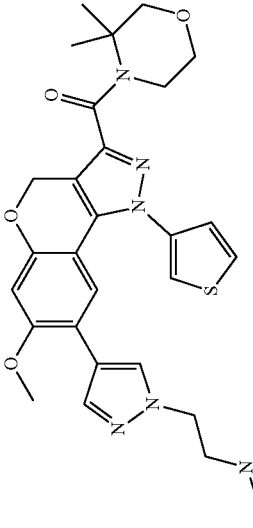 [8-(1-Allyl-1H-pyrazol-4-yl)-7-methoxy-1-thiophen-3-yl-1,4-dihydro-chromeno[4,3-c]pyrazol-3-yl]-(3,3-dimethyl-morpholin-4-yl)-methanone (207) | 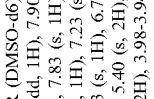 | 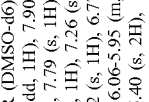 | m/z = 532 [M + H]⁺ | ¹H-NMR (DMSO-d6): δ 8.03 (dd, 1H), 7.90 (dd, 1H), 7.79 (s, 1H), 7.38 (dd, 1H), 7.26 (s, 1H), 6.82 (s, 1H), 6.77 (s, 1H), 6.06-5.95 (m, 1H), 5.40 (s, 2H), 5.24-5.11 (m, 2H), 4.73 (d, 2H), 3.98-3.94 (m, 2H), 3.85 (s, 3H), 3.75-3.71 (m, 2H), 3.42 (s, 2H), 1.42 (s, 6H). |

| Compound | Boronic acid Starting material | Amine Starting material | LC/MS | NMR |
|---|---|---|---|---|
| (3,3-Dimethyl-morpholin-4-yl)-{7-methoxy-8-[1-(3-methoxy-propyl)-1H-pyrazol-4-yl]-1-thiophen-3-yl-1,4-dihydro-chromeno[4,3-c]pyrazol-3-yl}-methanone (208) | | | m/z = 564 [M + H]+ | 1H-NMR (DMSO-d6): δ 8.04 (dd, 1H), 7.91 (dd, 1H), 7.80 (s, 1H), 7.39 (dd, 1H), 7.23 (s, 1H), 6.83 (s, 1H), 6.77 (s, 1H), 5.40 (s, 2H), 4.12 (t, 2H), 3.99-3.94 (m, 2H), 3.86 (s, 3H), 3.76-3.70 (m, 2H), 3.42 (s, 2H), 3.29-3.23 (m, 5H), 1.98 (quintet, 2H), 1.42 (s, 6H). |
| (3,3-Dimethyl-morpholin-4-yl)-[8-(1-[1,3]dioxolan-2-ylmethyl-1H-pyrazol-4-yl)-7-methoxy-1-thiophen-3-yl-1,4-dihydro-chromeno[4,3-c]pyrazol-3-yl]-methanone (209) | | | m/z = 578 [M + H]+ | 1H-NMR (DMSO-d6): δ 8.04 (dd, 1H), 7.90 (dd, 1H), 7.80 (s, 1H), 7.39 (dd, 1H), 7.26 (s, 1H), 6.82 (s, 1H), 6.77 (s, 1H), 5.40 (s, 2H), 5.14 (t, 1H), 4.22 (d, 2H), 3.99-3.94 (m, 2H), 3.88-3.81 (m, 7H), 3.76-3.71 (m, 2H), 3.42 (s, 2H), 1.42 (s, 6H). |

| Compound | Boronic acid Starting material | Amine Starting material | LC/MS | NMR |
|---|---|---|---|---|
| (3,3-Dimethyl-morpholin-4-yl)-[8-(1-ethyl-1H-pyrazol-4-yl)-7-methoxy-1-thiophen-3-yl-1,4-dihydro-chromeno[4,3-c]pyrazol-3-yl]-methanone (210) | | | m/z = 520 [M + H]⁺ | ¹H-NMR (DMSO-d6): δ 8.04 (dd, 1H), 7.91 (dd, 1H), 7.81 (s, 1H), 7.38 (dd, 1H), 7.22 (s, 1H), 6.83 (s, 1H), 6.76 (s, 1H), 5.40 (s, 2H), 4.14-4.06 (m, 6H), 3.98-3.94 (m, 2H), 3.86 (s, 3H), 3.76-3.71 (m, 2H), 3.42 (s, 2H), 1.42 (s, 6H), 1.36 (t, 3H). |
| (3,3-Dimethyl-morpholin-4-yl)-[7-methoxy-8-(1-propyl-1H-pyrazol-4-yl)-1-thiophen-3-yl-1,4-dihydro-chromeno[4,3-c]pyrazol-3-yl]-methanone (211) | | | m/z = 534 [M + H]⁺ | ¹H-NMR (DMSO-d6): δ 8.04 (dd, 1H), 7.91 (dd, 1H), 7.80 (s, 1H), 7.39 (dd, 1H), 7.23 (s, 1H), 6.83 (s, 1H), 6.76 (s, 1H), 5.40 (s, 2H), 4.03 (t, 2H), 3.99-3.94 (m, 2H), 3.86 (s, 3H), 3.76-3.71 (m, 2H), 3.42 (s, 2H), 1.77 (sextet, 2H), 1.42 (s, 6H), 0.82 (t, 3H). |

| Compound | Boronic acid Starting material | Amine Starting material | LC/MS | NMR |
|---|---|---|---|---|
| (3,3-Dimethyl-morpholin-4-yl)-[7-methoxy-8-(5-methyl-2-propyl-2H-pyrazol-3-yl)-1-thiophen-3-yl-1,4-dihydro-chromeno[4,3-c]pyrazol-3-yl]-methanone (212) | | | m/z = 548 [M + H]⁺ | ¹H-NMR (DMSO-d6): δ 7.94 (dd, 1H), 7.76 (dd, 1H), 7.30 (dd, 1H), 6.84 (s, 1H), 6.55 (s, 1H), 5.76 (s, 1H), 5.43 (s, 2H), 3.96-3.91 (m, 2H), 3.77-3.70 (m, 5H), 3.60 (t, 2H), 3.42 (s, 2H), 2.12 (s, 3H), 1.54 (sextet, 2H), 1.42 (s, 6H), 0.62 (t, 3H). |
| (3,3-Dimethyl-morpholin-4-yl)-[8-(2-ethyl-2H-pyrazol-3-yl)-7-methoxy-1-thiophen-3-yl-1,4-dihydro-chromeno[4,3-c]pyrazol-3-yl]-methanone (213) | | | m/z = 520 [M + H]⁺ | ¹H-NMR (DMSO-d6): δ 7.96 (dd, 1H), 7.77 (dd, 1H), 7.40 (d, 1H), 7.32 (dd, 1H), 6.87 (s, 1H), 6.56 (s, 1H), 5.97 (d, 1H), 5.45 (s, 2H), 3.97-3.93 (m, 2H), 3.80-3.71 (m, 7H), 3.42 (s, 2H), 1.42 (s, 6H), 1.17 (t, 3H). |

Example 8

7-Methoxy-8-(2-methyl-propenyl)-1-thiophen-3-yl-1,4-dihydro-chromeno[4,3-c]pyrazole-3-carboxylic acid methyl-[2-(2-oxo-oxazolidin-3-yl)-ethyl]-amide (23)

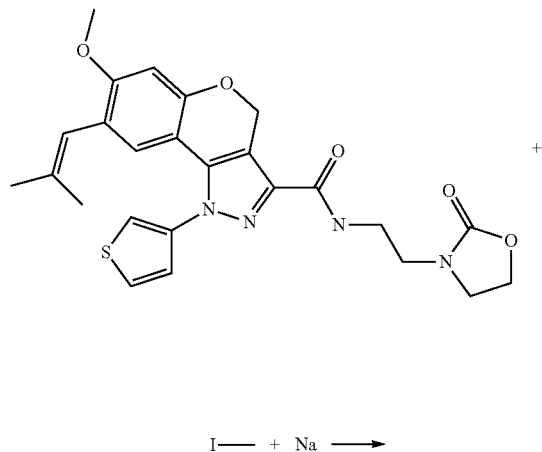

I— + Na ⟶

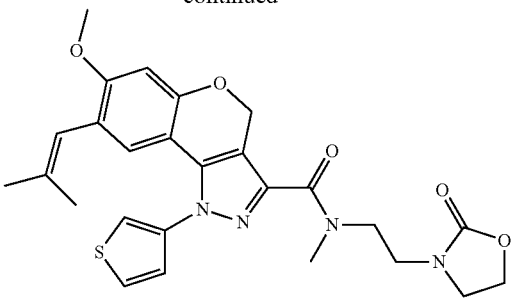

To 7-methoxy-8-(2-methyl-propenyl)-1-thiophen-3-yl-1,4-dihydro-chromeno[4,3-c]pyrazole-3-carboxylic acid [2-(2-oxo-oxazolidin-3-yl)-ethyl]-amide (22.00 mg; 0.04 mmol; 1.00 eq.) was added N,N-Dimethyl-formamide (0.50 ml) and sodium hydride (2.67 mg; 0.07 mmol; 1.50 eq.). Reaction was stirred at RT for 10 min then iodomethane (0.00 ml; 0.05 mmol; 1.10 eq.) (1 drop) was added and the reaction was stirred at RT for 15 min. Water was added and product was extracted with EtOAc and washed with water. Organic layer was dried, filtered, concentrated. Residue was dried on high vacuum then lyophilized to afford the desired product (22.5 mg, 99%) as an off white solid.

$^1$H NMR (400 MHz, CDCl$_3$) δ 7.56-7.42 (m, 2H), 7.24 (d, J=4.9 Hz, 1H), 6.73 (d, J=4.0 Hz, 1H), 6.57 (d, J=2.8 Hz, 1H), 6.12 (s, 1H), 5.55 (s, 1H), 5.51 (s, 1H), 4.38-4.31 (m, 1H), 4.20-4.10 (m, 2H), 3.82 (s, 3H), 3.81-3.72 (m, 2H), 3.62-3.55 (m, 3H), 3.53 (s, 1H), 3.46-3.38 (m, 1H), 3.17 (s, 1H), 1.85 (s, 3H), 1.53 (d, J=3.8 Hz, 3H). m/z: 509 [M+H]$^+$

The following compounds were prepared using procedures analogous to those disclosed in example 8 above:

| Compound | Starting material | LC/MS | NMR |
|---|---|---|---|
| 8-Isopropoxy-7-methoxy-1-thiophen-3-yl-1,4-dihydro-chromeno[4,3-c]pyrazole-3-carboxylic acid [2-(cyclobutanecarbonyl-methyl-amino)-ethyl]-methyl-amide (29) | | m/z: 539 [M + H]+ | 1H NMR (400 MHz, CDCl3) δ 7.60-7.47 (m, 2H), 7.26 (dd, J = 5.0, 1.4 Hz, 1H), 6.61 (s, 1H), 6.41 (d, J = 3.6 Hz, 1H), 5.54-5.45 (m, 2H), 4.10-4.00 (m, 1H), 3.98-3.86 (m, 1H), 3.84 (s, 3H), 3.60-3.51 (m, 1H), 3.51-3.42 (m, 2H), 3.33-3.25 (m, 1H), 3.15-3.10 (m, 1H), 2.95 (s, 3H), 2.73 (s, 2H), 2.42-2.23 (m, 2H), 2.23-2.04 (m, 2H), 2.04-1.79 (m, 2H), 1.22 (d, J = 6.1 Hz, 6H). |
| 8-Isopropoxy-7-methoxy-1-thiophen-3-yl-1,4-dihydro-chromeno[4,3-c]pyrazole-3-carboxylic acid [3-(cyclobutanecarbonyl-methyl-amino)-propyl]-methyl-amide (30) | | m/z: 553 [M + H]+ | 1H NMR (400 MHz, CDCl3) δ 7.59-7.44 (m, 2H), 7.26 (dd, J = 5.0, 1.4 Hz, 1H), 6.61 (s, 1H), 6.44-6.32 (m, 1H), 5.59-5.36 (m, 2H), 4.10-4.01 (m, 1H), 3.91 (dd, J = 19.2, 11.5 Hz, 2H), 3.84 (s, 3H), 3.59-3.51 (m, 1H), 3.47 (dd, J = 19.7, 6.8 Hz, 2H), 3.38 (t, J = 7.2 Hz, 1H), 3.33-3.26 (m, 1H), 3.16-3.06 (m, 3H), 2.95 (s, 2H), 2.73 (s, 1H), 2.43-2.22 (m, 2H), 2.21-2.06 (m, 2H), 2.06-1.76 (m, 2H), 1.22 (d, J = 6.1 Hz, 6H). |

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid (2-methoxy-1,1-dimethyl-ethyl)-methyl-amide (31) | | m/z: 482 [M + H]⁺ | ¹H NMR (400 MHz, CDCl₃) δ 7.52 (dd, J = 3.2, 1.4 Hz, 1H), 7.46 (dd, J = 5.1, 3.2 Hz, 1H), 7.23 (dd, J = 5.1, 1.4 Hz, 1H), 6.74 (s, 1H), 6.58 (s, 1H), 6.12 (s, 1H), 5.45 (s, 2H), 3.82 (s, 3H), 3.78 (s, 2H), 3.39 (s, 3H), 3.33 (s, 3H), 1.85 (s, 3H), 1.53 (d, J = 1.1 Hz, 3H), 1.51 (s, 6H). |
| 7-Methoxy-8-(2-methyl-propenyl)-1-thiophen-3-yl-1,4-dihydro-chromeno[4,3-c]pyrazole-3-carboxylic acid [3-(acetyl-methyl-amino)-propyl]-methyl-amide (32) | | m/z: 509 [M + H]⁺ | ¹H NMR (400 MHz, CDCl₃) δ 7.57-7.46 (m, 2H), 7.27-7.19 (m, 1H), 6.74 (s, 1H), 6.57 (s, 1H), 6.12 (s, 1H), 5.61-5.50 (m, 2H), 3.97-3.87 (m, 2H), 3.82 (s, 3H), 3.53 (dd, J = 23.0, 9.4 Hz, 4H), 3.38 (d, J = 6.5 Hz, 2H), 3.28 (s, 1H), 3.12 (d, J = 7.8 Hz, 3H), 2.97 (d, J = 5.7 Hz, 2H), 2.81 (d, J = 12.9 Hz, 1H), 1.85 (s, 3H), 1.53 (s, 3H). |

-continued

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid methyl-[3-(2-oxo-oxazolidin-3-yl)-propyl]-amide (33) | | m/z: 523 [M + H]⁺ | ¹H NMR (400 MHz, CDCl₃) δ 7.57-7.45 (m, 2H), 7.27-7.22 (m, 1H), 6.72 (d, J = 13.8 Hz, 1H), 6.58 (s, 1H), 6.12 (s, 1H), 5.54 (d, J = 10.5 Hz, 2H), 4.40-4.34 (m, 1H), 4.05-3.93 (m, 2H), 3.82 (s, H), 3.69-3.63 (m, 1H), 3.62-3.55 (m, 1H), 3.50 (s, 2H), 3.43-3.28 (m, 3H), 3.13 (s, 2H), 2.06-1.94 (m, 1H), 1.85 (s, 3H), 1.53 (s, 3H). |
| 7-Methoxy-8-(2-methyl-propenyl)-1-thiophen-3-yl-1,4-dihydro-chromeno[4,3-c]pyrazole-3-carboxylic acid [2-(acetyl-methyl-amino)-ethyl]-methyl-amide (34) | | m/z: 495 [M + H]⁺ | ¹H NMR (400 MHz, CDCl₃) δ 7.58-7.45 (m, 2H), 7.27-7.17 (m, 1H), 6.74 (s, 1H), 6.57 (s, 1H), 6.12 (s, 1H), 5.59-5.50 (m, 2H), 4.08 (dd, J = 13.5, 6.1 Hz, 1H), 3.82 (s, 3H), 3.67 (dd, J = 13.2, 7.7 Hz, 3H), 3.54 (d, J = 5.3 Hz, 1H), 3.20-3.11 (m, 3H), 2.88 (d, J = 2.8 Hz, 3H), 1.97 (s, 2H), 1.85 (s, 3H), 1.52 (d, J = 8.4 Hz, 3H). |

-continued

| Compound | Starting material | LC/MS | NMR |
|---|---|---|---|
| [7-Methoxy-8-(2-methyl-propenyl)-1-thiophen-3-yl-1,4-dihydro-chromeno[4,3-c]pyrazol-3-yl]-(3-methoxy-d3-pyrrolidin-1-yl)-methanone (49) | | m/z: 469 [M + H]⁺ | ¹H NMR (400 MHz, CDCl₃) δ 7.53-7.43 (m, 2H), 7.24 (d, J = 5.0 Hz, 1H), 6.74 (s, 1H), 6.57 (s, 1H), 6.12 (s, 1H), 5.62 (d, J = 1.6 Hz, 2H), 4.33-4.15 (m, 2H), 4.05 (t, J = 9.9 Hz, 2H), 3.82 (s, 3H), 3.80-3.66 (m, 2H), 2.14-1.92 (m, 1H), 1.85 (s, 3H), 1.54 (s, 3H). |
| (2-Methoxy-d3-methyl-2-methyl-pyrrolidin-1-yl)-[7-methoxy-8-(2-methyl-propenyl)-1-thiophen-3-yl-1,4-dihydro-chromeno[4,3-c]pyrazol-3-yl]-methanone (51) | | m/z: 497 [M + H]⁺ | ¹H NMR (400 MHz, CDCl₃) δ 7.53-7.42 (m, 2H), 7.23 (d, J = 5.0 Hz, 1H), 6.73 (s, 1H), 6.58 (s, 1H), 6.12 (s, 1H), 5.56 (s, 2H), 4.23-4.14 (m, 1H), 3.99 (dd, J = 17.8, 7.9 Hz, 2H), 3.82 (s, 3H), 3.71 (d, J = 9.5 Hz, 1H), 2.22 (dd, J = 13.5, 6.8 Hz, 1H), 1.91 (d, J = 6.6 Hz, 2H), 1.85 (s, 3H), 1.71 (dd, J = 12.4, 6.4 Hz, 1H), 1.54 (s, 6H). |

| Compound | Starting material | LC/MS | NMR |
|---|---|---|---|
| 7-Methoxy-8-(2-methyl-d3-propenyl)-1-thiophen-3-yl-1,4-dihydro-chromeno[4,3-c]pyrazole-3-carboxylic acid methyl-d3-[2-(2-oxo-oxazolidin-3-yl)-ethyl]-amide (56) | | m/z: 512 [M + H]⁺ | ¹H NMR (400 MHz, CDCl₃) δ 7.56-7.45 (m, 2H), 7.24 (d, J = 4.7 Hz, 1H), 6.73 (s, 1H), 6.57 (s, 1H), 6.12 (s, 1H), 5.53 (d, J = 17.1 Hz, 2H), 4.35 (t, J = 8.0 Hz, 1H), 4.22-4.11 (m, 2H), 3.82 (s, 3H), 3.81-3.72 (m, 2H), 3.62-3.53 (m, 2H), 3.42 (t, J = 7.8 Hz, 1H), 1.85 (s, 3H), 1.53 (s, 3H). |
| 7-Methoxy-8-(2-methyl-d3-propenyl)-1-thiophen-3-yl-1,4-dihydro-chromeno[4,3-c]pyrazole-3-carboxylic acid (2-methoxy-d3-1,1-dimethyl-ethyl)-methyl-amide (58) | | m/z: 488 [M + H]⁺ | ¹H NMR (400 MHz, CDCl₃) δ 7.52 (s, 1H), 7.46 (s, 1H), 7.23 (d, J = 4.8 Hz, 1H), 6.74 (s, 1H), 6.58 (s, 1H), 6.12 (s, 1H), 5.45 (s, 2H), 3.83 (s, 3H), 3.78 (s, 2H), 1.85 (s, 3H), 1.55-1.48 (m, 9H). |

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid (2-methoxy-d3-1,1-dimethyl-ethyl)-amide (59) | | m/z: 471 [M + H]⁺ | ¹H NMR (400 MHz, CDCl₃) δ 7.56-7.45 (m, 2H), 7.25 (d, J = 4.9 Hz, 1H), 6.96 (s, 1H), 6.69 (s, 1H), 6.57 (s, 1H), 6.11 (s, 1H), 5.62 (s, 2H), 3.82 (s, 3H), 3.52 (s, 2H), 1.85 (s, 3H), 1.52 (s, 3H), 1.48 (s, 6H). |
| 7-Methoxy-8-(2-methyl-propenyl)-1-thiophen-3-yl-1,4-dihydro-chromeno[4,3-c]pyrazole-3-carboxylic acid [2-(acetyl-methyl-d3-amino)-ethyl]-amide (60) | | m/z: 484 [M + H]⁺ | ¹H NMR (400 MHz, CDCl₃) δ 7.98 (s, 1H), 7.59-7.43 (m, 2H), 7.24 (d, J = 4.8 Hz, 1H), 6.76-6.66 (m, 1H), 6.57 (s, 1H), 6.12 (s, 1H), 5.50 (s, 2H), 4.01-3.87 (m, 1H), 3.82 (s, 3H), 3.62-3.41 (m, 3H), 2.02 (s, 3H), 1.85 (s, 3H), 1.52 (s, 3H). |

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid [2-(acetyl-methyl-d3-amino)-ethyl]-methyl-d3-amide (61) | | m/z: 515 [M + H]+ | 1H NMR (400 MHz, CDCl3) δ 7.51 (dd, J = 14.6, 7.7 Hz, 2H), 7.24 (d, J = 4.9 Hz, 1H), 6.73 (d, J = 5.1 Hz, 1H), 6.57 (s, 1H), 6.12 (s, 1H), 5.53 (dd, J = 16.7, 6.7 Hz, 2H), 4.09 (t, J = 6.9 Hz, 1H), 3.82 (s, 3H), 3.67 (d, J = 19.2 Hz, 3H), 2.00 (s, 3H), 1.85 (s, 3H), 1.56-1.46 (m, 3H). |
| 7-Methoxy-8-(2-methyl-propenyl)-1-thiophen-3-yl-1,4-dihydro-chromeno[4,3-c]pyrazole-3-carboxylic acid [3-(cyclobutanecarbonyl-methyl-d3-amino)-propyl]-methyl-d3-amide (69) | | m/z: 555 [M + H]+ | 1H NMR (400 MHz, CDCl3) δ 7.54 (dd, J = 29.4, 18.4 Hz, 2H), 7.25 (d, J = 4.3 Hz, 1H), 6.87-6.68 (m, 1H), 6.59 (s, 1H), 6.12 (s, 1H), 5.62 (s, 1H), 5.53 (d, J = 6.8 Hz, 1H), 4.00-3.92 (m, 1H), 3.80 (s, 3H), 3.67-3.59 (m, 1H), 3.55-3.38 (m, 1H), 3.37-3.23 (m, 2H), 3.07 (dd, J = 16.1, 8.8 Hz, 1H), 2.89 (s, 1H), 2.30 (dd, J = 18.3, 9.1 Hz, 1H), 2.19 (d, J = 8.0 Hz, 2H), 2.07-1.70 (m, 6H), 1.48 (s, 3H). |

| Compound | Starting material | LC/MS | NMR |
|---|---|---|---|
| 7-Methoxy-8-(1-methyl-d3-1H-pyrazol-4-yl)-1-thiophen-3-yl-1,4-dihydro-chromeno[4,3-c]pyrazole-3-carboxylic acid methyl-d3-[2-(2-oxo-oxazolidin-3-yl)-ethyl]-amide (78) | | m/z: 541 [M + H]+ | 1H NMR (400 MHz, CDCl3) δ 7.66 (s, 1H), 7.60-7.53 (m, 2H), 7.38 (d, J = 9.2 Hz, 1H), 7.29 (s, 1H), 6.99 (s, 1H), 6.65 (d, J = 4.5 Hz, 1H), 5.56 (d, J = 16.4 Hz, 2H), 4.39-4.32 (m, 1H), 4.23-4.13 (m, 2H), 3.91 (s, 3H), 3.83-3.74 (m, 2H), 3.63-3.53 (m, 2H), 3.49-3.41 (m, 1H). |
| 8-Isobutyl-7-methoxy-1-thiophen-3-yl-1,4-dihydro-chromeno[4,3-c]pyrazole-3-carboxylic acid [2-(acetyl-methyl-d3-amino)-ethyl]-methyl-d3-amide (82) | | m/z = 503 [M + H]+ | 1H NMR (DMSO-d6): δ 7.95 (d, 1H), 7.82 (s, 1H), 7.37-7.28 (m, 1H), 6.66 (d, 1H), 6.47-6.40 (m, 1H), 5.40-5.32 (m, 2H), 4.06-3.98 (m, 1H), 3.76 (s, 3H), 3.63-3.44 (m, 3H), 2.15 (d, 2H), 1.99 (d, 1H), 1.82 (d, 2H), 1.62 (septet, 1H), 0.74 (d, 6H). |

| Compound | Starting material | LC/MS | NMR |
|---|---|---|---|
| 8-Isobutyl-7-methoxy-1-thiophen-3-yl-1,4-dihydro-chromeno[4,3-c]pyrazole-3-carboxylic acid methyl-d3-[2-(2-oxo-oxazolidin-3-yl)-ethyl]-amide (214) | | m/z = 514 [M + H]⁺ | ¹H NMR (DMSO-d6): δ 7.96 (s, 1H), 7.82 (s, 1H), 7.34 (s, 1H), 6.66 (d, 1H), 6.44 (d, 1H), 5.35 (s, 2H), 4.23 (s, 1H), 4.06 (s, 2H), 3.76 (s, 3H), 3.71-3.59 (d, 2H), 3.50-3.38 (m, 3H), 2.15 (d, 2H), 1.69-1.55 (m, 1H), 0.75 (d, 6H). |
| 8-Isobutyl-7-methoxy-1-thiophen-3-yl-1,4-dihydro-chromeno[4,3-c]pyrazole-3-carboxylic acid (2-methoxy-d3-1,1-dimethyl-ethyl)-methyl-d3-amide (83) | | m/z = 490 [M + H]⁺ | ¹H NMR (DMSO-d6): δ 7.91 (s, 1H), 7.81 (s, 1H), 7.30 (s, 1H), 6.66 (s, 1H), 6.44 (s, 1H), 5.31 (s, 2H), 3.76 (s, 3H), 3.64 (s, 2H), 2.13 (d, 2H), 1.69-1.55 (m, 1H), 1.41 (s, 6H), 0.74 (d, 6H). |

| Compound | Starting material | LC/MS | NMR |
|---|---|---|---|
| 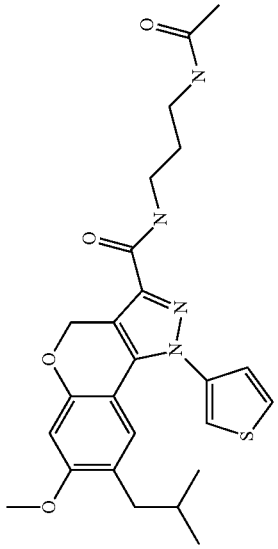 8-Isobutyl-7-methoxy-1-thiophen-3-yl-1,4-dihydro-chromeno[4,3-c]pyrazole-3-carboxylic acid [3-(acetyl-methyl-d3-amino)-propyl]-methyl-d3-amide (84) | | m/z = 517 [M + H]+ | 1H NMR (DMSO-d6): δ 8.01-7.92 (m, 1H), 7.82 (s, 1H), 7.39-7.29 (m, 1H), 6.66 (s, 1H), 6.47-6.40 (m, 1H), 5.38 (s, 2H), 3.77 (s, 4H), 3.50-3.38 (m, 1H), 3.27-3.17 (m, 1H), 2.15 (d, 2H), 2.01-1.56 (m, 6H), 0.74 (d, 6H). |
| 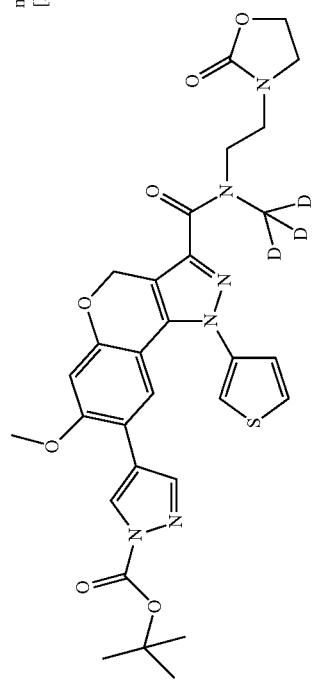 7-Methoxy-8-(1H-pyrazol-4-yl)-1-thiophen-3-yl-1,4-dihydro-chromeno[4,3-c]pyrazole-3-carboxylic acid methyl-d3-[2-(2-oxo-oxazolidin-3-yl)-ethyl]-amide (85) | 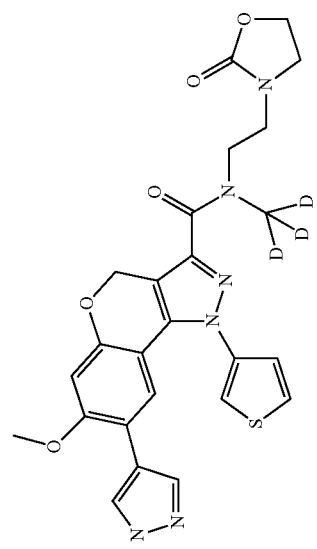 | m/z: 524 [M + H]+ | 1H NMR (400 MHz, CDCl3) δ 8.42 (s, 1H), 7.98 (s, 1H), 7.66-7.53 (m, 2H), 6.95 (s, 1H), 6.88 (s, 1H), 6.69 (dd, J = 10.0, 5.1 Hz, 1H), 5.67-5.56 (m, 2H), 4.36 (t, J = 7.8 Hz, 2H), 4.24-4.13 (m, 2H), 3.94 (s, 3H), 3.85-3.74 (m, 2H), 3.63-3.55 (m, 2H). |

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid (2-acetylamino-ethyl)-methyl-d3-amide (87) | | m/z = 484 [M + H]⁺ | ¹H-NMR (DMSO-d6): δ 8.38 (t, 0.3H), 8.04-7.78 (m, 3H), 7.40-7.31 (m, 1H), 6.69-6.57 (m, 2H), 6.03 (s, 1H), 5.53-5.36 (m, 2H), 3.93 (t, 1H), 3.75 (s, 3H), 3.49 (t, 1H), 3.30-3.15 (m, 6H), 1.84-1.72 (m, 5H), 1.62 (s, 1H), 1.43 (d, 3H). |
| (3,3-Dimethyl-morpholin-4-yl)-[7-methoxy-8-(1-methyl-d3-1H-pyrazol-4-yl)-1-thiophen-3-yl-1,4-dihydro-chromeno[4,3-c]pyrazol-3-yl]-methanone (96) | | m/z: 509 [M + H]⁺ | ¹H-NMR (400 MHz, CDCl₃) δ 7.66 (s, 1H), 7.58-7.53 (m, 2H), 7.38 (s, 1H), 7.28-7.24 (m, 1H), 6.98 (s, 1H), 6.66 (s, 1H), 5.51 (s, 2H), 4.14-4.08 (m, 2H), 3.91 (s, 3H), 3.89-3.85 (m, 2H), 3.51 (s, 2H), 1.55 (s, 6H). |

-continued

| Compound | Starting material | LC/MS | NMR |
|---|---|---|---|
| 7-Methoxy-8-(2-methyl-propenyl)-1-thiophen-3-yl-1,4-dihydro-chromeno[4,3-c]pyrazole-3-carboxylic acid methyl-d3-((1R,3S)-3-methyl-d3-carbamoyl-cyclohexyl)-amide (107) | | m/z = 541 [M + H]+ | 1H-NMR (DMSO-d6): δ 7.98 (s, 1H), 7.84-7.80 (m, 1H), 7.69 (s, 1H), 7.57 (s, 1H), 7.34 (d, 1H), 6.69-6.59 (m, 1H), 6.03 (s, 1H), 5.39 (d, 2H), 4.71 (s, 1H), 4.39 (s, 1H), 4.09 (s, 1H), 3.76 (s, 3H), 3.18 (s, 5H), 2.21 (d, 1H), 1.88-1.19 (m, 6H). |
| 7-Methoxy-8-(1-methyl-1H-pyrrol-3-yl)-1-thiophen-3-yl-1,4-dihydro-chromeno[4,3-c]pyrazole-3-carboxylic acid (3-methoxy-d3-methyl-oxetan-3-yl)-methyl-d3-amide (113) | | m/z = 527 [M + H]+ | 1H-NMR (DMSO-d6): δ 8.04 (dd, 1H), 7.90 (dd, 1H), 7.39 (dd, 1H), 7.00 (t, 1H), 6.85 (s, 1H), 6.71 (s, 1H), 6.63 (t, 1H), 5.81-5.78 (m, 1H), 5.40 (s, 2H), 4.69 (d, 2H), 4.39 (d, 2H), 3.88 (s, 2H), 3.84 (s, 3H), 3.59 (s, 3H). |

-continued

| Compound | Starting material | LC/MS | NMR |
|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid (3-methoxy-d3-methyl-oxetan-3-yl)-methyl-d3-amide (114) | | m/z = 528 [M + H]+ | 1H-NMR (DMSO-d6): δ 8.02-7.95 (m, 1H), 7.84 (dd, 1H), 7.60 (d, 1H), 7.47 (s, 1H), 7.34 (d, 1H), 6.76 (s, 1H), 6.49 (d, 1H), 5.44 (s, 2H), 4.70 (d, 2H), 4.40 (d, 2H), 3.88 (s, 2H), 3.84 (s, 3H), 3.78 (s, 3H). |
| 7-Methoxy-8-(1-methyl-1H-pyrrol-3-yl)-1-thiophen-3-yl-1,4-dihydro-chromeno[4,3-c]pyrazole-3-carboxylic acid methyl-d3-(3-methyl-oxetan-3-yl)-amide (115) | | m/z = 494 [M + H]+ | 1H-NMR (DMSO-d6): δ 8.08-8.00 (m, 1H), 7.90 (dd, 1H), 7.39 (d, 1H), 7.00 (s, 1H), 6.85 (s, 1H), 6.71 (s, 1H), 6.63 (t, 1H), 5.80 (s, 1H), 5.40 (s, 2H), 4.69 (d, 2H), 4.24 (d, 2H), 3.83 (s, 3H), 3.59 (s, 3H), 1.63 (s, 3H). |

| Compound | Starting material | LC/MS | NMR |
|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid methyl-d3-(3-methyl-oxetan-3-yl)-amide (116) | | m/z = 495 [M + H]⁺ | ¹H-NMR (DMSO-d6): δ 7.98 (dd, 1H), 7.84 (dd, 1H), 7.60 (d, 1H), 7.47 (s, 1H), 7.34 (dd, 1H), 6.76 (s, 1H), 6.49 (d, 1H), 5.43 (s, 2H), 4.69 (d, 2H), 4.24 (d, 2H), 3.84 (s, 3H), 3.78 (s, 3H), 1.63 (s, 3H). |
| 7-Methoxy-8-(2-methyl-2H-pyrazol-3-yl)-1-thiophen-3-yl-1,4-dihydro-chromeno[4,3-c]pyrazole-3-carboxylic acid methyl-d3-(3-methyl-oxetan-3-yl)-amide (118) | | m/z = 495 [M + H]⁺ | ¹H-NMR (DMSO-d6): δ 8.00 (dd, 1H), 7.81 (dd, 1H), 7.39-7.34 (m, 2H), 6.87 (s, 1H), 6.60 (s, 1H), 6.01 (d, 1H), 5.49 (s, 2H), 4.69 (d, 2H), 4.24 (d, 2H), 3.80 (s, 3H), 3.52 (s, 3H), 1.63 (s, 3H). |

| Compound | Starting material | LC/MS | NMR |
|---|---|---|---|
| 7-Methoxy-8-(2-methyl-2H-pyrazol-3-yl)-1-thiophen-3-yl-1,4-dihydro-chromeno[4,3-c]pyrazole-3-carboxylic acid (3-methoxy-d3-methyl-oxetan-3-yl)-methyl-d3-amide (119) | 7-Methoxy-8-(2-methyl-2H-pyrazol-3-yl)-1-thiophen-3-yl-1,4-dihydro-chromeno[4,3-c]pyrazole-3-carboxylic acid (3-methoxy-d3-methyl-oxetan-3-yl)-methyl-d3-amide (119) | m/z = 528 [M + H]+ | 1H-NMR (DMSO-d6): δ 8.00 (dd, 1H), 7.81 (dd, 1H), 7.39-7.34 (dd, 2H), 6.87 (s, 1H), 6.60 (s, 1H), 6.01 (d, 1H), 5.49 (s, 2H), 4.69 (d, 2H), 4.39 (d, 2H), 3.88 (s, 2H), 3.80 (s, 3H), 3.53 (s, 3H). |
| 7-Methoxy-8-(1-methyl-1H-pyrazol-3-yl)-1-thiophen-3-yl-1,4-dihydro-chromeno[4,3-c]pyrazole-3-carboxylic acid methyl-d3-(tetrahydro-furan-3-yl)-amide (140) | 7-Methoxy-8-(1-methyl-1H-pyrazol-3-yl)-1-thiophen-3-yl-1,4-dihydro-chromeno[4,3-c]pyrazole-3-carboxylic acid methyl-d3-(tetrahydro-furan-3-yl)-amide (140) | m/z = 495 [M + H]+ | 1H-NMR (DMSO-d6): δ 7.97 (dd, 1H), 7.83 (dd, 1H), 7.60 (d, 1H), 7.50 (s, 1H), 7.34 (s, 1H), 6.76 (s, 1H), 6.50 (d, 1H), 5.59 (s, 1H), 5.43 (s, 2H), 5.20 (s, 1H), 4.01-3.91 (m, 1H), 3.89-3.54 (m, 10H), 2.26-2.17 (m, 1H), 1.95 (s, 1H). |

| Compound | Starting material | LC/MS | NMR |
|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid (3-methoxy-d3-cyclobutyl)-methyl-d3-amide (142) | | m/z = 511 [M + H]+ | 1H-NMR (DMSO-d6): δ 8.06-8.00 (m, 1H), 7.92-7.87 (m, 1H), 7.42-7.36 (m, 1H), 7.00 (t, 1H), 6.88 (s, 1H), 6.71 (s, 1H), 6.64 (t, 1H), 5.81 (s, 1H), 5.37 (s, 2H), 5.12-4.86 (m, 1H), 4.46 (s, 1H), 3.97-3.79 (m, 3.5H), 3.70-3.50 (m, 4H), 2.47-2.38 (m, 1H), 2.24-1.98 (m, 2H). |
| 8-(1-methyl, 3-methyl-d3-1H-pyrazol-4-yl)-7-methoxy-1-thiophen-3-yl-1,4-dihydro-chromeno[4,3-c]pyrazole-3-carboxylic acid methyl-d3-(tetrahydro-furan-3-yl)-amide (143) | | m/z = 512 [M + H]+ | 1H-NMR (DMSO-d6): δ 8.02-7.97 (m, 1H), 7.81 (dd, 1H), 7.56 (s, 1H), 7.36 (s, 1H), 7.17 (s, 1H), 6.79-6.69 (m, 1H), 6.63-6.55 (m, 1H), 5.58 (s, 1H), 5.42 (s, 2H), 5.19 (s, 1H), 3.99-3.92 (m, 1H), 3.81-3.53 (m, 4H), 2.26-2.14 (m, 1H), 2.03-1.82 (m, 4H). |

-continued

| Compound | Starting material | LC/MS | NMR |
|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid methyl-d3-(tetrahydro-furan-3-yl)-amide (146) | | m/z = 494 [M + H]+ | 1H-NMR (DMSO-d6): δ 8.03 (dd, 1H), 7.89 (dd, 1H), 7.40 (s, 1H), 7.01 (t, 1H), 6.93-6.84 (m, 1H), 6.71 (s, 1H), 6.64 (t, 1H), 5.81 (s, 1H), 5.60 (s, 1H), 5.39 (s, 2H), 5.19 (s, 1H), 3.99-3.92 (m, 1H), 3.84 (s, 3H), 3.80-3.53 (m, 7H), 2.26-2.16 (m, 1H), 1.97 (s, 1H). |
| 8-Isobutyl-7-methoxy-1-thiophen-3-yl-1,4-dihydro-chromeno[4,3-c]pyrazole-3-carboxylic acid (3-methoxy-d3-methyl-oxetan-3-yl)-methyl-d3-amide (162) | | m/z = 504 [M + H]+ | 1H-NMR (DMSO-d6): δ 7.96 (dd, 1H), 7.83 (dd, 1H), 7.33 (s, 1H), 6.66 (s, 1H), 6.42 (s, 1H), 5.37 (s, 2H), 4.69 (d, 2H), 4.39 (d, 2H), 3.88 (s, 2H), 3.76 (s, 3H), 2.14 (d, 2H), 1.62 (septet, 1H), 0.74 (d, 6H). |

| Compound | Starting material | LC/MS | NMR |
|---|---|---|---|
| 8-Isobutyl-7-methoxy-1-thiophen-3-yl-1,4-dihydro-chromeno[4,3-c]pyrazole-3-carboxylic acid methyl-d3-(3-methyl-oxetan-3-yl)-amide (163) | | m/z = 471 [M + H]+ | 1H-NMR (DMSO-d6): δ 7.96 (dd, 1H), 7.83 (dd, 1H), 7.33 (dd, 1H), 6.66 (s, 1H), 6.42 (s, 1H), 5.37 (s, 2H), 4.69 (d, 2H), 4.24 (d, 2H), 3.76 (s, 3H), 2.14 (d, 2H), 1.66-1.60 (m, 4H), 0.74 (d, 6H). |
| 7-Methoxy-8-(1-methyl-1H-pyrazol-3-yl)-1-thiophen-3-yl-1,4-dihydro-chromeno[4,3-c]pyrazole-3-carboxylic acid (3-methoxy-d3-oxetan-3-ylmethyl)-methyl-d3-amide (167) | | m/z = 528 [M + H]+ | 1H-NMR (DMSO-d6): δ 8.00-7.93 (m, 1H), 7.85-7.80 (m, 1H), 7.60 (d, 1H), 7.33 (d, 1H), 6.76 (s, 1H), 6.50 (d, 1H), 5.76 (s, 1H), 5.43 (s, 2H), 4.59-4.41 (m, 4H), 3.99 (s, 1H), 3.84 (s, 3H), 3.80-3.76 (m, 3H), 3.69 (s, 1H). |

| Compound | Starting material | LC/MS | NMR |
|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid (3-methoxy-d3-oxetan-3-ylmethyl)-methyl-d3-amide (168) | | m/z = 527 [M + H]+ | 1H-NMR (DMSO-d6): δ 8.06-7.99 (m, 1H), 7.92-7.87 (m, 1H), 7.41-7.36 (m, 1H), 7.00 (s, 1H), 6.94-6.84 (m, 1H), 6.71 (s, 1H), 6.63 (t, 1H), 5.80 (s, 1H), 5.40 (s, 2H), 4.58-4.40 (m, 5H), 3.99 (s, 1H), 3.84 (s, 3H), 3.59 (s, 3H). |
| 7-Methoxy-8-(1-methyl-1H-pyrazol-3-yl)-1-thiophen-3-yl-1,4-dihydro-chromeno[4,3-c]pyrazole-3-carboxylic acid ((1S,3R)-3-methoxy-d3-cyclopentyl)-methyl-d3-amide (177) | | m/z = 526 [M + H]+ | 1H-NMR (DMSO-d6): δ 7.96 (s, 1H), 7.83 (s, 1H), 7.60 (s, 1H), 7.51 (d, 1H), 7.34 (s, 1H), 6.76 (s, 1H), 6.50 (s, 1H), 5.48-5.36 (m, 2H), 5.25 (s, 1H), 4.97 (s, 1H), 3.88-3.67 (m, 7H), 2.14 (s, 1H), 1.85-1.49 (m, 5H). |

| Compound | Starting material | LC/MS | NMR |
|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid ((1S,3R)-3-methoxy-d3-cyclopentyl)-methyl-d3-amide (178) | | m/z = 525 [M + H]⁺ | ¹H-NMR (DMSO-d6): δ 8.02 (s, 1H), 7.90 (s, 1H), 7.39 (s, 1H), 7.01 (s, 1H), 6.94-6.84 (m, 1H), 6.71 (s, 1H), 6.64 (s, 1H), 5.81 (s, 1H), 5.44-5.32 (m, 2H), 5.24 (s, 1H), 4.97 (s, 1H), 3.87-3.67 (m, 4H), 3.59 (s, 3H), 2.13 (s, 1H), 1.87-1.49 (m, 5H). |
| (2-Methoxy-d3-methyl-2-methyl-pyrrolidin-1-yl)-[7-methoxy-8-(1-methyl-1H-pyrazol-3-yl)-1-thiophen-3-yl-1,4-dihydro-chromeno[4,3-c]pyrazol-3-yl]-methanone (182) | | m/z = 523 [M + H]⁺ | |

| Compound | Starting material | LC/MS | NMR |
|---|---|---|---|
| (2-Methoxy-d3-methyl-2-methyl-pyrrolidin-1-yl)-[7-methoxy-8-(1-methyl-1H-pyrrol-3-yl)-1-thiophen-3-yl-1,4-dihydro-chromeno[4,3-c]pyrazol-3-yl]-methanone (184) | | m/z = 522 [M + H]+ | ¹H-NMR (DMSO-d6): δ 8.01 (s, 1H), 7.89 (s, 1H), 7.38 (s, 1H), 7.00 (s, 1H), 6.85 (s, 1H), 6.71 (s, 1H), 6.63 (s, 1H), 5.80 (s, 1H), 5.44 (s, 2H), 4.11-4.02 (m, 1H), 3.90-3.81 (m, 5H), 3.62-3.54 (m, 4H), 2.17-2.07 (m, 1H), 1.88-1.74 (m, 2H), 1.68-1.59 (m, 1H), 1.42 (s, 3H). |
| 7-Methoxy-8-(1-methyl-1H-pyrazol-3-yl)-1-thiophen-3-yl-1,4-dihydro-chromeno[4,3-c]pyrazole-3-carboxylic acid methyl-d3-(3-methyl-azetidin-3-yl)-amide (193) | | m/z = 494 [M + H]+ | ¹H-NMR (DMSO-d6): δ 8.23 (s, 1H), 8.02 (dd, 1H), 7.86 (dd, 1H), 7.60 (d, 1H), 7.42 (s, 1H), 7.34 (dd, 1H), 6.76 (s, 1H), 6.49 (d, 1H), 5.54 (s, 2H), 5.18 (s, 1H), 3.84 (s, 3H), 3.77 (s, 3H), 3.44-3.36 (m, 4H), 1.05 (s, 3H). |

-continued

| Compound | Starting material | LC/MS | NMR |
|---|---|---|---|
| 7-Methoxy-8-(1-methyl-1H-pyrazol-3-yl)-1-thiophen-3-yl-1,4-dihydro-chromeno[4,3-c]pyrazole-3-carboxylic acid ((1S,3S)-3-methoxy-d3-cyclopentyl)-methyl-d3-amide (196) | | m/z = 526 [M + H]+ | ¹H-NMR (DMSO-d6): δ 8.00-7.90 (m, 1H), 7.83 (dd, 1H), 7.63-7.46 (m, 2H), 7.32 (dd, 1H), 6.76 (s, 1H), 6.50 (d, 1H), 5.50-5.26 (m, 2.5H), 5.02 (s, 0.5H), 3.91-3.75 (m, 7H), 2.02-1.51 (m, 6H). |
| 7-Methoxy-8-(1-methyl-1H-pyrrol-3-yl)-1-thiophen-3-yl-1,4-dihydro-chromeno[4,3-c]pyrazole-3-carboxylic acid ((1S,3S)-3-methoxy-d3-cyclopentyl)-methyl-d3-amide (197) | | m/z = 525 [M + H]+ | ¹H-NMR (DMSO-d6): δ 8.00 (s, 1H), 7.89 (dd, 1H), 7.37 (d, 1H), 7.00 (d, 1H), 6.89 (d, 1H), 6.71 (s, 1H), 6.64 (t, 1H), 5.81 (s, 1H), 5.45-5.24 (m, 2.5H), 5.01 (s, 0.5H), 3.84 (s, 4H), 3.64-3.57 (m, 4H), 2.03-1.50 (m, 8H). |

| Compound | Starting material | LC/MS | NMR |
|---|---|---|---|
| 7-Methoxy-8-(1-methyl-1H-pyrrol-3-yl)-1-thiophen-3-yl-1,4-dihydro-chromeno[4,3-c]pyrazole-3-carboxylic acid [3-(2-methoxy-d3-ethyl)-oxetan-3-yl]-methyl-d3-amide (198) | 7-Methoxy-8-(1-methyl-1H-pyrrol-3-yl)-1-thiophen-3-yl-1,4-dihydro-chromeno[4,3-c]pyrazole-3-carboxylic acid [3-(2-methoxy-ethyl)-oxetan-3-yl]-amide | m/z = 541 [M + H]+ | 1H-NMR (DMSO-d6): δ 8.03 (dd, 1H), 7.89 (dd, 1H), 7.38 (dd, 1H), 7.00 (t, 1H), 6.86 (s, 1H), 6.72 (s, 1H), 6.63 (t, 1H), 5.80 (dd, 1H), 5.37 (s, 2H), 4.09 (d, 1H), 3.85-3.72 (m, 7H), 3.67-3.56 (m, 6H). |
| 7-Methoxy-8-(propane-2-sulfonyl)-1-thiophen-3-yl-1,4-dihydro-chromeno[4,3-c]pyrazole-3-carboxylic acid methyl-d3-(3-methyl-oxetan-3-yl)-amide (199) | 7-Methoxy-8-(propane-2-sulfonyl)-1-thiophen-3-yl-1,4-dihydro-chromeno[4,3-c]pyrazole-3-carboxylic acid methyl-(3-methyl-oxetan-3-yl)-amide | m/z = 521 [M + H]+ | 1H-NMR (DMSO-d6): δ 7.99 (dd, 1H), 7.85 (dd, 1H), 7.33 (dd, 1H), 7.22 (s, 1H), 6.93 (s, 1H), 5.57 (s, 2H), 4.69 (d, 2H), 4.24 (d, 2H), 3.90 (s, 3H), 3.45 (septet, 1H), 1.62 (s, 3H), 1.08 (d, 6H). |

-continued
| Compound | Starting material | LC/MS | NMR |
|---|---|---|---|
| 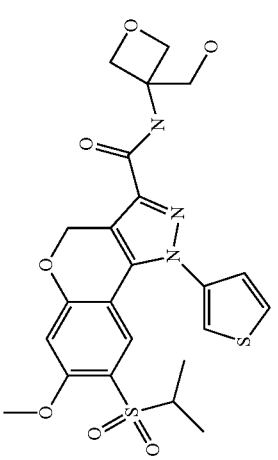<br>7-Methoxy-8-(propane-2-sulfonyl)-1-thiophen-3-yl-1,4-dihydro-chromeno[4,3-c]pyrazole-3-carboxylic acid (3-methoxy-d3-methyl-oxetan-3-yl)-methyl-d3-amide (200) | 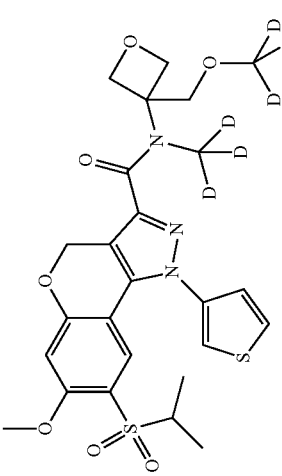 | m/z = 554 [M + H]+ | 1H-NMR (DMSO-d6): δ 7.99 (dd, 1H), 7.85 (dd, 1H), 7.33 (dd, 1H), 7.22 (s, 1H), 6.94 (s, 1H), 5.57 (s, 2H), 4.69 (d, 2H), 4.39 (d, 2H), 3.93-3.85 (m, 5H), 3.45 (septet, 1H), 1.08 (d, 6H). |

Example 9

(8-Isobutyl-7-methoxy-1-thiophen-3-yl-1,4-dihydro-chromeno[4,3-c]pyrazol-3-yl)-[4-(tetrahydro-furan-2-carbonyl)-[1,4]diazepan-1-yl]-methanone (21)

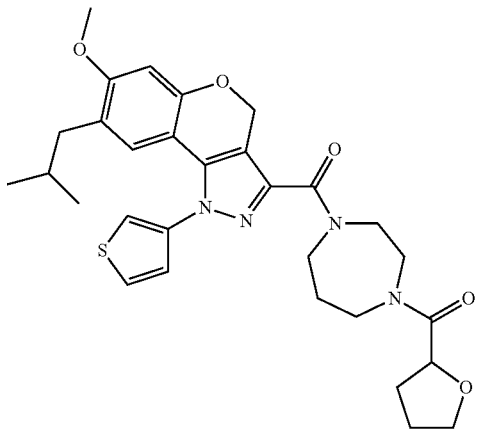 [SMILES: COc1cc2c(cc1CC(C)C)-c1c(c(C(=O)N3CCCN(C(=O)C4CCCO4)CC3)nn1-c1ccsc1)CO2]

Step 1

To 8-isobutyl-7-methoxy-1-(3-thienyl)-1,4-dihydro-chromeno[4,3-c]pyrazole-3-carboxylic acid (70.00 mg; 0.18 mmol; 1.00 eq.) in DCM (1.00 ml; 15.60 mmol; 85.68 eq.) was added N,N-Diisopropylethylamine (0.04 ml; 0.22 mmol; 1.20 eq.) 1-boc-hexahydro-1,4-diazepine (0.04 ml; 0.22 mmol; 1.20 eq.) and 2,4,6-tripropyl-1,3,5,2,4,6-trioxatriphosphinane 2,4,6-trioxide (0.08 ml; 0.27 mmol; 1.50 eq.). After stirring at room temperature for 2 h, the reaction mixture washed with water and 1N HCL. The organic layer was dried with Na$_2$SO$_4$, filtered, concentrated to afford 4-(8-Isobutyl-7-methoxy-1-thiophen-3-yl-1,4-dihydro-chromeno[4,3-c]pyrazole-3-carbonyl)-[1,4]diazepane-1-carboxylic acid tert-butyl ester (103.00 mg; 0.18 mmol) as a white foam. To 4-(8-Isobutyl-7-methoxy-1-thiophen-3-yl-1,4-dihydro-chromeno[4,3-c]pyrazole-3-carbonyl)-[1,4]diazepane-1-carboxylic acid tert-butyl ester (103.00 mg; 0.18 mmol) in methanol (1.00 ml; 24.69 mmol; 135.58 eq.) was added hydrogen chloride (0.46 ml; 1.82 mmol; 10.00 eq.) (4M in dioxane). After stirring for 4 h the reaction was mixture was concentrated to dryness and diluted with water. Mixture was lyophilized to afford [1,4]Diazepan-1-yl-(8-isobutyl-7-methoxy-1-thiophen-3-yl-1,4-dihydro-chromeno[4,3-c]pyrazol-3-yl)-methanone as a white solid.

Step 2

To [1,4]diazepan-1-yl-(8-isobutyl-7-methoxy-1-thiophen-3-yl-1,4-dihydro-chromeno[4,3-c]pyrazol-3-yl)-methanone (30.00 mg; 0.06 mmol; 1.00 eq.) in DCM (1.00 ml; 15.60 mmol; 242.64 eq.) was added N,N-Diisopropylethylamine (0.01 ml; 0.08 mmol; 1.20 eq.), tetrahydro-2-furoic acid (0.01 ml; 0.13 mmol; 2.00 eq.) and 2,4,6-tripropyl-1,3,5,2,4,6-trioxatriphosphinane 2,4,6-trioxide (0.03 ml; 0.10 mmol; 1.50 eq.). After stirring for 30 min at room temperature the reaction was concentrated to dryness and purified by flash chromatography to afford the desired compound (10.7 mg, 30%) as a white solid.

$^1$H NMR (400 MHz, CDCl$_3$) δ 7.51-7.44 (m, 2H), 7.50-7.44 (m, 1H), 7.25-7.21 (m, 1H), 6.59 (d, J=7.0 Hz, 1H), 6.56 (d, J=2.7 Hz, 1H), 5.50 (dd, J=4.9, 3.5 Hz, 2H), 4.70-4.58 (m, 1H), 4.53-4.41 (m, 1H), 4.41-4.22 (m, 1H), 4.19-4.09 (m, 1H), 4.08-3.82 (m, 4H), 3.79 (s, 3H), 3.71-3.59 (m, 2H), 3.58-3.42 (m, 1H), 2.36-2.26 (m, 1H), 2.26-2.20 (m, 2H), 2.19-1.83 (m, 3H), 1.78-1.60 (m, 2H), 0.81 (d, J=6.6 Hz, 6H). m/z: 565 [M+H]$^+$

Example 10

7-Methoxy-8-(1H-pyrazol-4-yl)-1-thiophen-3-yl-1,4-dihydro-chromeno[4,3-c]pyrazole-3-carboxylic acid methylamide (22)

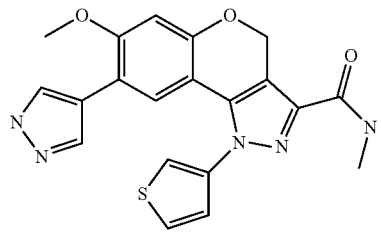 [SMILES: CNC(=O)c1nn(-c2ccsc2)c2c1COc1cc(OC)c(-c3cn[nH]c3)cc1-2]

Step 1

To 8-bromo-7-methoxy-1-thiophen-3-yl-1,4-dihydro-chromeno[4,3-c]pyrazole-3-carboxylic acid (100.00 mg; 0.25 mmol; 1.00 eq.) in a microwave vial was added 4-(4,4,5,5-tetramethyl-1,3,2-dioxaborolan-2-yl)-pyrazole-1-carboxylic acid tert-butyl ester (108.35 mg; 0.37 mmol; 1.50 eq.), [1,1'-bis(diphenylphosphino)ferrocene]dichloropalladium(ii), complex with dichloromethane (1:1) (20.05 mg; 0.02 mmol; 0.10 eq.), and cesium carbonate (0.25 ml; 0.49 mmol; 2.00 eq.) (3 Molar solution in water). The vessel was sealed and vacuumed and backfilled with nitrogen (3 times). Reaction was microwaved at 100° C. for 30 min. Mixture was diluted with EtOAc and washed with water and 1N HCl. Organic layer was dried (Na$_2$SO$_4$), filtered, concentrated to afford 8-(1-tert-Butoxycarbonyl-1H-pyrazol-4-yl)-7-methoxy-1-thiophen-3-yl-1,4-dihydro-chromeno[4,3-c] pyrazole-3-carboxylic acid as a crude product.

Step 2

To 8-(1-tert-Butoxycarbonyl-1H-pyrazol-4-yl)-7-methoxy-1-thiophen-3-yl-1,4-dihydro-chromeno[4,3-c]pyrazole-3-carboxylic acid (121.00 mg; 0.24 mmol; 1.00 eq.) in DCM (1.50 ml; 23.40 mmol; 95.64 eq.) was added DIPEA (0.09 ml; 0.49 mmol; 2.00 eq.), o-(benzotriazol-1-yl)-n,n,n',n'-tetramethyluronium tetrafluoroborate (157.13 mg; 0.49 mmol; 2.00 eq.), and n-tert-butylmethylamine (0.06 ml; 0.49 mmol; 2.00 eq.). After stirring for 30 min at room temperature the mixture was concentrated to dryness and purified by flash chromatography to afford 4-[3-(tert-Butyl-methyl-carbamoyl)-7-methoxy-1-thiophen-3-yl-1,4-dihydro-chromeno[4,3-c]pyrazol-8-yl]-pyrazole-1-carboxylic acid tert-butyl ester as a white solid (99 mg, 72%).

Step 3

To 4-[3-(tert-Butyl-methyl-carbamoyl)-7-methoxy-1-thiophen-3-yl-1,4-dihydro-chromeno[4,3-c]pyrazol-8-yl]-pyrazole-1-carboxylic acid tert-butyl ester (99.00 mg; 0.18 mmol) in methanol (3.00 ml; 74.06 mmol; 302.68 eq.) was added hydrochloric acid (0.20 ml; 0.80 mmol; 3.27 eq.) (4M in dioxane). After stirring at room temperature for 1 h, the mixture was concentrated and purified by flash chromatography to afford the desired product (33.8 mg, 34%) as a white solid.

$^1$H NMR (400 MHz, DMSO) δ 12.83 (s, 1H), 8.33 (dd, J=9.4, 4.6 Hz, 1H), 8.07 (dd, J=3.2, 1.4 Hz, 1H), 7.92 (dd, J=5.1, 3.2 Hz, 1H), 7.77 (s, 1H), 7.41 (dd, J=5.1, 1.4 Hz, 1H), 7.32 (s, 1H), 6.85 (s, 1H), 6.76 (s, 1H), 5.52 (s, 2H), 3.86 (s, 3H), 2.75 (d, J=4.7 Hz, 3H). m/z: 408 [M+H]$^+$

Example 11

[4-(Azetidine-1-carbonyl)-azepan-1-yl]-(8-isopropoxy-7-methoxy-1-thiophen-3-yl-1,4-dihydro-chromeno[4,3-c]pyrazol-3-yl)-methanone (26)

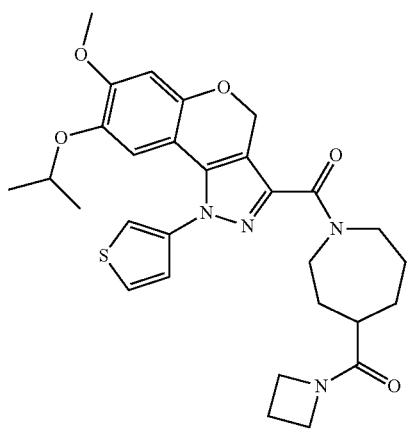 [SMILES: COc1cc2c(cc1OC(C)C)-c1c(c(C(=O)N3CCCC(C(=O)N4CCC4)CC3)nn1-c1ccsc1)CO2]

To 1-(8-isopropoxy-7-methoxy-1-(thiophen-3-yl)-1,4-dihydrochromeno[4,3-c]pyrazole-3-carbonyl)azepane-4-carboxylic acid (45.00 mg; 0.09 mmol; 1.00 eq.) in DCM (2.00 ml; 31.20 mmol; 354.72 eq.) was added DIPEA (0.02 ml; 0.13 mmol; 1.50 eq.), Azetidine (0.01 ml; 0.13 mmol; 1.50 eq.) and 2,4,6-tripropyl-[1,3,5,2,4,6]trioxatriphosphinane 2,4,6-trioxide (0.08 ml; 0.13 mmol; 1.50 eq.). After stirring at room temperature for 30 min the reaction mixture was concentrated to dryness and purified by flash chromatography to afford the desired product (24.5 mg, 51%) as a white solid.

$^1$H NMR (400 MHz, CDCl$_3$) δ 7.54-7.45 (m, 2H), 7.24 (t, J=5.0 Hz, 1H), 6.61 (s, 1H), 6.43 (d, J=5.8 Hz, 1H), 5.55-5.41 (m, 2H), 4.59 (d, J=14.3 Hz, 1H), 4.23-3.86 (m, 4H), 3.83 (s, 3H), 3.77-3.49 (m, 1H), 3.35-3.27 (m, 1H), 2.42-2.07 (m, 4H), 2.03-1.68 (m, 6H), 1.27 (t, J=7.1 Hz, 1H), 1.21 (d, J=6.1 Hz, 6H). m/z: 551 [M+H]

Example 12

8-Isopropoxy-7-methoxy-1-thiophen-3-yl-1,4-dihydro-chromeno[4,3-c]pyrazole-3-carboxylic acid (3-amino-propyl)-amide (27)

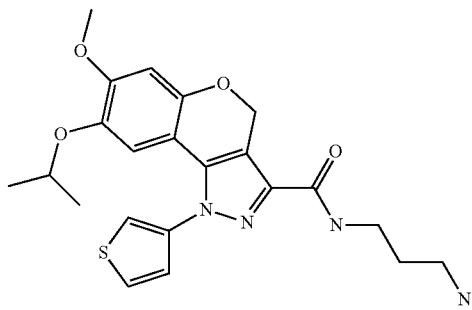 [SMILES: COc1cc2c(cc1OC(C)C)-c1c(c(C(=O)NCCCN)nn1-c1ccsc1)CO2]

Step 1

To 8-isopropoxy-7-methoxy-1-thiophen-3-yl-1,4-dihydro-chromeno[4,3-c]pyrazole-3-carboxylic acid (120.00 mg; 0.31 mmol; 1.00 eq.) in DCM (1.00 ml; 15.60 mmol; 50.24 eq.) was added N,N-Diisopropylethylamine (0.07 ml; 0.37 mmol; 1.20 eq.), n-boc-1,3-diaminopropane (81.16 mg; 0.47 mmol; 1.50 eq.) and 2,4,6-tripropyl-1,3,5,2,4,6-trioxatriphosphinane 2,4,6-trioxide (0.14 ml; 0.47 mmol; 1.50 eq.). After stirring for 30 min at room temperature, the reaction mixture was concentrated to dryness and purified by flash chromatography to afford {3-[(8-Isopropoxy-7-methoxy-1-thiophen-3-yl-1,4-dihydro-chromeno[4,3-c]pyrazole-3-carbonyl)-amino]-propyl}-carbamic acid tert-butyl ester (170 mg, 100%) as a white solid.

Step 2

To {3-[(8-Isopropoxy-7-methoxy-1-thiophen-3-yl-1,4-dihydro-chromeno[4,3-c]pyrazole-3-carbonyl)-amino]-propyl}-carbamic acid tert-butyl ester (172.70 mg; 0.32 mmol) in methanol (4.00 ml; 98.75 mmol; 317.98 eq.) was added hydrochloric acid in dioxane (0.31 ml; 1.24 mmol; 4.00 eq.). After stirring at room temperature for 18 h the reaction mixture was concentrated to dryness and purified by flash chromatography to afford the desired compound (71.3 mg, 52%) as a white solid.

$^1$H NMR (400 MHz, CDCl$_3$) δ 8.77-8.64 (m, 2H), 7.55 (d, J=7.2 Hz, 2H), 6.62 (s, 1H), 6.36 (s, 1H), 5.51 (s, 2H), 4.13-3.94 (m, 2H), 3.85 (s, 3H), 3.65-3.59 (m, 2H), 3.23-3.07 (m, 2H), 2.21-2.09 (m, 1H), 1.21 (d, J=6.0 Hz, 6H). m/z: 443 [M+H]$^+$

Example 13

8-Isopropoxy-7-methoxy-1-thiophen-3-yl-1,4-dihydro-chromeno[4,3-c]pyrazole-3-carboxylic acid [3-(cyclobutanecarbonyl-amino)-propyl]-amide (28)

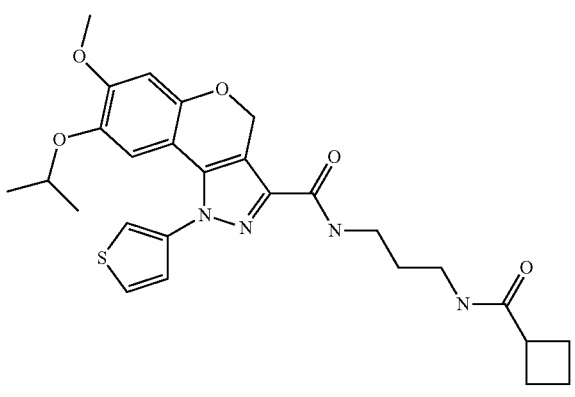 [SMILES: COc1cc2c(cc1OC(C)C)-c1c(c(C(=O)NCCCNC(=O)C3CCC3)nn1-c1ccsc1)CO2]

To 8-isopropoxy-7-methoxy-1-thiophen-3-yl-1,4-dihydro-chromeno[4,3-c]pyrazole-3-carboxylic acid (3-amino-propyl)-amide (27) (65.00 mg; 0.15 mmol; 1.00 eq.) in DCM (1.00 ml; 15.60 mmol; 106.21 eq.) was added N,N-Diisopropylethylamine (0.03 ml; 0.18 mmol; 1.20 eq.) cyclobutanecarboxylic acid (0.14 ml; 1.50 mmol; 10.21 eq.) and 2,4,6-tripropyl-1,3,5,2,4,6-trioxatriphosphinane 2,4,6-trioxide (0.13 ml; 0.22 mmol; 1.50 eq.). After stirring at room temperature for 18 h the reaction mixture was concentrated to dryness and purified by flash chromatography to afford the desired compound (55.8 mg, 72%) as a white solid.

$^1$H NMR (400 MHz, CDCl$_3$) δ 7.57-7.46 (m, 2H), 7.23 (d, J=5.0 Hz, 1H), 7.16 (t, J=6.3 Hz, 1H), 6.59 (s, 1H), 6.35 (m, 2H), 5.54 (s, 2H), 4.02 (dt, J=12.1, 6.0 Hz, 1H), 3.82 (s, 3H), 3.46 (q, J=6.2 Hz, 1H), 3.31 (q, J=6.0 Hz, 2H), 3.03 (p, J=8.6 Hz, 1H), 2.36-2.22 (m, 2H), 2.20-2.10 (m, 2H), 2.01-1.80 (m, 2H), 1.79-1.67 (m, 2H), 1.19 (d, J=6.1 Hz, 6H). m/z: 525 [M+H]$^+$

Example 14

Cyclobutanecarboxylic acid {1-[7-methoxy-8-(2-methyl-propenyl)-1-thiophen-3-yl-1,4-dihydro-chromeno[4,3-c]pyrazole-3-carbonyl]-azepan-4-yl}-amide (37)

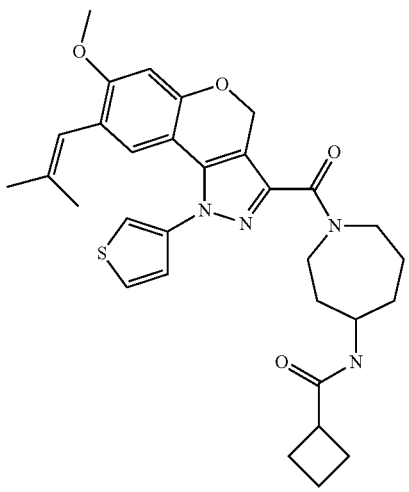 [SMILES: COc1cc2c(cc1C=C(C)C)-c1c(c(C(=O)N3CCCC(NC(=O)C4CCC4)CC3)nn1-c1ccsc1)CO2]

To (4-amino-azepan-1-yl)-[7-methoxy-8-(2-methyl-propenyl)-1-thiophen-3-yl-1,4-dihydro-chromeno[4,3-c]pyrazol-3-yl]-methanone (55.00 mg; 0.11 mmol; 1.00 eq.) in DCM (1.00 ml; 15.60 mmol; 135.76 eq.) was added N,N-Diisopropylethylamine (0.02 ml; 0.14 mmol; 1.20 eq.) cyclobutanecarboxylic acid (0.14 ml; 1.50 mmol; 13.05 eq.) and 2,4,6-tripropyl-1,3,5,2,4,6-trioxatriphosphinane 2,4,6-trioxide (0.10 ml; 0.17 mmol; 1.50 eq.). After stirring for 30 min at room temperature the reaction mixture was washed with NaHCO$_3$, and extracted with DCM. The organic layer was concentrated and purified by flash chromatography to afford the desired compound (60.3 mg, 94%) as a white solid.

$^1$H NMR (400 MHz, CDCl$_3$) δ 7.53-7.44 (m, 2H), 7.23 (dd, J=5.0, 1.3 Hz, 1H), 6.76 (s, 1H), 6.57 (s, 1H), 6.12 (s, 1H), 5.60-5.45 (m, 3H), 4.61-4.49 (m, 1H), 4.43-4.30 (m, 1H), 4.18-3.99 (m, 2H), 3.82 (s, 3H), 3.60-3.48 (m, 1H), 3.45-3.34 (m, 1H), 3.26 (t, J=10.3 Hz, 1H), 3.00-2.81 (m, 1H), 2.31-2.06 (m, 4H), 2.01-1.87 (m, 2H), 1.85 (s, 3H), 1.72-1.59 (m, 4H), 1.54 (s, 3H). m/z: 547 [M+H]$^+$

Example 15

8-(1,2-Dihydroxy-2-methyl-propyl)-7-methoxy-1-thiophen-3-yl-1,4-dihydro-chromeno[4,3-c]pyrazole-3-carboxylic acid tert-butyl-methyl-amide (38)

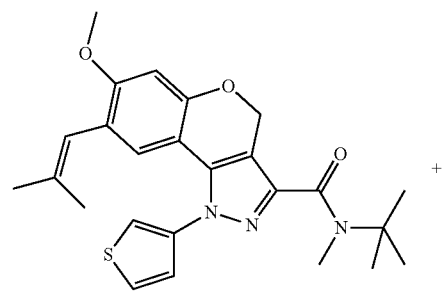

-continued

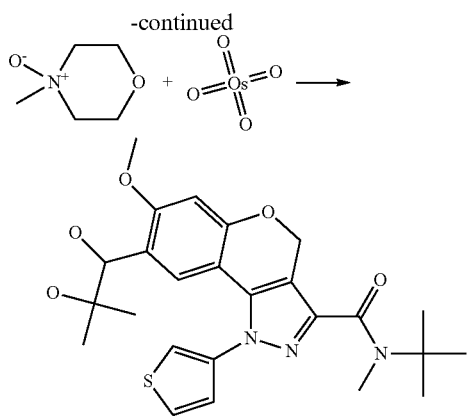

To 7-methoxy-8-(2-methyl-propenyl)-1-thiophen-3-yl-1,4-dihydro-chromeno[4,3-c]pyrazole-3-carboxylic acid tert-butyl-methyl-amide (30.00 mg; 0.07 mmol; 1.00 eq.) in water (0.10 ml), and acetone (0.40 ml) was added 4-methylmorpholine 4-oxide (23.35 mg; 0.20 mmol; 3.00 eq.) and osmium tetroxide (0.51 mg; 0.00 mmol; 0.03 eq.). After stirring for 1 h at room temperature the mixture was quenched with saturated sodium sulfide and extracted with EtOAc. The organic layer was dried (Na$_2$SO$_4$), filtered, concentrated and purified by flash chromatography to afford the desired compound (22.5 mg, 70%) as a white solid.

$^1$H NMR (400 MHz, CDCl$_3$) δ 7.51 (dd, J=3.2, 1.3 Hz, 1H), 7.47 (dd, J=5.1, 3.2 Hz, 1H), 7.21 (dd, J=5.1, 1.3 Hz, 1H), 6.90 (s, 1H), 6.56 (s, 1H), 5.53-5.38 (m, 2H), 4.69 (s, 1H), 3.81 (s, 3H), 3.27 (s, 3H), 2.67 (s, 1H), 1.52 (s, 9H), 1.28 (dd, J=6.0, 3.0 Hz, 1H), 1.15 (s, 3H), 0.97 (s, 3H). m/z: 486 [M+H]$^+$

Example 16

1-[7-Methoxy-8-(2-methyl-propenyl)-1-thiophen-3-yl-1,4-dihydro-chromeno[4,3-c]pyrazole-3-carbonyl]-azepane-4-carboxylic acid dimethylamide (41)

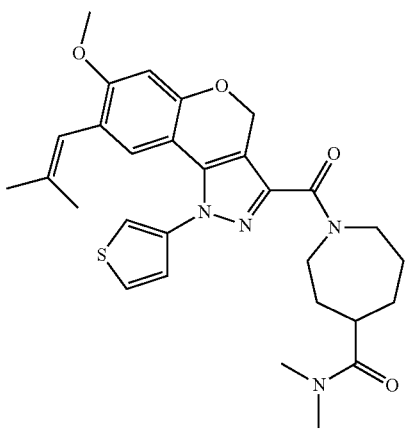 [SMILES: COc1cc2c(cc1C=C(C)C)-c1c(c(C(=O)N3CCCC(C(=O)N(C)C)CC3)nn1-c1ccsc1)CO2]

To 1-[7-methoxy-8-(2-methyl-propenyl)-1-thiophen-3-yl-1,4-dihydro-chromeno[4,3-c]pyrazole-3-carbonyl]-azepane-4-carboxylic acid (100.00 mg; 0.20 mmol; 1.00 eq.) in DCM (1.00 ml; 15.60 mmol; 79.19 eq.) was added N,N-Diisopropylethylamine (0.04 ml; 0.24 mmol; 1.20 eq.), dimethylamine hydrochloride (24.10 mg; 0.30 mmol; 1.50 eq.) and 2,4,6-tripropyl-1,3,5,2,4,6-trioxatriphosphinane 2,4,6-trioxide (0.17 ml; 0.30 mmol; 1.50 eq.). After stirring for 30 min at room temperature the reaction mixture was concentrated and purified by flash chromatography to afford the desired compound (92.3 mg, 88%) as a white solid.

$^1$H NMR (500 MHz, cdcl$_3$) δ 7.46-7.34 (m, 2H), 7.14 (ddd, J=13.8, 4.9, 1.4 Hz, 1H), 6.67 (d, J=12.0 Hz, 1H), 6.49 (d, J=1.8 Hz, 1H), 6.03 (s, 1H), 5.52-5.41 (m, 2H), 4.61-4.55 (m, 1H), 4.22-4.10 (m, 1H), 3.98-3.85 (m, 1H), 3.73 (s, 3H), 3.55-3.48 (m, 1H), 3.45-3.37 (m, 1H), 3.22-3.14 (m, 1H), 2.96 (s, 1H), 2.88 (d, J=8.1 Hz, 3H), 2.83 (s, 1H), 2.71-2.60 (m, 1H), 2.14-2.04 (m, 1H), 1.95-1.83 (m, 2H), 1.76 (s, 3H), 1.70-1.53 (m, 2H), 1.45 (d, J=4.8 Hz, 3H). m/z: 535 [M+H]$^+$ Example 17

1-[7-Methoxy-8-(2-methyl-propenyl)-1-thiophen-3-yl-1,4-dihydro-chromeno[4,3-c]pyrazole-3-carbonyl]-azepane-4-carboxylic acid methylamide (42)

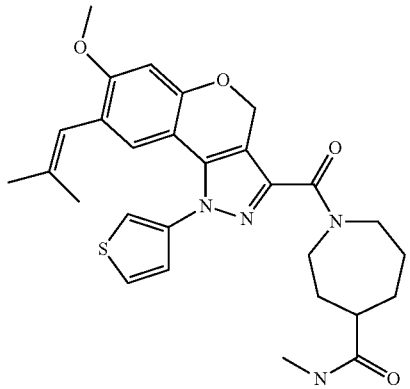 [SMILES: CNC(=O)C1CCCN(C(=O)c2nn(-c3ccsc3)c3c2COc2cc(OC)c(C=C(C)C)cc2-3)CC1]

In a similar manner to example 16, 1-[7-methoxy-8-(2-methyl-propenyl)-1-thiophen-3-yl-1,4-dihydro-chromeno[4,3-c]pyrazole-3-carbonyl]-azepane-4-carboxylic acid methylamide was obtained from 1-[7-Methoxy-8-(2-methyl-propenyl)-1-thiophen-3-yl-1,4-dihydro-chromeno[4,3-c]pyrazole-3-carbonyl]-azepane-4-carboxylic acid (100.00 mg; 0.20 mmol; 1.00 eq.) in DCM (1.00 ml; 15.60 mmol; 79.19 eq.), and methylamine hydrochloride (13.30 mg; 0.20 mmol; 1.00 eq.). The desired compound was obtained in 52% yield (53.5 mg) as a white solid.

$^1$H NMR (500 MHz, cdcl$_3$) δ 7.49-7.43 (m, 2H), 7.21 (d, J=5.1 Hz, 1H), 6.74 (s, 1H), 6.56 (s, 1H), 6.10 (s, 1H), 5.55 (t, J=4.9 Hz, 1H), 5.52 (t, J=4.1 Hz, 2H), 4.49-4.43 (m, 1H), 4.18 (dt, J=14.5, 5.4 Hz, 1H), 4.07-4.00 (m, 1H), 3.95 (dt, J=9.5, 4.4 Hz, 1H), 3.85-3.82 (m, 1H), 3.80 (s, 3H), 3.72-3.63 (m, 1H), 3.49-3.42 (m, 1H), 2.78 (dd, J=14.0, 4.8 Hz, 3H), 2.34-2.12 (m, 1H), 2.05-1.91 (m, 1H), 1.84 (d, J=1.2 Hz, 3H), 1.80-1.68 (m, 2H), 1.54-1.51 (s, 3H). m/z: 521 [M+H]$^+$

Example 18

1-[7-methoxy-8-(2-methyl-propenyl)-1-thiophen-3-yl-1,4-dihydro-chromeno[4,3-c]pyrazole-3-carbonyl]-azepane-4-carboxylic acid amide (43)

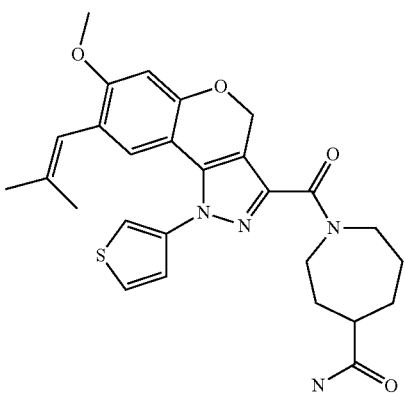 [SMILES: COc1cc2c(cc1C=C(C)C)-c1c(c(C(=O)N3CCCC(C(N)=O)CC3)nn1-c1ccsc1)CO2]

To 1-[7-methoxy-8-(2-methyl-propenyl)-1-thiophen-3-yl-1,4-dihydro-chromeno[4,3-c]pyrazole-3-carbonyl]-azepane-4-carboxylic acid (75.00 mg; 0.15 mmol; 1.00 eq.) in DMSO (1.00 ml) was added 1,1'-carbonylbis(1H-imidazole) (119.72 mg; 0.74 mmol; 5.00 eq.). Reaction was stirred at room temperature for 18 h, then ammonium acetate (34.17 mg; 0.44 mmol; 3.00 eq.) was added and the reaction was continued to stir at room temperature for 2 h. After completion, water was added to the mixture and solid formed was filtered, rinsed with water to afford the desired compound (62.5 mg, 84%) as a white solid.

$^1$H NMR (500 MHz, cdcl$_3$) δ 7.44-7.34 (m, 2H), 7.15-7.11 (m, 1H), 6.67 (s, 1H), 6.49 (s, 1H), 6.03 (s, 1H), 5.47-5.43 (m, 2H), 5.13 (s, 1H), 4.75 (s, 1H), 4.44-4.36 (m, 1H), 4.12 (dt, J=14.7, 5.3 Hz, 1H), 4.03-3.95 (m, 1H), 3.88 (d, J=14.3 Hz, 1H), 3.83-3.74 (m, 1H), 3.73 (s, 3H), 3.66-3.56 (m, 1H), 3.43-3.37 (m, 1H), 2.36-2.25 (m, 1H), 2.23-2.11 (m, 1H), 2.03-1.87 (m, 2H), 1.76 (d, J=1.0 Hz, 3H), 1.45 (s, 3H). m/z: 507 [M+H]$^+$

Example 19

7-methoxy-8-(2-methyl-propenyl)-1-thiophen-3-yl-1,4-dihydro-chromeno[4,3-c]pyrazole-3-carboxylic acid [3-(cyclobutanecarbonyl-amino)-propyl]-amide (57)

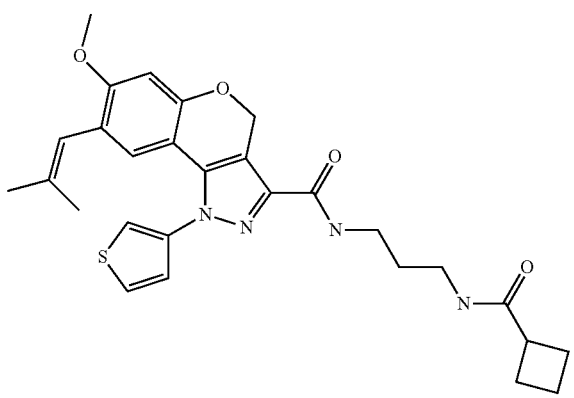 [SMILES: COc1cc2c(cc1C=C(C)C)-c1c(c(C(=O)NCCCNC(=O)C3CCC3)nn1-c1ccsc1)CO2]

Step 1

In a similar manner to example 12 step 1, (3-{[7-Methoxy-8-(2-methyl-propenyl)-1-thiophen-3-yl-1,4-dihydro-chromeno[4,3-c]pyrazole-3-carbonyl]-amino}-propyl)-carbamic acid tert-butyl ester was obtained from 7-methoxy-8-(2-methyl-propenyl)-1-thiophen-3-yl-1,4-dihydro-chromeno[4,3-c]pyrazole-3-carboxylic acid (150 mg, 0.39 mmol) and N-boc-1,3-diaminopropane (102.5 mg, 0.59 mmol, 1.5 eq.).

Step 2

In a similar manner to example 12 step 2, 7-methoxy-8-(2-methyl-propenyl)-1-thiophen-3-yl-1,4-dihydro-chromeno[4,3-c]pyrazole-3-carboxylic acid (3-amino-propyl)-amide was obtained from (3-{[7-Methoxy-8-(2-methyl-propenyl)-1-thiophen-3-yl-1,4-dihydro-chromeno[4,3-c]pyrazole-3-carbonyl]-amino}-propyl)-carbamic acid tert-butyl ester and HCl (4M in dioxane).

Step 3

In a similar manner to example 12, step 1, 7-methoxy-8-(2-methyl-propenyl)-1-thiophen-3-yl-1,4-dihydro-chromeno[4,3-c]pyrazole-3-carboxylic acid [3-(cyclobutanecarbonyl-amino)-propyl]-amide was obtained from 7-Methoxy-8-(2-methyl-propenyl)-1-thiophen-3-yl-1,4-dihydro-chromeno[4,3-c]pyrazole-3-carboxylic acid (3-amino-propyl)-amide (100 mg, 0.23 mmol) and cyclobutanecarboxylic acid (0.14 ml; 1.50 mmol; 6.58 eq.). The desired compound was obtained in 97% yield (115 mg) as a white solid.

$^1$H NMR (400 MHz, CDCl$_3$) δ 7.55 (s, 1H), 7.53-7.48 (m, 1H), 7.25 (d, J=4.7 Hz, 1H), 7.11 (t, J=7.1 Hz, 1H), 6.71 (s, 1H), 6.58 (s, 1H), 6.32-6.25 (m, 1H), 6.12 (s, 1H), 5.62 (s, 2H), 3.83 (s, 3H), 3.49 (dd, J=12.3, 5.9 Hz, 2H), 3.34 (dd, J=12.1, 6.0 Hz, 2H), 3.12-3.00 (m, 1H), 2.32 (dt, J=19.0, 9.7 Hz, 2H), 2.19 (dd, J=18.8, 9.9 Hz, 2H), 1.98 (dd, J=18.7, 8.5 Hz, 2H), 1.85 (s, 3H), 1.79-1.71 (m, 2H), 1.52 (s, 3H). m/z: 521 [M+H]$^+$

Scheme 3:

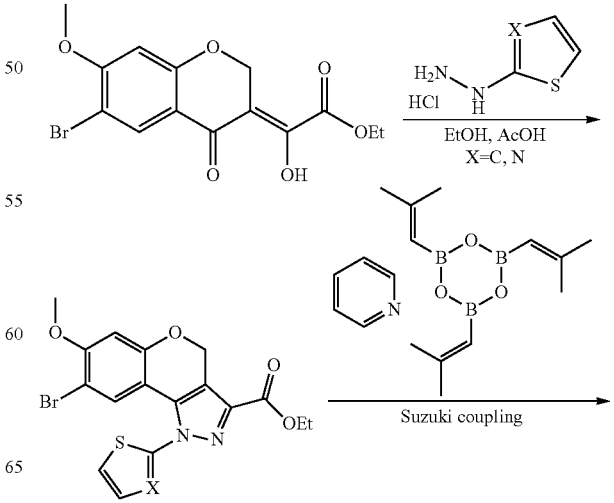

321
-continued

322
-continued

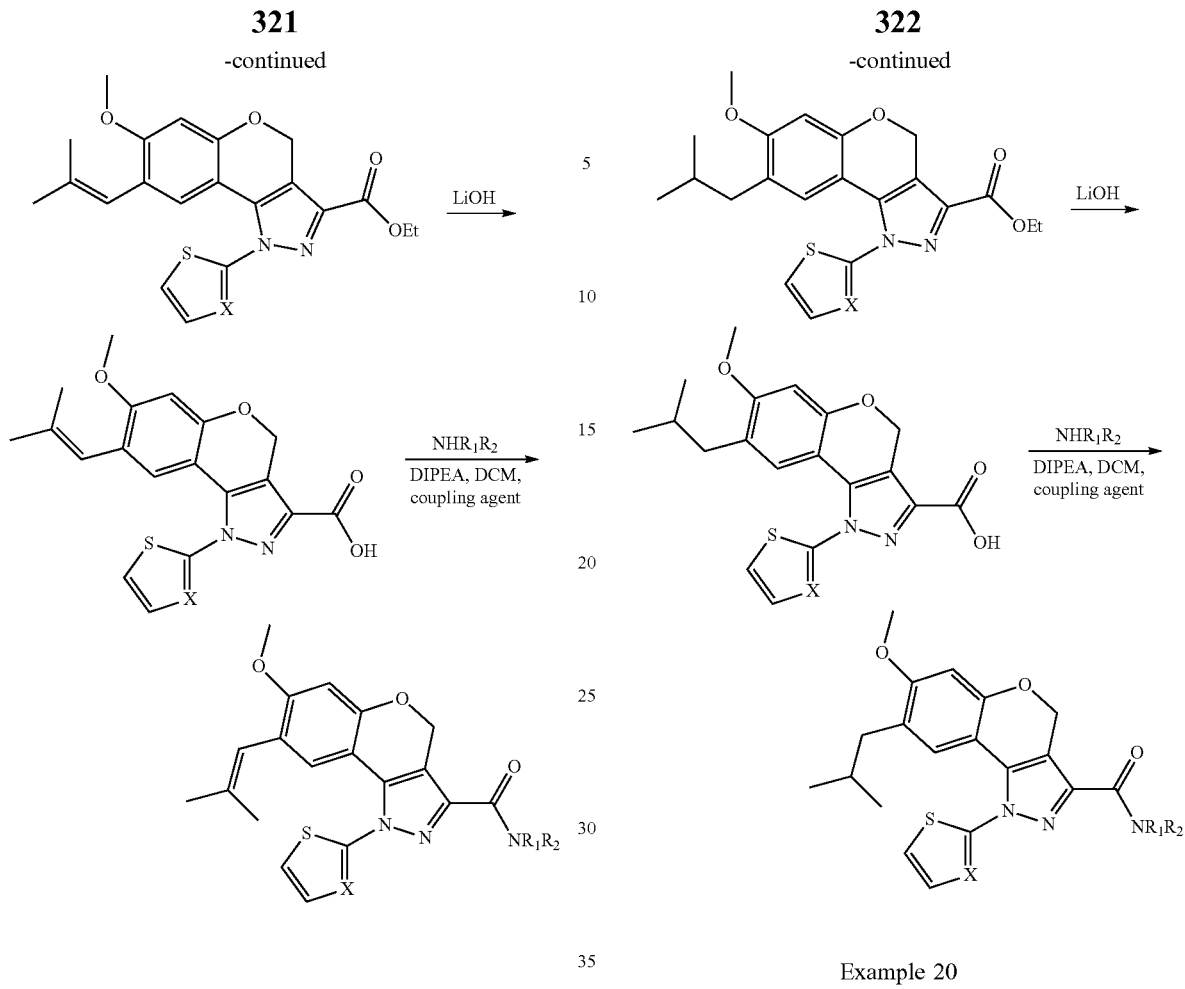

Example 20

7-Methoxy-8-(2-methyl-propenyl)-1-thiazol-2-yl-1,
4-dihydro-chromeno[4,3-c]pyrazole-3-carboxylic
acid tert-butyl-methyl-amide (89)

Step 1: 2-Hydrazino-1,3-thiazole hydrochloride

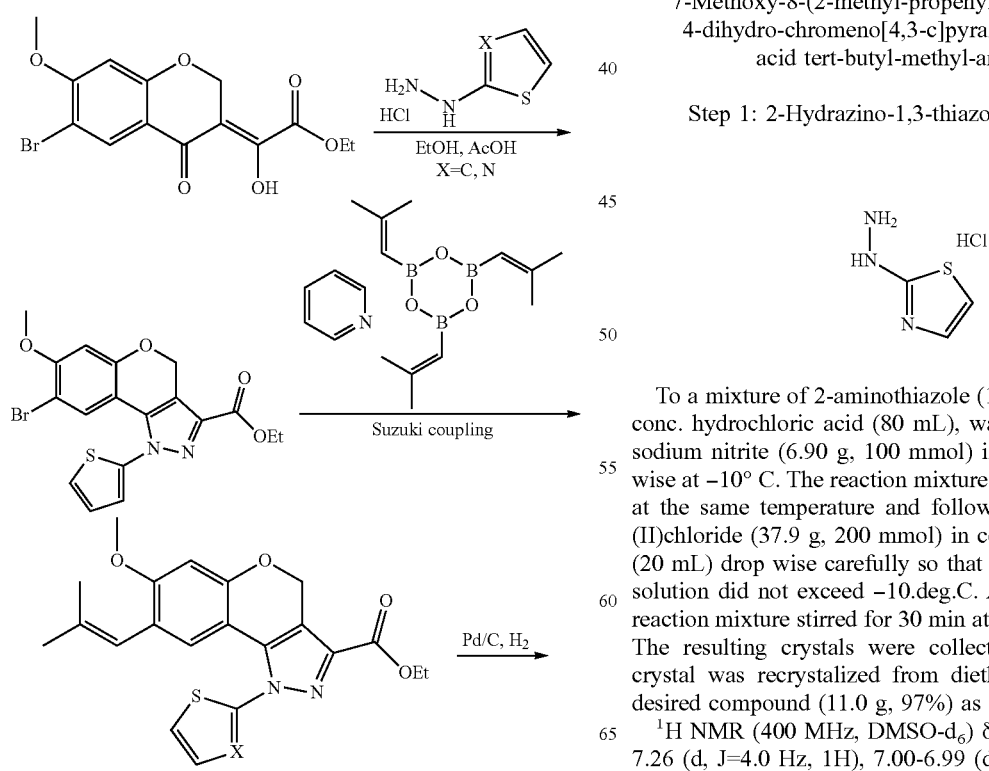

To a mixture of 2-aminothiazole (10.0 g, 100 mmol) and conc. hydrochloric acid (80 mL), was added a solution of sodium nitrite (6.90 g, 100 mmol) in water (50 mL) drop wise at −10° C. The reaction mixture was stirred for 10 min at the same temperature and followed by addition of tin (II)chloride (37.9 g, 200 mmol) in conc. hydrochloric acid (20 mL) drop wise carefully so that the temperature of the solution did not exceed −10.deg.C. After the addition, the reaction mixture stirred for 30 min at the same temperature. The resulting crystals were collected by filtration. The crystal was recrystalized from diethylether to afford the desired compound (11.0 g, 97%) as brown solid.

$^1$H NMR (400 MHz, DMSO-d$_6$) δ 10.74 (bs, 1H), 7.27-7.26 (d, J=4.0 Hz, 1H), 7.00-6.99 (d, J=4.0 Hz, 1H), 3.45 (bs, 3H). m/z: 116 [M+H]$^+$

Step 2: Ethyl 8-bromo-7-methoxy-1-(1,3-thiazol-2-yl)-1,4-dihydrochromeno[4,3-c]pyrazole-3-carboxylate

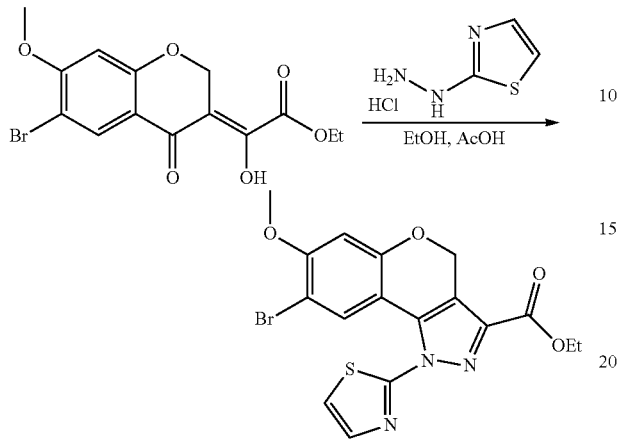

To a solution of ethyl-(6-bromo-7-methoxy-4-oxo-2H-chromen-3(4H)-ylidene)(hydroxy)acetate (3.0 g, 0.0084 mol) in a mixture of Ethanol (100 mL) and Acetic acid (100 mL) was added 2-Hydrazino-1,3-thiazole hydrochloride (1.9 g, 0.0126 mol) at RT under nitrogen. The reaction mixture was stirred at 100° C. for 4 h. The reaction mixture was concentrated under high vacuum. The residue was dissolved with ethyl acetate (40 mL), washed with water (20 mL), brine (20 mL), dried over sodium sulphate and concentrated under vacuum. The crude product was purified by column chromatography using pet ether/ethyl acetate as eluent to afford the desired compound (1.5 g, 41%) as pale yellow solid.

$^1$H NMR (400 MHz, DMSO-$d_6$) δ 8.61 (s, 1H), 7.86-7.85 (d, J=1.4 Hz, 2H), 6.86 (s, 1H), 5.45 (s, 2H), 4.37-4.32 (dd, J=7.0, 14.2, 2H), 3.86 (s, 3H), 1.34-1.31 (t, J=7.1, 14.2, 3H). m/z: 438 [M+H]$^+$

Step 3: Ethyl 7-methoxy-8-(2-methylprop-1-en-1-yl)-1-(1,3-thiazol-2-yl)-1,4-dihydrochromeno[4,3-c]pyrazole-3-carboxylate

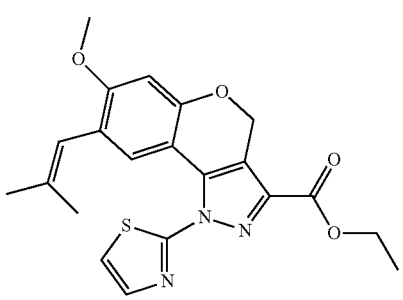 [SMILES: CCOC(=O)c1nn(-c2nccs2)c2c1COc1cc(OC)c(C=C(C)C)cc1-2]

To a solution of ethyl 8-bromo-7-methoxy-1-(1,3-thiazol-2yl)-1,4-dihydrochromeno[4,3-c]pyrazole-3-carboxylate (2.6 g, 0.0059 mol) in THF (100 mL) was added 2,4,6-Tris-(2-methyl-propenyl)-cyclotriboroxanepyridine complex (2.9 g, 0.0089 mol), bis(triphenylphospine)palladium (II) dichloride (417 mg, 0.0006 mol) and potassium tri phosphate (2.0 g, 0.0149 mol) at RT under nitrogen. The reaction mixture was degassed with nitrogen for 10 min and water (10 mL) was added at RT. The reaction mixture was stirred at 90° C. for 12 h. The reaction mixture was filtered through celite and washed with DCM (50 mL). The filtrate was concentrated under vacuum; crude product was dissolved in DCM (200 mL), washed with water (20 ml), brine (20 mL) and dried over sodium sulphate. The organic solvent was removed under vacuum; crude product was purified by column chromatography over (60-120) mesh silica gel and pet ether: ethyl acetate as eluent to afford the desired compound (2.2 g, 90%) as a pale yellow solid.

$^1$H NMR (400 MHz, DMSO-$d_6$) δ 7.94 (s, 1H), 7.87-7.86 (d, J=3.5 Hz, 1H), 7.82-7.81 (d, J=3.5 Hz, 1H), 6.69 (s, 1H), 6.01 (s, 1H), 5.42 (s, 2H), 4.35-4.33 (d, J=7.1 Hz, 2H), 3.77 (s, 3H), 1.82 (s, 3H), 1.70 (s, 3H), 1.34-1.31 (t, J=7.1, 14.2 Hz, 3H). m/z: 412 [M+H]

Step 4: 7-Methoxy-8-(2-methylprop-1-en-1-yl)-1-(1,3-thiazol-2-yl)-1,4-dihydro-chromeno[4,3-c]pyrazole-3-carboxylic acid

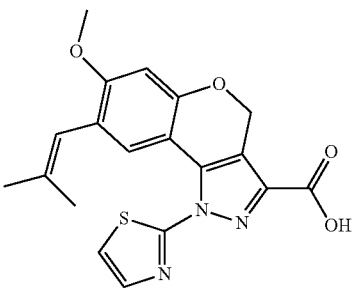 [SMILES: COc1cc2c(cc1C=C(C)C)-c1c(c(C(=O)O)nn1-c1nccs1)CO2]

To a solution of ethyl 7-methoxy-8-(2-methylprop-1-en-1-yl)-1-(1,3-thiazol-2-yl)-1,4-dihydrochromeno[4,3-c]pyrazole-3-carboxylate (1 g, 0.0024 mol) in mixture of THF (35 mL), H$_2$O (10 mL), MeOH (5 mL) was added LiOH.H$_2$O (302 mg, 0.0073 mol) at RT. The reaction mixture was stirred at RT for 4 h. The reaction mixture was evaporated and acidified with 1.5N HCl solution. The separated solid was filtered and dried under high vacuum to afford the desired compound (900 mg, 97%) as an off-white solid.

$^1$H NMR (400 MHz, DMSO-$d_6$) δ 13.57 (bs, 1H), 8.00 (s, 1H), 7.85-7.84 (d, J=3.5 Hz, 1H), 7.80 (d, J=3.5 Hz, 1H), 6.69 (s, 1H), 6.11 (s, 1H), 5.41 (s, 2H), 3.77 (s, 3H), 1.83 (s, 3H), 1.71 (s, 3H). m/z: 384 [M+H]$^+$

Step 5: 7-Methoxy-8-(2-methyl-propenyl)-1-thiazol-2-yl-1,4-dihydro-chromeno[4,3-c]pyrazole-3-carboxylic acid tert-butyl-methyl-amide

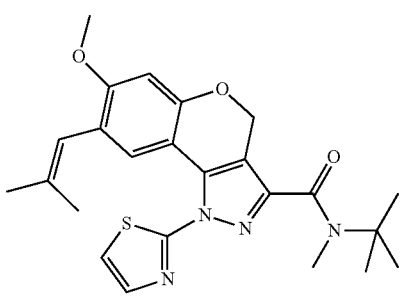 [SMILES: COc1cc2c(cc1C=C(C)C)-c1c(c(C(=O)N(C)C(C)(C)C)nn1-c1nccs1)CO2]

To a solution of 7-Methoxy-8-(2-methylprop-1-en-1-yl)-1-(1,3-thiazol-2-yl)-1,4-dihydro-chromeno[4,3-c]pyrazole- 3-carboxylic acid (900 mg, 0.0023 mol) in DCM (50 mL) was added N-tert-butyl methyl amine (225 mg, 0.0028 mol), HATU (1.1 g, 0.0028 mol) and diisopropyl ethyl amine (0.6 mL, 0.0035 mol) at RT under nitrogen. The reaction mixture was stirred at RT for 16 h. The reaction mixture was quenched to sodium bicarbonate (10 mL, 10%), extracted with DCM (2×50 mL). The combined organic layer was washed with NaHCO$_3$ solution (1×100 mL, 10% solution), brine (100 mL) and dried over anhydrous sodium sulphate. The solvent was removed under vacuum; the crude product was purified by column chromatography using pet ether and ethyl acetate (9:1) as eluent to afford the desired compound (850 mg, 80%) as an off-white solid.

$^1$H NMR (400 MHz, DMSO-d$_6$) δ 8.14 (s, 1H), 7.79-7.76 (dd, J=3.5, 6.3 Hz, 2H), 6.70 (s, 1H), 6.12 (s, 1H), 5.25 (s, 2H), 3.77 (s, 3H), 3.12 (s, 3H), 1.84 (s, 3H), 1.74 (s, 3H), 1.44 (s, 9H). m/z: 453 [M+H]$^+$

Example 21

7-Methoxy-8-(2-methyl-propenyl)-1-thiophen-2-yl-1,4-dihydro-chromeno[4,3-c]pyrazole-3-carboxylic acid tert-butyl-methyl-amide (90)

Step 1: tert-Butyl 1-(2-thienyl)hydrazinecarboxylate

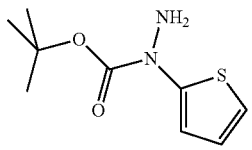

To a solution of 2-Bromo thiophene (10 g, 0.0613 mol) in DMSO (200 mL) was added tert-butyl carbazate (16.3 g, 0.1227 mol), cesium carbonate (40 g, 0.1227 mol) followed by CuI (1.2 g, 0.0061 mol) and 4-Hydroxy-L-Proline (1.6 g, 0.0123 mol) at RT under nitrogen. The reaction mixture was stirred at 80° C. for 14 h. The reaction mixture was cooled to RT, quenched with water (100 mL) and extracted with ethyl acetate (3×200 mL). The combined organic layer was washed with water (100 mL×2), brine (100 mL), dried over sodium sulphate and evaporated under vacuum. The crude product was purified by column chromatography by using pet ether and ethyl acetate (7:3) as eluent to afford the desired compound (3.0 g, 40%) as a brown liquid.

$^1$H NMR (400 MHz, DMSO-d$_6$) δ 6.89-6.87 (dd, J=1.7, 5.4 Hz, 1H), 6.81-6.79 (dd, J=3.4, 7.2 Hz, 2H), 5.38 (s, 2H), 1.49 (s, 9H). m/z: 115 [M+H]$^+$

Step 2: 2-Thienylhydrazine hydrochloride

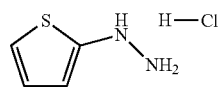

To a stirred solution of tert-Butyl 1-(2-thienyl)hydrazinecarboxylate (4.3 g, 0.0201 mol) in dichloromethane (20 mL) was added HCl in dioxane (30 mL) at RT under nitrogen. The reaction mixture was stirred at RT for 8 h. The organic solvent was removed under reduced pressure to afford the desired compound (2.9 g, 96%) as pale brown solid.

$^1$H NMR (400 MHz, DMSO-d$_6$) δ 10.17 (bs, 3H), 8.41 (bs, 1H), 7.07-7.05 (dd, J=1.4, 5.4 Hz, 1H), 6.85-6.83 (dd, J=3.6, 5.4 Hz, 1H), 6.72-6.71 (dd, J=1.4, 3.7 Hz, 1H). m/z: 115 [M+H]$^+$

Step 3: Ethyl 8-bromo-7-methoxy-1-(2-thienyl)-1,4-dihydrochromeno[4,3-c]pyrazole-3-carboxylate

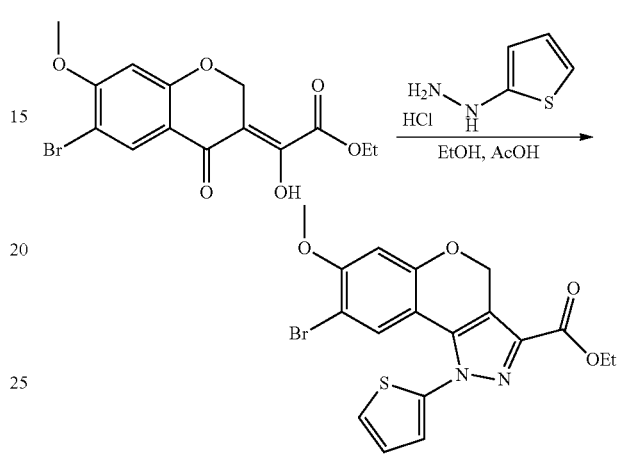

To a solution of ethyl-(6-bromo-7-methoxy-4-oxo-2H-chromen-3(4H)-ylidene)(hydroxy)acetate (6.0 g, 0.0168 mol) in a mixture of Ethanol (100 mL) and acetic acid (100 mL) was added 2-thienylhydrazine hydrochloride (2.9 g, 0.0252 mol) at RT under nitrogen. The reaction mixture was stirred at 100° C. for 4 h. The reaction mixture was concentrated under high vacuum. The residue was dissolved with ethyl acetate (40 mL), washed with water (20 mL), brine (20 mL), dried over sodium sulphate and concentrated under vacuum. The crude product was purified by column chromatography using pet ether/ethyl acetate as eluent to afford desired compound (4.0 g, 55%) as a pale yellow solid.

$^1$H NMR (400 MHz, DMSO-d$_6$) δ 7.84-7.82 (dd, J=1.2, 5.5 Hz, 1H), 7.49-7.47 (dd, J=1.2, 3.6 Hz, 1H), 7.24-7.22 (dd, J=3.8, 5.4 Hz, 1H), 6.83 (s, 1H), 6.72 (s, 1H), 5.51 (s, 2H), 4.33-4.28 (dd, J=7.1, 14.2 Hz. 2H), 3.82 (s, 3H), 1.32-1.28 (t, J=7.1, 14.2 Hz, 3H). m/z: 437 [M+H]

Step 4: 7-Methoxy-8-(2-methyl-propenyl)-1-thiophen-2-yl-1,4-dihydro-chromeno[4,3-c]pyrazole-3-carboxylic acid ethyl ester

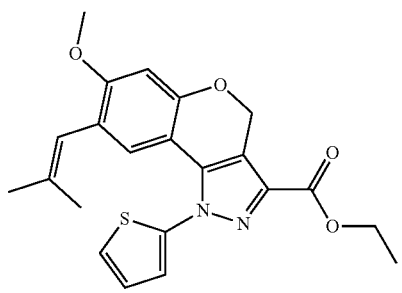 [SMILES: CCOC(=O)c1nn(-c2cccs2)c2c1COc1cc(OC)c(C=C(C)C)cc1-2]

To a solution of Ethyl 8-bromo-7-methoxy-1-(2-thienyl)-1,4-dihydrochromeno[4,3-c]pyrazole-3-carboxylate (3.8 g, 0.0087 mol) in THF (100 mL) was added 2,4,6-Tris-(2-methyl-propenyl)-cyclotriboroxanepyridine complex (4.3 g, 0.0131 mol), bis(triphenylphospine)palladium (II) dichloride (306 mg, 0.0004 mol) and potassium tri phosphate (2.4 g, 0.0174 mol) at RT under nitrogen. The reaction mixture was degassed with nitrogen for 10 min and water (10 mL) was added at RT. The reaction mixture was stirred at 90° C. for 12 h. The reaction mixture was filtered through celite and washed with DCM (50 mL). The filtrate was concentrated under vacuum; the crude product was dissolved in DCM (200 mL), washed with water (20 ml), brine (20 mL) and dried over sodium sulphate. The organic solvent was removed under vacuum; crude product was purified by column chromatography using pet ether: ethyl acetate as eluent to afford the desired compound (2.5 g, 70%) as pale yellow solid.

$^1$H NMR (400 MHz, DMSO-$d_6$) δ 7.79-7.77 (dd, J=1.4, 5.5 Hz, 1H), 7.46-7.45 (dd, J=1.5, 3.7 Hz, 1H), 7.20-7.18 (dd, J=3.7, 5.6 Hz, 1H), 6.66 (s, 1H), 6.56 (s, 1H), 6.00 (s, 1H), 5.47 (s, 2H), 4.33-4.27 (dd, J=7.1, 14.2 Hz, 2H), 3.74 (s, 3H), 1.73 (d, J=1.1 Hz, 3H), 1.39 (d, J=1.2 Hz, 3H), 1.32-1.28 (t, J=7.1, 14.2 Hz, 3H). m/z: 411 [M+H]$^+$

Step 5: 7-Methoxy-8-(2-methyl-propenyl)-1-thiophen-2-yl-1,4-dihydro-chromeno[4,3-c]pyrazole-3-carboxylic acid

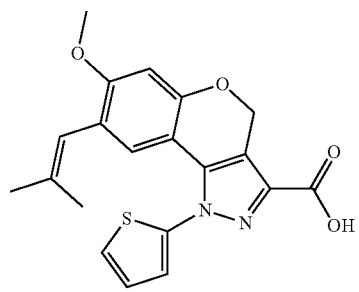 [SMILES: COc1cc2c(cc1C=C(C)C)-c1c(c(C(=O)O)nn1-c1cccs1)CO2]

To a solution of 7-methoxy-8-(2-methyl-propenyl)-1-thiophen-2-yl-1,4-dihydro-chromeno[4,3-c]pyrazole-3-carboxylic acid ethyl ester (1 g, 0.0024 mol) in mixture of THF (35 mL), H$_2$O (10 mL), MeOH (5 mL) was added LiOH.H$_2$O (303 mg, 0.0073 mol) at RT. The reaction mixture was stirred at RT for 4 h. The reaction mixture was evaporated and acidified with 1.5N HCl solution. The separated solid was filtered and dried under high vacuum to afford the desired compound (800 mg, 75%) as an off-white solid.

$^1$H NMR (400 MHz, DMSO-$d_6$) δ 13.30 (bs, 1H), 7.78-7.76 (dd, J=1.4, 5.6 Hz, 1H), 7.45-7.44 (dd, J=1.4, 3.7 Hz, 1H), 7.19-7.17 (dd, J=3.7, 5.5 Hz, 1H), 6.66 (s, 1H), 6.56 (s, 1H), 6.00 (s, 1H), 5.46 (s, 2H), 3.73 (s, 3H), 1.73 (s, 3H), 1.39 (s, 3H). m/z: 383 [M+H]$^+$

Step 6: 7-Methoxy-8-(2-methyl-propenyl)-1-thiophen-2-yl-1,4-dihydro-chromeno[4,3-c]pyrazole-3-carboxylic acid tert-butyl-methyl-amide

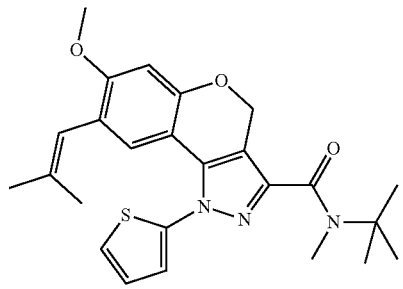 [SMILES: COc1cc2c(cc1C=C(C)C)-c1c(c(C(=O)N(C)C(C)(C)C)nn1-c1cccs1)CO2]

To a solution of 7-methoxy-8-(2-methyl-propenyl)-1-thiophen-2-yl-1,4-dihydro-chromeno[4,3-c]pyrazole-3-carboxylic acid (800 mg, 0.0021 mol) in DCM (50 mL) was added N-tert-butyl methylamine (220 mg, 0.0025 mol), HATU (950 mg, 0.0025 mol) and diisopropylethylamine (0.6 mL, 0.0032 mol) at RT under nitrogen. The reaction mixture was stirred at RT for 16 h. The reaction mixture was quenched to sodium bicarbonate (10 mL, 10%), extracted with DCM (2×50 mL). The combined organic layer was washed with NaHCO$_3$ solution (1×100 mL, 10% solution), brine (100 mL) and dried over anhydrous sodium sulphate. The solvent was removed under vacuum; the crude product was purified by column chromatography using pet ether and ethyl acetate (9:1) as eluent to afford the desired compound (850 mg, 90%) as a white solid.

$^1$H NMR (400 MHz, DMSO-$d_6$) δ 7.75-7.73 (dd, J=1.4, 5.5 Hz, 1H), 7.42-7.41 (dd, J=1.4, 3.6 Hz, 1H), 7.18-7.15 (dd, J=3.8, 5.6 Hz, 1H), 6.66 (s, 1H), 6.59 (s, 1H), 6.01 (s, 1H), 5.33 (s, 2H), 3.73 (s, 3H), 3.12 (s, 3H) 1.73 (s, 3H), 1.41 (s, 12H). m/z: 452 [M+H]$^+$

Example 22

8-Isobutyl-7-methoxy-1-thiophen-2-yl-1,4-dihydro-chromeno[4,3-c]pyrazole-3-carboxylic acid tert-butyl-methyl-amide (91)

Step 1: 8-Isobutyl-7-methoxy-1-thiophen-2-yl-1,4-dihydro-chromeno[4,3-c]pyrazole-3-carboxylic acid ethyl ester

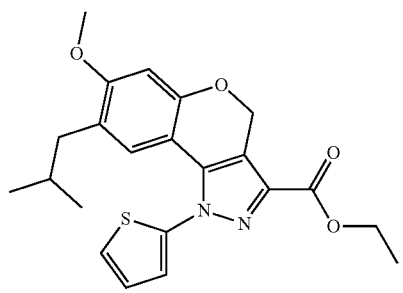 [SMILES: CCOC(=O)c1nn(-c2cccs2)c2c1COc1cc(OC)c(CC(C)C)cc1-2]

To a solution of 7-methoxy-8-(2-methyl-propenyl)-1-thiophen-2-yl-1,4-dihydro-chromeno[4,3-c]pyrazole-3-carboxylic acid ethyl ester (1.2 g, 0.0027 mol) in methanol and ethyl acetate mixture (100 mL) was added palladium on carbon (20%, 0.24 g). The reaction mixture was hydrogenated under 3 bar of pressure for 8 h at RT. The reaction mixture was filtered through celite to remove the catalyst and the filtrate was concentrated under vacuum. The residue was purified by column chromatography using pet ether/ethyl acetate as eluent to afford the desired compound (1.1 g, 90%) as an off white solid.

$^1$H NMR (400 MHz, DMSO-d$_6$) δ 7.81-7.79 (dd, J=1.4, 5.5 Hz, 1H), 7.43-7.41 (dd, J=1.4, 3.7 Hz, 1H), 7.20-7.18 (dd, J=3.7, 5.5 Hz, 1H), 6.65 (s, 1H), 6.36 (s, 1H), 5.44 (s, 2H), 4.33-4.27 (dd, J=7.0, 14.2 Hz, 2H), 3.74 (s, 3H), 2.12-2.10 (d, J=6.9 Hz, 2H), 1.59-1.56 (m, 1H), 1.32-1.28 (t, J=7.1, 14.2 Hz, 3H), 0.86-0.85 (d, J=6.6 Hz, 6H).

Step 2: 8-Isobutyl-7-methoxy-1-thiophen-2-yl-1,4-dihydro-chromeno[4,3-c]pyrazole-3-carboxylic acid

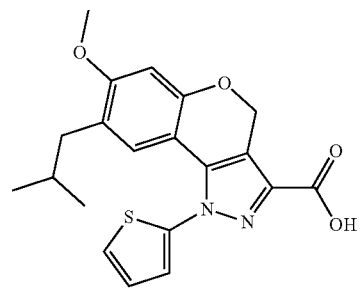 [SMILES: COc1cc2c(cc1CC(C)C)-c1c(c(C(=O)O)nn1-c1cccs1)CO2]

To a solution of 8-isobutyl-7-methoxy-1-thiophen-2-yl-1,4-dihydro-chromeno[4,3-c]pyrazole-3-carboxylic acid ethyl ester (1.1 g, 0.0027 mol) in mixture of THF (35 mL), H$_2$O (10 mL), MeOH (5 mL) was added LiOH.H$_2$O (332 mg, 0.0080 mol) at RT. The reaction mixture was stirred at RT for 4 h. The reaction mixture was evaporated and acidified with 1.5N HCl solution. The separated solid out was filtered to afford the desired compound (900 mg, 88%) as an off-white solid.

$^1$H NMR (400 MHz, DMSO-d$_6$) δ 13.33 (bs, 1H), 7.79-7.78 (dd, J=1.4, 5.5 Hz, 1H), 7.41-7.40 (dd, J=1.4, 3.7 Hz, 1H), 7.19-7.17 (dd, J=3.8, 5.5 Hz, 1H), 6.65 (s, 1H), 6.36 (s, 1H), 5.43 (s, 2H), 3.73 (s, 3H), 2.12-2.10 (d, J=7.0 Hz, 2H), 1.59-1.56 (m, 1H), 0.71-0.70 (d, J=6.6 Hz 6H) m/z: 385 [M+H]$^+$

Step 3: 8-Isobutyl-7-methoxy-1-thiophen-2-yl-1,4-dihydro-chromeno[4,3-c]pyrazole-3-carboxylic acid tert-butyl-methyl-amide

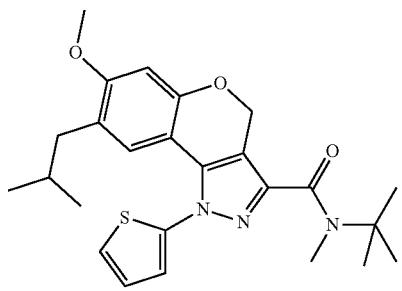 [SMILES: COc1cc2c(cc1CC(C)C)-c1c(c(C(=O)N(C)C(C)(C)C)nn1-c1cccs1)CO2]

To a solution of 8-isobutyl-7-methoxy-1-thiophen-2-yl-1,4-dihydro-chromeno[4,3-c]pyrazole-3-carboxylic acid (900 mg, 0.0023 mol) in DCM (50 mL) was added N-tert-butyl methyl amine (245 mg, 0.0028 mol), HATU (1.0 g, 0.0028 mol) and diisopropyl ethyl amine (0.6 mL, 0.0038 mol) at RT under nitrogen. The reaction mixture was stirred at RT for 16 h. The reaction mixture was quenched to sodium bicarbonate (10 mL, 10%), extracted with DCM (2×50 mL). The combined organic layer was washed with NaHCO$_3$ solution (100 mL, 10% solution), brine (100 mL) and dried over anhydrous sodium sulphate. The solvent was removed under vacuum; the crude product was purified by column chromatography using pet ether and ethyl acetate (9:1) as eluent to afford the desired compound (800 mg, 75%) as a white solid.

$^1$H NMR (400 MHz, DMSO-d$_6$) δ 7.76-7.75 (dd, J=1.4, 5.5 Hz, 1H), 7.38-7.37 (dd, J=1.4, 3.7 Hz, 1H), 7.18-7.15 (dd, J=3.7, 5.6 Hz, 1H), 6.64 (s, 1H), 6.39 (s, 1H), 5.30 (s, 2H), 3.73 (s, 3H), 3.12 (s, 3H), 3.12 (s, 3H), 2.12-2.10 (d, J=7.0 Hz, 2H), 1.60-1.56 (m, 1H), 1.41 (s, 9H) 0.71-0.70 (d, J=6.6 Hz 6H). m/z: 454 [M+H]$^+$

Scheme 5:

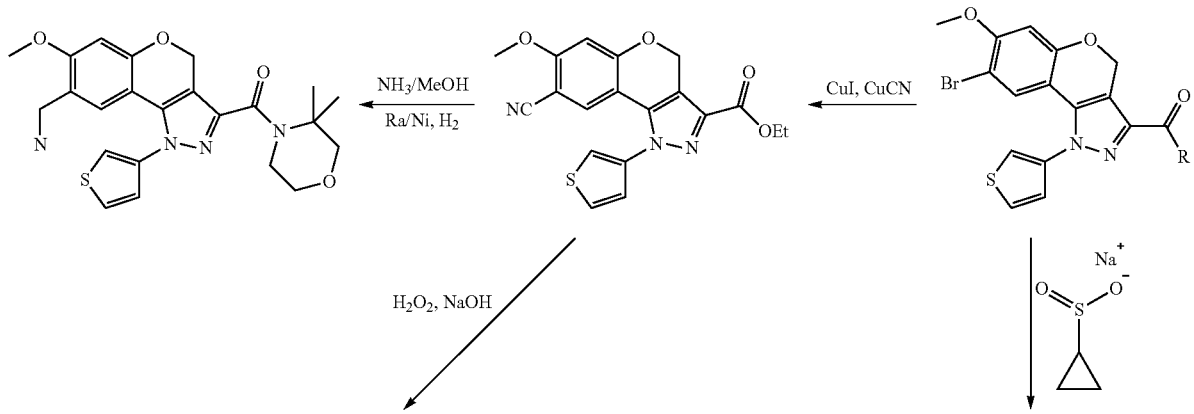

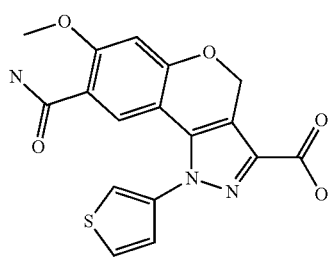
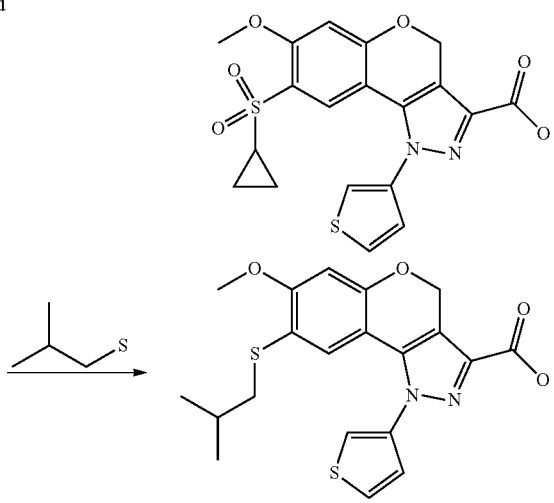

-continued

Example 23

(3,3-Dimethyl-morpholin-4-yl)-(8-isobutylsulfanyl-7-methoxy-1-thiophen-3-yl-1,4-dihydro-chromeno[4,3-c]pyrazol-3-yl)-methanone (97)

Step 1: 8-Isobutylsulfanyl-7-methoxy-1-thiophen-3-yl-1,4-dihydro-chromeno[4,3-c]pyrazole-3-carboxylic acid

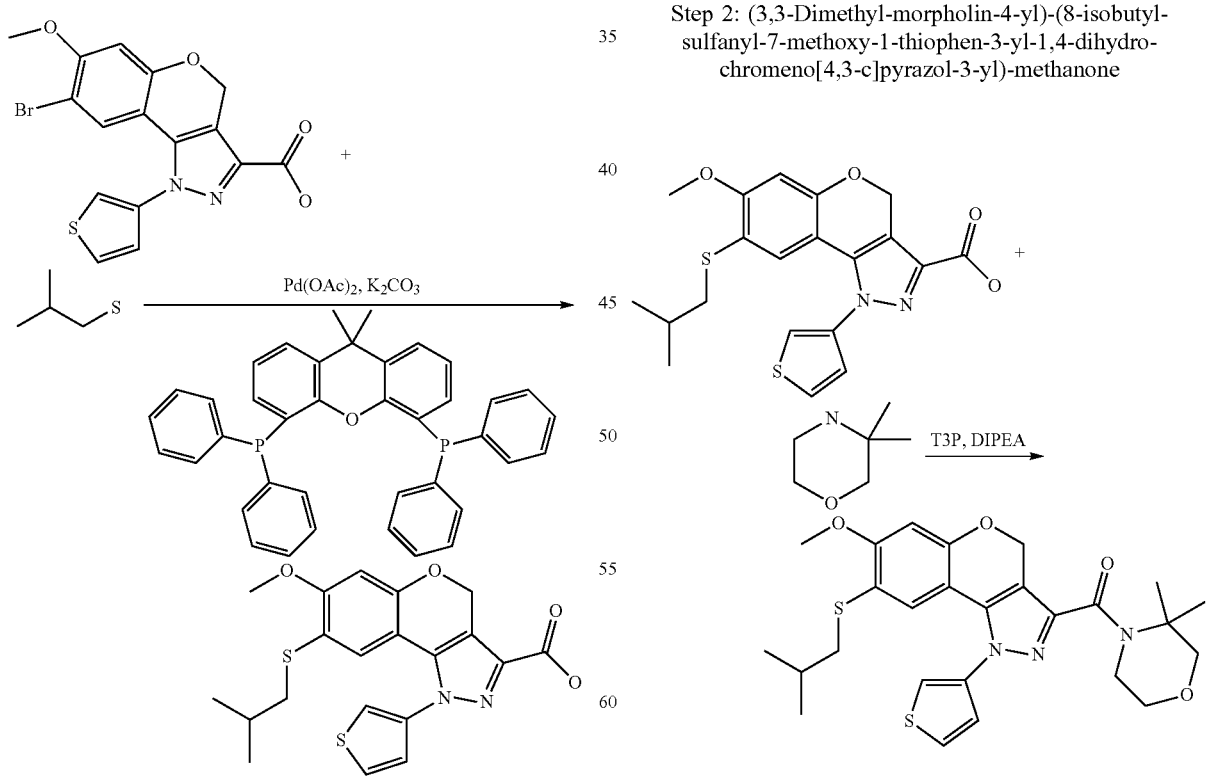

To 8-bromo-7-methoxy-1-thiophen-3-yl-1,4-dihydro-chromeno[4,3-c]pyrazole-3-carboxylic acid (100.00 mg; 0.25 mmol; 1.00 eq.) suspended in [1,4]Dioxane (3.00 ml) was added 2-Methyl-propane-1-thiol (33.22 mg; 0.37 mmol; 1.50 eq.), palladium acetate (2.76 mg; 0.01 mmol; 0.05 eq.), 4,5-Bis-diphenylphosphanyl-9,9-dimethyl-9H-xanthene (14.21 mg; 0.02 mmol; 0.10 eq.), and potassium carbonate (101.81 mg; 0.74 mmol; 3.00 eq.). The reaction was heated at 120° C. for 8 days. Mixture was diluted with EtOAc and washed with brine. The organic layer was dried ($Na_2SO_4$), filtered, concentrated to afford product 8-Isobutylsulfanyl-7-methoxy-1-thiophen-3-yl-1,4-dihydro-chromeno[4,3-c]pyrazole-3-carboxylic acid as a yellow crude product.

Step 2: (3,3-Dimethyl-morpholin-4-yl)-(8-isobutyl-sulfanyl-7-methoxy-1-thiophen-3-yl-1,4-dihydro-chromeno[4,3-c]pyrazol-3-yl)-methanone To 8-isobutylsulfanyl-7-methoxy-1-thiophen-3-yl-1,4-dihydro-chromeno[4,3-c]pyrazole-3-carboxylic acid (80.00 mg; 0.19 mmol; 1.00 eq.) suspended in DCM (3.00 ml; 46.80 mmol; 243.67 eq.) was added 2,4,6-tripropyl-1,3,5,2, 4,6-trioxatriphosphinane 2,4,6-trioxide (0.17 ml; 0.29 mmol; 1.50 eq.), 3,3-Dimethyl-morpholine (0.14 ml; 0.29 mmol; 1.50 eq.) and Ethyl-diisopropyl-amine (0.10 ml; 0.58 mmol; 3.00 eq.). The reaction was stirred at RT for 1 h. Mixture was concentrated and purified by flash chromatography to afford the desired product (40 mg, 40%) as a white solid.

$^1$H-NMR (DMSO-d6): δ 8.02-7.98 (s, 1H), 7.88-7.83 (m, 1H), 7.35 (dd, 1H), 6.72 (s, 1H), 6.60 (s, 1H), 5.37 (s, 2H), 3.94 (m, 2H), 3.80 (s, 3H), 3.72 (t, 2H), 3.42 (s, 2H), 2.34 (d, 2H), 1.60 (septet, 1H), 1.42 (s, 6H), 0.91 (d, 6H). m/z=514 [M+H]$^+$ Example 24

8-isopropylsulfanyl-7-methoxy-1-thiophen-3-yl-1,4-dihydro-chromeno[4,3-c]pyrazole-3-carboxylic acid tert-butyl-methyl-amide (52)

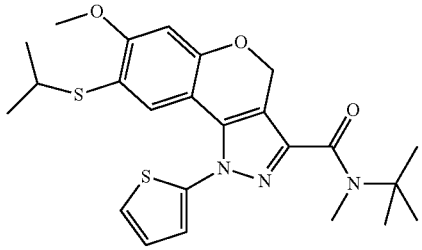 [SMILES: COc1cc2c(cc1SC(C)C)-c1c(c(C(=O)N(C)C(C)(C)C)nn1-c1cccs1)CO2]

In a similar manner to example 23, 8-isopropylsulfanyl-7-methoxy-1-thiophen-3-yl-1,4-dihydro-chromeno[4,3-c]pyrazole-3-carboxylic acid tert-butyl-methyl-amide was obtained from 8-Isopropylsulfanyl-7-methoxy-1-thiophen-3-yl-1,4-dihydro-chromeno[4,3-c]pyrazole-3-carboxylic acid (170 mg, 0.42 mmol), and n-tert-butylmethylamine (73.63 mg, 0.84 mmol, 2 eq.) as a white solid in 15% yield (29 mg). m/z=472 [M+H]$^+$, HPLC retention time=6.45 min.

Example 25

7-methoxy-8-(propane-2-sulfonyl)-1-thiophen-3-yl-1,4-dihydro-chromeno[4,3-c]pyrazole-3-carboxylic acid tert-butyl-methyl-amide (79)

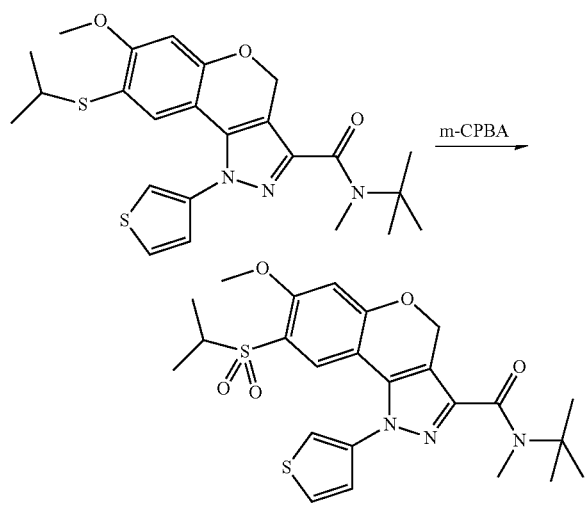

To 8-isopropylsulfanyl-7-methoxy-1-thiophen-3-yl-1,4-dihydro-chromeno[4,3-c]pyrazole-3-carboxylic acid tert-butyl-methyl-amide (24 mg, 0.05 mmol) in DCM (2 mL) was added 3-chloroperbenzoic acid (11.40 mg; 0.05 mmol; 1.00 eq.). The reaction was stirred at RT for 2 h. The mixture was purified by flash chromatography to afford the desired product (8 mg, 32%) as a white solid. m/z=504 [M+H]$^+$, HPLC retention time=4.40 min.

Example 26

8-Cyclopropanesulfonyl-7-methoxy-1-thiophen-3-yl-1,4-dihydro-chromeno[4,3-c]pyrazol-3-yl)-(3,3-dimethyl-morpholin-4-yl)-methanone (106

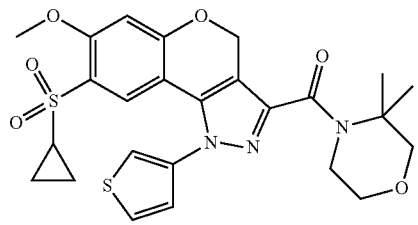 [SMILES: COc1cc2c(cc1S(=O)(=O)C1CC1)-c1c(c(C(=O)N3CCOCC3(C)C)nn1-c1ccsc1)CO2]

Step 1: 8-(cyclopropylsulfonyl)-7-methoxy-1-(thiophen-3-yl)-1,4-dihydrochromeno[4,3-c]pyrazole-3-carboxylic acid

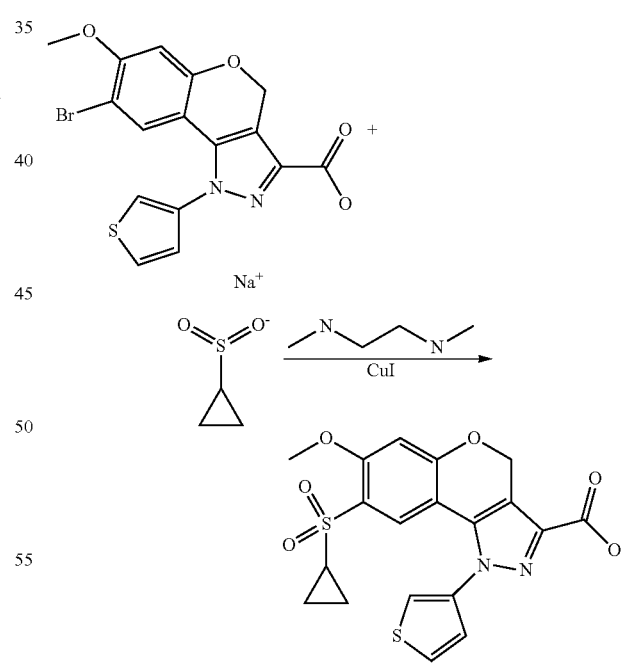

To 8-Bromo-7-methoxy-1-thiophen-3-yl-1,4-dihydro-chromeno[4,3-c]pyrazole-3-carboxylic acid (100.00 mg; 0.25 mmol; 1.00 eq.) suspended in N,N-Dimethyl-formamide (3.00 ml) was added cyclopropanesulfinic acid sodium (47.19 mg; 0.37 mmol; 1.50 eq.), copper iodide (23.38 mg; 0.12 mmol; 0.50 eq.), and N,N'-Dimethyl-ethane-1,2-diamine (0.04 ml; 0.37 mmol; 1.50 eq.). The reaction mixture was heated to 90° C. for 18 h. The mixture was filtered, concentrated and lyophilized to afford 8-(cyclopropylsulfonyl)-7-methoxy-1-(thiophen-3-yl)-1,4-dihydrochromeno[4,3-c]pyrazole-3-carboxylic acid as a blue crude solid.

Step 2: (8-Cyclopropanesulfonyl-7-methoxy-1-thiophen-3-yl-1,4-dihydro-chromeno[4,3-c]pyrazol-3-yl)-(3,3-dimethyl-morpholin-4-yl)-methanone In a similar manner to example 23 above step 2, (8-cyclopropanesulfonyl-7-methoxy-1-thiophen-3-yl-1,4-dihydro-chromeno[4,3-c]pyrazol-3-yl)-(3,3-dimethyl-morpholin-4-yl)-methanone was obtained from 8-(cyclopropylsulfonyl)-7-methoxy-1-(thiophen-3-yl)-1,4-dihydrochromeno[4,3-c]pyrazole-3-carboxylic acid (30.00 mg; 0.07 mmol; 1.00 eq.) and 3,3-dimethyl-morpholine (0.05 ml; 0.10 mmol; 1.50 eq.). The desired compound was obtained in a yield of 12 mg (33%) as a blue solid.

LCMS: m/z=530 [M+H]$^+$ HPLC retention time=3.24 min.

Example 27

(3,3-Dimethyl-morpholin-4-yl)-[7-methoxy-8-(propane-2-sulfonyl)-1-thiophen-3-yl-1,4-dihydro-chromeno[4,3-c]pyrazol-3-yl]-methanone (112)

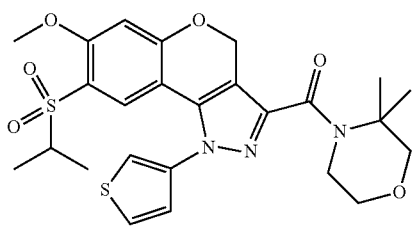 [SMILES: COc1cc2c(cc1S(=O)(=O)C(C)C)-c1c(c(C(=O)N3CCOCC3(C)C)nn1-c1ccsc1)CO2]

Step 1: 7-methoxy-8-(propane-2-sulfonyl)-1-thiophen-3-yl-1,4-dihydro-chromeno[4,3-c]pyrazole-3-carboxylic acid In a similar manner to example 26 (step 1), 7-methoxy-8-(propane-2-sulfonyl)-1-thiophen-3-yl-1,4-dihydro-chromeno[4,3-c]pyrazole-3-carboxylic acid was obtained from 8-bromo-7-methoxy-1-thiophen-3-yl-1,4-dihydro-chromeno[4,3-c]pyrazole-3-carboxylic acid (100.00 mg; 0.25 mmol; 1.00 eq.) and propane-2-sulfinic acid sodium (47.94 mg; 0.37 mmol; 1.50 eq.) as a crude blue solid.

Step 2: (3,3-Dimethyl-morpholin-4-yl)-[7-methoxy-8-(propane-2-sulfonyl)-1-thiophen-3-yl-1,4-dihydro-chromeno[4,3-c]pyrazol-3-yl]-methanone In a similar manner to example 26 (step 2), (3,3-Dimethyl-morpholin-4-yl)-[7-methoxy-8-(propane-2-sulfonyl)-1-thiophen-3-yl-1,4-dihydro-chromeno[4,3-c]pyrazol-3-yl]-methanone was obtained from 7-Methoxy-8-(propane-2-sulfonyl)-1-thiophen-3-yl-1,4-dihydro-chromeno[4,3-c]pyrazole-3-carboxylic acid (100.00 mg; 0.23 mmol; 1.00 eq.), and 3,3-Dimethyl-morpholine (0.17 ml; 0.35 mmol; 1.50 eq.) in 8.2% yield (10 mg) as a blue solid. LCMS: m/z=532 [M+H]$^+$, HPLC retention time=3.25 min.

Example 28

(3,3-Dimethyl-morpholin-4-yl)-[7-methoxy-8-(2-methyl-propane-1-sulfonyl)-1-thiophen-3-yl-1,4-dihydro-chromeno[4,3-c]pyrazol-3-yl]-methanone (127)

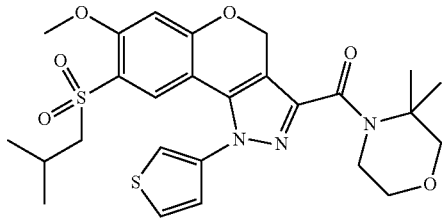 [SMILES: COc1cc2c(cc1S(=O)(=O)CC(C)C)-c1c(c(C(=O)N3CCOCC3(C)C)nn1-c1ccsc1)CO2]

Step 1: 7-Methoxy-8-(2-methyl-propane-1-sulfonyl)-1-thiophen-3-yl-1,4-dihydro-chromeno[4,3-c]pyrazole-3-carboxylic acid In a similar manner to example 26 (step 1), 7-Methoxy-8-(2-methyl-propane-1-sulfonyl)-1-thiophen-3-yl-1,4-dihydro-chromeno[4,3-c]pyrazole-3-carboxylic acid was obtained from 8-Bromo-7-methoxy-1-thiophen-3-yl-1,4-dihydro-chromeno[4,3-c]pyrazole-3-carboxylic acid (100.00 mg; 0.25 mmol; 1.00 eq.) and 2-Methyl-propane-1-sulfinic acid sodium (53.10 mg; 0.37 mmol; 1.50 eq.) as a blue crude solid.

Step 2: (3,3-Dimethyl-morpholin-4-yl)-[7-methoxy-8-(2-methyl-propane-1-sulfonyl)-1-thiophen-3-yl-1,4-dihydro-chromeno[4,3-c]pyrazol-3-yl]-methanone In a similar manner to example 26 (step 2), (3,3-Dimethyl-morpholin-4-yl)-[7-methoxy-8-(2-methyl-propane-1-sulfonyl)-1-thiophen-3-yl-1,4-dihydro-chromeno[4,3-c]pyrazol-3-yl]-methanone was obtained from 7-Methoxy-8-(2-methyl-propane-1-sulfonyl)-1-thiophen-3-yl-1,4-dihydro-chromeno[4,3-c]pyrazole-3-carboxylic acid (30.00 mg; 0.07 mmol; 1.00 eq.), and 3,3-Dimethyl-morpholine (46.22 mg; 0.40 mmol; 6.00 eq.) as a white solid in 13.7% yield (5 mg).

LCMS: m/z=546 [M+H]$^+$, HPLC retention time=3.56 min.

Example 29

7-Methoxy-8-(propane-2-sulfonyl)-1-thiophen-3-yl-1,4-dihydro-chromeno[4,3-c]pyrazole-3-carboxylic acid (3-hydroxymethyl-oxetan-3-yl)-amide (187)

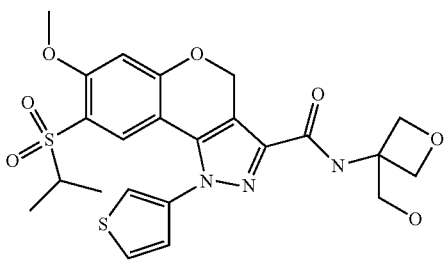 [SMILES: COc1cc2c(cc1S(=O)(=O)C(C)C)-c1c(c(C(=O)NC3(CO)COC3)nn1-c1ccsc1)CO2]

In a similar manner to example 27, 7-methoxy-8-(propane-2-sulfonyl)-1-thiophen-3-yl-1,4-dihydro-chromeno[4,3-c]pyrazole-3-carboxylic acid (3-hydroxymethyl-oxetan-3-yl)-amide was obtained from 7-Methoxy-8-(propane-2-sulfonyl)-1-thiophen-3-yl-1,4-dihydro-chromeno[4,3-c]pyrazole-3-carboxylic acid (70.00 mg; 0.16 mmol; 1.00 eq.) and (3-Amino-oxetan-3-yl)-methanol (24.92 mg; 0.24 mmol; 1.50 eq.) as white solid in 25% yield (21 mg).

$^1$H-NMR (DMSO-d6): δ 8.77 (s, 1H), 8.02 (dd, 1H), 7.86 (dd, 1H), 7.34 (dd, 1H), 7.19 (s, 1H), 6.93 (s, 1H), 5.64 (s, 2H), 5.14 (s, 1H), 4.67 (d, 2H), 4.51 (d, 2H), 3.90 (s, 3H), 3.68 (d, 2H), 3.45 (septet, 1H), 1.08 (d, 6H). m/z=520 [M+H]$^+$ Example 30

7-Methoxy-8-(propane-2-sulfonyl)-1-thiophen-3-yl-1,4-dihydro-chromeno[4,3-c]pyrazole-3-carboxylic acid (3-methyl-oxetan-3-yl)-amide (188)

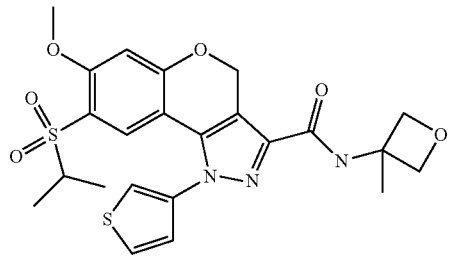 [SMILES: COc1cc2c(cc1S(=O)(=O)C(C)C)-c1c(c(C(=O)NC3(C)COC3)nn1-c1ccsc1)CO2]

In a similar manner to example 27, 7-methoxy-8-(propane-2-sulfonyl)-1-thiophen-3-yl-1,4-dihydro-chromeno[4,3-c]pyrazole-3-carboxylic acid (3-methyl-oxetan-3-yl)-amide was obtained from 7-Methoxy-8-(propane-2-sulfonyl)-1-thiophen-3-yl-1,4-dihydro-chromeno[4,3-c]pyrazole-3-carboxylic acid (70.00 mg; 0.16 mmol; 1.00 eq.) and 3-Methyl-oxetan-3-ylamine hydrochloride (29.87 mg; 0.24 mmol; 1.50 eq.) as a white solid in 34% yield (28 mg).

$^1$H-NMR (DMSO-d6): δ 8.95 (s, 1H), 8.03 (dd, 1H), 7.85 (dd, 1H), 7.34 (dd, 1H), 7.18 (s, 1H), 6.93 (s, 1H), 5.64 (s, 2H), 4.71 (d, 2H), 4.31 (d, 2H), 3.90 (s, 3H), 3.45 (septet, 1H), 1.59 (s, 3H), 1.07 (d, 6H). m/z=504 [M+H]$^+$ Example 31

(3,3-Dimethyl-morpholin-4-yl)-[8-(1-hydroxy-2-methyl-propyl)-7-methoxy-1-thiophen-3-yl-1,4-dihydro-chromeno[4,3-c]pyrazol-3-yl]-methanone (131)

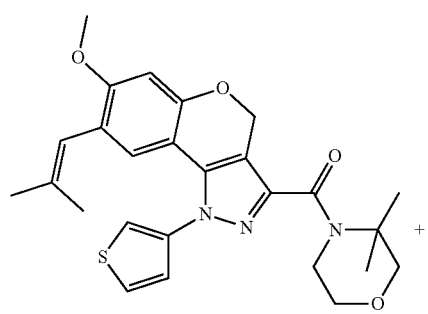

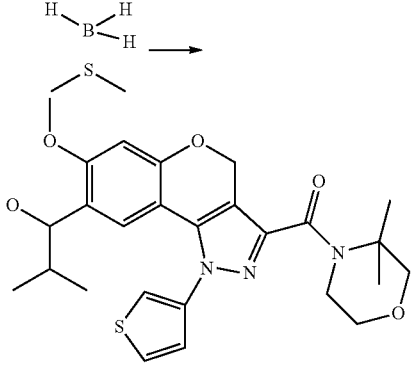

To (3,3-dimethyl-morpholin-4-yl)-[7-methoxy-8-(2-methyl-propenyl)-1-thiophen-3-yl-1,4-dihydro-chromeno[4,3-c]pyrazol-3-yl]-methanone (70.00 mg; 0.15 mmol; 1.00 eq.) suspended in THF (3.00 ml), was added methylsulfanylmethane; with borane (16.63 mg; 0.22 mmol; 1.50 eq.). The reaction was stirred at RT for 2 h. Then NaOH (2N solution) was added very slowly. The reaction mixture was purified using reverse phase prep-HPLC (45-60% CH$_3$CN in 0.1% NH$_4$OH in H$_2$O) to afford the desired product (19 mg, 26%) as a white solid.

$^1$H-NMR (DMSO-d6): δ 7.86 (dd, 1H), 7.78 (dd, 1H), 7.28 (dd, 1H), 6.92 (s, 1H), 6.65 (s, 1H), 5.39 (d, 1H), 5.26 (d, 1H), 4.56 (d, 1H), 4.50 (t, 1H), 4.03-3.96 (m, 1H), 3.93-3.85 (m, 1H), 3.77-3.70 (m, 5H), 3.42 (s, 2H), 1.61 (sextet, 1H), 1.42 (d, 6H), 0.74 (d, 3H), 0.68 (d, 3H). m/z=498 [M+H]$^+$ Example 32

(3,3-Dimethyl-morpholin-4-yl)-[7-methoxy-1-thiophen-3-yl-8-(5-trimethylsilanyl-5H-[1,2,4]triazol-3-yl)-1,4-dihydro-chromeno[4,3-c]pyrazol-3-yl]-methanone (139)

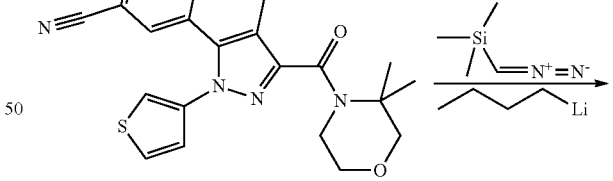

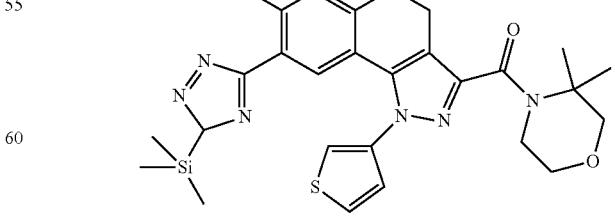

To diazomethyl-trimethyl-silane (0.17 ml; 0.33 mmol; 3.00 eq.) suspended in Ethoxy-ethane (3.00 ml) at 0° C. was added n-butyl lithium (0.09 ml; 0.22 mmol; 2.00 eq.). The reaction mixture was stirred at 0° C. for 30 min then 3-(3,3-Dimethyl-morpholine-4-carbonyl)-7-methoxy-1-thiophen-3-yl-1,4-dihydro-chromeno[4,3-c]pyrazole-8-carbonitrile (50.00 mg; 0.11 mmol; 1.00 eq.) was added and the reaction was stirred at 0° C. for another 30 min. The reaction mixture was warmed to RT and stirred at RT for 1 h. The mixture was concentrated and purified by column chromatography to afford the desired product (18 mg, 29%) as a white solid.

$^1$H-NMR (DMSO-d6): δ 7.92 (dd, 1H), 7.72 (dd, 1H), 7.28 (dd, 1H), 6.79 (s, 1H), 6.73 (s, 1H), 5.43 (s, 2H), 3.96-3.92 (m, 2H), 3.74-3.68 (m, 5H), 3.42 (s, 2H), 3.18 (s, 1H), 1.43 (s, 6H), 0.06 (s, 9H). m/z=565 [M+H]$^+$

Example 33

(3,3-Dimethyl-morpholin-4-yl)-[7-methoxy-1-thiophen-3-yl-8-(5H-[1,2,4]triazol-3-yl)-1,4-dihydro-chromeno[4,3-c]pyrazol-3-yl]-methanone (161)

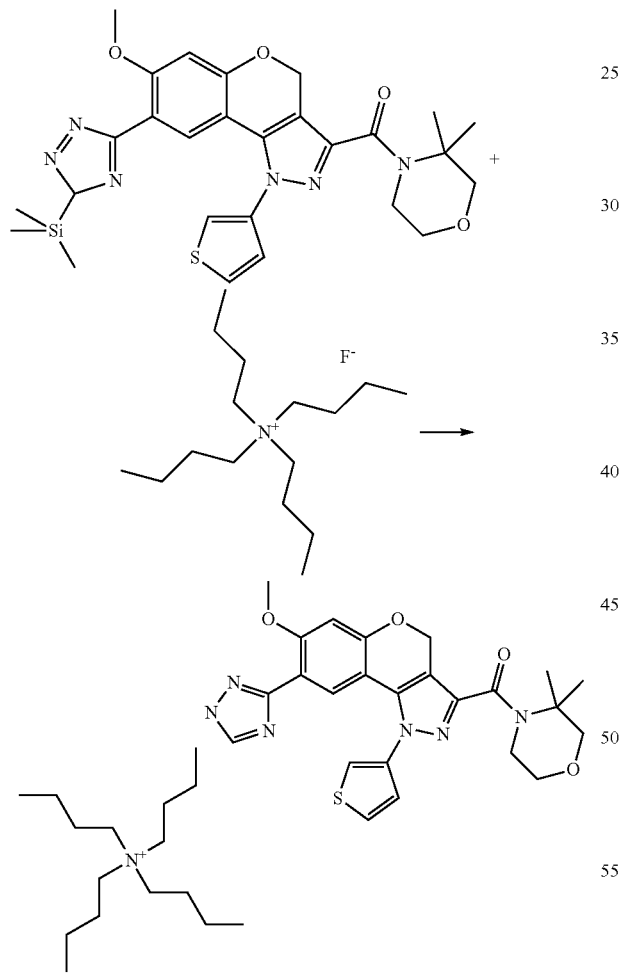

To (3,3-dimethyl-morpholin-4-yl)-[7-methoxy-1-thiophen-3-yl-8-(5-trimethylsilanyl-5H-[1,2,4]triazol-3-yl)-1,4-dihydro-chromeno[4,3-c]pyrazol-3-yl]-methanone (34.00 mg; 0.06 mmol; 1.00 eq.) dissolved in THF (3.00 ml) was added tetrabutyl-ammonium fluoride (1M in THF) (0.30 ml; 0.30 mmol; 5.00 eq.) and the reaction was stirred at RT for 18 h. Reaction mixture was concentrated and purified by reverse phase prep-HPLC (35-40% CH$_3$CN in 0.1% NH$_4$OH in H$_2$O) to afford the desired product (36 mg, 82%) as a white solid.

$^1$H-NMR (DMSO-d6) (tetrabutyl ammonium salt): δ 7.89 (dd, 1H), 7.79 (dd, 1H), 7.73 (s, 1H), 7.53 (s, 1H), 7.31 (dd, 1H), 6.70 (s, 1H), 5.31 (s, 2H), 3.96 (t, 2H), 3.83 (s, 3H), 3.73 (t, 2H), 3.43 (s, 2H), 3.20-3.13 (m, 9H), 1.64-1.52 (m, 9H), 1.43 (s, 6H), 1.33 (sextet, 9H), 0.94 (t, 12H). m/z=493 [M+H]$^+$ Example 34 (8-Aminomethyl-7-methoxy-1-thiophen-3-yl-1,4-dihydro-chromeno[4,3-c]pyrazol-3-yl)-(3,3-dimethyl-morpholin-4-yl)-methanone (166)

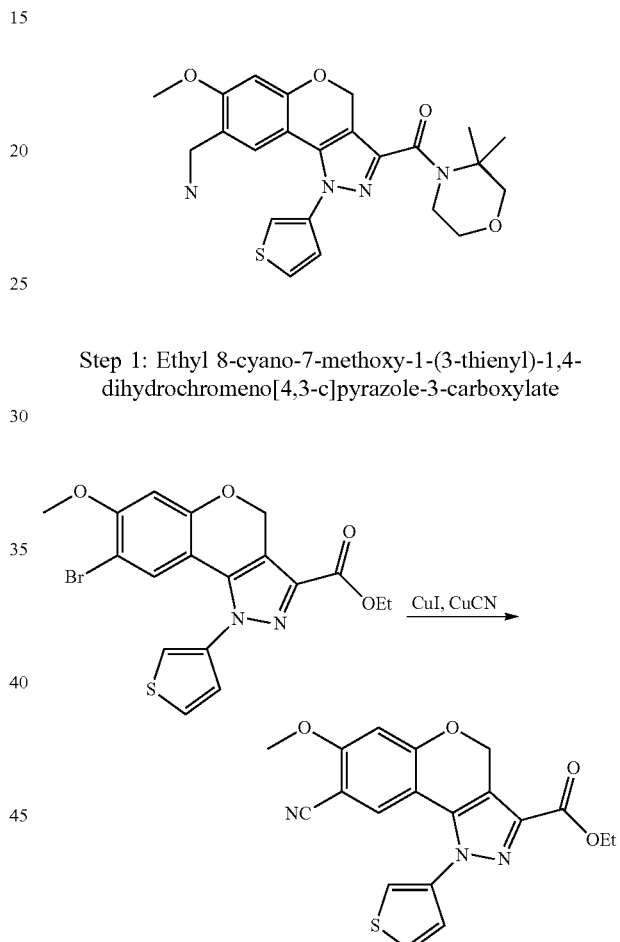

Step 1: Ethyl 8-cyano-7-methoxy-1-(3-thienyl)-1,4-dihydrochromeno[4,3-c]pyrazole-3-carboxylate To a solution of ethyl 8-bromo-7-methoxy-1-(3-thienyl)-1,4-dihydrochromeno[4,3-c]pyrazole-3-carboxylate (2 g, 0.0459 mol) in NMP (50 mL), was added CuI (90 mg, 0.5 mmol) and followed by CuCN (825 mg, 9.1 mmol) in a sealed tube. The reaction mixture was heated to 160° C. for 16 h. The reaction mixture was filtered through celite and the filtrate was concentrated. The crude product was purified by column chromatography by using dichloromethane/methanol (9:1) as eluent. The product was triturated with acetonitrile and filtered, to afford of the desired compound (0.7 g, 83%) as a white solid.

$^1$H NMR (400 MHz, DMSO) δ 8.05-8.04 (dd, J=1.4, 3.1 Hz, 1H), 7.90-7.88 (dd, J=3.2, 5.1 Hz, 1H), 7.37-7.35 (dd, J=1.4, 5.1 Hz, 1H), 5.63 (s, 1H), 4.33-4.28 (m, 2H), 3.89 (s, 1H), 1.32-1.28 (t, J=12.9 Hz, 3H). m/z=382 [M+H]$^+$

Step 2: 8-Cyano-7-methoxy-1-thiophen-3-yl-1,4-dihydro-chromeno[4,3-c]pyrazole-3-carboxylic acid To 8-cyano-7-methoxy-1-thiophen-3-yl-1,4-dihydro-chromeno[4,3-c]pyrazole-3-carboxylic acid ethyl ester (300.00 mg; 0.79 mmol; 1.00 eq.) dissolved in Methanol (6.00 ml; 177.52 mmol; 225.69 eq.) was added potassium hydroxide (66.20 mg; 1.18 mmol; 1.50 eq.) and water (0.60 ml). The reaction mixture was heated to 50° C. for 2 h. The reaction was concentrated and lyophilized to afford the crude desired product as a gray solid.

Step 3: 3-(3,3-Dimethyl-morpholine-4-carbonyl)-7-methoxy-1-thiophen-3-yl-1,4-dihydro-chromeno[4,3-c]pyrazole-8-carbonitrile (86)

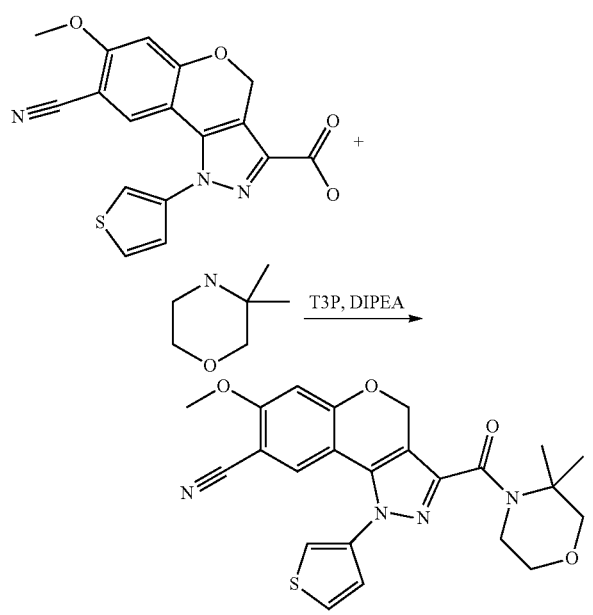

To 8-cyano-7-methoxy-1-thiophen-3-yl-1,4-dihydro-chromeno[4,3-c]pyrazole-3-carboxylic acid (270.00 mg; 0.76 mmol; 1.00 eq.) suspended in DCM (6.00 ml; 93.60 mmol; 122.50 eq.) was added 2,4,6-tripropyl-1,3,5,2,4,6-trioxatriphosphinane 2,4,6-trioxide (1.35 ml; 2.29 mmol; 3.00 eq.), 3,3-Dimethyl-morpholine (176.01 mg; 1.53 mmol; 2.00 eq.) and ethyl-diisopropyl-amine (0.38 ml; 2.29 mmol; 3.00 eq.). The reaction was stirred at RT for 1 h. Mixture was concentrated and purified by flash chromatography to afford the desired product (309 mg, 90%) as a white solid. LCMS: m/z=451 [M+H]+

Step 4: (8-Aminomethyl-7-methoxy-1-thiophen-3-yl-1,4-dihydro-chromeno[4,3-c]pyrazol-3-yl)-(3,3-dimethyl-morpholin-4-yl)-methanone

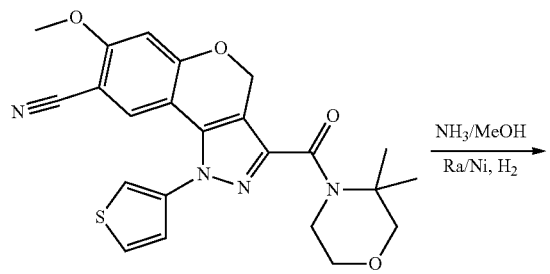

3-(3,3-dimethyl-morpholine-4-carbonyl)-7-methoxy-1-thiophen-3-yl-1,4-dihydro-chromeno[4,3-c]pyrazole-8-carbonitrile (50.00 mg; 0.11 mmol; 1.00 eq.) was dissolved in amonia in methanol (10.00 ml; 20.00 mmol; 180.20 eq.) and the reaction mixture was run through an H-cube under full $H_2$ pressure using Raney nickel cartridge at 70° C. for 2 h. The mixture was concentrated and purified by reverse phase prep-HPLC (35-45% $CH_3CN$ in 0.1% $NH_4OH$ in $H_2O$) to afford the desired product as white solid (7 mg, 14%). LCMS: m/z=455 [M+H]+, HPLC retention time=2.71 min.

Example 35

N-[3-(3,3-Dimethyl-morpholine-4-carbonyl)-7-methoxy-1-thiophen-3-yl-1,4-dihydro-chromeno[4,3-c]pyrazol-8-ylmethyl]-acetamide (175)

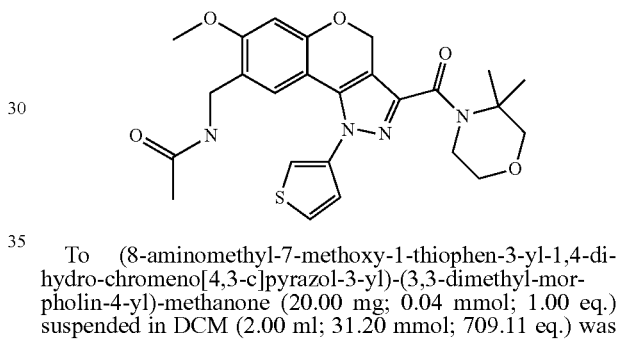

To (8-aminomethyl-7-methoxy-1-thiophen-3-yl-1,4-dihydro-chromeno[4,3-c]pyrazol-3-yl)-(3,3-dimethyl-morpholin-4-yl)-methanone (20.00 mg; 0.04 mmol; 1.00 eq.) suspended in DCM (2.00 ml; 31.20 mmol; 709.11 eq.) was added 2,4,6-tripropyl-1,3,5,2,4,6-trioxatriphosphinane 2,4,6-trioxide (0.04 ml; 0.07 mmol; 1.50 eq.), acetic acid (3.96 mg; 0.07 mmol; 1.50 eq.) and ethyl-diisopropyl-amine (0.02 ml; 0.13 mmol; 3.00 eq.). The reaction mixture was stirred at RT for 1 h. The mixture was concentrated and purified by reverse phase prep-HPLC (32-38% $CH_3CN$ in 0.1% $NH_4OH$ in $H_2O$) to afford the desired product (4 mg, 18%) as a white solid.

$^1$H-NMR (DMSO-d6): δ 7.91-7.76 (m, 2H), 7.28-7.22 (m, 1H), 6.74-6.61 (m, 2H), 5.37-5.26 (m, 2H), 4.14 (s, 0.5H), 3.96 (d, 3.5H), 3.84-3.69 (m, 5H), 3.42 (s, 2H), 2.05 (s, 0.5H), 1.91 (s, 0.5H), 1.86-1.76 (m, 3H), 1.42 (s, 6H). m/z=497 [M+H]+

Example 36

8-Cyano-7-methoxy-1-thiophen-3-yl-1,4-dihydro-chromeno[4,3-c]pyrazole-3-carboxylic acid tert-butyl-methyl-amide (12)

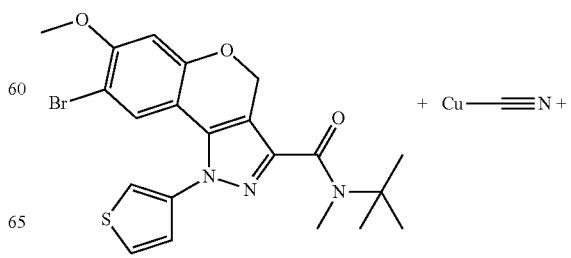

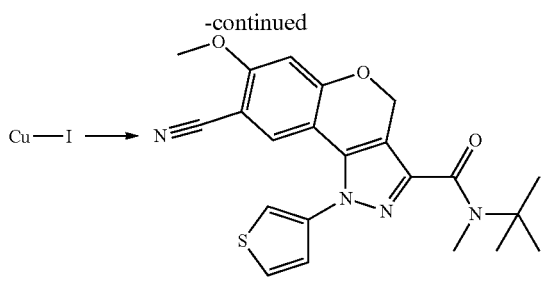

To 8-bromo-7-methoxy-1-thiophen-3-yl-1,4-dihydro-chromeno[4,3-c]pyrazole-3-carboxylic acid tert-butyl-methyl-amide (210 mg, 0.44 mmol) in NMP (5 mL) was added CuCN 43.5 mg, 0.48 mmol, 1.1 eq.) and CuI (8.4 mg, 0.044 mmol 0.1 eq.). The reaction was microwaved at 170° C. for 70 min. The mixture was purified by reverse phase prep HPLC to afford the desired product (10 mg, 5%) as a white solid.

$^1$H NMR (400 MHz, CDCl$_3$) δ 7.54 (ddd, J=4.7, 4.1, 2.4 Hz, 2H), 7.19 (dd, J=5.0, 1.5 Hz, 1H), 6.97 (s, 1H), 6.62 (s, 1H), 5.58 (s, 2H), 3.92 (s, 3H), 3.28 (s, 3H), 1.53 (s, 9H). m/z=423 [M+H]$^+$ Example 37

7-methoxy-8-(1-methyl-1H-pyrrol-3-yl)-1-thiophen-3-yl-1,4-dihydro-chromeno[4,3-c]pyrazole-3-carboxylic acid (2-hydroxy-1-hydroxymethyl-1-methyl-ethyl)-amide (179)

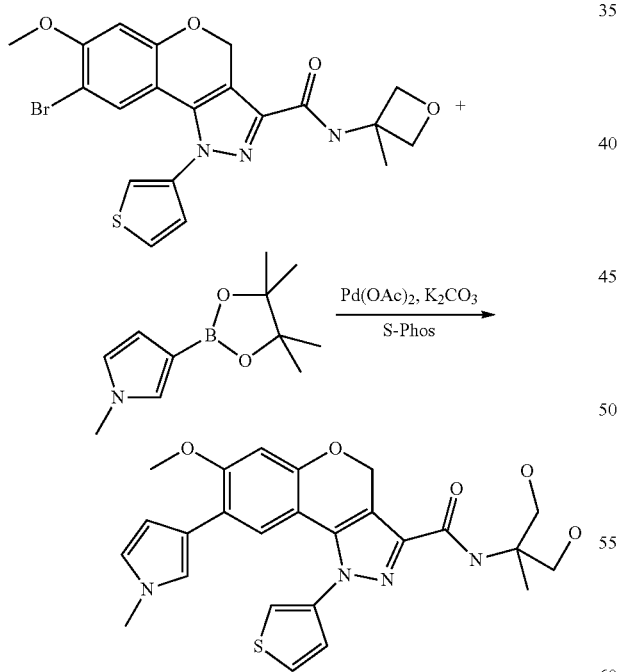

To 8-bromo-7-methoxy-1-thiophen-3-yl-1,4-dihydro-chromeno[4,3-c]pyrazole-3-carboxylic acid (3-methyl-oxetan-3-yl)-amide (1.00 g; 2.10 mmol; 1.00 eq.) was added 1-Methyl-3-(4,4,5,5-tetramethyl-[1,3,2]dioxaborolan-2-yl)-1H-pyrrole (652.08 mg; 3.15 mmol; 1.50 eq.), palladium acetate (23.57 mg; 0.10 mmol; 0.05 eq.), dicyclohexyl-(2', 6'-dimethoxy-biphenyl-2-yl)-phosphane (86.18 mg; 0.21 mmol; 0.10 eq.), potassium carbonate (870.42 mg; 6.30 mmol; 3.00 eq.), dioxane (10.00 ml) and water (1.00 ml). The reaction mixture was heated at 120° C. for 24 h. The mixture was concentrated, filtered and purified by reverse phase prep-HPLC (35-45% CH$_3$CN in 0.1% NH$_4$OH in H$_2$O) to afford the hydrolyzed product (14 mg, 1.3%) as a white solid.

$^1$H-NMR (DMSO-d6): δ 8.06 (s, 1H), 7.90 (s, 1H), 7.39 (s, 1H), 7.31 (s, 1H), 7.00 (s, 1H), 6.79 (s, 1H), 6.71 (s, 1H), 6.63 (s, 1H), 5.77 (s, 1H), 5.49 (s, 2H), 4.95 (s, 2H), 3.83 (s, 3H), 3.65-3.56 (m, 5H), 3.53-3.45 (m, 2H), 1.30 (s, 3H). m/z=495 [M+H]

Example 38

7-Methoxy-8-(1-methyl-1H-pyrazol-3-yl)-1-thiophen-3-yl-1,4-dihydro-chromeno[4,3-c]pyrazole-3-carboxylic acid (2-hydroxy-1-hydroxymethyl-1-methyl-ethyl)-amide (185)

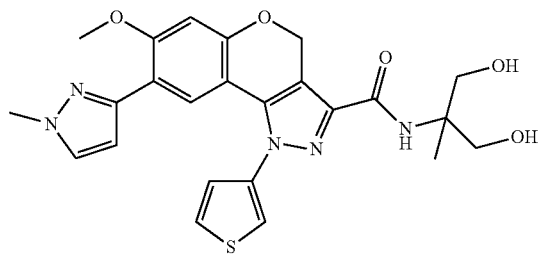 [SMILES: COc1cc2c(cc1-c1ccn(C)n1)-c1c(c(C(=O)NC(C)(CO)CO)nn1-c1ccsc1)CO2]

Using a procedure similar to example 37, 7-methoxy-8-(1-methyl-1H-pyrazol-3-yl)-1-thiophen-3-yl-1,4-dihydro-chromeno[4,3-c]pyrazole-3-carboxylic acid (2-hydroxy-1-hydroxymethyl-1-methyl-ethyl)-amide was obtained from 8-Bromo-7-methoxy-1-thiophen-3-yl-1,4-dihydro-chromeno[4,3-c]pyrazole-3-carboxylic acid (3-methyl-oxetan-3-yl)-amide (1.00 g; 2.10 mmol; 1.00 eq.) and 1-Methyl-3-(4,4,5,5-tetramethyl-[1,3,2]dioxaborolan-2-yl)-1H-pyrazole (655.19 mg; 3.15 mmol; 1.50 eq.), as a white solid in 2% yield (20 mg).

$^1$H-NMR (DMSO-d6): δ 8.01 (s, 1H), 7.85 (d, 1H), 7.60 (s, 1H), 7.41 (s, 1H), 7.32 (s, 2H), 6.76 (s, 1H), 6.49 (s, 1H), 5.53 (s, 2H), 4.95 (s, 2H), 3.84 (s, 3H), 3.78 (s, 3H), 3.66-3.57 (m, 2H), 3.53-3.45 (m, 2H), 1.30 (s, 3H). m/z=496 [M+H]$^+$

Example 39

7-Methoxy-8-(tetrahydro-furan-3-yl)-1-thiophen-3-yl-1,4-dihydro-chromeno[4,3-c]pyrazole-3-carboxylic acid tert-butyl-methyl-amide (194)

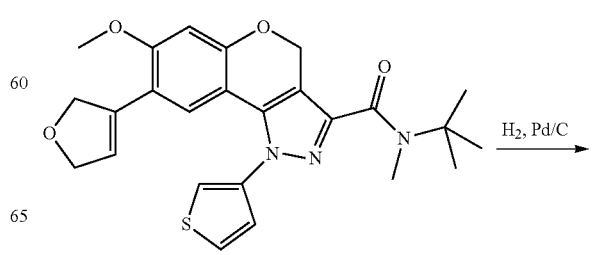

-continued

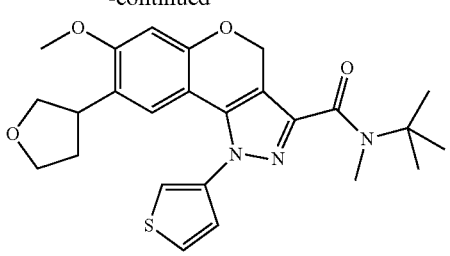

To 8-(2,5-dihydro-furan-3-yl)-7-methoxy-1-thiophen-3-yl-1,4-dihydro-chromeno[4,3-c]pyrazole-3-carboxylic acid tert-butyl-methyl-amide (30.00 mg; 0.06 mmol; 1.00 eq.) suspended in acetic acid (3.00 ml) was added palladium on carbon (0.02 ml; 0.32 mmol; 5.00 eq.). The flask was capped with a rubber septum and topped with a hydrogen balloon. The reaction mixture was stirred at RT for 18 h. Triethylamine was added, the mixture was filtered through celite and the mixture was purified by reverse phase prep-HPLC (55-63% $CH_3CN$ in 0.1% $NH_4OH$ in $H_2O$) to afford the desired product (11 mg, 37%) as a white solid.

$^1$H-NMR (DMSO-d6): δ 7.95 (dd, 1H), 7.84 (dd, 1H), 7.32 (dd, 1H), 6.69 (s, 1H), 6.60 (s, 1H), 5.34 (d, 2H), 3.85 (t, 1H), 3.79 (s, 3H), 3.71-3.57 (m, 2H), 3.43 (quintet, 1H), 3.21-3.15 (m, 4H), 2.10-2.00 (m, 1H), 1.56-1.40 (m, 10H). m/z=468 $[M+H]^+$ Example 40

7-Methoxy-8-(tetrahydro-furan-2-yl)-1-thiophen-3-yl-1,4-dihydro-chromeno[4,3-c]pyrazole-3-carboxylic acid tert-butyl-methyl-amide (201)

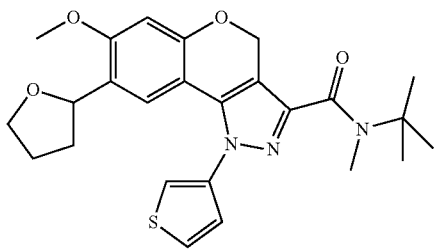 [SMILES: COc1cc2c(cc1C1CCCO1)-c1c(c(C(=O)N(C)C(C)(C)C)nn1-c1ccsc1)CO2]

In a similar manner to example 39, 7-methoxy-8-(tetrahydro-furan-2-yl)-1-thiophen-3-yl-1,4-dihydro-chromeno[4,3-c]pyrazole-3-carboxylic acid tert-butyl-methyl-amide was obtained from 8-(4,5-Dihydro-furan-2-yl)-7-methoxy-1-thiophen-3-yl-1,4-dihydro-chromeno[4,3-c]pyrazole-3-carboxylic acid tert-butyl-methyl-amide (65.00 mg; 0.14 mmol; 1.00 eq.) as a white solid in 9% yield (6 mg).

$^1$H-NMR (DMSO-d6): δ 7.93 (dd, 1H), 7.82 (dd, 1H), 7.30 (dd, 1H), 6.75 (s, 1H), 6.66 (s, 1H), 5.33 (q, 2H), 4.90 (dd, 1H), 3.77 (s, 3H), 3.65-3.58 (m, 2H), 3.17 (s, 3H), 2.18-2.07 (m, 1H), 1.85-1.74 (m, 1H), 1.70-1.59 (m, 1H), 1.50-1.40 (m, 10H). m/z=468 $[M+H]^+$

Example 41

7-Methoxy-8-(1-methyl-1H-pyrazol-3-yl)-1-thiophen-3-yl-1,4-dihydro-chromeno[4,3-c]pyrazole-3-carboxylic acid (1S,3S)-3-amino-cyclopentyl ester (180)

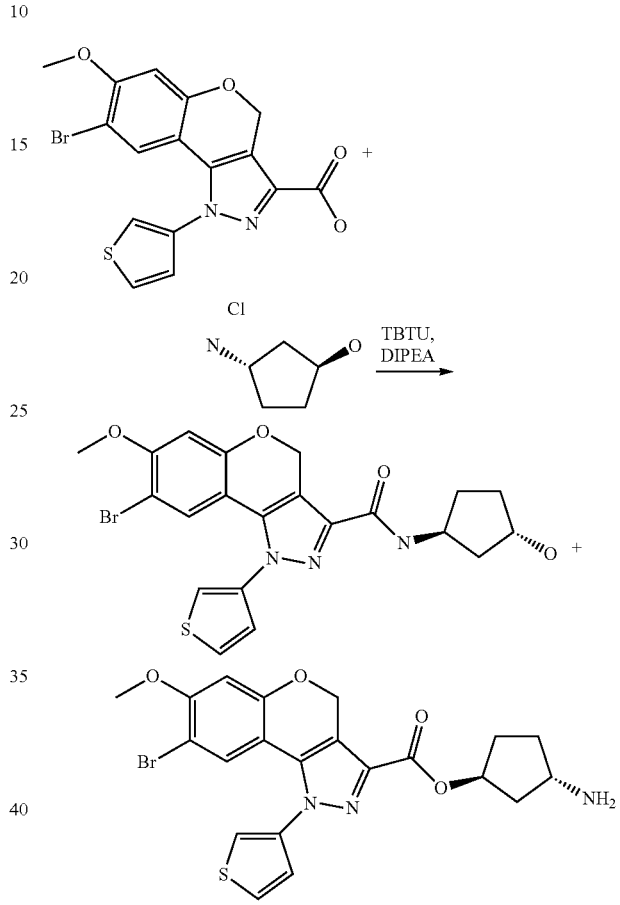

Step 1

To 8-bromo-7-methoxy-1-thiophen-3-yl-1,4-dihydro-chromeno[4,3-c]pyrazole-3-carboxylic acid (500.00 mg; 1.23 mmol; 1.00 eq.) suspended in DCM (10.00 ml; 156.01 mmol; 127.06 eq.) was added (1S,3S)-3-amino-cyclopentanol hydrochloride (253.43 mg; 1.84 mmol; 1.50 eq.), [(benzotriazol-1-yloxy)-dimethylamino-methylene]-dimethyl-ammonium tetrafluoroborate (788.43 mg; 2.46 mmol; 2.00 eq.), and ethyl-diisopropyl-amine (0.61 ml; 3.68 mmol; 3.00 eq.). The reaction was stirred at RT for 1 h. The mixture was concentrated and purified by flash chromatography to afford a mixture of 8-bromo-7-methoxy-1-thiophen-3-yl-1,4-dihydro-chromeno[4,3-c]pyrazole-3-carboxylic acid ((1S,3S)-3-hydroxy-cyclopentyl)-amide and 8-bromo-7-methoxy-1-thiophen-3-yl-1,4-dihydro-chromeno[4,3-c]pyrazole-3-carboxylic acid (1S,3S)-3-amino-cyclopentyl ester (total 247 mg, 41%) as a white solid.

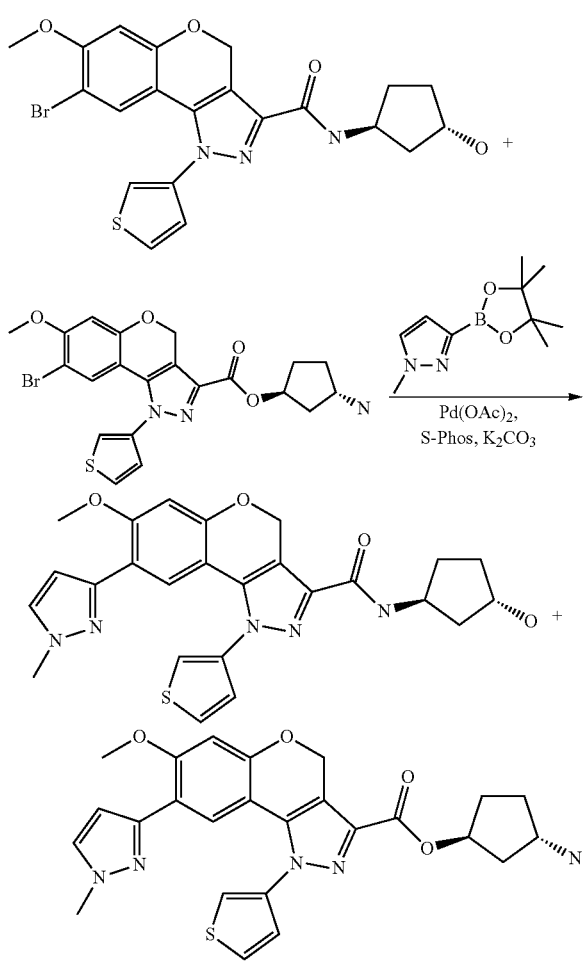

Step 2

To a mixture of 8-bromo-7-methoxy-1-thiophen-3-yl-1,4-dihydro-chromeno[4,3-c]pyrazole-3-carboxylic acid ((1S,3S)-3-hydroxy-cyclopentyl)-amide and 8-bromo-7-methoxy-1-thiophen-3-yl-1,4-dihydro-chromeno[4,3-c]pyrazole-3-carboxylic acid (1S,3S)-3-amino-cyclopentyl ester (120.00 mg; 0.24 mmol; 1.00 eq.) was added 1-methyl-3-(4,4,5,5-tetramethyl-[1,3,2]dioxaborolan-2-yl)-1H-pyrazole (76.37 mg; 0.37 mmol; 1.50 eq.), palladium acetate (2.75 mg; 0.01 mmol; 0.05 eq.), dicyclohexyl-(2',6'-dimethoxy-biphenyl-2-yl)-phosphane (10.05 mg; 0.02 mmol; 0.10 eq.), potassium carbonate (101.46 mg; 0.73 mmol; 3.00 eq.), dioxane (4.00 ml) and water (0.40 ml). The reaction mixture was heated at 140° C. for 18 h. The mixture was concentrated and a portion of it was purified by flash chromatography (KPNH, 80-100% EtOAc/Hexanes, 0-20% MeOH/EtOAc) to afford 7-methoxy-8-(1-methyl-1H-pyrazol-3-yl)-1-thiophen-3-yl-1,4-dihydro-chromeno[4,3-c]pyrazole-3-carboxylic acid ((1S,3S)-3-hydroxy-cyclopentyl)-amide (78 mg, 65%) as a white solid. The rest of the crude material was purified by reverse phase prep-HPLC (35-45% CH$_3$CN in 0.1% NH$_4$OH in H$_2$O) to afford 7-methoxy-8-(1-methyl-1H-pyrazol-3-yl)-1-thiophen-3-yl-1,4-dihydro-chromeno[4,3-c]pyrazole-3-carboxylic acid (1S,3S)-3-amino-cyclopentyl ester (5 mg, 4.2%) as a white solid.

$^1$H-NMR (DMSO-d6): δ 7.94 (s, 1H), 7.82 (s, 1H), 7.60 (s, 1H), 7.50 (s, 1H), 7.33 (s, 1H), 6.77 (s, 1H), 6.50 (s, 1H), 5.38 (s, 2H), 4.96 (s, 1H), 3.85 (s, 3H), 3.78 (s, 3H), 3.63 (s, 1H), 1.32 (d, 12H). m/z=492 [M+H]$^+$

Example 42

7-Methoxy-8-(1-methyl-1H-pyrrol-3-yl)-1-thiophen-3-yl-1,4-dihydro-chromeno[4,3-c]pyrazole-3-carboxylic acid (1S,3S)-3-amino-cyclopentyl ester (181)

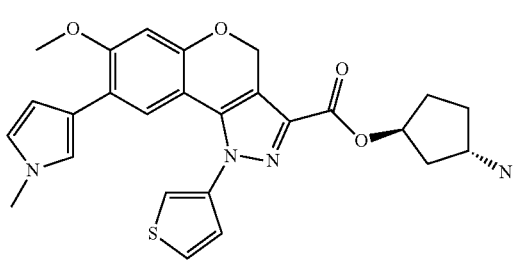 [SMILES: COc1cc2c(cc1-c1ccn(C)c1)-c1c(c(C(=O)O[C@H]3CC[C@H](N)C3)nn1-c1ccsc1)CO2]

In a similar manner to example 41, 7-methoxy-8-(1-methyl-1H-pyrrol-3-yl)-1-thiophen-3-yl-1,4-dihydro-chromeno[4,3-c]pyrazole-3-carboxylic acid (1S,3S)-3-amino-cyclopentyl ester was obtained from 8-bromo-7-methoxy-1-thiophen-3-yl-1,4-dihydro-chromeno[4,3-c]pyrazole-3-carboxylic acid (1S,3S)-3-amino-cyclopentyl ester, in 3% yield (3 mg) as a white solid.

$^1$H-NMR (DMSO-d6): δ 8.01 (s, 1H), 7.88 (s, 1H), 7.38 (s, 1H), 7.01 (s, 1H), 6.88 (s, 1H), 6.72 (s, 1H), 6.64 (s, 1H), 5.81 (s, 1H), 5.34 (s, 2H), 4.98 (s, 1H), 4.09 (s, 5H), 3.84 (s, 3H), 3.59 (s, 4H), 1.48-1.14 (m, 12H). m/z=491 [M+H]$^+$

Example 43

7-Methoxy-1-thiophen-3-yl-1,4-dihydro-chromeno[4,3-c]pyrazole-3-carboxylic acid tert-butyl-methyl-amide (133)

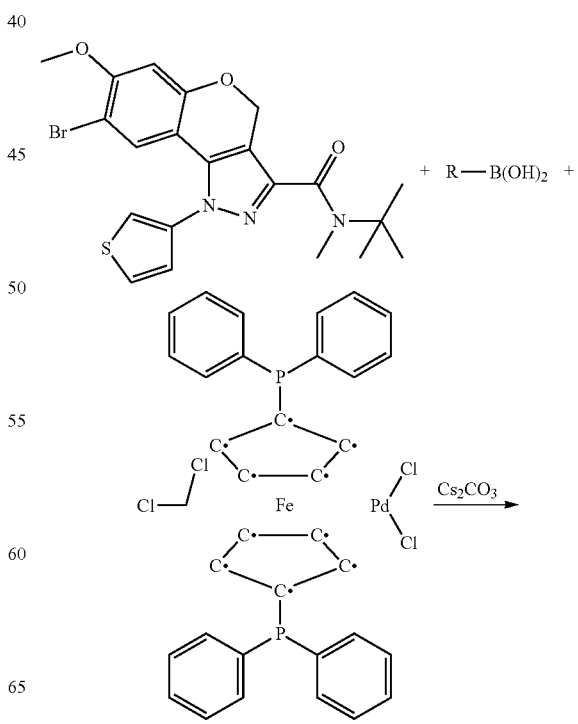

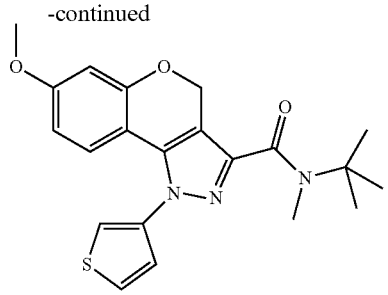

To 8-bromo-7-methoxy-1-thiophen-3-yl-1,4-dihydro-chromeno[4,3-c]pyrazole-3-carboxylic acid tert-butyl-methyl-amide (70.00 mg; 0.15 mmol; 1.00 eq.), was added boronic acid, [1,1'-bis(diphenylphosphino)ferrocene]dichloropalladium(ii), complex with dichloromethane (1:1) (24.00 mg; 0.03 mmol; 0.20 eq.), cesium carbonate (143.63 mg; 0.44 mmol; 3.00 eq.) dioxane (2.00 ml; 23.47 mmol; 159.74 eq.) and water (0.20 ml). The reaction was heated to 120° C. for 18 h. The reaction mixture was concentrated, purified by reverse phase using prep-HPLC (45-55% CH$_3$CN in 0.1% NH$_4$OH in H$_2$O) to afford 7-methoxy-1-thiophen-3-yl-1,4-dihydro-chromeno[4,3-c]pyrazole-3-carboxylic acid tert-butyl-methyl-amide as the major product as a white solid (30 mg, 51%).

$^1$H-NMR (DMSO-d6): δ 7.94 (dd, 1H), 7.81 (dd, 1H), 7.32 (dd, 1H), 6.67 (d, 1H), 6.62 (d, 1H), 6.47 (dd, 1H), 5.33 (s, 2H), 3.73 (s, 3H), 3.17 (s, 3H), 1.44 (s, 9H). m/z=398 [M+H]$^+$

Example 44

(2-Methoxymethyl-2-methyl-pyrrolidin-1-yl)-(7-methoxy-1-thiophen-3-yl-1,4-dihydro-chromeno[4,3-c]pyrazol-3-yl)-methanone (183)

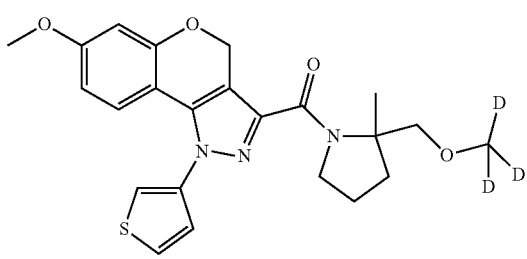 [SMILES: [2H]C([2H])([2H])OCC1(C)CCCN1C(=O)c1nn(-c2ccsc2)c2c1COc1cc(OC)ccc1-2]

In a similar manner to example 43, (2-methoxymethyl-2-methyl-pyrrolidin-1-yl)-(7-methoxy-1-thiophen-3-yl-1,4-dihydro-chromeno[4,3-c]pyrazol-3-yl)-methanone was obtained from (2-Hydroxymethyl-2-methyl-pyrrolidin-1-yl)-(7-methoxy-1-thiophen-3-yl-1,4-dihydro-chromeno[4,3-c]pyrazol-3-yl)-methanone as a white solid (13 mg, 50%).

$^1$H-NMR (DMSO-d6): δ 7.95 (s, 1H), 7.82 (s, 1H), 7.32 (s, 1H), 6.69-6.60 (m, 2H), 6.49-6.44 (m, 1H), 5.43 (s, 2H), 4.05 (s, 1H), 3.90-3.79 (m, 2H), 3.73 (s, 3H), 3.59-3.52 (m, 1H), 2.16-2.07 (m, 1H), 1.88-1.72 (m, 2H), 1.68-1.58 (m, 1H), 1.42 (s, 3H). m/z=443 [M+H]$^+$

Example 45

(3,3-Dimethyl-morpholin-4-yl)-(7-methoxy-1-thiophen-3-yl-1,4-dihydro-chromeno[4,3-c]pyrazol-3-yl)-methanone (128)

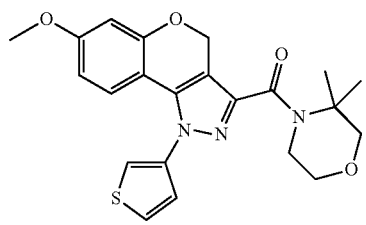

In a similar manner to example 43, (3,3-Dimethyl-morpholin-4-yl)-(7-methoxy-1-thiophen-3-yl-1,4-dihydro-chromeno[4,3-c]pyrazol-3-yl)-methanone was obtained from (8-Bromo-7-methoxy-1-thiophen-3-yl-1,4-dihydro-chromeno[4,3-c]pyrazol-3-yl)-(3,3-dimethyl-morpholin-4-yl)-methanone as a white solid (13 mg, 46%).

LCMS: m/z=427 [M+H]$^+$, HPLC retention time=3.65 min.

Example 46

7-Methoxy-1-thiophen-3-yl-1,4-dihydro-chromeno[4,3-c]pyrazole-3,8-dicarboxylic acid 8-amide 3-(tert-butyl-methyl-amide) (50)

Step 1: 8-Carbamoyl-7-methoxy-1-thiophen-3-yl-1,4-dihydro-chromeno[4,3-c]pyrazole-3-carboxylic acid

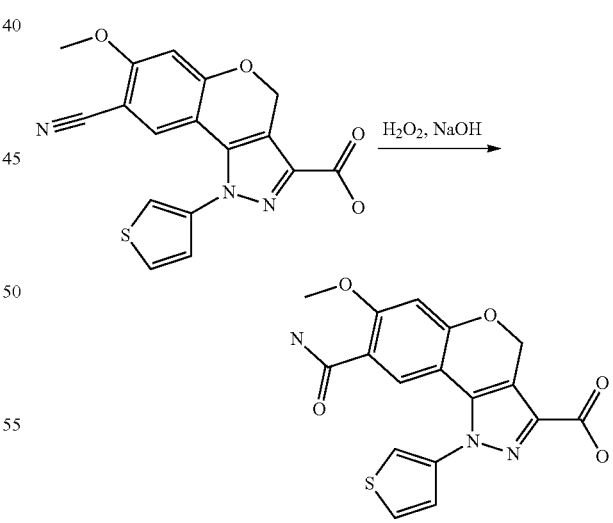

To 8-cyano-7-methoxy-1-thiophen-3-yl-1,4-dihydro-chromeno[4,3-c]pyrazole-3-carboxylic acid (45.00 mg; 0.13 mmol; 1.00 eq.) (example 34) in DMSO (4 mL) was added H$_2$O$_2$ (0.12 ml; 1.27 mmol; 10.00 eq.) and 2.0M NaOH aq (0.64 ml; 1.27 mmol; 10.00 eq.). The reaction was stirred at RT for 2 h. The mixture was purified by reverse phase HPLC to afford the desired product (17 mg, 35%) as a white solid.

351

Step 2: 7-Methoxy-1-thiophen-3-yl-1,4-dihydro-chromeno[4,3-c]pyrazole-3,8-dicarboxylic acid 8-amide 3-(tert-butyl-methyl-amide)

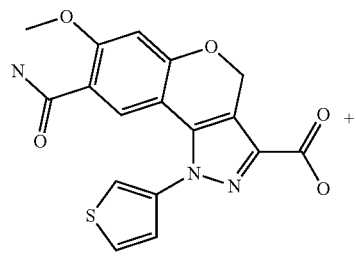

 HATU, DIPEA

352

-continued

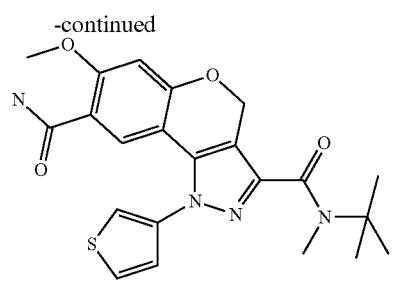

To 8-carbamoyl-7-methoxy-1-thiophen-3-yl-1,4-dihydro-chromeno[4,3-c]pyrazole-3-carboxylic acid (17 mg, 0.05 mmol) in DCM (1.00 ml; 46.80 mmol; 1022.39 eq.) was added DIPEA (0.02 ml; 0.09 mmol; 2.00 eq.), o-(benzotri-azol-1-yl)-n,n,n',n'-tetramethyluronium tetrafluoroborate (29.40 mg; 0.09 mmol; 2.00 eq.), and N-tert-butylmethyl-amine (0.01 ml; 0.09 mmol; 2.00 eq.). Reaction was stirred at RT for 30 min. The mixture was concentrated and purified by reverse phase prepHPLC to afford the desired product (2.5 mg, 11%) as a white solid.

$^1$H NMR (400 MHz, MeOD) δ 7.88 (s, 1H), 7.71 (s, 1H), 7.69-7.56 (m, 1H), 7.26 (d, J=4.9 Hz, 1H), 6.79 (s, 1H), 5.46 (s, 2H), 3.98 (s, 3H), 3.23 (s, 3H), 1.54 (s, 9H). m/z=441 [M+H]$^+$

Example 47

The following compounds were prepared using procedures analogous to those disclosed in Example 1:

| Compound | Boronic acid Starting material | Amine Starting material | LC/MS | NMR |
|---|---|---|---|---|
| (8-(1-cyclopropyl-1H-pyrazol-4-yl)-7-methoxy-1-(thiophen-3-yl)-1,4-dihydrochromeno[4,3-c]pyrazol-3-yl)(3,3-dimethylmorpholino)methanone (215) | | | m/z: 532 [M + H]$^+$ | $^1$H NMR (DMSO-d6): δ 8.03 (dd, 1H), 7.91 (dd, 1H), 7.82 (s, 1H), 7.38 (d, 1H), 7.21 (s, 1H), 6.79 (d, 2H), 5.40 (s, 2H), 3.96 (t, 2H), 3.86 (s, 3H), 3.73 (t, 3H), 3.42 (s, 2H), 1.42 (s, 6H), 1.05-0.93 (m, 4H). |
| 1-(4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazin-1-yl)ethanone (216) | | | m/z: 547 [M + H]$^+$ | $^1$H NMR (DMSO-d6): δ 7.96 (s, 1H), 7.83 (s, 1H), 7.60 (s, 1H), 7.46 (s, 1H), 7.35-7.30 (m, 1H), 6.76 (s, 1H), 6.49 (s, 1H), 5.41 (s, 2H), 4.27 (t, 1H), 4.19 (t, 1H), 3.84 (s, 3H), 3.77 (s, 3H), 3.65-3.57 (m, 3H), 3.44 (t, 1H), 2.00 (d, 3H), 1.49 (d, 6H). |

| Compound | Boronic acid Starting material | Amine Starting material | LC/MS | NMR |
|---|---|---|---|---|
| 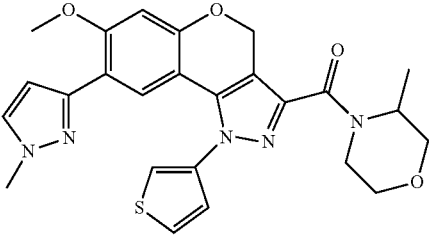 [SMILES: COc1cc2c(cc1-c1ccn(C)n1)-c1c(c(C(=O)N3CCOCC3C)nn1-c1ccsc1)CO2]<br>(7-methoxy-8-(1-methyl-1H-pyrazol-3-yl)-1-(thiophen-3-yl)-1,4-dihydrochromeno[4,3-c]pyrazol-3-yl)(3-methylmorpholino)methanone (218) | 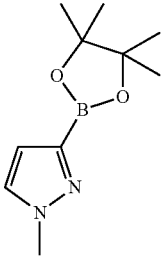 |  | m/z: 492 [M + H]+ HPLC retention time: 4.91 min | |

Example 48

N-(1,3-dihydroxy-2-methylpropan-2-yl)-7-methoxy-N-methyl-8-(1-methyl-1H-pyrazol-3-yl)-1-(thiophen-3-yl)-1,4-dihydrochromeno[4,3-c]pyrazole-3-carboxamide (217)

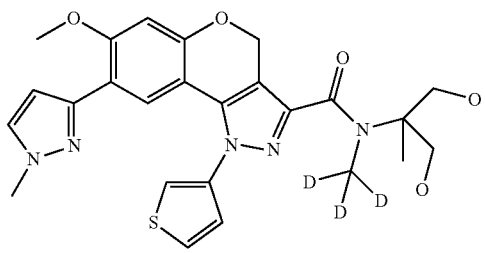 [SMILES: [2H]C([2H])([2H])N(C(=O)c1nn(-c2ccsc2)c2c1COc1cc(OC)c(-c3ccn(C)n3)cc1-2)C(C)(CO)CO]

Compound 116 (MSC2501240) (30.00 mg; 0.06 mmol; 1.00 eq.) was dissolved in hydrochloric acid in water (2.00 ml). The reaction mixture was stirred at room temperature overnight. The mixture was applied to a prep-HPLC (32-38% $CH_3CN$ in 0.1% $NH_4OH$ in $H_2O$) to afford the desired product 7-Methoxy-8-(1-methyl-1H-pyrazol-3-yl)-1-thiophen-3-yl-1,4-dihydro-chromeno[4,3-c]pyrazole-3-carboxylic acid (2-hydroxy-1-hydroxymethyl-1-methyl-ethyl)-methyl-amide (19.00 mg; 0.04 mmol) as a white solid (61%). LCMS: m/z=513 [M+H]+, HPLC retention time: 2.67 min.

Example 49

$EC_{50}$ of Cyclic AMP Production in CHO FSHR Cells+$EC_{20}$ FSH (Assay A)

2500 Cho-FSHR-LUC-1-1-43 cells were plated per well in 5 μl of phenol red free DMEM/F12+1% FBS. Cells were plated in 384 well, solid white low volume plates (Greiner 784075) by Multidrop. Cells were assayed by adding 100 μl of 2× $EC_{20}$ FSH/IBMX in DMEM/F12+0.1% BSA) by Multidrop to 2 μl of test compound stamped in 384 well plates (compounds are diluted 1:50). The final FSH concentration was 0.265 μM, and the final IBMX concentration was 200 μM. The compound plate map was as follows: Column 1: 2 μl of DMSO; Column 2: 2 μl of DMSO; Columns 3-12 and 13-24: 2 μl of test compound, diluted 1:4 in 100% DMSO, or 2 μl of FSH, diluted 1:4 in DMEM/F12+0.1% BSA. The starting concentration for FSH was 50 nM (final concentration was 0.5 nM). Furthermore, Column 23 contained 2 μl of $EC_{100}$ FSH reference (100×) (diluted in DMEM/F12+0.1% BSA) at a final concentration of 0.5 nM, and Column 24 contained 2 μl of 1 mM AS707664/2 reference compound 2. 5 μl of compound+$EC_{20}$ FSH mixture were transferred to cell plates (1:2 dilution into 5 μl of cell media) The plates were incubated at 37° C. for 1 h. 10 μl of mixed HTRF (CisBio #62AM4PEC) reagents were added per well and incubated at room temperature for 1 h. The plates were read on Envision using the cAMP HTRF—low volume 384 well protocol. The readout was the calculated fluorescence ratio (665 nm/620 nm). Values given in percent (%) indicate the percental effect (response) at a certain concentration of agonist relative to the maximum response of the FSH standard. The results are provided below.

Example 50

Rat Granulosa $EC_{50}$ FSH (Assay B)

The assay was performed pursuant to the teaching of Yanofsky et al. (2006) Allosteric activation of the follicle-stimulating hormone (FSH) receptor by selective, nonpeptide agonists (JBC 281(19): 13226-13233, which is incorporated by reference in the disclosure of the invention). The results are provided below.

The data is interpreted according to the following:

| | |
|---|---|
| + | >5 μM; |
| ++ | >1-5 μM; |
| +++ | >0.1-1 μM; |
| ++++ | <0.1 μM. |

| Compound number | Assay A | Assay B |
|---|---|---|
| 1 | ++++ | ++++ |
| 2 | ++++ | 54% @ 30 μM |

| No. | Col A | Col B |
|---|---|---|
| 3 | ++++ | ++ |
| 4 | +++ | 62% @ 6 μM |
| 5 | ++++ | ++ |
| 6 | ++++ | ++ |
| 7 | ++ | 43.5% @ 6 μM |
| 8 | + | |
| 9 | ++ | 40.5% @ 30 μM |
| 10 | +++ | ++ |
| 11 | ++ | |
| 12 | ++++ | ++ |
| 13 | +++ | ++ |
| 14 | ++ | |
| 15 | + | |
| 16 | + | |
| 17 | +++ | + |
| 18 | ++ | 30% @ 30 μM |
| 19 | ++++ | ++ |
| 20 | +++ | +++ |
| 21 | +++ | + |
| 22 | ++ | |
| 23 | ++++ | ++++ |
| 24 | ++++ | ++ |
| 25 | + | |
| 26 | ++ | + |
| 27 | + | |
| 28 | + | + |
| 29 | ++++ | |
| 30 | +++ | |
| 31 | ++++ | |
| 32 | +++ | |
| 33 | +++ | |
| 34 | ++++ | |
| 35 | ++ | |
| 36 | +++ | |
| 37 | ++ | |
| 38 | ++ | |
| 39 | ++++ | |
| 40 | ++++ | |
| 41 | +++ | |
| 42 | +++ | |
| 43 | ++++ | |
| 44 | +++ | |
| 45 | +++ | |
| 46 | ++ | |
| 47 | ++ | |
| 48 | ++++ | |
| 49 | +++ | |
| 50 | ++++ | +++ |
| 51 | ++++ | |
| 52 | ++++ | +++ |
| 53 | ++++ | |
| 54 | +++ | |
| 55 | ++++ | |
| 56 | ++++ | |
| 57 | ++ | |
| 58 | ++++ | |
| 59 | +++ | |
| 60 | +++ | |
| 61 | ++++ | |
| 62 | +++ | |
| 63 | ++++ | +++ |
| 64 | ++++ | |
| 65 | ++++ | |
| 66 | ++++ | |
| 67 | ++++ | |
| 68 | ++++ | |
| 69 | +++ | |
| 70 | ++++ | |
| 71 | ++++ | |
| 72 | ++++ | |
| 73 | ++++ | |
| 74 | ++++ | |
| 75 | ++++ | |
| 76 | ++++ | |
| 77 | ++++ | |
| 78 | ++++ | |
| 79 | ++++ | + |
| 80 | ++++ | |
| 81 | ++++ | |
| 82 | ++++ | ++ |
| 83 | ++++ | +++ |
| 84 | + | |
| 85 | ++++ | |
| 86 | ++++ | |
| 87 | +++ | |
| 88 | ++++ | |
| 89 | ++++ | |
| 90 | ++++ | |
| 91 | ++++ | ++ |
| 92 | ++++ | |
| 93 | ++++ | +++ |
| 94 | ++++ | +++ |
| 95 | ++++ | +++ |
| 96 | ++++ | +++ |
| 97 | +++ | +++ |
| 98 | ++++ | ++ |
| 99 | +++ | +++ |
| 100 | +++ | |
| 101 | ++++ | |
| 102 | +++ | |
| 103 | +++ | |
| 104 | ++ | |
| 105 | ++++ | ++++ |
| 106 | +++ | |
| 107 | + | |
| 108 | ++++ | ++ |
| 109 | +++ | |
| 110 | ++++ | |
| 111 | +++ | |
| 112 | ++ | |
| 113 | ++++ | +++ |
| 114 | ++++ | ++ |
| 115 | ++++ | +++ |
| 116 | ++++ | ++ |
| 117 | +++ | |
| 118 | ++++ | |
| 119 | ++++ | ++ |
| 120 | ++++ | |
| 121 | ++++ | + |
| 122 | ++++ | + |
| 123 | ++++ | |
| 124 | ++++ | |
| 125 | ++++ | ++ |
| 126 | ++++ | +++ |
| 127 | + | |
| 128 | + | |
| 129 | ++++ | |
| 130 | ++++ | |
| 131 | ++++ | ++ |
| 132 | ++++ | +++ |
| 133 | ++ | |
| 134 | +++ | |
| 135 | ++ | |
| 136 | + | |
| 137 | ++ | |
| 138 | + | |
| 139 | ++++ | ++ |
| 140 | ++ | |
| 141 | ++ | |
| 142 | + | |
| 143 | +++ | |
| 144 | ++++ | |
| 145 | +++ | |
| 146 | +++ | +++ |
| 147 | ++++ | +++ |
| 148 | ++++ | +++ |
| 149 | ++++ | +++ |
| 150 | ++++ | +++ |
| 151 | ++++ | +++ |
| 152 | ++++ | |
| 153 | ++++ | ++++ |
| 154 | ++++ | ++ |
| 155 | + | |
| 156 | +++ | |
| 157 | +++ | +++ |
| 158 | ++ | |
| 159 | ++++ | ++++ |
| 160 | ++++ | ++++ |

-continued

| | | |
|---|---|---|
| 161 | ++++ | ++++ |
| 162 | ++++ | +++ |
| 163 | ++++ | +++ |
| 164 | ++ | |
| 165 | + | |
| 166 | ++ | |
| 167 | +++ | +++ |
| 168 | ++++ | +++ |
| 169 | ++++ | +++ |
| 170 | ++++ | ++ |
| 171 | +++ | |
| 172 | + | |
| 173 | + | |
| 174 | +++ | |
| 175 | +++ | + |
| 176 | ++++ | |
| 177 | ++ | |
| 178 | ++ | |
| 179 | +++ | |
| 180 | ++++ | |
| 181 | ++++ | |
| 182 | ++++ | ++++ |
| 183 | +++ | |
| 184 | ++++ | ++++ |
| 185 | +++ | |
| 186 | ++++ | +++ |
| 187 | + | |
| 188 | + | |
| 189 | ++++ | ++++ |
| 190 | ++++ | |
| 191 | ++++ | |
| 192 | ++++ | |
| 193 | + | |
| 194 | ++++ | +++ |
| 195 | ++++ | |
| 196 | + | |
| 197 | ++ | |
| 198 | ++++ | ++++ |
| 199 | ++++ | |
| 200 | ++++ | + |
| 201 | +++ | ++ |
| 202 | +++ | +++ |
| 203 | +++ | |
| 204 | ++++ | |
| 205 | ++++ | ++++ |
| 206 | +++ | |
| 207 | ++++ | |
| 208 | ++++ | ++++ |
| 209 | ++++ | ++++ |
| 210 | ++++ | + |
| 211 | ++++ | ++++ |
| 212 | ++++ | |
| 213 | ++++ | |
| 214 | ++++ | ++ |
| 215 | ++++ | +++ |
| 216 | ++++ | |
| 217 | ++ | |
| 218 | ++++ | +++ |

Example 51

Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by t appended claims rather than by the specific embodiments that have been represented by way of example.

We claim:
1. A compound of formula I-c,

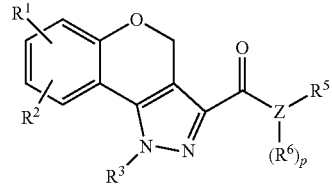

or a pharmaceutically acceptable salt thereof, wherein:
Z is N;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^1$ is —OR, $R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^3$ is a 5-6 membered monocyclic heteroaryl ring having 1-4 heteroatoms independently selected from nitrogen, oxygen, or sulfur; which is optionally substituted;

$R^5$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^6$ is hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

or $R^5$ and $R^6$, together with the atom to which each is attached, form a 3-8 membered heterocyclic ring having 1-4 heteroatoms independently selected from nitrogen, oxygen, or sulfur, or a 3-8 membered heteroaryl ring having 1-4 heteroatoms independently selected from nitrogen, oxygen, or sulfur; each of which is optionally substituted;

and p is 0 or 1.

2. The compound of claim 1, wherein $R^1$ is —OR, and R is $C_{1-6}$ aliphatic.

3. The compound of claim 1, wherein $R^2$ is hydrogen, Br, CN,

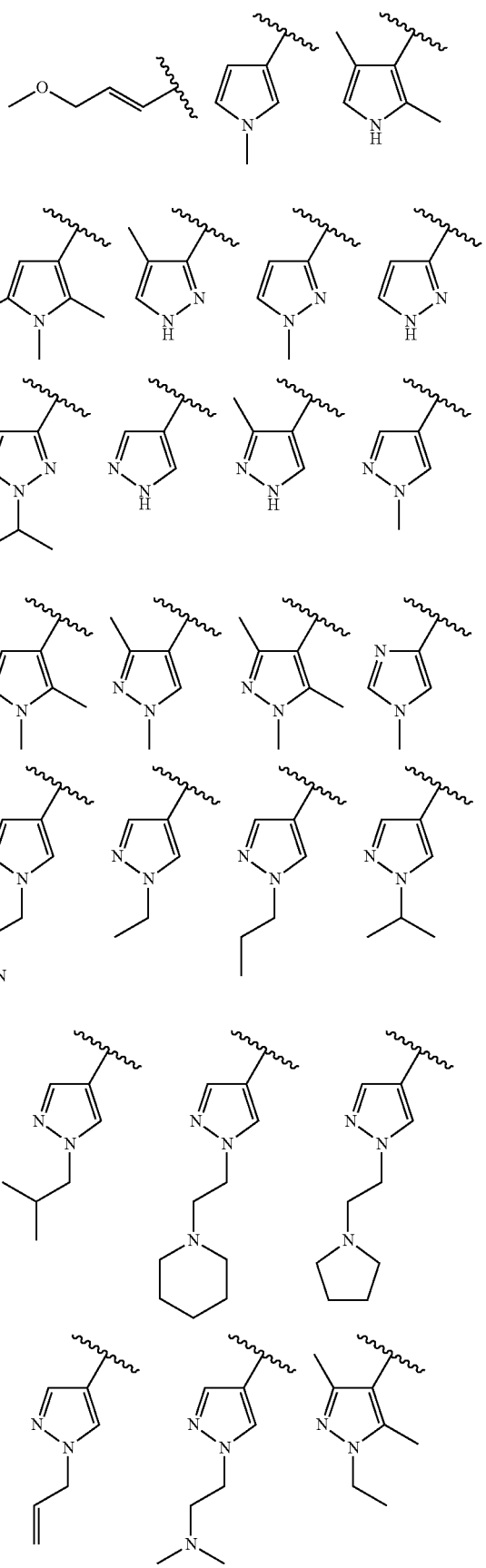

-continued
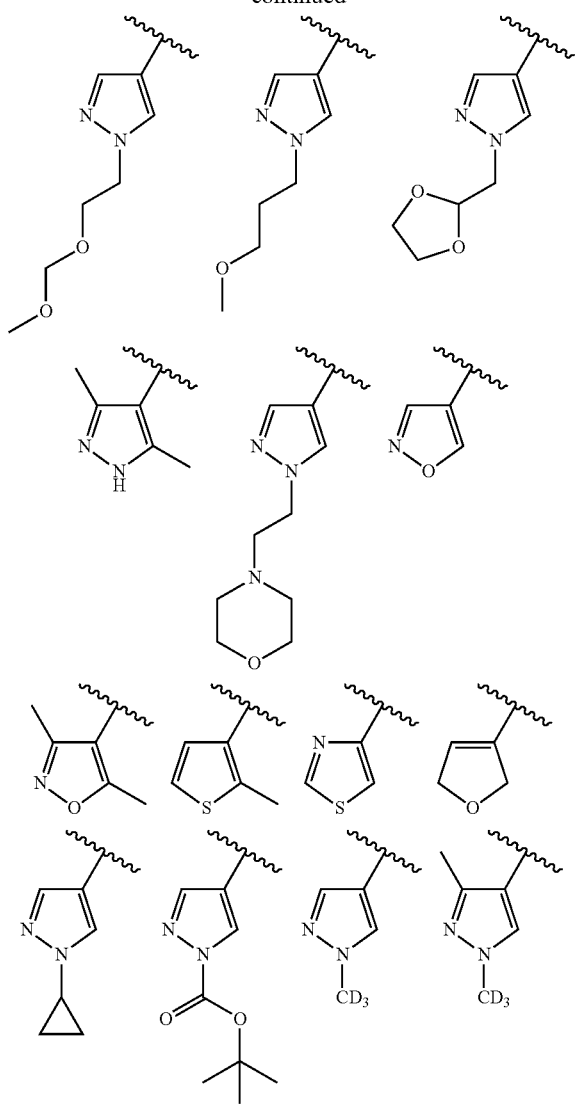
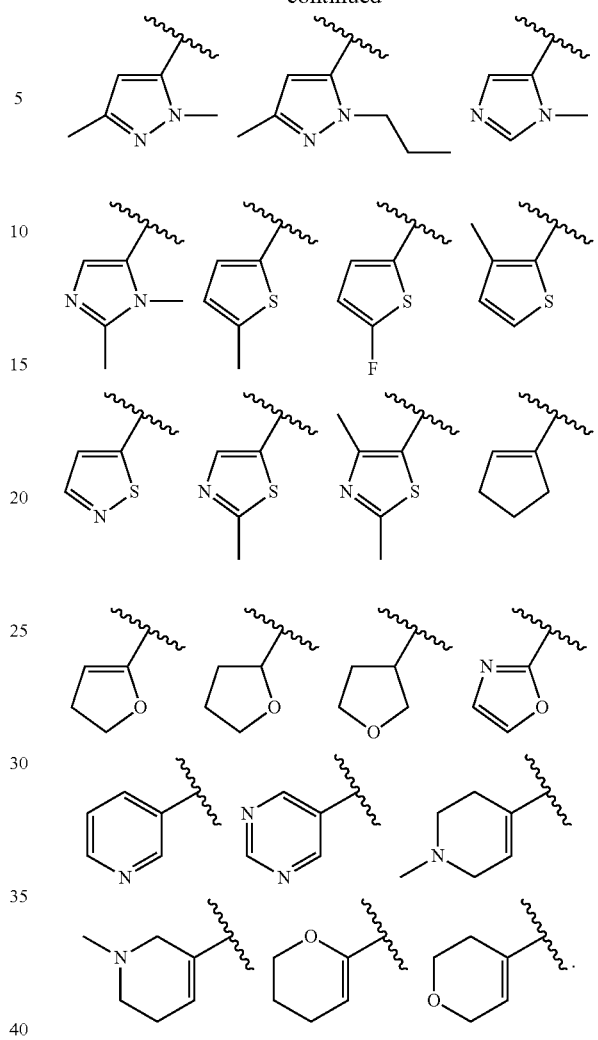
4. The compound of claim 3, wherein $R^2$ is
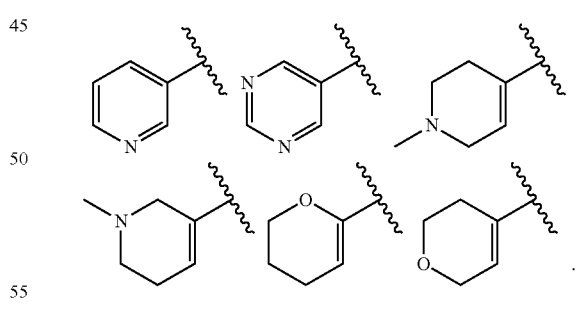
5. The compound of claim 3, wherein $R^2$ is
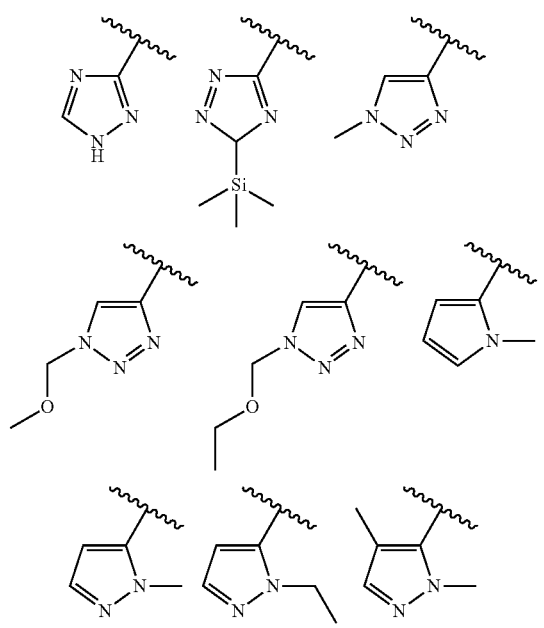

363
-continued
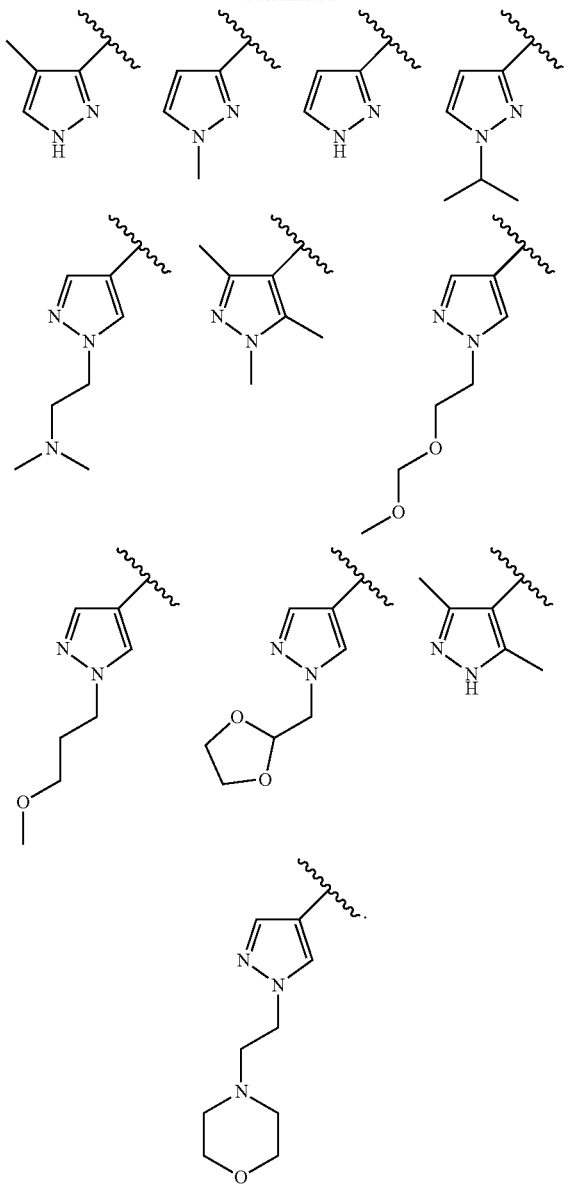
6. The compound of claim 1, wherein $R^3$ is
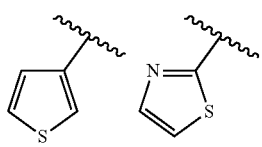
7. The compound of claim 1, wherein $R^5$ is methyl, t-butyl, —CD₃,
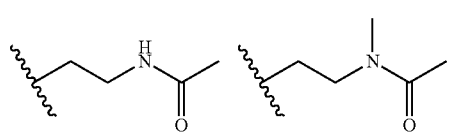
364
-continued
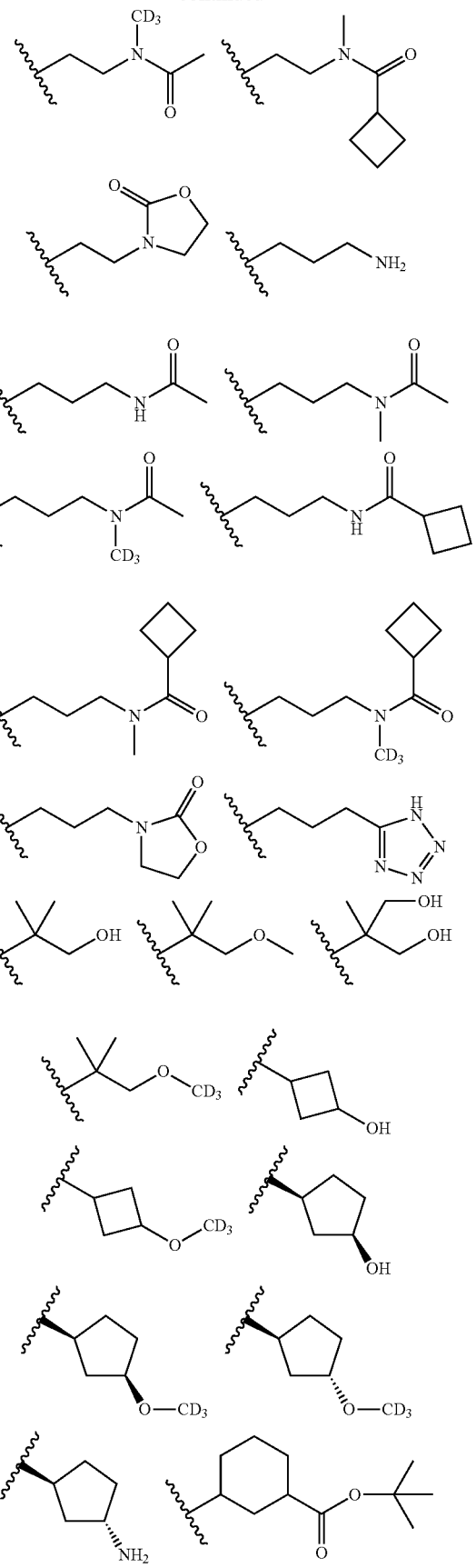

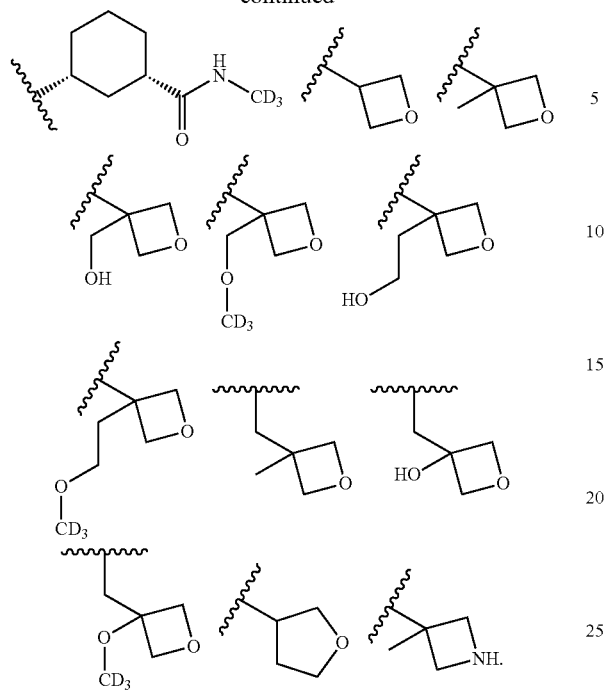
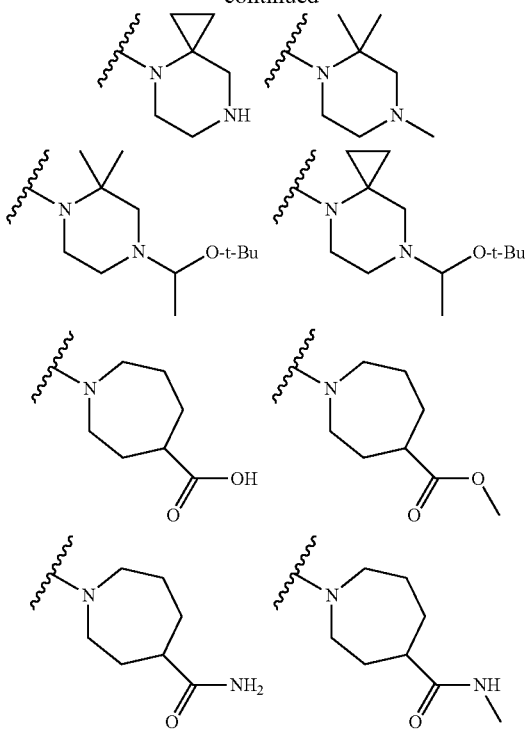
8. The compound of claim 7, wherein $R^5$ is t-butyl, and $R^6$ is an optionally substituted $C_{1-6}$ aliphatic.
9. The compound of claim 1, wherein Z is N and the ring formed by Z, $R^5$ and $R^6$ is
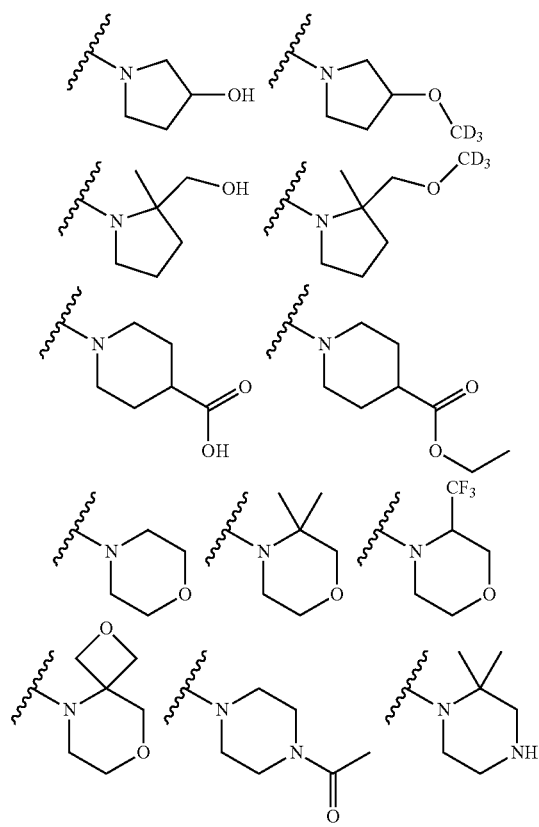
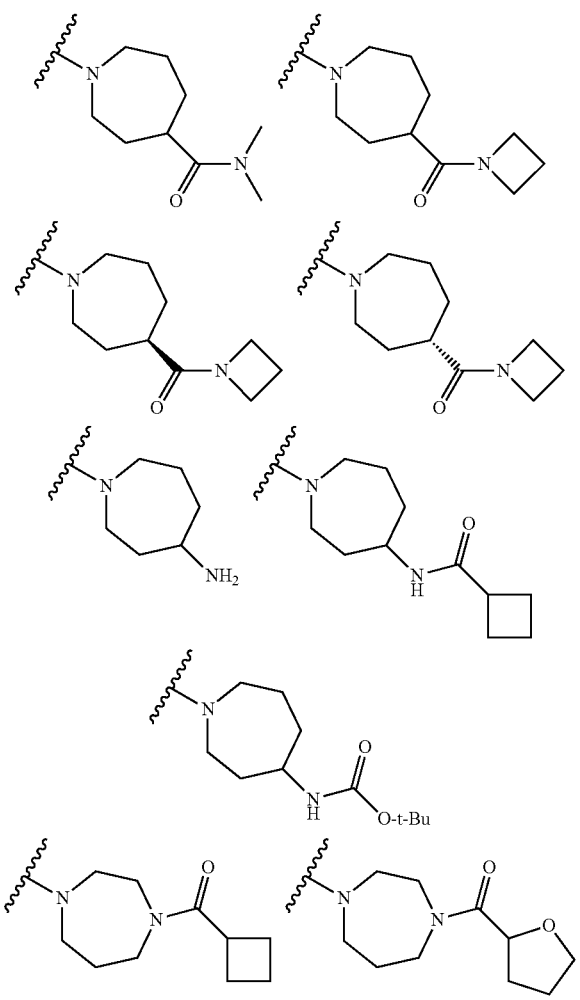

-continued

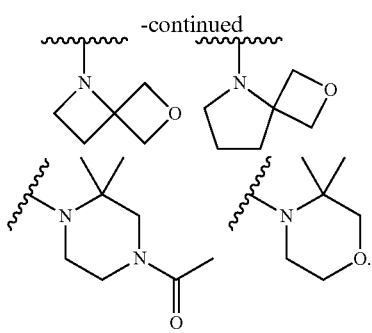

10. The compound of claim 9, wherein Z is N and the ring formed by Z, R⁵ and R⁶ is

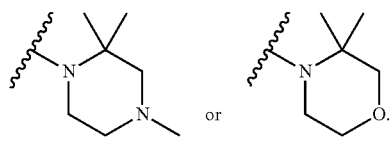

11. The compound of claim 1, wherein $R^6$ is hydrogen, methyl, t-butyl, or —CD₃.

12. The compound of claim 1, of formula I-f:

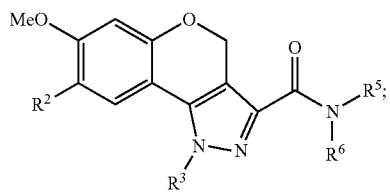

or a pharmaceutically acceptable salt thereof.

13. The compound of claim 12, wherein $R^2$ is 5-6 membered monocyclic heteroaryl ring having 1-4 heteroatoms independently selected from nitrogen, oxygen, or sulfur; which is optionally substituted; and $R^3$ is an optionally substituted 5-6 membered monocyclic heteroaryl ring having 1-4 heteroatoms independently selected from nitrogen, oxygen, or sulfur.

14. The compound of claim 1, of formula I-h:

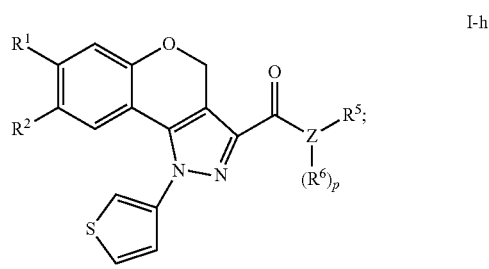

or a pharmaceutically acceptable salt thereof.

15. The compound of claim 14, wherein $R^1$ is —OR and R is $C_{1-6}$ aliphatic; and $R^2$ is 5-6 membered monocyclic heteroaryl ring having 1-4 heteroatoms independently selected from nitrogen, oxygen, or sulfur; which is optionally substituted.

16. The compound of claim 1, selected from Table 1:

TABLE 1

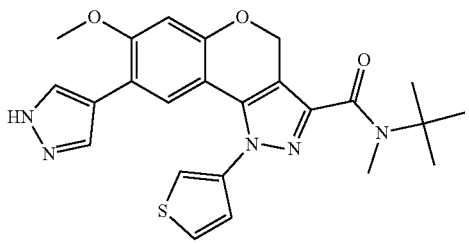 [SMILES: COc1cc2c(cc1-c1cn[nH]c1)-c1c(c(C(=O)N(C)C(C)(C)C)nn1-c1ccsc1)CO2]

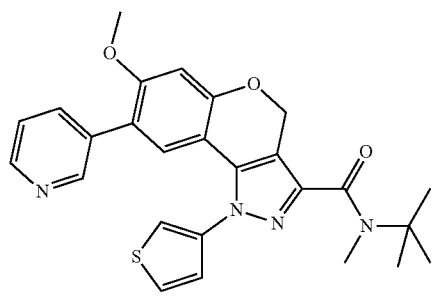 [SMILES: COc1cc2c(cc1-c1cccnc1)-c1c(c(C(=O)N(C)C(C)(C)C)nn1-c1ccsc1)CO2]

TABLE 1-continued
| | |
|---|---|
| 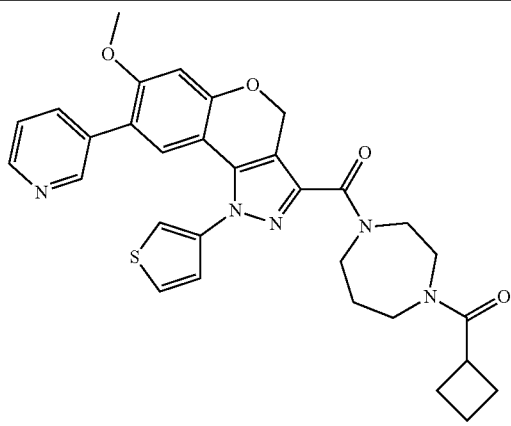 | 3 |
| 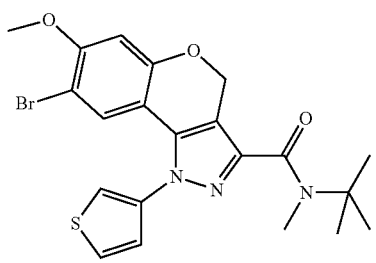 [SMILES: COc1cc2c(cc1Br)-c1c(c(C(=O)N(C)C(C)(C)C)nn1-c1ccsc1)CO2] | 4 |
| 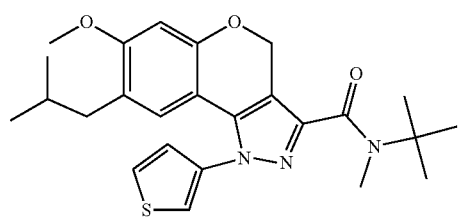 [SMILES: COc1cc2c(cc1CC(C)C)-c1c(c(C(=O)N(C)C(C)(C)C)nn1-c1ccsc1)CO2] | 5 |
| 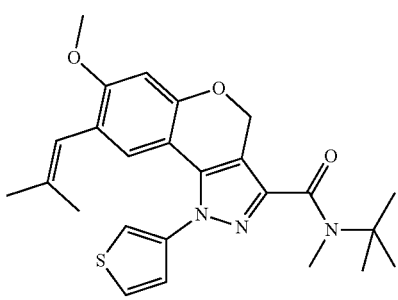 [SMILES: COc1cc2c(cc1C=C(C)C)-c1c(c(C(=O)N(C)C(C)(C)C)nn1-c1ccsc1)CO2] | 6 |
| 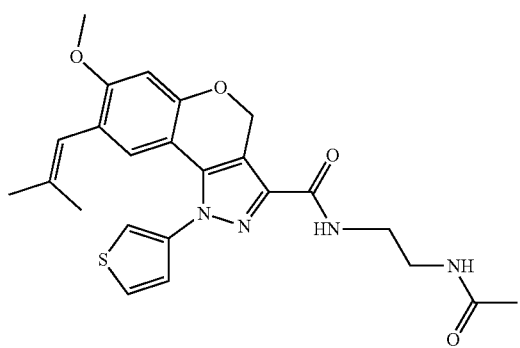 [SMILES: COc1cc2c(cc1C=C(C)C)-c1c(c(C(=O)NCCNC(C)=O)nn1-c1ccsc1)CO2] | 7 |

TABLE 1-continued
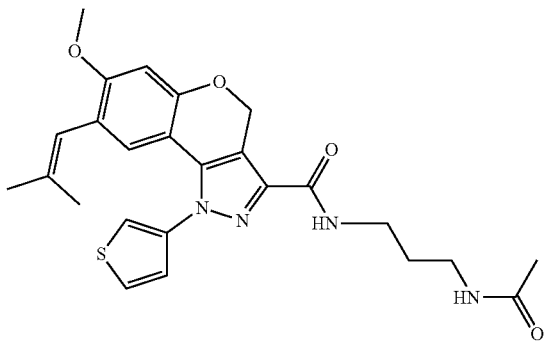 [SMILES: COc1cc2c(cc1C=C(C)C)-c1c(c(C(=O)NCCCNC(C)=O)nn1-c1ccsc1)CO2]
8
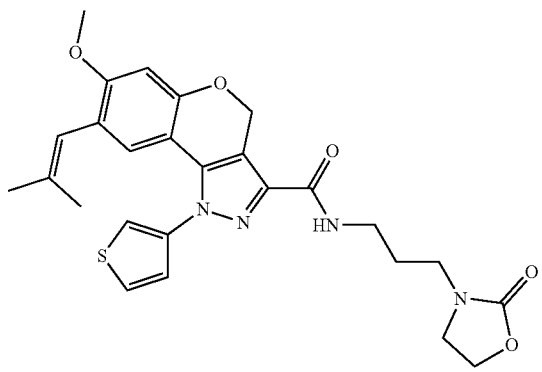 [SMILES: COc1cc2c(cc1C=C(C)C)-c1c(c(C(=O)NCCCN3CCOC3=O)nn1-c1ccsc1)CO2]
9
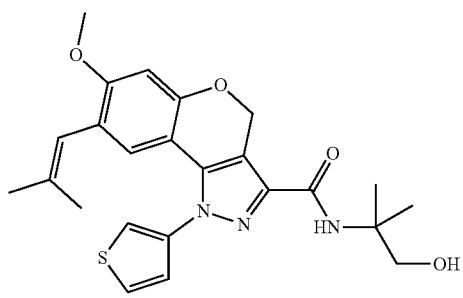 [SMILES: COc1cc2c(cc1C=C(C)C)-c1c(c(C(=O)NC(C)(C)CO)nn1-c1ccsc1)CO2]
10
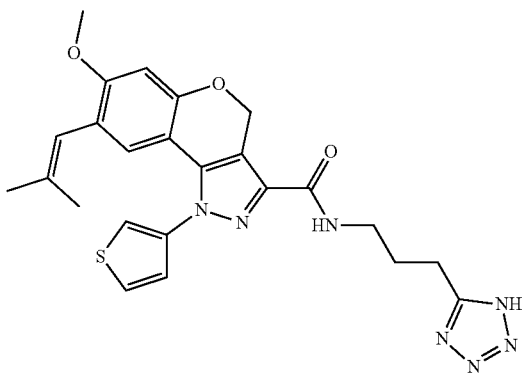 [SMILES: COc1cc2c(cc1C=C(C)C)-c1c(c(C(=O)NCCCc3nnn[nH]3)nn1-c1ccsc1)CO2]
11
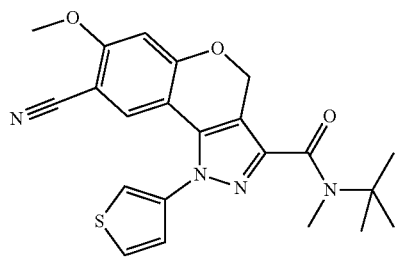 [SMILES: COc1cc2c(cc1C#N)-c1c(c(C(=O)N(C)C(C)(C)C)nn1-c1ccsc1)CO2]
12

TABLE 1-continued
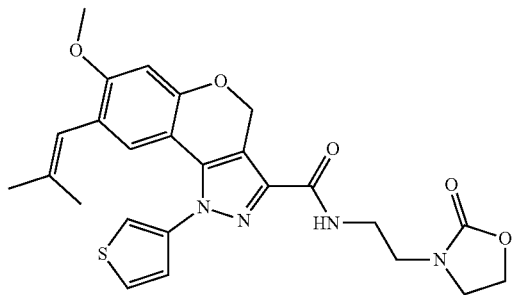 [SMILES: COc1cc2c(cc1C=C(C)C)-c1c(c(C(=O)NCCN3CCOC3=O)nn1-c1ccsc1)CO2]
13
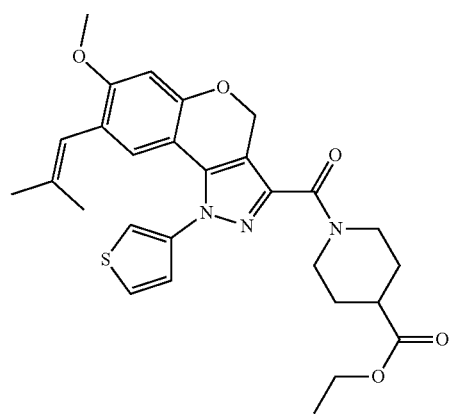 [SMILES: CCOC(=O)C1CCN(C(=O)c2nn(-c3ccsc3)c3c2COc2cc(OC)c(C=C(C)C)cc2-3)CC1]
14
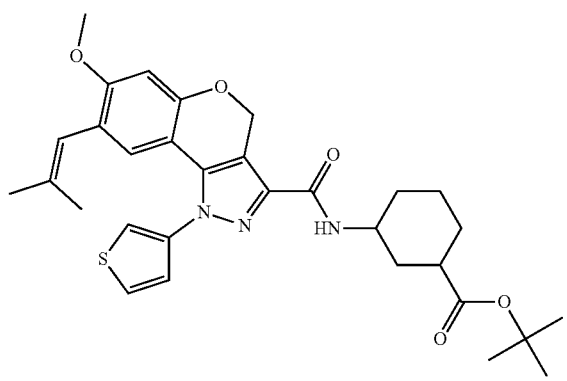 [SMILES: COc1cc2c(cc1C=C(C)C)-c1c(c(C(=O)NC3CCCC(C(=O)OC(C)(C)C)C3)nn1-c1ccsc1)CO2]
15
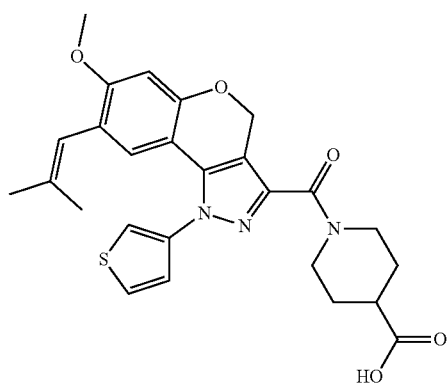 [SMILES: COc1cc2c(cc1C=C(C)C)-c1c(c(C(=O)N3CCC(C(=O)O)CC3)nn1-c1ccsc1)CO2]
16

TABLE 1-continued
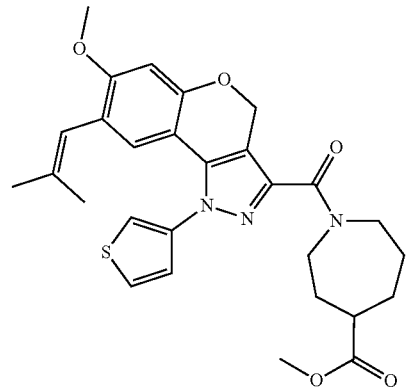 [SMILES: COC(=O)C1CCCN(C(=O)c2nn(-c3ccsc3)c3c2COc2cc(OC)c(C=C(C)C)cc2-3)CC1]
17
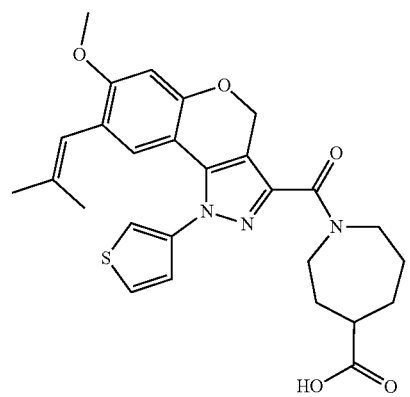 [SMILES: COc1cc2c(cc1C=C(C)C)-c1c(c(C(=O)N3CCCC(C(=O)O)CC3)nn1-c1ccsc1)CO2]
18
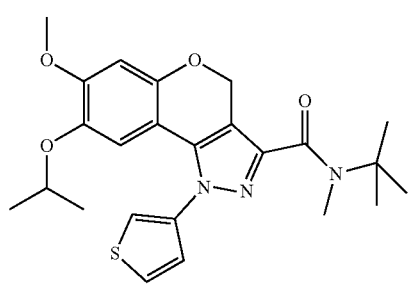 [SMILES: COc1cc2c(cc1OC(C)C)-c1c(c(C(=O)N(C)C(C)(C)C)nn1-c1ccsc1)CO2]
19
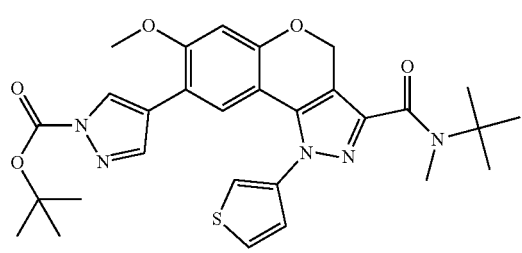 [SMILES: COc1cc2c(cc1-c1cnn(C(=O)OC(C)(C)C)c1)-c1c(c(C(=O)N(C)C(C)(C)C)nn1-c1ccsc1)CO2]
20

TABLE 1-continued
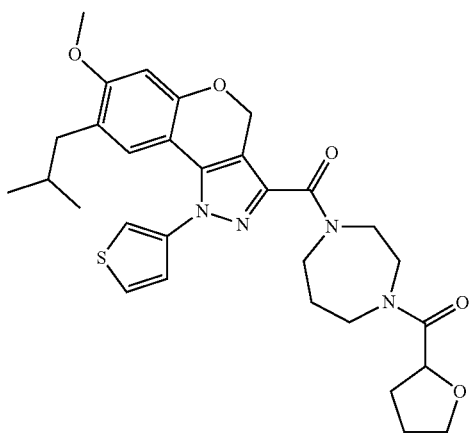 [SMILES: COc1cc2c(cc1CC(C)C)-c1c(c(C(=O)N3CCCN(C(=O)C4CCCO4)CC3)nn1-c1ccsc1)CO2]
21
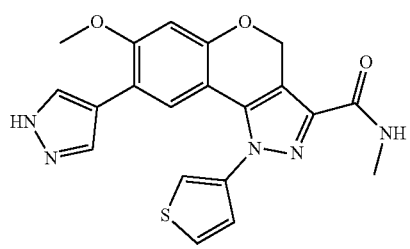 [SMILES: CNC(=O)c1nn(-c2ccsc2)c2c1COc1cc(OC)c(-c3cn[nH]c3)cc1-2]
22
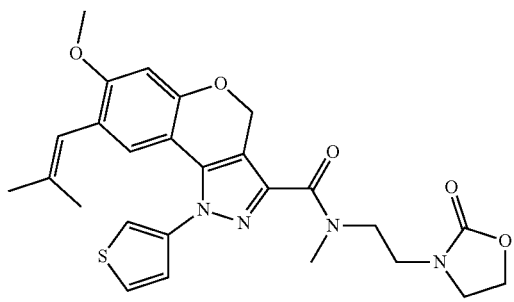 [SMILES: COc1cc2c(cc1C=C(C)C)-c1c(c(C(=O)N(C)CCN3CCOC3=O)nn1-c1ccsc1)CO2]
23
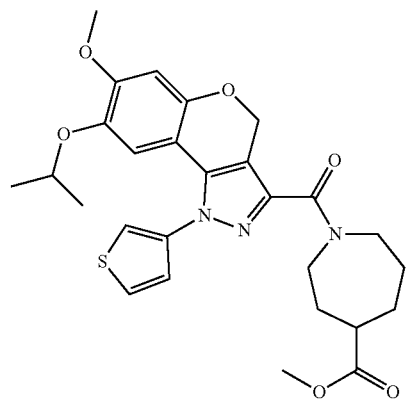 [SMILES: COC(=O)C1CCCN(C(=O)c2nn(-c3ccsc3)c3c2COc2cc(OC)c(OC(C)C)cc2-3)CC1]
24

TABLE 1-continued
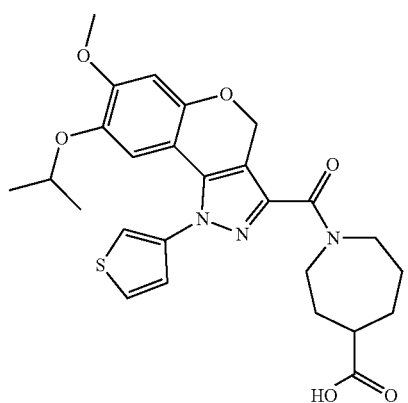 [SMILES: COc1cc2c(cc1OC(C)C)-c1c(c(C(=O)N3CCCC(C(=O)O)CC3)nn1-c1ccsc1)CO2]
25
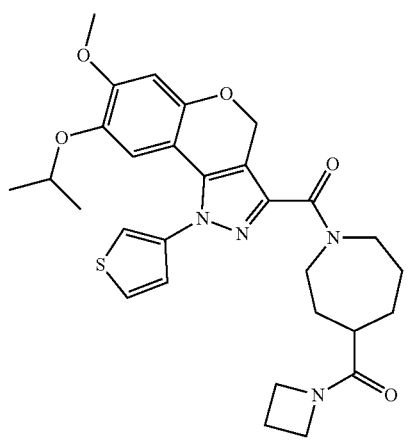 [SMILES: COc1cc2c(cc1OC(C)C)-c1c(c(C(=O)N3CCCC(C(=O)N4CCC4)CC3)nn1-c1ccsc1)CO2]
26
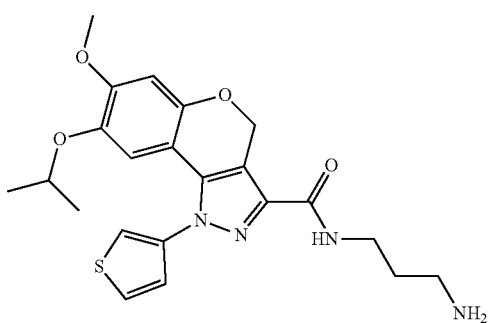 [SMILES: COc1cc2c(cc1OC(C)C)-c1c(c(C(=O)NCCCN)nn1-c1ccsc1)CO2]
27
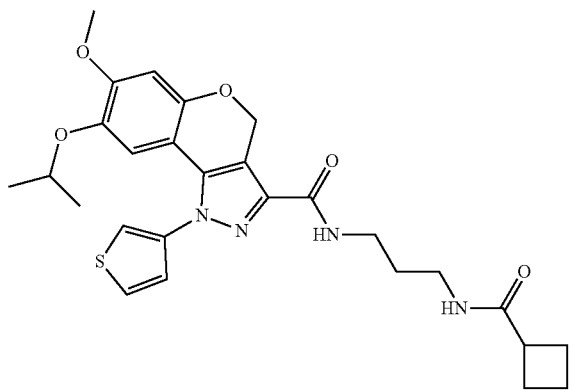 [SMILES: COc1cc2c(cc1OC(C)C)-c1c(c(C(=O)NCCCNC(=O)C3CCC3)nn1-c1ccsc1)CO2]
28

TABLE 1-continued
| | |
|---|---|
| 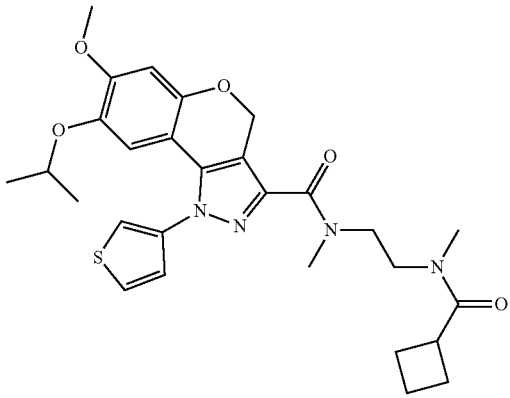 [SMILES: COc1cc2c(cc1OC(C)C)-c1c(c(C(=O)N(C)CCN(C)C(=O)C3CCC3)nn1-c1ccsc1)CO2] | 29 |
| 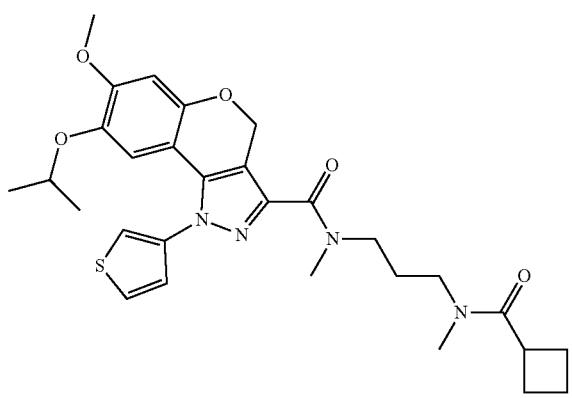 [SMILES: COc1cc2c(cc1OC(C)C)-c1c(c(C(=O)N(C)CCCN(C)C(=O)C3CCC3)nn1-c1ccsc1)CO2] | 30 |
| 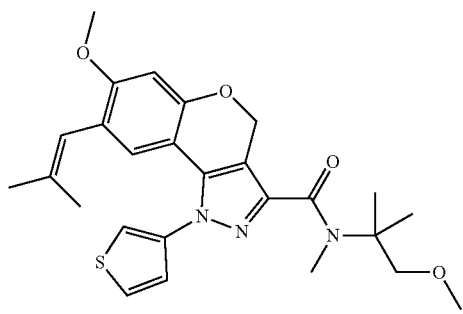 [SMILES: COCC(C)(C)N(C)C(=O)c1nn(-c2ccsc2)c2c1COc1cc(OC)c(C=C(C)C)cc1-2] | 31 |
| 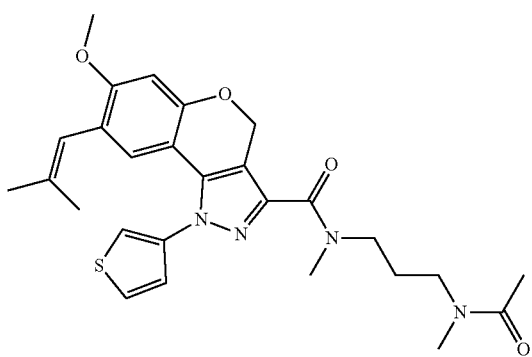 [SMILES: COc1cc2c(cc1C=C(C)C)-c1c(c(C(=O)N(C)CCCN(C)C(C)=O)nn1-c1ccsc1)CO2] | 32 |

TABLE 1-continued
| | |
|---|---|
| 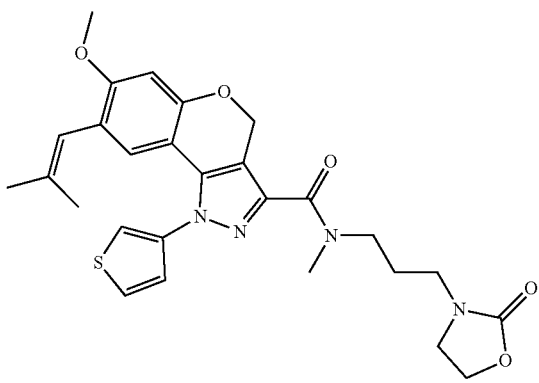 [SMILES: COc1cc2c(cc1C=C(C)C)-c1c(c(C(=O)N(C)CCCN3CCOC3=O)nn1-c1ccsc1)CO2] | 33 |
| 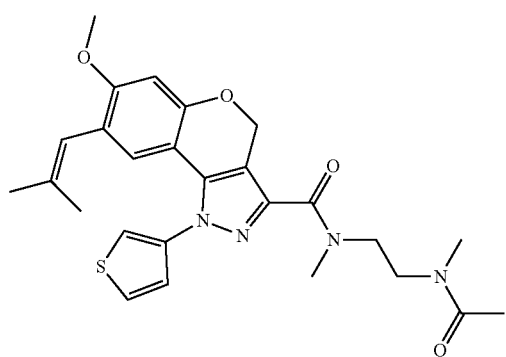 [SMILES: COc1cc2c(cc1C=C(C)C)-c1c(c(C(=O)N(C)CCN(C)C(C)=O)nn1-c1ccsc1)CO2] | 34 |
| 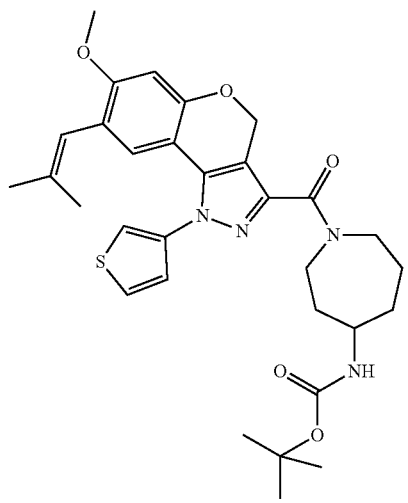 [SMILES: COc1cc2c(cc1C=C(C)C)-c1c(c(C(=O)N3CCCC(NC(=O)OC(C)(C)C)CC3)nn1-c1ccsc1)CO2] | 35 |
| 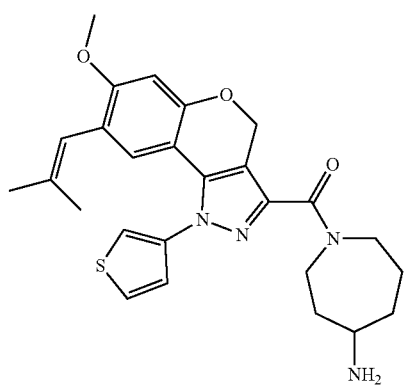 [SMILES: COc1cc2c(cc1C=C(C)C)-c1c(c(C(=O)N3CCCC(N)CC3)nn1-c1ccsc1)CO2] | 36 |

TABLE 1-continued
| | |
|---|---|
| 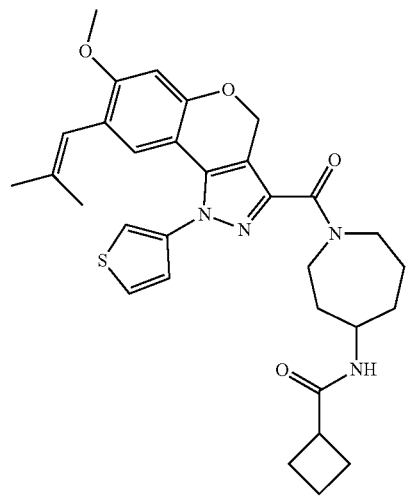 [SMILES: COc1cc2c(cc1C=C(C)C)-c1c(c(C(=O)N3CCCC(NC(=O)C4CCC4)CC3)nn1-c1ccsc1)CO2] | 37 |
| 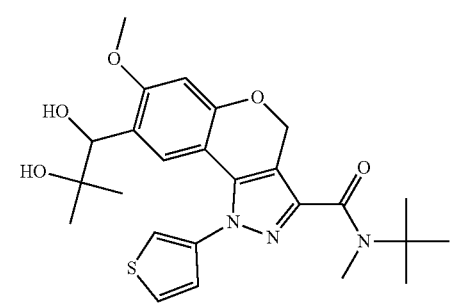 [SMILES: COc1cc2c(cc1C(O)C(C)(C)O)-c1c(c(C(=O)N(C)C(C)(C)C)nn1-c1ccsc1)CO2] | 38 |
| 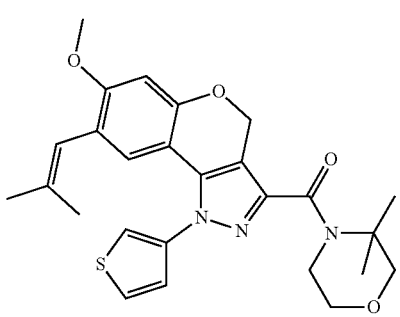 | 39 |
| 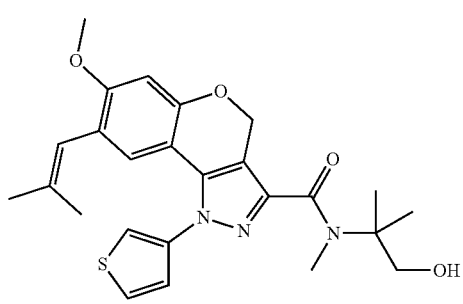 [SMILES: COc1cc2c(cc1C=C(C)C)-c1c(c(C(=O)N(C)C(C)(C)CO)nn1-c1ccsc1)CO2] | 40 |

TABLE 1-continued
| | |
|---|---|
| 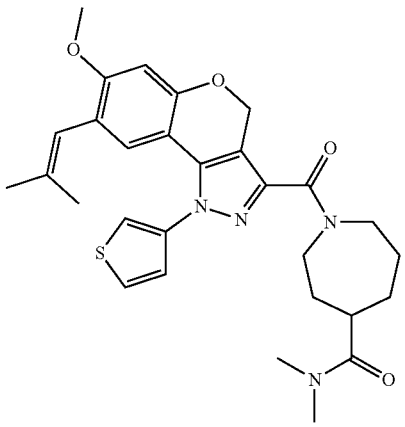 [SMILES: COc1cc2c(cc1C=C(C)C)-c1c(c(C(=O)N3CCCC(C(=O)N(C)C)CC3)nn1-c1ccsc1)CO2] | 41 |
| 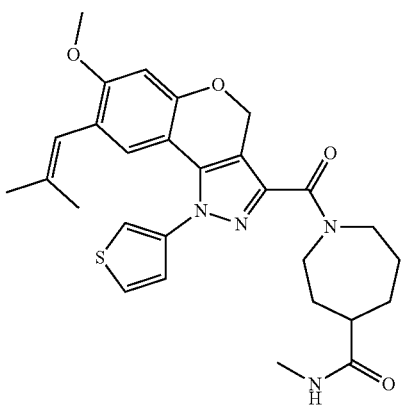 [SMILES: CNC(=O)C1CCCN(C(=O)c2nn(-c3ccsc3)c3c2COc2cc(OC)c(C=C(C)C)cc2-3)CC1] | 42 |
| 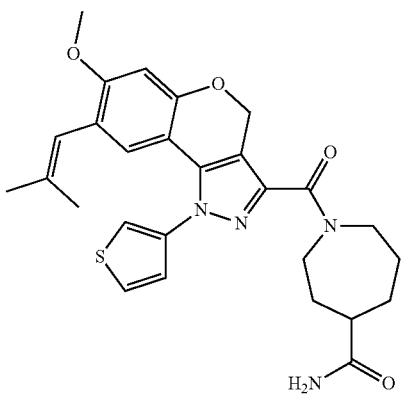 [SMILES: COc1cc2c(cc1C=C(C)C)-c1c(c(C(=O)N3CCCC(C(N)=O)CC3)nn1-c1ccsc1)CO2] | 43 |
| 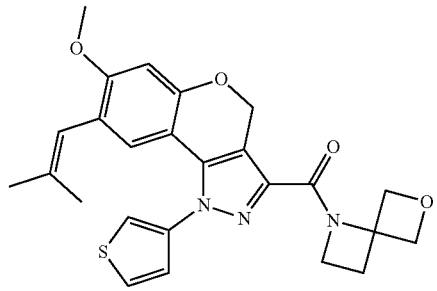 [SMILES: COc1cc2c(cc1C=C(C)C)-c1c(c(C(=O)N3CCC34COC4)nn1-c1ccsc1)CO2] | 44 |

TABLE 1-continued
| | |
|---|---|
| 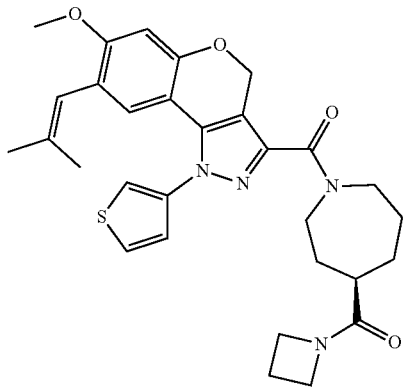 [SMILES: COc1cc2c(cc1C=C(C)C)-c1c(c(C(=O)N3CCC[C@@H](C(=O)N4CCC4)CC3)nn1-c1ccsc1)CO2] | 45 |
| 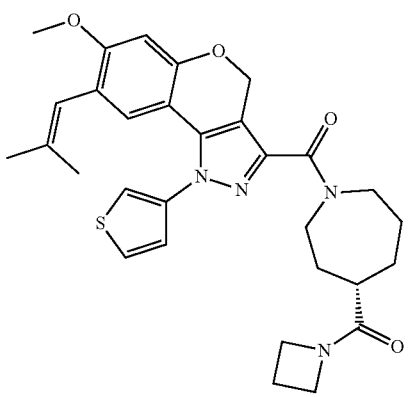 [SMILES: COc1cc2c(cc1C=C(C)C)-c1c(c(C(=O)N3CCC[C@H](C(=O)N4CCC4)CC3)nn1-c1ccsc1)CO2] | 46 |
| 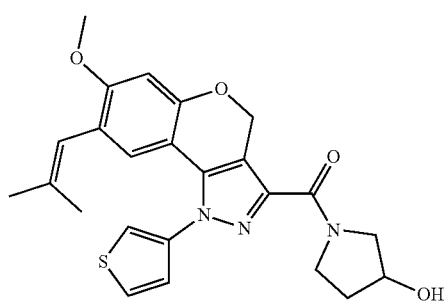 [SMILES: COc1cc2c(cc1C=C(C)C)-c1c(c(C(=O)N3CCC(O)C3)nn1-c1ccsc1)CO2] | 47 |
| 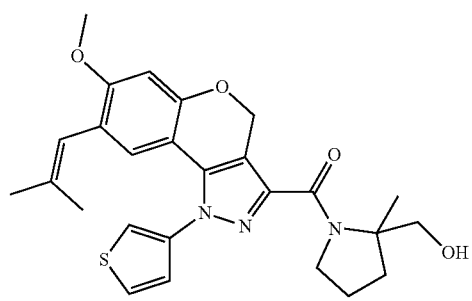 [SMILES: COc1cc2c(cc1C=C(C)C)-c1c(c(C(=O)N3CCCC3(C)CO)nn1-c1ccsc1)CO2] | 48 |

TABLE 1-continued
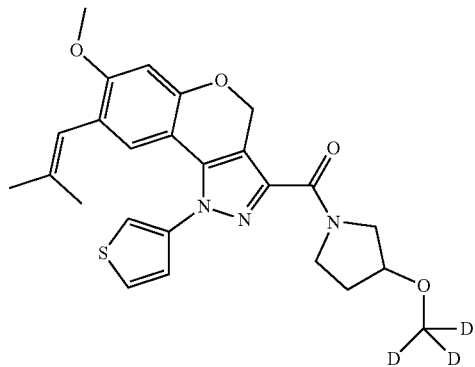 [SMILES: [2H]C([2H])([2H])OC1CCN(C(=O)c2nn(-c3ccsc3)c3c2COc2cc(OC)c(C=C(C)C)cc2-3)C1]
49
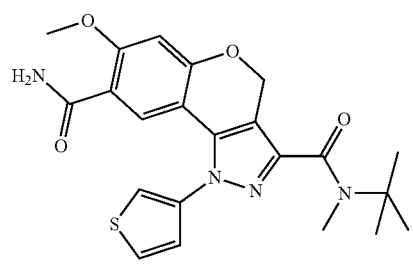 [SMILES: COc1cc2c(cc1C(N)=O)-c1c(c(C(=O)N(C)C(C)(C)C)nn1-c1ccsc1)CO2]
50
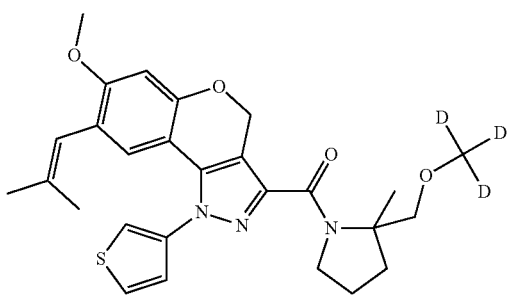 [SMILES: [2H]C([2H])([2H])OCC1(C)CCCN1C(=O)c1nn(-c2ccsc2)c2c1COc1cc(OC)c(C=C(C)C)cc1-2]
51
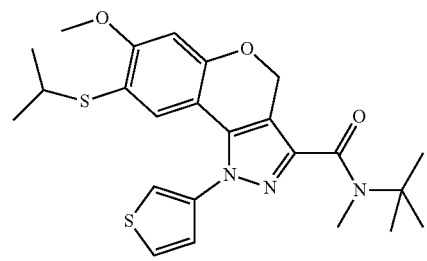 [SMILES: COc1cc2c(cc1SC(C)C)-c1c(c(C(=O)N(C)C(C)(C)C)nn1-c1ccsc1)CO2]
52
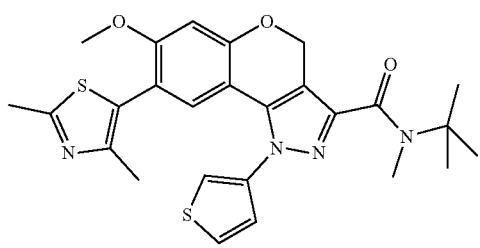 [SMILES: COc1cc2c(cc1-c1sc(C)nc1C)-c1c(c(C(=O)N(C)C(C)(C)C)nn1-c1ccsc1)CO2]
53

TABLE 1-continued
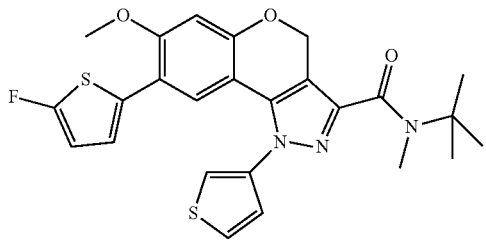 [SMILES: COc1cc2c(cc1-c1ccc(F)s1)-c1c(c(C(=O)N(C)C(C)(C)C)nn1-c1ccsc1)CO2] 54
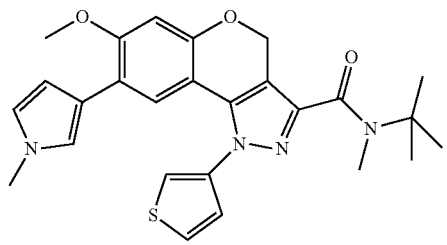 [SMILES: COc1cc2c(cc1-c1ccn(C)c1)-c1c(c(C(=O)N(C)C(C)(C)C)nn1-c1ccsc1)CO2] 55
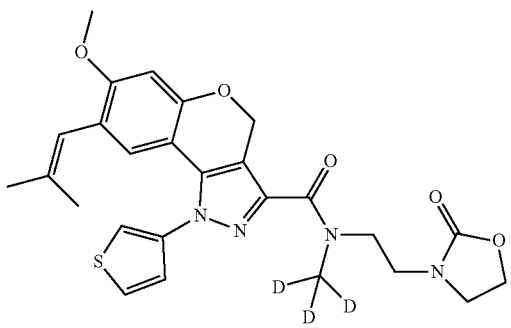 [SMILES: [2H]C([2H])([2H])N(CCN1CCOC1=O)C(=O)c1nn(-c2ccsc2)c2c1COc1cc(OC)c(C=C(C)C)cc1-2] 56
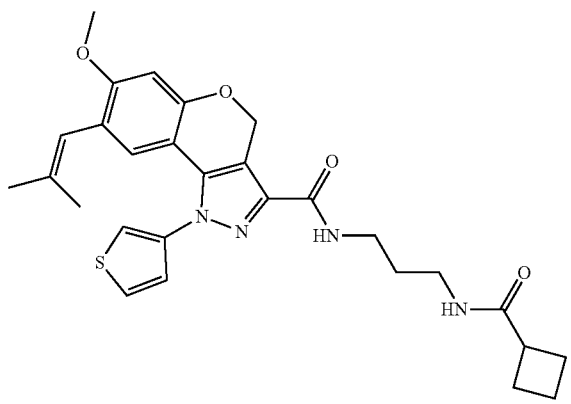 [SMILES: COc1cc2c(cc1C=C(C)C)-c1c(c(C(=O)NCCCNC(=O)C3CCC3)nn1-c1ccsc1)CO2] 57
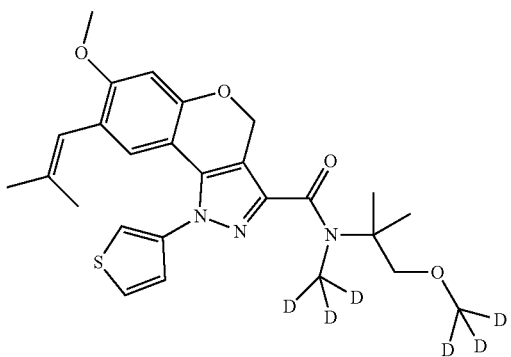 [SMILES: [2H]C([2H])([2H])OCC(C)(C)N(C(=O)c1nn(-c2ccsc2)c2c1COc1cc(OC)c(C=C(C)C)cc1-2)C([2H])([2H])[2H]] 58

TABLE 1-continued
59
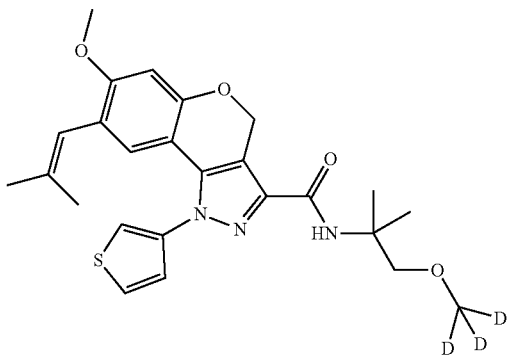 [SMILES: [2H]C([2H])([2H])OCC(C)(C)NC(=O)c1nn(-c2ccsc2)c2c1COc1cc(OC)c(C=C(C)C)cc1-2]
60
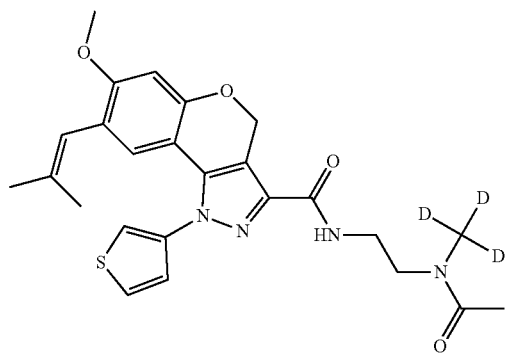 [SMILES: [2H]C([2H])([2H])N(CCNC(=O)c1nn(-c2ccsc2)c2c1COc1cc(OC)c(C=C(C)C)cc1-2)C(C)=O]
61
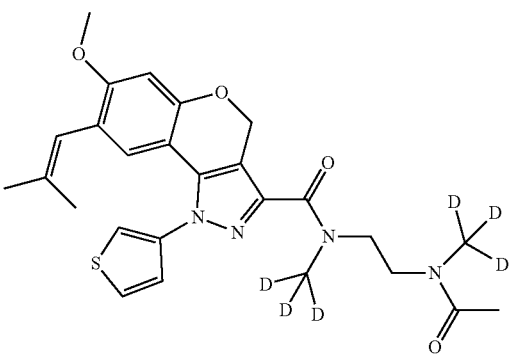 [SMILES: [2H]C([2H])([2H])N(CCN(C(=O)c1nn(-c2ccsc2)c2c1COc1cc(OC)c(C=C(C)C)cc1-2)C([2H])([2H])[2H])C(C)=O]
62
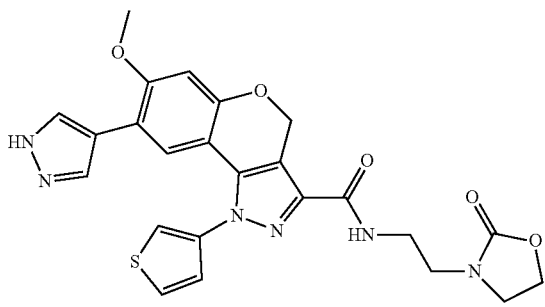 [SMILES: COc1cc2c(cc1-c1cn[nH]c1)-c1c(c(C(=O)NCCN3CCOC3=O)nn1-c1ccsc1)CO2]
63
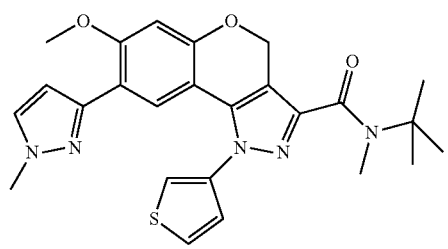 [SMILES: COc1cc2c(cc1-c1ccn(C)n1)-c1c(c(C(=O)N(C)C(C)(C)C)nn1-c1ccsc1)CO2]

TABLE 1-continued
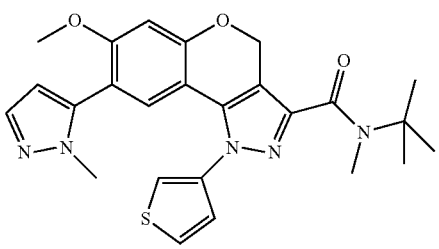 [SMILES: COc1cc2c(cc1-c1ccnn1C)-c1c(c(C(=O)N(C)C(C)(C)C)nn1-c1ccsc1)CO2]
64
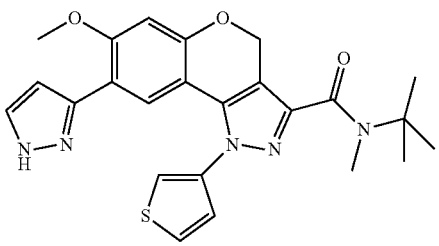 [SMILES: COc1cc2c(cc1-c1cc[nH]n1)-c1c(c(C(=O)N(C)C(C)(C)C)nn1-c1ccsc1)CO2]
65
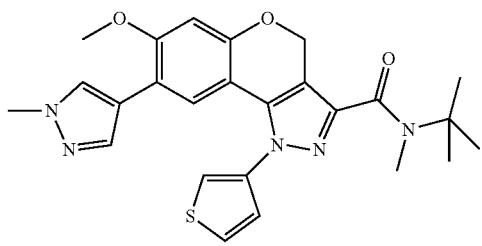 [SMILES: COc1cc2c(cc1-c1cnn(C)c1)-c1c(c(C(=O)N(C)C(C)(C)C)nn1-c1ccsc1)CO2]
66
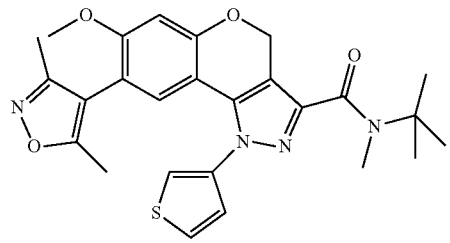 [SMILES: COc1cc2c(cc1-c1c(C)noc1C)-c1c(c(C(=O)N(C)C(C)(C)C)nn1-c1ccsc1)CO2]
67
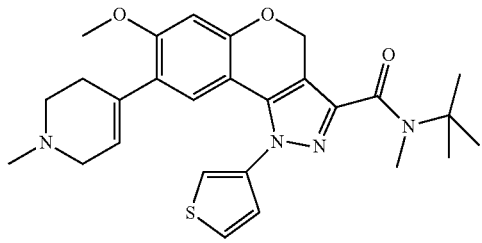 [SMILES: COc1cc2c(cc1C1=CCN(C)CC1)-c1c(c(C(=O)N(C)C(C)(C)C)nn1-c1ccsc1)CO2]
68
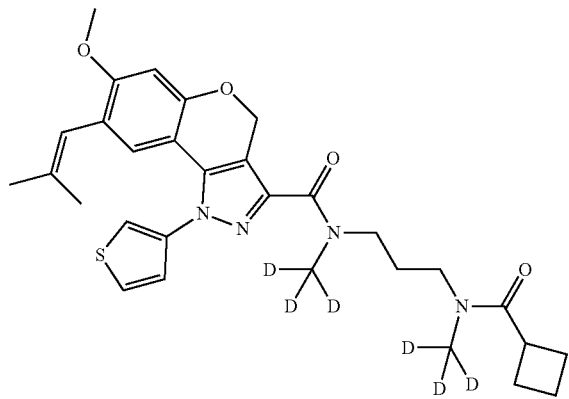 [SMILES: [2H]C([2H])([2H])N(CCCN(C(=O)C1CCC1)C([2H])([2H])[2H])C(=O)c1nn(-c2ccsc2)c2c1COc1cc(OC)c(C=C(C)C)cc1-2]
69

TABLE 1-continued
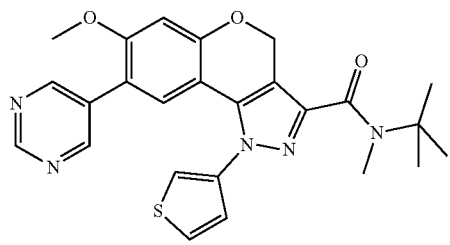 [SMILES: COc1cc2c(cc1-c1cncnc1)-c1c(c(C(=O)N(C)C(C)(C)C)nn1-c1ccsc1)CO2] 70
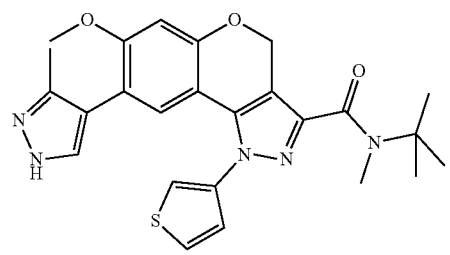 [SMILES: COc1cc2c(cc1-c1c[nH]nc1C)-c1c(c(C(=O)N(C)C(C)(C)C)nn1-c1ccsc1)CO2] 71
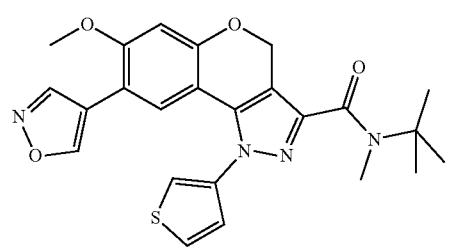 [SMILES: COc1cc2c(cc1-c1cnoc1)-c1c(c(C(=O)N(C)C(C)(C)C)nn1-c1ccsc1)CO2] 72
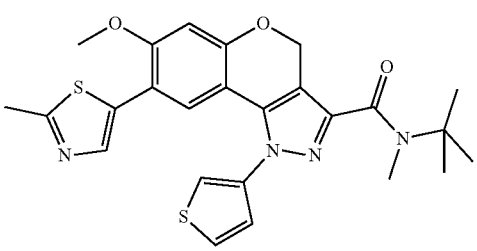 [SMILES: COc1cc2c(cc1-c1cnc(C)s1)-c1c(c(C(=O)N(C)C(C)(C)C)nn1-c1ccsc1)CO2] 73
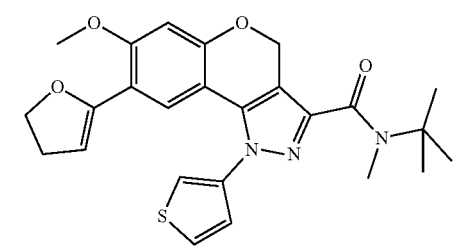 [SMILES: COc1cc2c(cc1C1=CCCO1)-c1c(c(C(=O)N(C)C(C)(C)C)nn1-c1ccsc1)CO2] 74
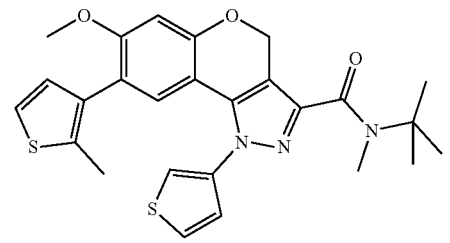 [SMILES: COc1cc2c(cc1-c1ccsc1C)-c1c(c(C(=O)N(C)C(C)(C)C)nn1-c1ccsc1)CO2] 75

TABLE 1-continued
| | |
|---|---|
| 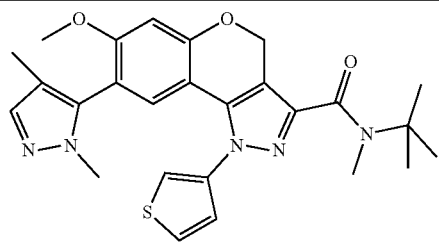 | 76 |
| 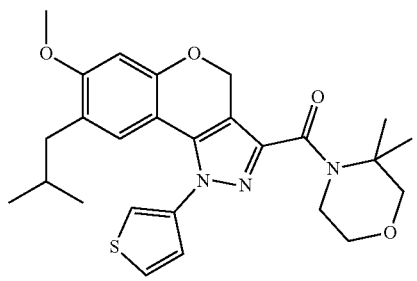 [SMILES: COc1cc2c(cc1CC(C)C)-c1c(c(C(=O)N3CCOCC3(C)C)nn1-c1ccsc1)CO2] | 77 |
| 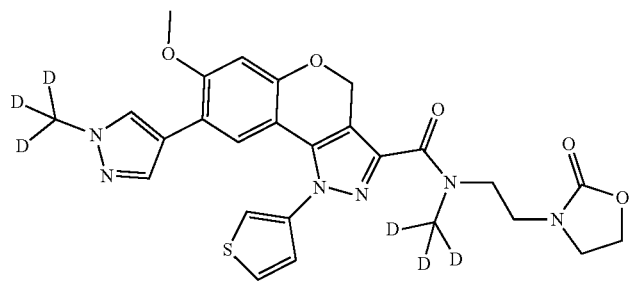 [SMILES: [2H]C([2H])([2H])N(CCN1CCOC1=O)C(=O)c1nn(-c2ccsc2)c2c1COc1cc(OC)c(-c3cnn(C([2H])([2H])[2H])c3)cc1-2] | 78 |
| 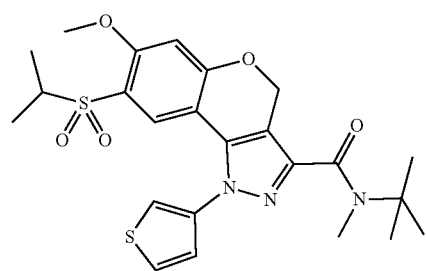 [SMILES: COc1cc2c(cc1S(=O)(=O)C(C)C)-c1c(c(C(=O)N(C)C(C)(C)C)nn1-c1ccsc1)CO2] | 79 |
| 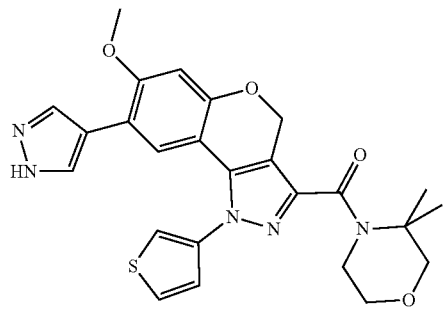 [SMILES: COc1cc2c(cc1-c1cn[nH]c1)-c1c(c(C(=O)N3CCOCC3(C)C)nn1-c1ccsc1)CO2] | 80 |
| 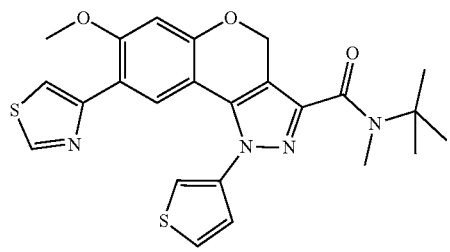 [SMILES: COc1cc2c(cc1-c1cscn1)-c1c(c(C(=O)N(C)C(C)(C)C)nn1-c1ccsc1)CO2] | 81 |

TABLE 1-continued
| | |
|---|---|
| 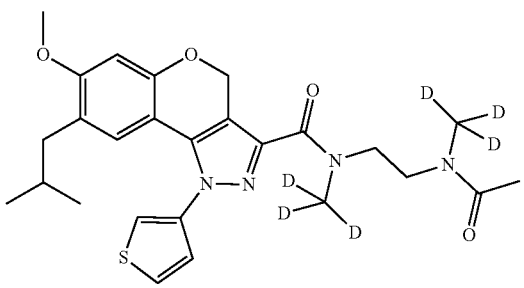 [SMILES: [2H]C([2H])([2H])N(CCN(C(=O)c1nn(-c2ccsc2)c2c1COc1cc(OC)c(CC(C)C)cc1-2)C([2H])([2H])[2H])C(C)=O] | 82 |
| 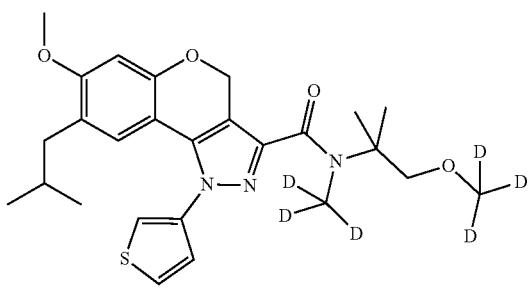 [SMILES: [2H]C([2H])([2H])OCC(C)(C)N(C(=O)c1nn(-c2ccsc2)c2c1COc1cc(OC)c(CC(C)C)cc1-2)C([2H])([2H])[2H]] | 83 |
| 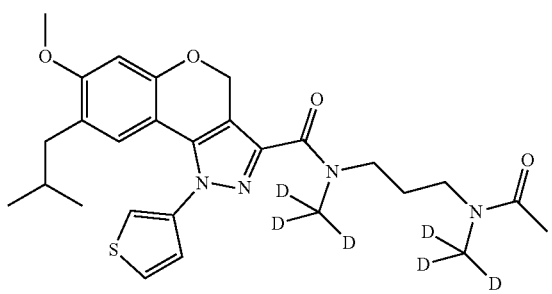 [SMILES: [2H]C([2H])([2H])N(CCCN(C(=O)c1nn(-c2ccsc2)c2c1COc1cc(OC)c(CC(C)C)cc1-2)C([2H])([2H])[2H])C(C)=O] | 84 |
| 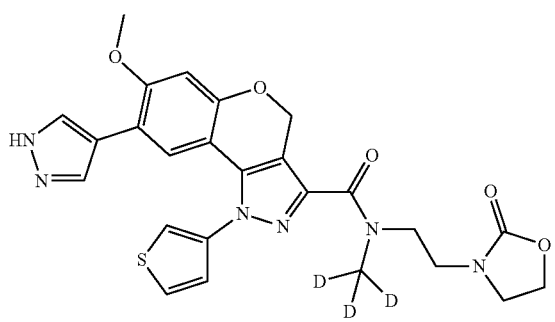 [SMILES: [2H]C([2H])([2H])N(CCN1CCOC1=O)C(=O)c1nn(-c2ccsc2)c2c1COc1cc(OC)c(-c3cn[nH]c3)cc1-2] | 85 |
| 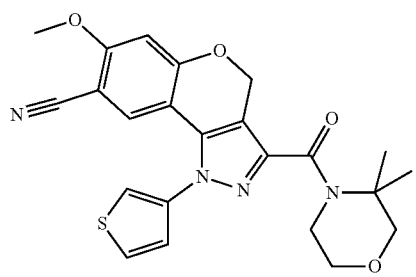 [SMILES: COc1cc2c(cc1C#N)-c1c(c(C(=O)N3CCOCC3(C)C)nn1-c1ccsc1)CO2] | 86 |

TABLE 1-continued
| | |
|---|---|
| 87 | 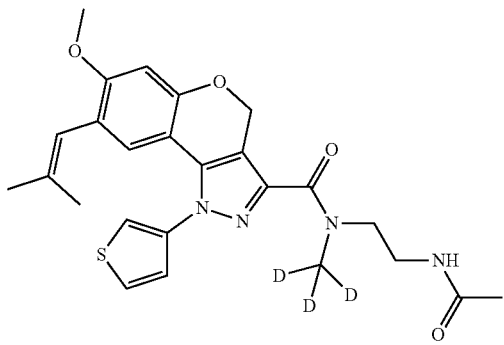 [SMILES: [2H]C([2H])([2H])N(CCNC(C)=O)C(=O)c1nn(-c2ccsc2)c2c1COc1cc(OC)c(C=C(C)C)cc1-2] |
| 88 | 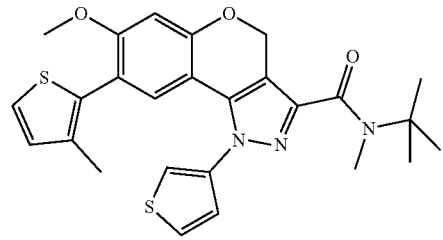 [SMILES: COc1cc2c(cc1-c1sccc1C)-c1c(c(C(=O)N(C)C(C)(C)C)nn1-c1ccsc1)CO2] |
| 89 | 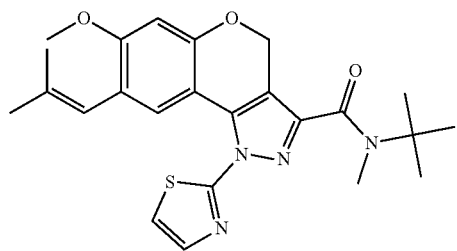 [SMILES: COc1cc2c(cc1C=C(C)C)-c1c(c(C(=O)N(C)C(C)(C)C)nn1-c1nccs1)CO2] |
| 90 | 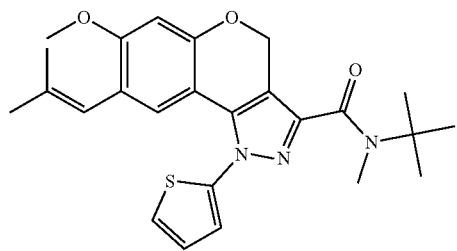 [SMILES: COc1cc2c(cc1C=C(C)C)-c1c(c(C(=O)N(C)C(C)(C)C)nn1-c1cccs1)CO2] |
| 91 | 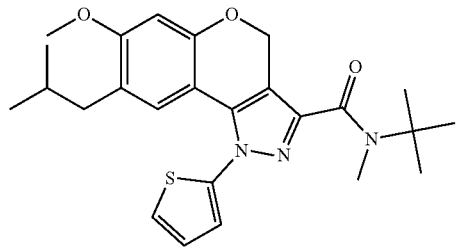 [SMILES: COc1cc2c(cc1CC(C)C)-c1c(c(C(=O)N(C)C(C)(C)C)nn1-c1cccs1)CO2] |
| 92 | 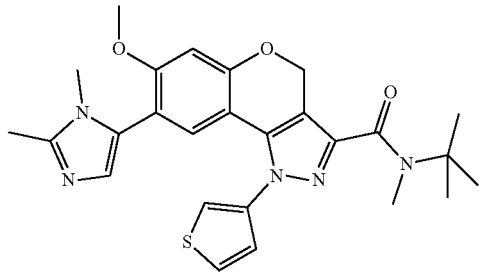 [SMILES: COc1cc2c(cc1-c1cnc(C)n1C)-c1c(c(C(=O)N(C)C(C)(C)C)nn1-c1ccsc1)CO2] |

TABLE 1-continued
| | |
|---|---|
| 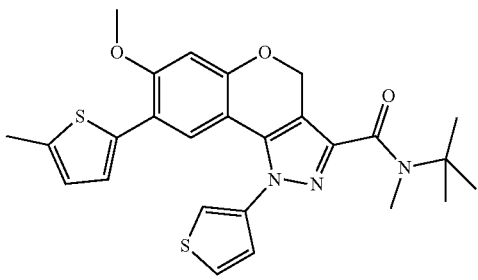 [SMILES: COc1cc2c(cc1-c1ccc(C)s1)-c1c(c(C(=O)N(C)C(C)(C)C)nn1-c1ccsc1)CO2] | 93 |
| 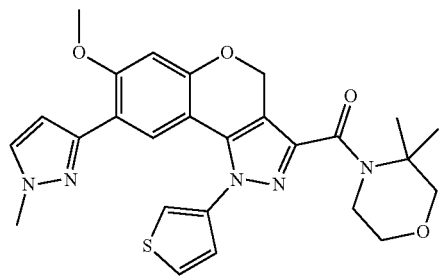 [SMILES: COc1cc2c(cc1-c1ccn(C)n1)-c1c(c(C(=O)N3CCOCC3(C)C)nn1-c1ccsc1)CO2] | 94 |
| 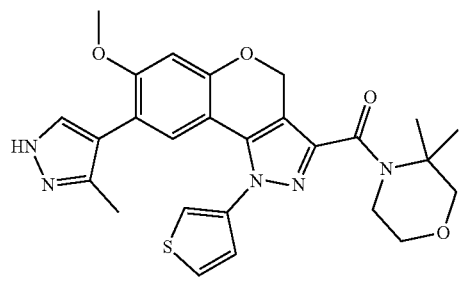 [SMILES: COc1cc2c(cc1-c1c[nH]nc1C)-c1c(c(C(=O)N3CCOCC3(C)C)nn1-c1ccsc1)CO2] | 95 |
| 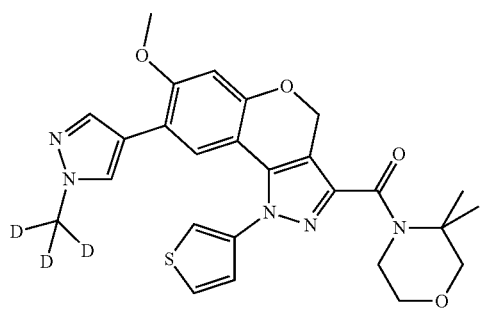 [SMILES: [2H]C([2H])([2H])n1cc(-c2cc3c(cc2OC)OCc2c(C(=O)N4CCOCC4(C)C)nn(-c4ccsc4)c2-3)cn1] | 96 |
| 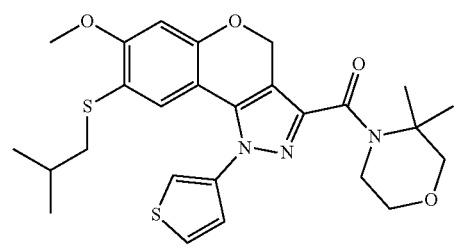 [SMILES: COc1cc2c(cc1SCC(C)C)-c1c(c(C(=O)N3CCOCC3(C)C)nn1-c1ccsc1)CO2] | 97 |
| 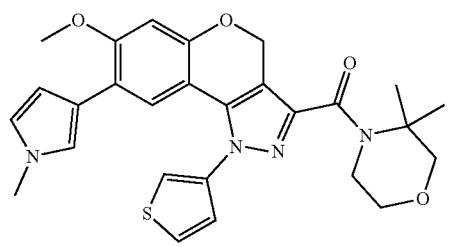 [SMILES: COc1cc2c(cc1-c1ccn(C)c1)-c1c(c(C(=O)N3CCOCC3(C)C)nn1-c1ccsc1)CO2] | 98 |

TABLE 1-continued
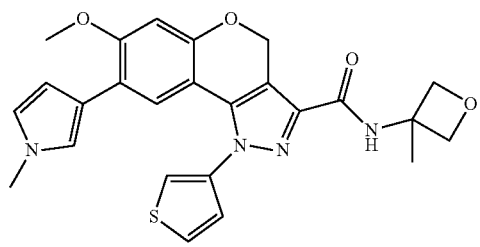 [SMILES: COc1cc2c(cc1-c1ccn(C)c1)-c1c(c(C(=O)NC3(C)COC3)nn1-c1ccsc1)CO2] 99
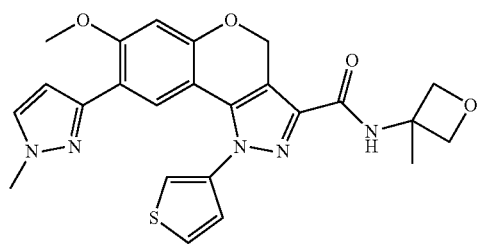 [SMILES: COc1cc2c(cc1-c1ccn(C)n1)-c1c(c(C(=O)NC3(C)COC3)nn1-c1ccsc1)CO2] 100
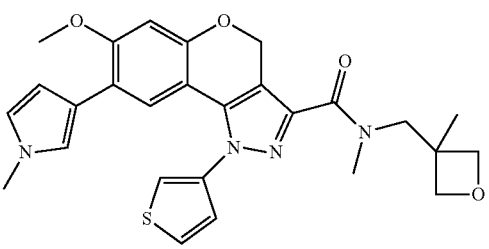 [SMILES: COc1cc2c(cc1-c1ccn(C)c1)-c1c(c(C(=O)N(C)CC3(C)COC3)nn1-c1ccsc1)CO2] 101
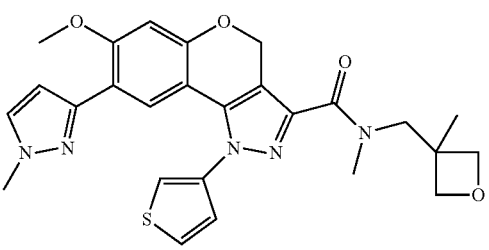 [SMILES: COc1cc2c(cc1-c1ccn(C)n1)-c1c(c(C(=O)N(C)CC3(C)COC3)nn1-c1ccsc1)CO2] 102
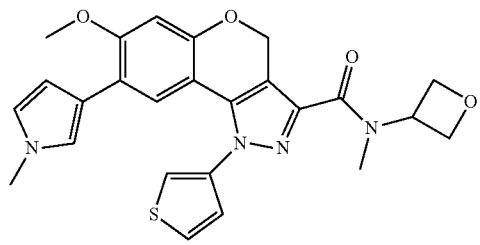 [SMILES: COc1cc2c(cc1-c1ccn(C)c1)-c1c(c(C(=O)N(C)C3COC3)nn1-c1ccsc1)CO2] 103
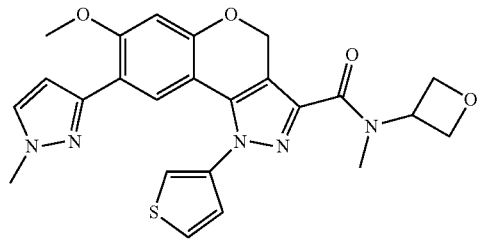 [SMILES: COc1cc2c(cc1-c1ccn(C)n1)-c1c(c(C(=O)N(C)C3COC3)nn1-c1ccsc1)CO2] 104

TABLE 1-continued
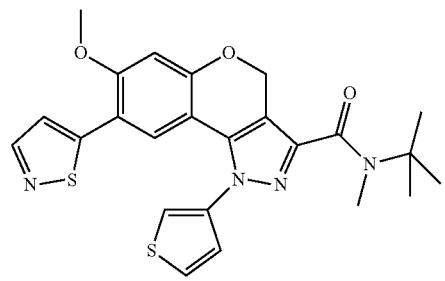 [SMILES: COc1cc2c(cc1-c1ccns1)-c1c(c(C(=O)N(C)C(C)(C)C)nn1-c1ccsc1)CO2]
105
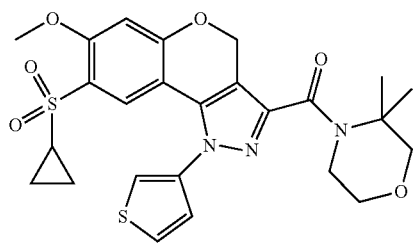
106
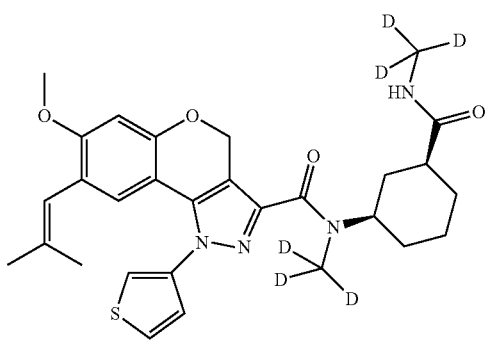 [SMILES: [2H]C([2H])([2H])NC(=O)[C@H]1CCC[C@@H](N(C(=O)c2nn(-c3ccsc3)c3c2COc2cc(OC)c(C=C(C)C)cc2-3)C([2H])([2H])[2H])C1]
107
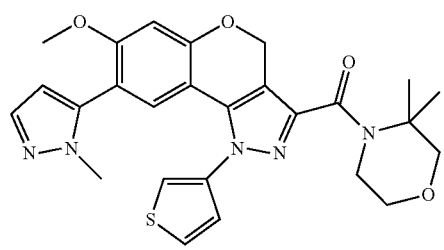 [SMILES: COc1cc2c(cc1-c1ccnn1C)-c1c(c(C(=O)N3CCOCC3(C)C)nn1-c1ccsc1)CO2]
108
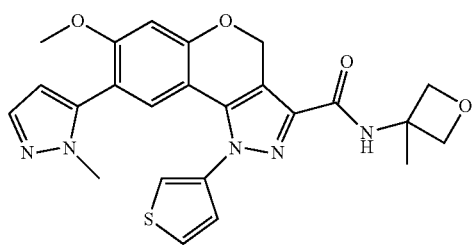 [SMILES: COc1cc2c(cc1-c1ccnn1C)-c1c(c(C(=O)NC3(C)COC3)nn1-c1ccsc1)CO2]
109
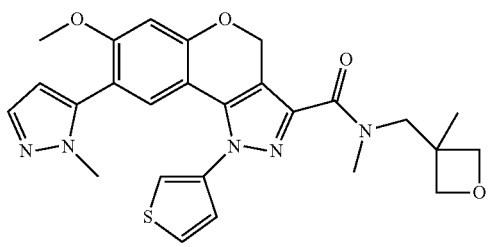 [SMILES: COc1cc2c(cc1-c1ccnn1C)-c1c(c(C(=O)N(C)CC3(C)COC3)nn1-c1ccsc1)CO2]
110

TABLE 1-continued
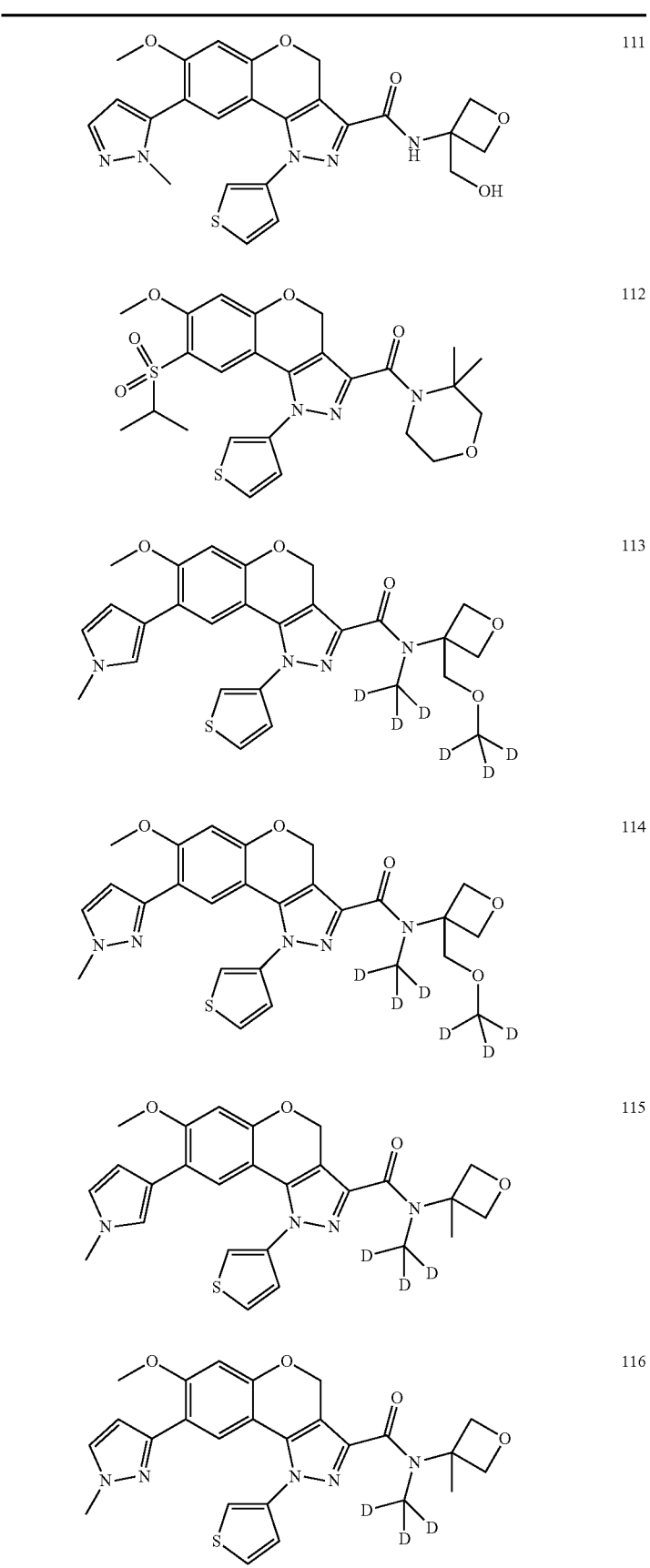
111
112
113
114
115
116

TABLE 1-continued
| | |
|---|---|
| 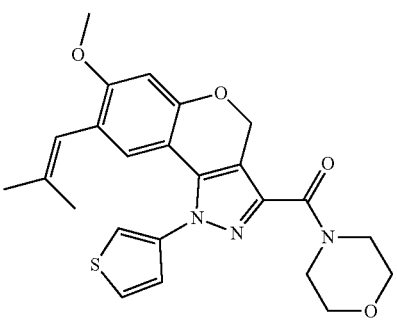 [SMILES: COc1cc2c(cc1C=C(C)C)-c1c(c(C(=O)N3CCOCC3)nn1-c1ccsc1)CO2] | 117 |
| 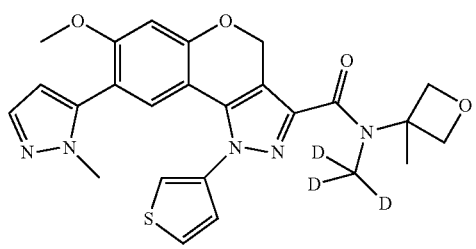 [SMILES: [2H]C([2H])([2H])N(C(=O)c1nn(-c2ccsc2)c2c1COc1cc(OC)c(-c3ccnn3C)cc1-2)C1(C)COC1] | 118 |
| 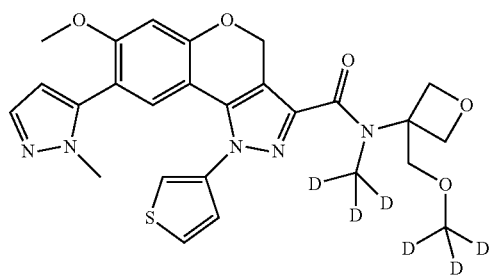 [SMILES: [2H]C([2H])([2H])OCC1(N(C(=O)c2nn(-c3ccsc3)c3c2COc2cc(OC)c(-c4ccnn4C)cc2-3)C([2H])([2H])[2H])COC1] | 119 |
| 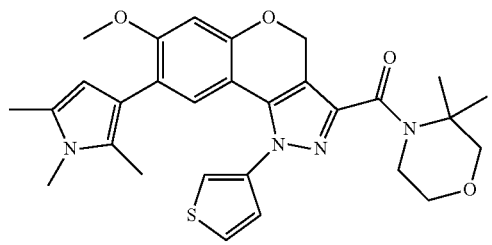 | 120 |
| 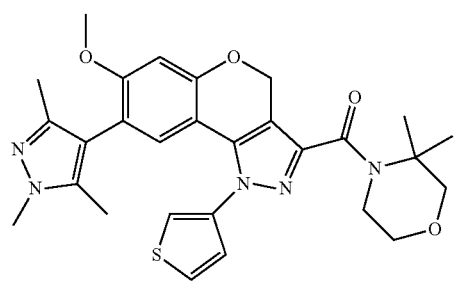 | 121 |

TABLE 1-continued
| | |
|---|---|
| 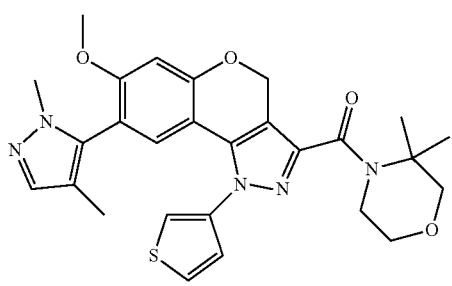 [SMILES: COc1cc2c(cc1-c1c(C)cnn1C)-c1c(c(C(=O)N3CCOCC3(C)C)nn1-c1ccsc1)CO2] | 122 |
| 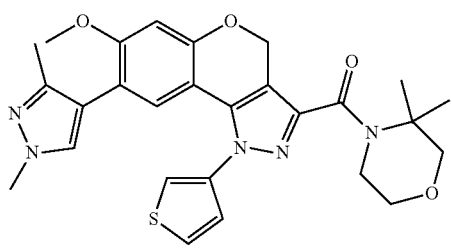 | 123 |
| 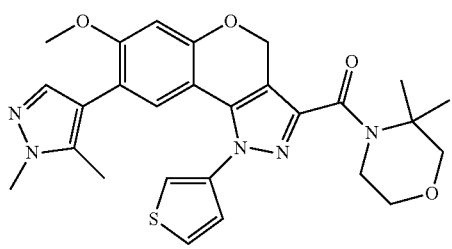 | 124 |
| 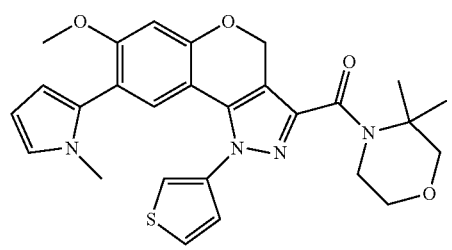 [SMILES: COc1cc2c(cc1-c1cccn1C)-c1c(c(C(=O)N3CCOCC3(C)C)nn1-c1ccsc1)CO2] | 125 |
| 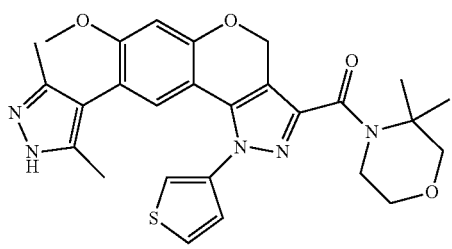 [SMILES: COc1cc2c(cc1-c1c(C)n[nH]c1C)-c1c(c(C(=O)N3CCOCC3(C)C)nn1-c1ccsc1)CO2] | 126 |
| 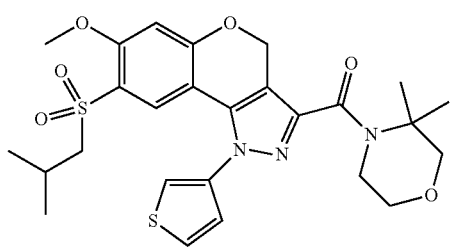 [SMILES: COc1cc2c(cc1S(=O)(=O)CC(C)C)-c1c(c(C(=O)N3CCOCC3(C)C)nn1-c1ccsc1)CO2] | 127 |

TABLE 1-continued
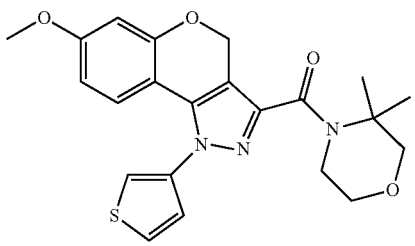
128
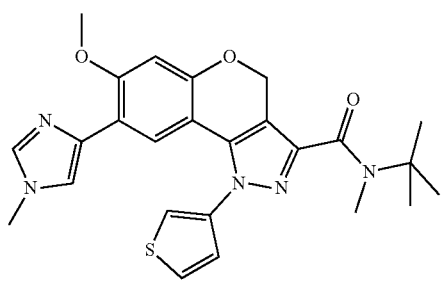 [SMILES: COc1cc2c(cc1-c1cn(C)cn1)-c1c(c(C(=O)N(C)C(C)(C)C)nn1-c1ccsc1)CO2]
129
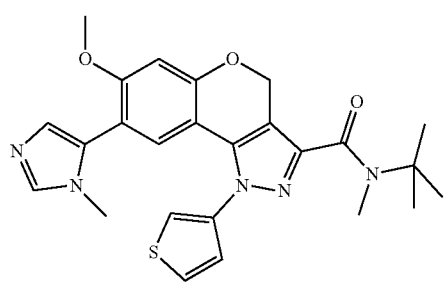 [SMILES: COc1cc2c(cc1-c1cncn1C)-c1c(c(C(=O)N(C)C(C)(C)C)nn1-c1ccsc1)CO2]
130
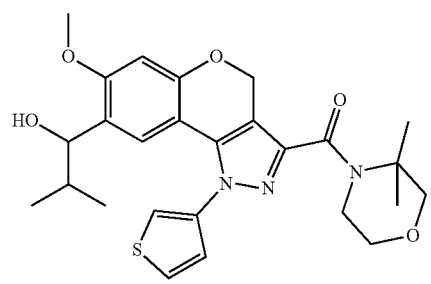
131
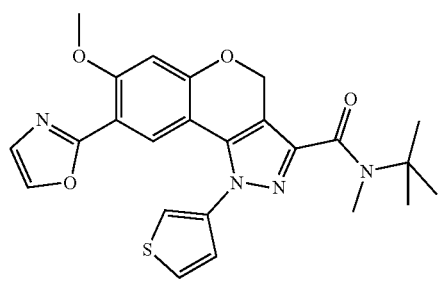 [SMILES: COc1cc2c(cc1-c1ncco1)-c1c(c(C(=O)N(C)C(C)(C)C)nn1-c1ccsc1)CO2]
132

TABLE 1-continued
| | |
|---|---|
| 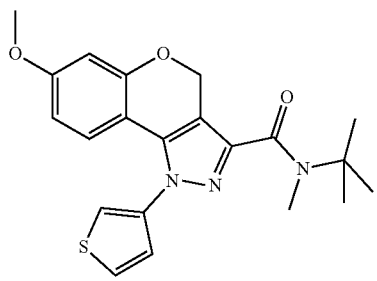 [SMILES: COc1ccc2c(c1)OCc1c(C(=O)N(C)C(C)(C)C)nn(-c3ccsc3)c1-2] | 133 |
| 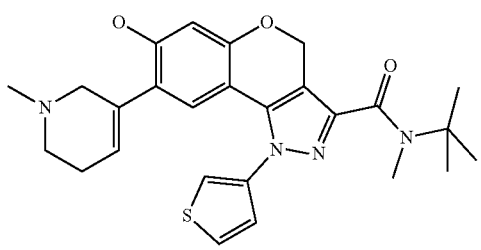 [SMILES: CN1CCC=C(c2cc3c(cc2O)OCc2c(C(=O)N(C)C(C)(C)C)nn(-c4ccsc4)c2-3)C1] | 134 |
| 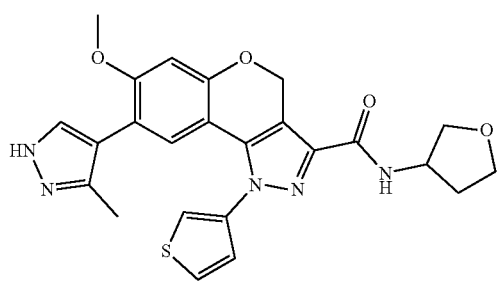 [SMILES: COc1cc2c(cc1-c1c[nH]nc1C)-c1c(c(C(=O)NC3CCOC3)nn1-c1ccsc1)CO2] | 135 |
| 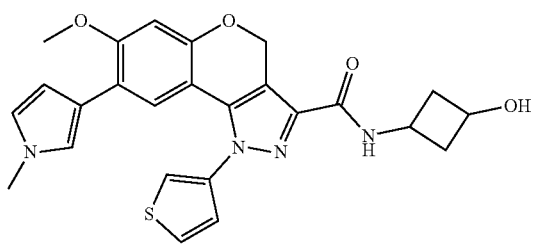 [SMILES: COc1cc2c(cc1-c1ccn(C)c1)-c1c(c(C(=O)NC3CC(O)C3)nn1-c1ccsc1)CO2] | 136 |
| 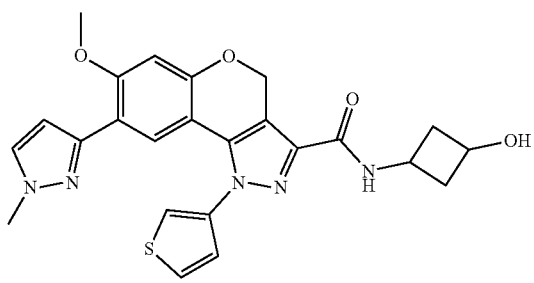 [SMILES: COc1cc2c(cc1-c1ccn(C)n1)-c1c(c(C(=O)NC3CC(O)C3)nn1-c1ccsc1)CO2] | 137 |
| 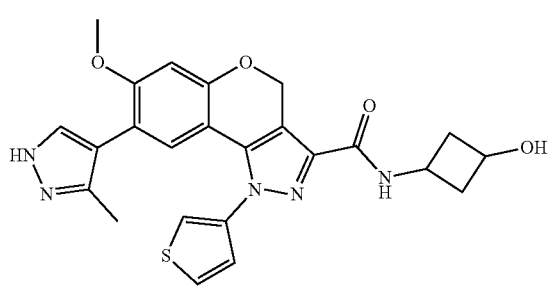 [SMILES: COc1cc2c(cc1-c1c[nH]nc1C)-c1c(c(C(=O)NC3CC(O)C3)nn1-c1ccsc1)CO2] | 138 |

TABLE 1-continued
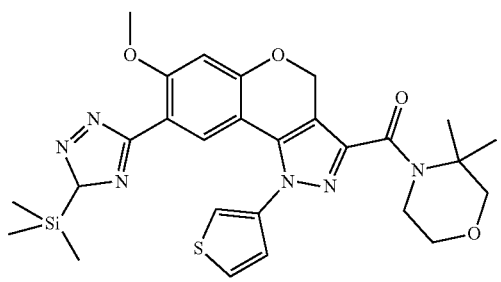
139
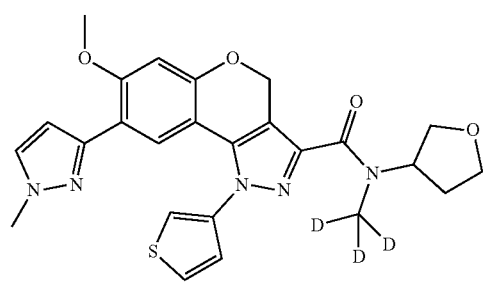 [SMILES: [2H]C([2H])([2H])N(C(=O)c1nn(-c2ccsc2)c2c1COc1cc(OC)c(-c3ccn(C)n3)cc1-2)C1CCOC1]
140
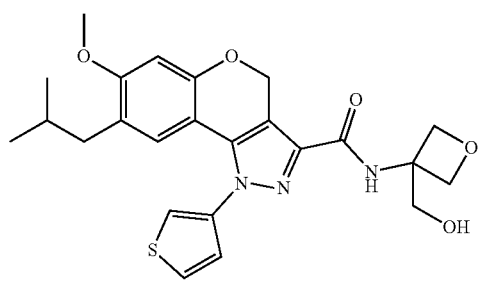 [SMILES: COc1cc2c(cc1CC(C)C)-c1c(c(C(=O)NC3(CO)COC3)nn1-c1ccsc1)CO2]
141
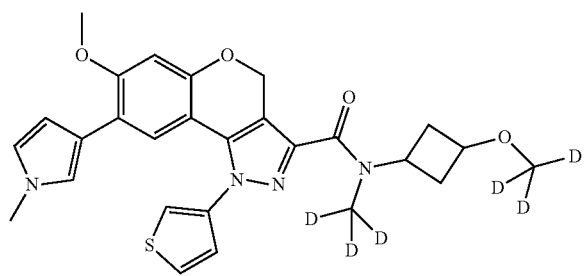 [SMILES: [2H]C([2H])([2H])OC1CC(N(C(=O)c2nn(-c3ccsc3)c3c2COc2cc(OC)c(-c4ccn(C)c4)cc2-3)C([2H])([2H])[2H])C1]
142
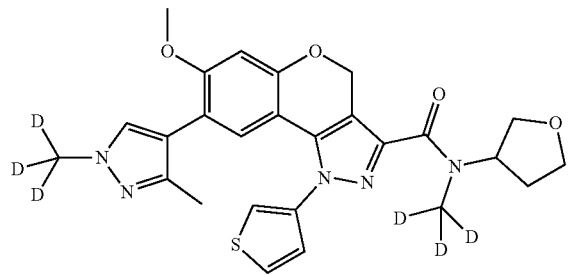 [SMILES: [2H]C([2H])([2H])N(C(=O)c1nn(-c2ccsc2)c2c1COc1cc(OC)c(-c3cn(C([2H])([2H])[2H])nc3C)cc1-2)C1CCOC1]
143

TABLE 1-continued
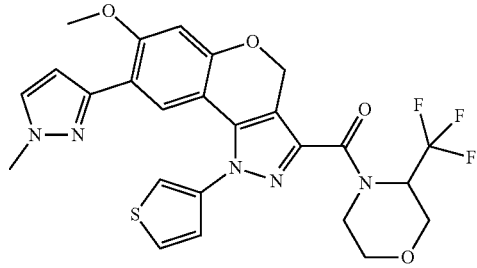 [SMILES: COc1cc2c(cc1-c1ccn(C)n1)-c1c(c(C(=O)N3CCOCC3C(F)(F)F)nn1-c1ccsc1)CO2] 144
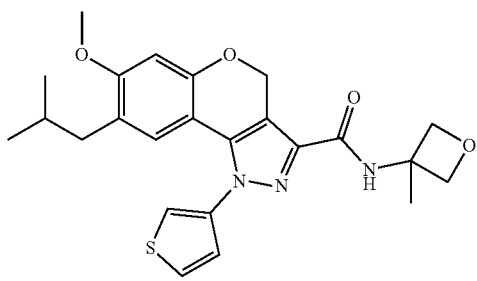 [SMILES: COc1cc2c(cc1CC(C)C)-c1c(c(C(=O)NC3(C)COC3)nn1-c1ccsc1)CO2] 145
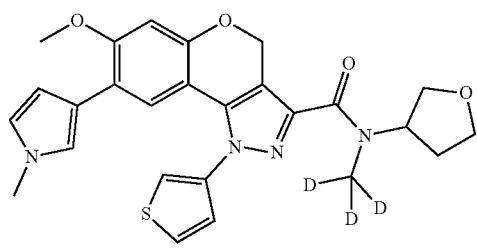 [SMILES: [2H]C([2H])([2H])N(C(=O)c1nn(-c2ccsc2)c2c1COc1cc(OC)c(-c3ccn(C)c3)cc1-2)C1CCOC1] 146
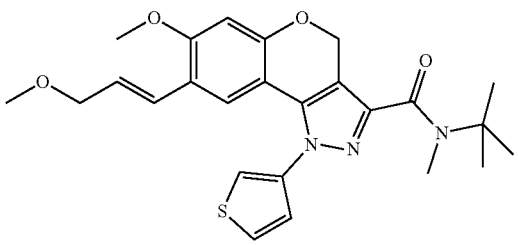 [SMILES: COC/C=C/c1cc2c(cc1OC)OCc1c(C(=O)N(C)C(C)(C)C)nn(-c3ccsc3)c1-2] 147
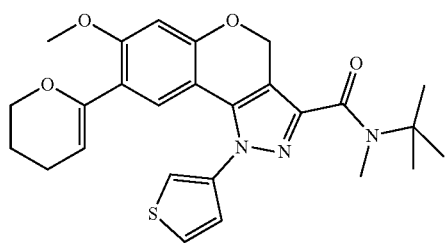 [SMILES: COc1cc2c(cc1C1=CCCCO1)-c1c(c(C(=O)N(C)C(C)(C)C)nn1-c1ccsc1)CO2] 148
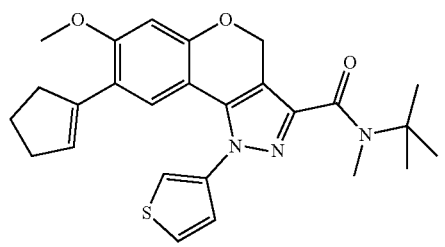 [SMILES: COc1cc2c(cc1C1=CCCC1)-c1c(c(C(=O)N(C)C(C)(C)C)nn1-c1ccsc1)CO2] 149

TABLE 1-continued
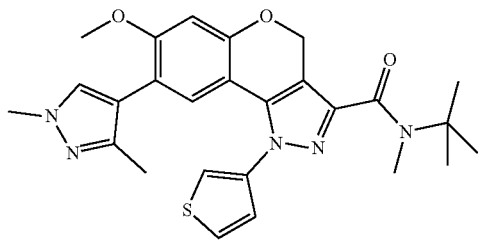 [SMILES: COc1cc2c(cc1-c1cn(C)nc1C)-c1c(c(C(=O)N(C)C(C)(C)C)nn1-c1ccsc1)CO2] 150
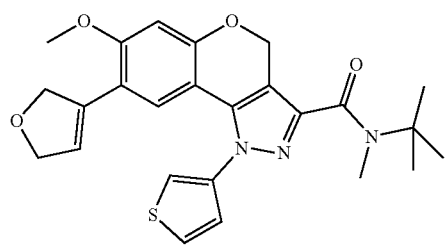 [SMILES: COc1cc2c(cc1C1=CCOC1)-c1c(c(C(=O)N(C)C(C)(C)C)nn1-c1ccsc1)CO2] 151
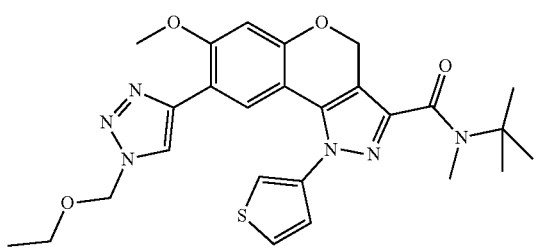 [SMILES: CCOCn1cc(-c2cc3c(cc2OC)OCc2c(C(=O)N(C)C(C)(C)C)nn(-c4ccsc4)c2-3)nn1] 152
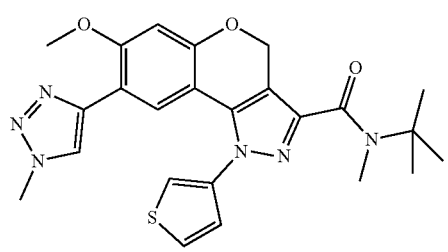 [SMILES: COc1cc2c(cc1-c1cn(C)nn1)-c1c(c(C(=O)N(C)C(C)(C)C)nn1-c1ccsc1)CO2] 153
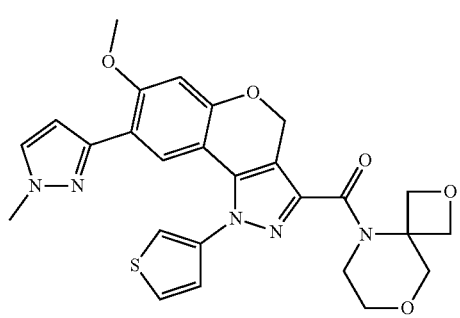 [SMILES: COc1cc2c(cc1-c1ccn(C)n1)-c1c(c(C(=O)N3CCOCC34COC4)nn1-c1ccsc1)CO2] 154

TABLE 1-continued
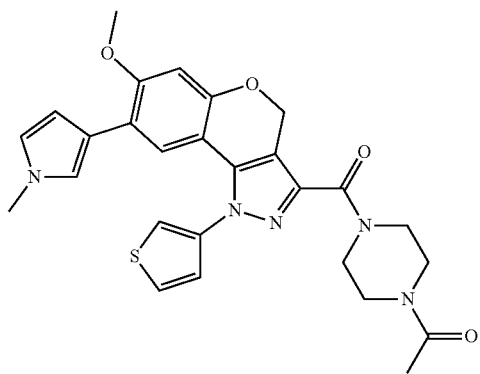 [SMILES: COc1cc2c(cc1-c1ccn(C)c1)-c1c(c(C(=O)N3CCN(C(C)=O)CC3)nn1-c1ccsc1)CO2]
155
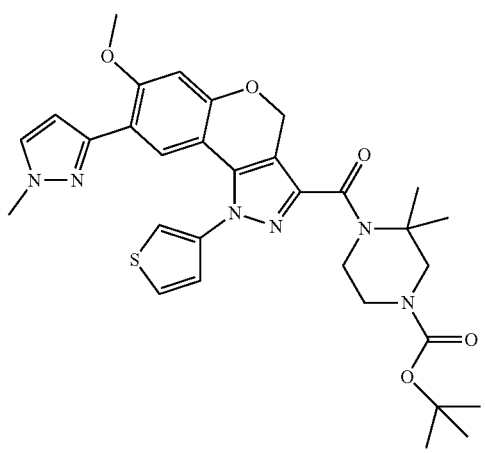 [SMILES: COc1cc2c(cc1-c1ccn(C)n1)-c1c(c(C(=O)N3CCN(C(=O)OC(C)(C)C)CC3(C)C)nn1-c1ccsc1)CO2]
156
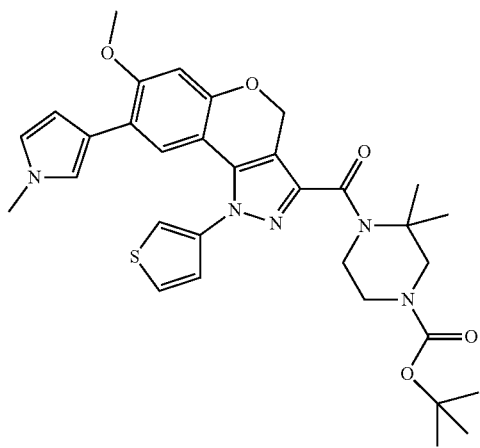 [SMILES: COc1cc2c(cc1-c1ccn(C)c1)-c1c(c(C(=O)N3CCN(C(=O)OC(C)(C)C)CC3(C)C)nn1-c1ccsc1)CO2]
157

TABLE 1-continued
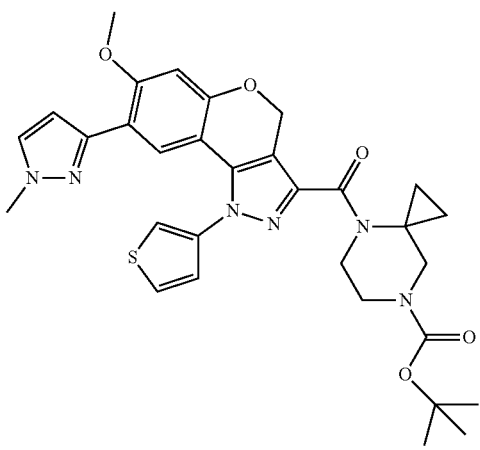 [SMILES: COc1cc2c(cc1-c1ccn(C)n1)-c1c(c(C(=O)N3CCN(C(=O)OC(C)(C)C)CC34CC4)nn1-c1ccsc1)CO2]
158
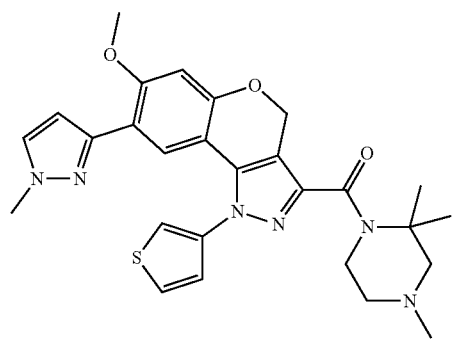
159
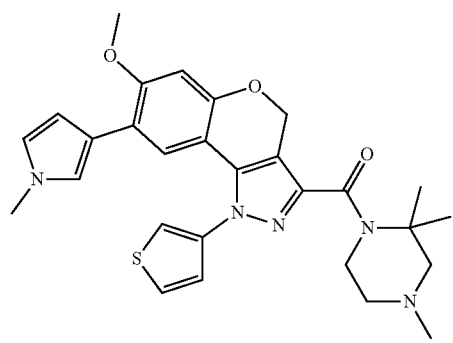
160
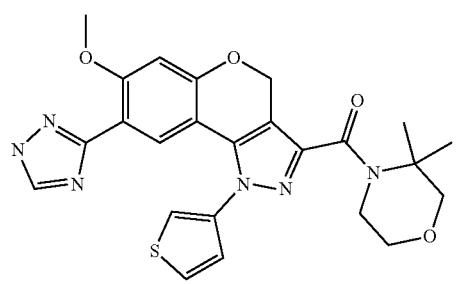 [SMILES: COc1cc2c(cc1-c1nc[nH]n1)-c1c(c(C(=O)N3CCOCC3(C)C)nn1-c1ccsc1)CO2]
161

TABLE 1-continued
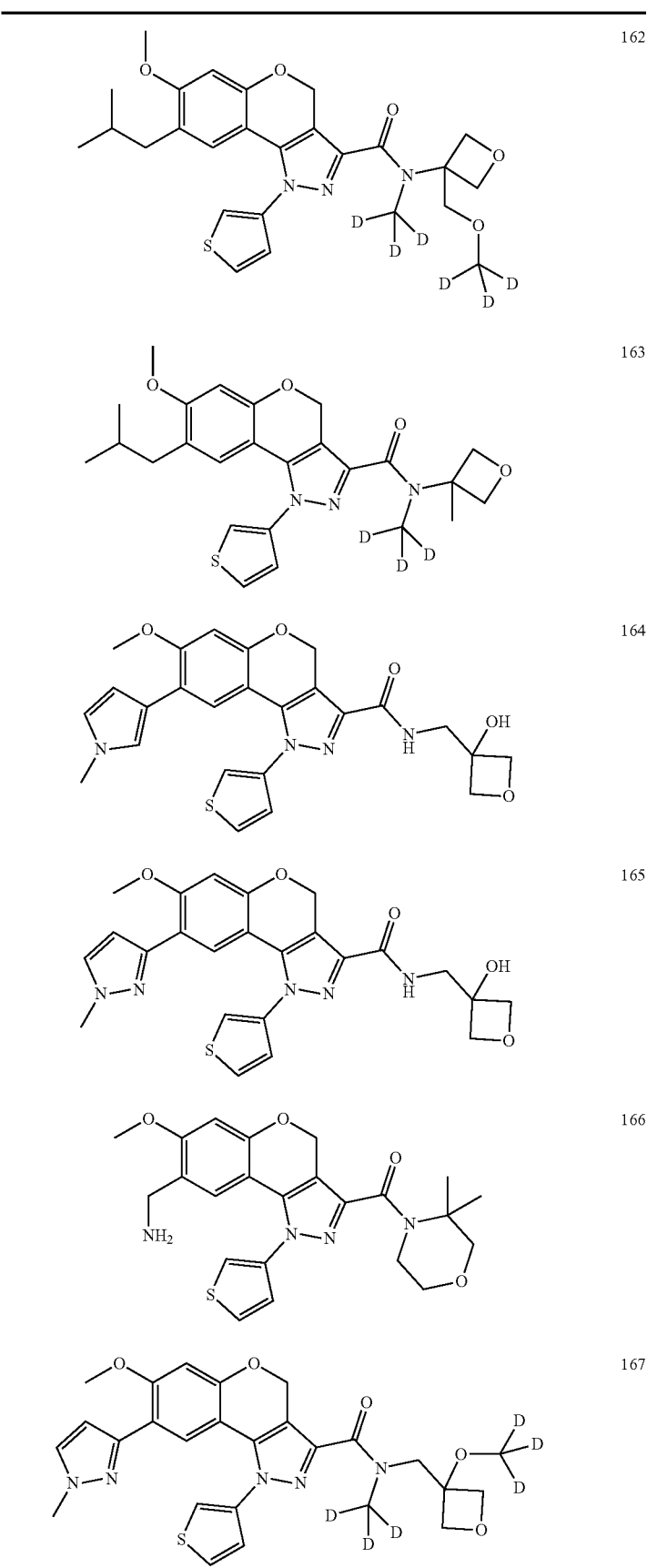

TABLE 1-continued
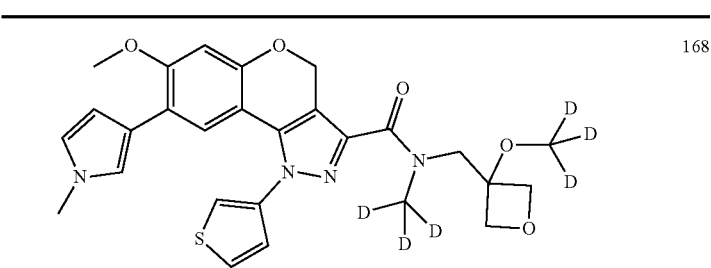
168
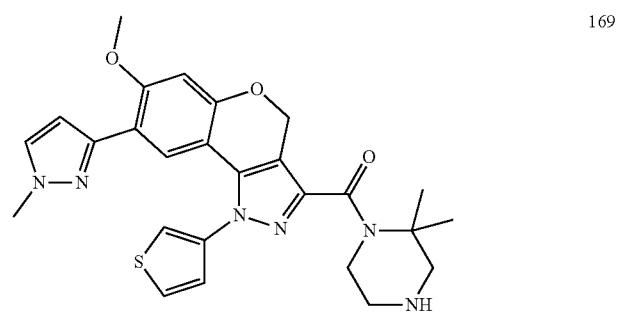
169
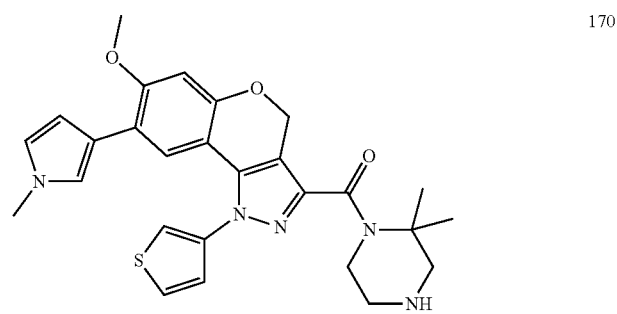
170
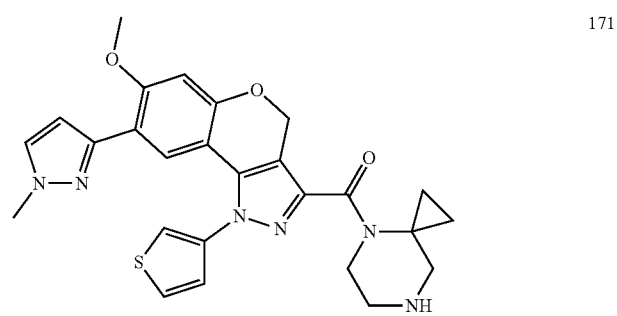
171
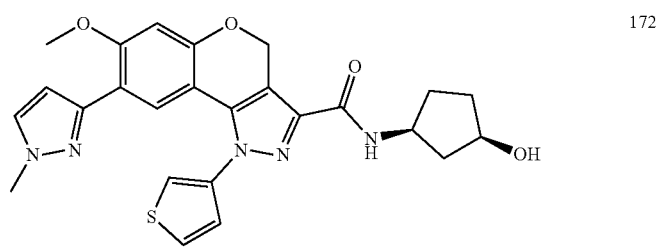
172

TABLE 1-continued
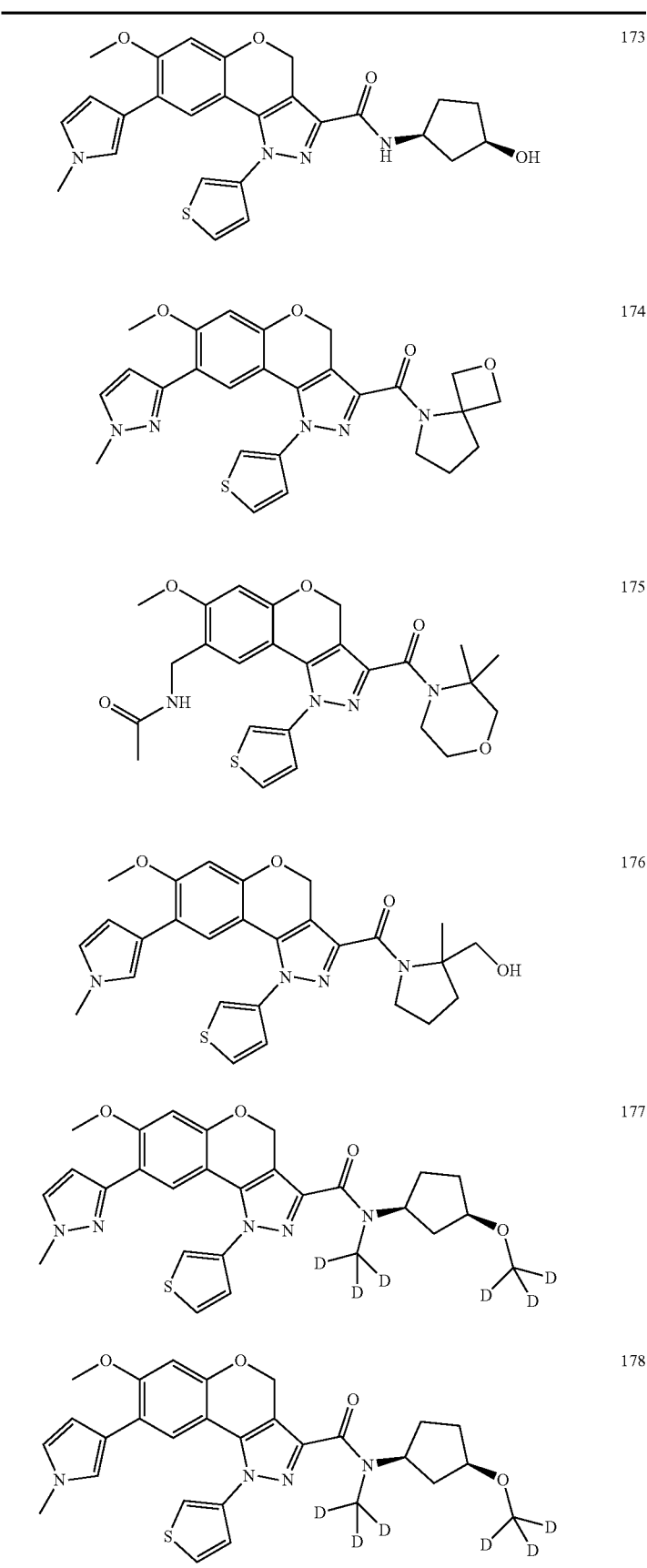

TABLE 1-continued
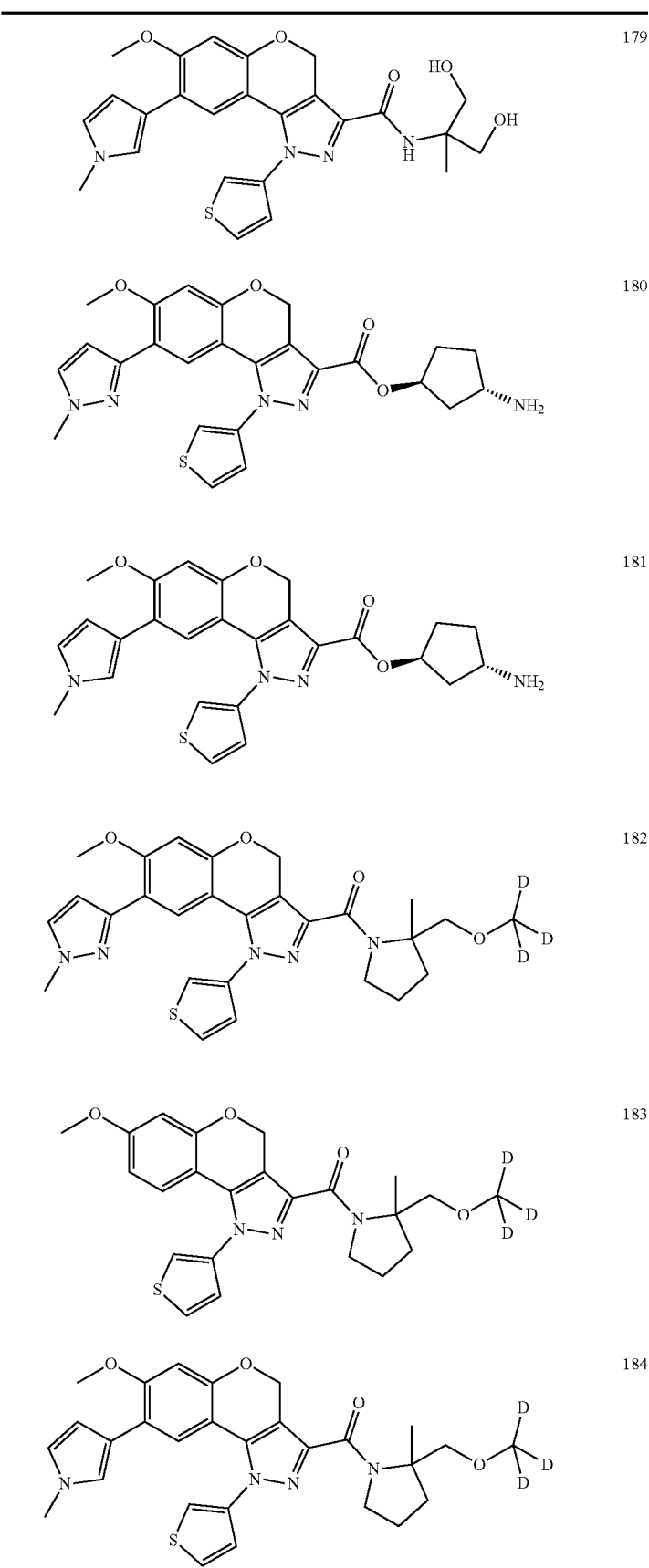

TABLE 1-continued
| | |
|---|---|
| 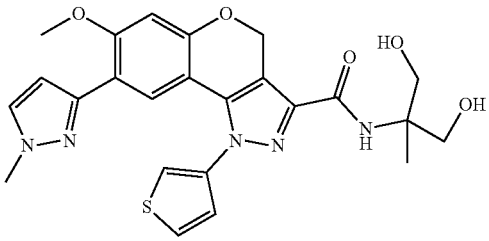 [SMILES: COc1cc2c(cc1-c1ccn(C)n1)-c1c(c(C(=O)NC(C)(CO)CO)nn1-c1ccsc1)CO2] | 185 |
| 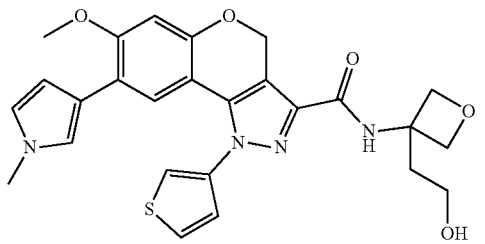 [SMILES: COc1cc2c(cc1-c1ccn(C)c1)-c1c(c(C(=O)NC3(CCO)COC3)nn1-c1ccsc1)CO2] | 186 |
| 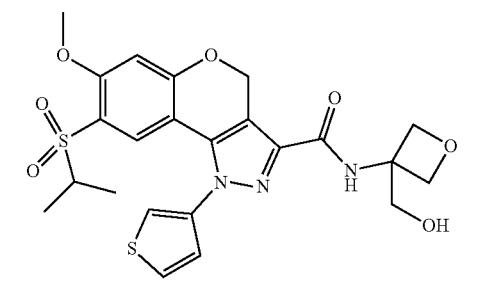 [SMILES: COc1cc2c(cc1S(=O)(=O)C(C)C)-c1c(c(C(=O)NC3(CO)COC3)nn1-c1ccsc1)CO2] | 187 |
| 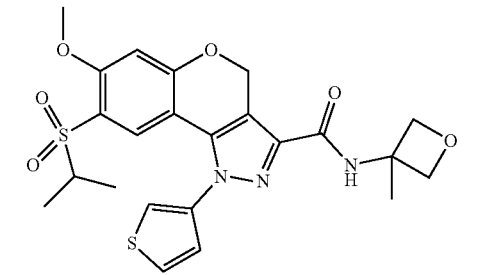 [SMILES: COc1cc2c(cc1S(=O)(=O)C(C)C)-c1c(c(C(=O)NC3(C)COC3)nn1-c1ccsc1)CO2] | 188 |
| 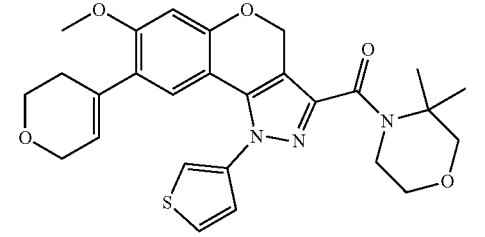 [SMILES: COc1cc2c(cc1C1=CCOCC1)-c1c(c(C(=O)N3CCOCC3(C)C)nn1-c1ccsc1)CO2] | 189 |
| 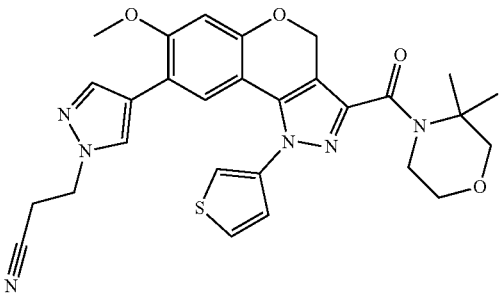 [SMILES: COc1cc2c(cc1-c1cnn(CCC#N)c1)-c1c(c(C(=O)N3CCOCC3(C)C)nn1-c1ccsc1)CO2] | 190 |

TABLE 1-continued
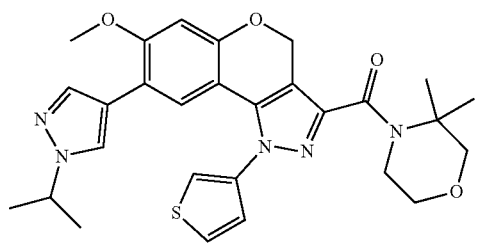 [SMILES: COc1cc2c(cc1-c1cnn(C(C)C)c1)-c1c(c(C(=O)N3CCOCC3(C)C)nn1-c1ccsc1)CO2] 191
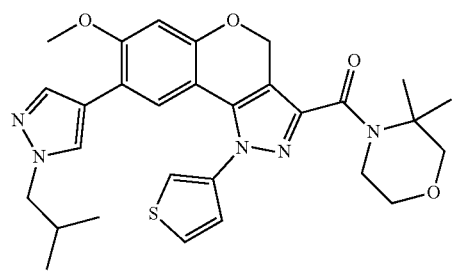 [SMILES: COc1cc2c(cc1-c1cnn(CC(C)C)c1)-c1c(c(C(=O)N3CCOCC3(C)C)nn1-c1ccsc1)CO2] 192
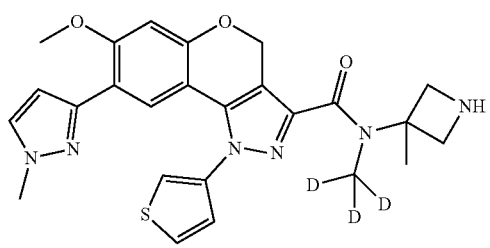 [SMILES: [2H]C([2H])([2H])N(C(=O)c1nn(-c2ccsc2)c2c1COc1cc(OC)c(-c3ccn(C)n3)cc1-2)C1(C)CNC1] 193
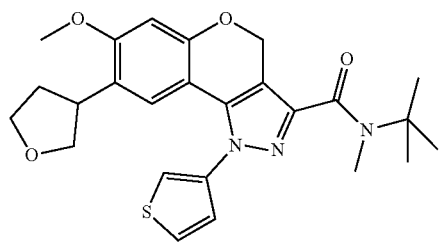 [SMILES: COc1cc2c(cc1C1CCOC1)-c1c(c(C(=O)N(C)C(C)(C)C)nn1-c1ccsc1)CO2] 194
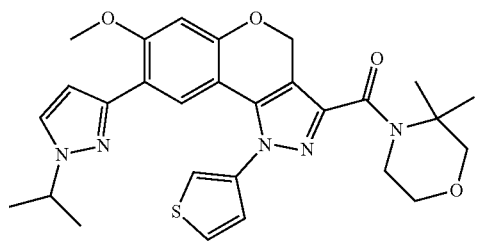 [SMILES: COc1cc2c(cc1-c1ccn(C(C)C)n1)-c1c(c(C(=O)N3CCOCC3(C)C)nn1-c1ccsc1)CO2] 195
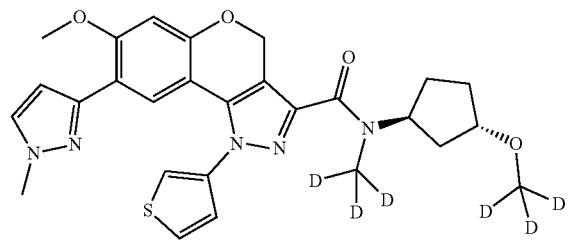 [SMILES: [2H]C([2H])([2H])O[C@H]1CC[C@H](N(C(=O)c2nn(-c3ccsc3)c3c2COc2cc(OC)c(-c4ccn(C)n4)cc2-3)C([2H])([2H])[2H])C1] 196

TABLE 1-continued
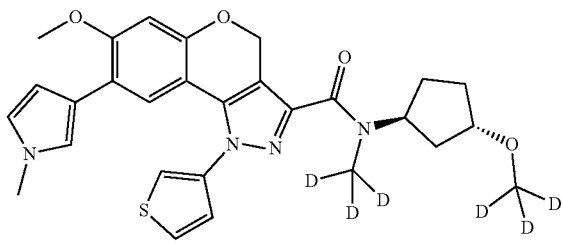 [SMILES: [2H]C([2H])([2H])O[C@H]1CC[C@H](N(C(=O)c2nn(-c3ccsc3)c3c2COc2cc(OC)c(-c4ccn(C)c4)cc2-3)C([2H])([2H])[2H])C1] 197
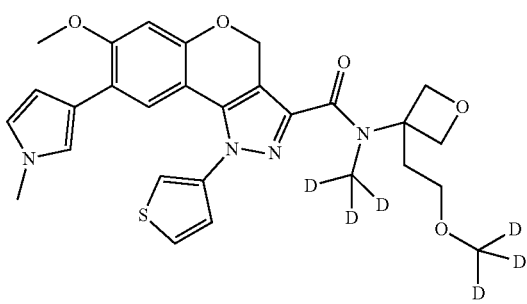 [SMILES: [2H]C([2H])([2H])OCCC1(N(C(=O)c2nn(-c3ccsc3)c3c2COc2cc(OC)c(-c4ccn(C)c4)cc2-3)C([2H])([2H])[2H])COC1] 198
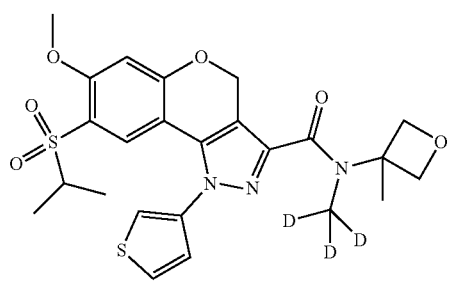 [SMILES: [2H]C([2H])([2H])N(C(=O)c1nn(-c2ccsc2)c2c1COc1cc(OC)c(S(=O)(=O)C(C)C)cc1-2)C1(C)COC1] 199
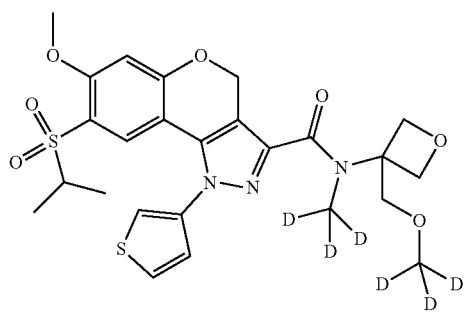 [SMILES: [2H]C([2H])([2H])OCC1(N(C(=O)c2nn(-c3ccsc3)c3c2COc2cc(OC)c(S(=O)(=O)C(C)C)cc2-3)C([2H])([2H])[2H])COC1] 200
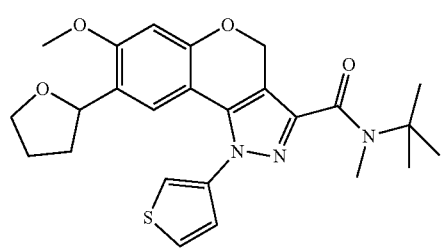 [SMILES: COc1cc2c(cc1C1CCCO1)-c1c(c(C(=O)N(C)C(C)(C)C)nn1-c1ccsc1)CO2] 201

TABLE 1-continued
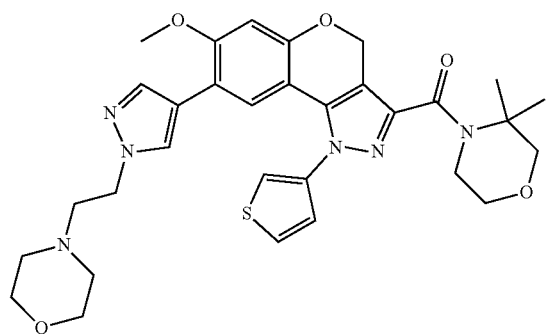 [SMILES: COc1cc2c(cc1-c1cnn(CCN3CCOCC3)c1)-c1c(c(C(=O)N3CCOCC3(C)C)nn1-c1ccsc1)CO2]
202
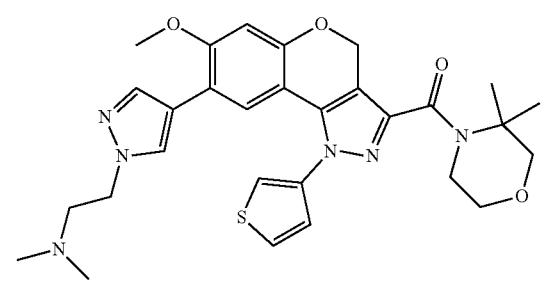
203
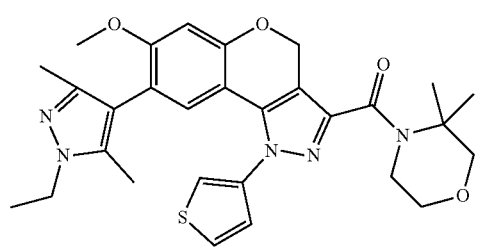 [SMILES: CCn1nc(C)c(-c2cc3c(cc2OC)OCc2c(C(=O)N4CCOCC4(C)C)nn(-c4ccsc4)c2-3)c1C]
204
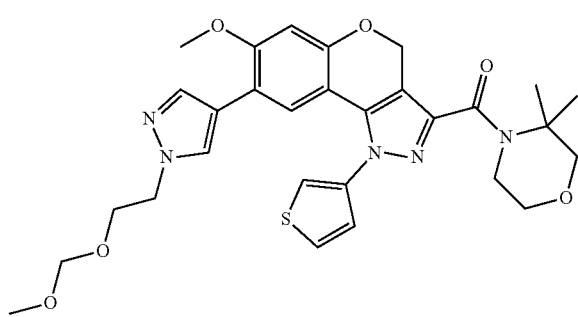
205
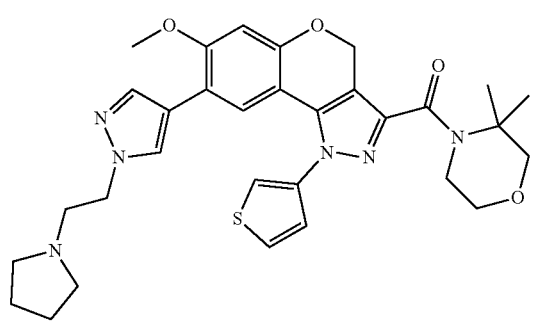 [SMILES: COc1cc2c(cc1-c1cnn(CCN3CCCC3)c1)-c1c(c(C(=O)N3CCOCC3(C)C)nn1-c1ccsc1)CO2]
206

TABLE 1-continued
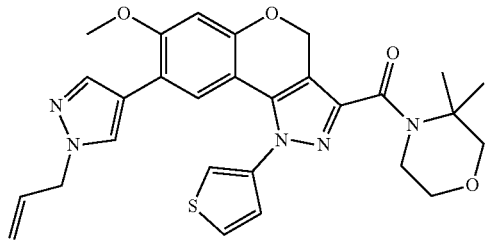 [SMILES: C=CCn1cc(-c2cc3c(cc2OC)OCc2c(C(=O)N4CCOCC4(C)C)nn(-c4ccsc4)c2-3)cn1]
207
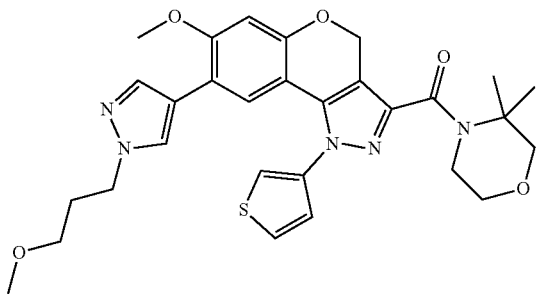
208
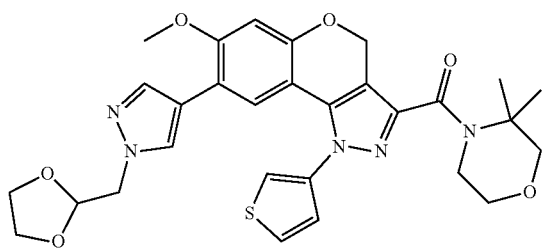 [SMILES: COc1cc2c(cc1-c1cnn(CC3OCCO3)c1)-c1c(c(C(=O)N3CCOCC3(C)C)nn1-c1ccsc1)CO2]
209
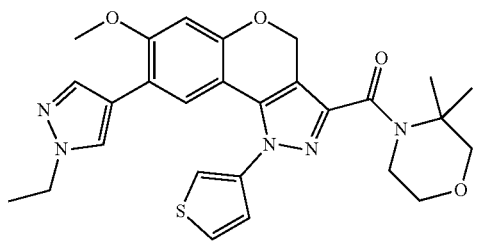 [SMILES: CCn1cc(-c2cc3c(cc2OC)OCc2c(C(=O)N4CCOCC4(C)C)nn(-c4ccsc4)c2-3)cn1]
210
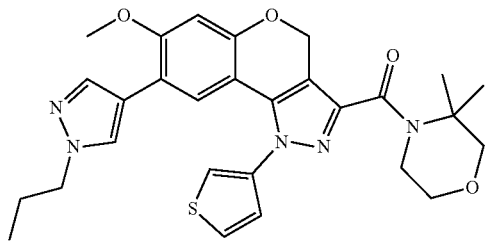 [SMILES: CCCn1cc(-c2cc3c(cc2OC)OCc2c(C(=O)N4CCOCC4(C)C)nn(-c4ccsc4)c2-3)cn1]
211
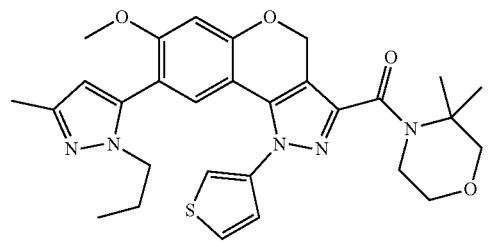
212

TABLE 1-continued
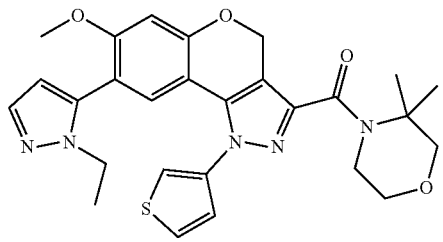 [SMILES: CCn1nccc1-c1cc2c(cc1OC)OCc1c(C(=O)N3CCOCC3(C)C)nn(-c3ccsc3)c1-2] 213
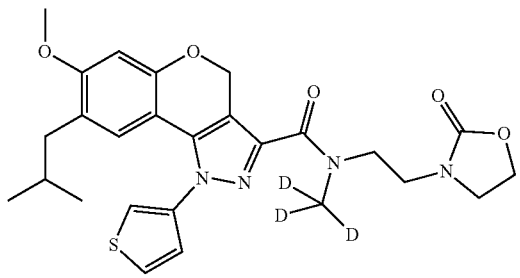 [SMILES: [2H]C([2H])([2H])N(CCN1CCOC1=O)C(=O)c1nn(-c2ccsc2)c2c1COc1cc(OC)c(CC(C)C)cc1-2] 214
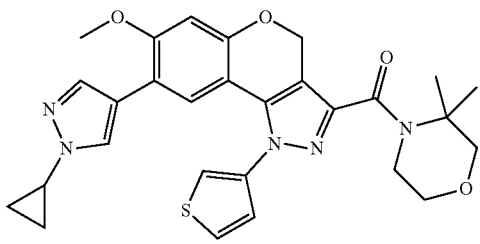 [SMILES: COc1cc2c(cc1-c1cnn(C3CC3)c1)-c1c(c(C(=O)N3CCOCC3(C)C)nn1-c1ccsc1)CO2] 215
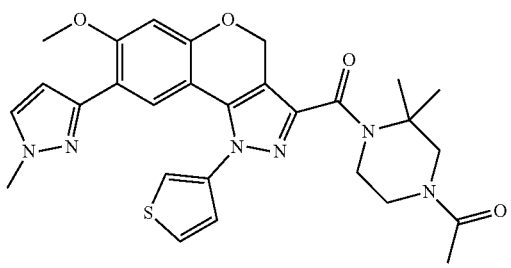 [SMILES: COc1cc2c(cc1-c1ccn(C)n1)-c1c(c(C(=O)N3CCN(C(C)=O)CC3(C)C)nn1-c1ccsc1)CO2] 216
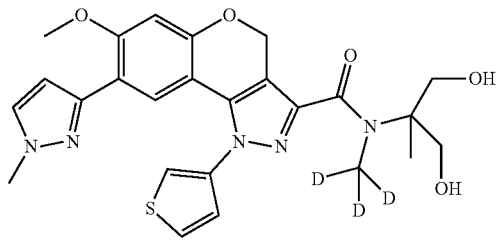 [SMILES: [2H]C([2H])([2H])N(C(=O)c1nn(-c2ccsc2)c2c1COc1cc(OC)c(-c3ccn(C)n3)cc1-2)C(C)(CO)CO] 217
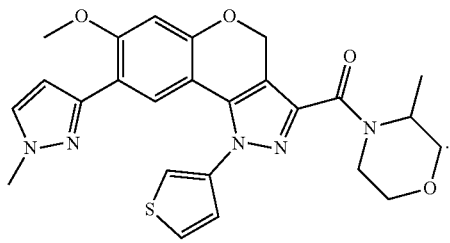 [SMILES: COc1cc2c(cc1-c1ccn(C)n1)-c1c(c(C(=O)N3CCOCC3C)nn1-c1ccsc1)CO2] 218

17. A pharmaceutical composition comprising a compound of claim 1, and a pharmaceutically acceptable adjuvant, carrier, or vehicle.

18. A method for treating a FSHR-mediated disorder in a patient in need thereof, comprising the step of administering to said patient a compound of claim 1.

19. A method for treating fertility disorders in a subject, comprising the step of administering to said subject a compound of claim 1 or a physiologically acceptable salt thereof.

* * * * *

UNITED STATES PATENT AND TRADEMARK OFFICE
CERTIFICATE OF CORRECTION

PATENT NO. : 10,081,637 B2
APPLICATION NO. : 14/900209
DATED : September 25, 2018
INVENTOR(S) : Henry Yu et al.

Page 1 of 1

It is certified that error appears in the above-identified patent and that said Letters Patent is hereby corrected as shown below:

In the Specification

Column 99, delete compounds 180 and 181

Column 346, delete entire column

Column 347, delete entire column

Column 348, delete Lines 1-32

Column 357, delete compound 180 at Line 17

Column 357, delete compound 181 at Line 18

In the Claims

Column 439, delete compounds 180 and 181

Signed and Sealed this
Eighteenth Day of December, 2018

Andrei Iancu
*Director of the United States Patent and Trademark Office*